United States Patent
Nagamori et al.

(10) Patent No.: US 10,752,596 B2
(45) Date of Patent: Aug. 25, 2020

(54) NITROGEN-CONTAINING HETEROARYL COMPOUND AND PHARMACEUTICAL USE THEREOF

(71) Applicant: JAPAN TOBACCO INC., Tokyo (JP)

(72) Inventors: Hironobu Nagamori, Takatsuki (JP); Tatsuya Nishimaru, Takatsuki (JP); Masaki Takagi, Takatsuki (JP); Ikuo Mitani, Takatsuki (JP); Yuichi Nakagawa, Takatsuki (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/150,989

(22) Filed: Oct. 3, 2018

(65) Prior Publication Data

US 2019/0152926 A1 May 23, 2019

(30) Foreign Application Priority Data

Oct. 4, 2017 (JP) ................................. 2017-194005

(51) Int. Cl.
| | | |
|---|---|---|
| *C07D 241/12* | (2006.01) | |
| *C07D 213/46* | (2006.01) | |
| *A61P 19/06* | (2006.01) | |
| *C07D 405/10* | (2006.01) | |
| *A61P 43/00* | (2006.01) | |
| *A61K 31/4965* | (2006.01) | |
| *C07D 217/16* | (2006.01) | |
| *A61K 31/497* | (2006.01) | |
| *C07D 213/55* | (2006.01) | |
| *A61K 31/4433* | (2006.01) | |
| *A61K 31/4418* | (2006.01) | |
| *C07D 405/04* | (2006.01) | |
| *A61K 31/472* | (2006.01) | |

(52) U.S. Cl.
CPC ........ *C07D 241/12* (2013.01); *A61K 31/4418* (2013.01); *A61K 31/4433* (2013.01); *A61K 31/472* (2013.01); *A61K 31/497* (2013.01); *A61K 31/4965* (2013.01); *A61P 19/06* (2018.01); *A61P 43/00* (2018.01); *C07D 213/46* (2013.01); *C07D 213/55* (2013.01); *C07D 217/16* (2013.01); *C07D 405/04* (2013.01); *C07D 405/10* (2013.01)

(58) Field of Classification Search
CPC ...... C07D 241/12; C07D 213/46; A61P 19/06
See application file for complete search history.

(56) References Cited

U.S. PATENT DOCUMENTS

| | | | |
|---|---|---|---|
| 5,861,419 A | 1/1999 | Dube et al. | |
| 6,001,843 A | 12/1999 | Dube et al. | |
| 6,071,936 A | 6/2000 | Dube et al. | |
| 6,562,828 B1 * | 5/2003 | Katoh | C07D 401/04 514/256 |
| 6,596,736 B2 | 7/2003 | Dube et al. | |
| 6,812,346 B2 | 11/2004 | Dube et al. | |
| 7,060,715 B2 | 6/2006 | Dube et al. | |
| 9,181,162 B2 | 11/2015 | Chen et al. | |
| 10,000,443 B2 | 6/2018 | Chen et al. | |
| 2003/0065011 A1 | 4/2003 | Dube et al. | |
| 2004/0029921 A1 | 2/2004 | Dube et al. | |
| 2005/0009875 A1 | 1/2005 | Dube et al. | |
| 2005/0070545 A1 * | 3/2005 | Fox | C07D 487/04 514/248 |
| 2007/0078135 A1 | 4/2007 | Yuan et al. | |
| 2011/0077267 A1 * | 3/2011 | Mitani | C07D 471/04 514/303 |
| 2012/0121536 A1 | 5/2012 | Chen et al. | |
| 2016/0137585 A1 | 5/2016 | Chen et al. | |
| 2018/0346406 A1 | 12/2018 | Chen et al. | |

FOREIGN PATENT DOCUMENTS

| | | |
|---|---|---|
| CN | 104306363 A | 1/2015 |
| JP | H11-514008 A | 11/1999 |
| JP | 2007-176933 A | 7/2007 |
| JP | 2008-536950 A | 9/2008 |
| WO | WO 2008/126901 A1 | 10/2008 |
| WO | WO 2011/119866 A1 | 9/2011 |

OTHER PUBLICATIONS

Wu et al., "3-(Piperidin-4-ylmethoxy)pyridine Containing Compounds Are Potent Inhibitors of Lysine Specific Demethylase 1," *J. Med. Chem*, 59(1): 253-263 (2016).
Japanese Patent Office, International Search Report in International Patent Application No. PCT/JP2018/037007 (dated Dec. 25, 2018).

* cited by examiner

*Primary Examiner* — Mark L Shibuya
*Assistant Examiner* — Ebenezer O Sackey
(74) *Attorney, Agent, or Firm* — Leydig, Voit & Mayer, Ltd.

(57) ABSTRACT

The invention provides a compound having a GLUT9 inhibitory activity. The compound is of Formula [I]

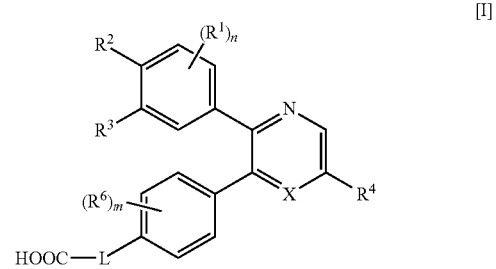

wherein each symbol is as defined in the specification, or a pharmaceutically acceptable salt thereof.

32 Claims, No Drawings

NITROGEN-CONTAINING HETEROARYL COMPOUND AND PHARMACEUTICAL USE THEREOF

CROSS-REFERENCE TO RELATED APPLICATIONS

This patent application claims the benefit of Japanese Patent Application No. 2017-194005, filed on Oct. 4, 2017, which is incorporated by reference in its entirety herein.

TECHNICAL FIELD

The present invention relates to a nitrogen-containing heteroaryl compound having a GLUT9 inhibitory activity, or a pharmaceutically acceptable salt thereof, a pharmaceutical composition containing the same, and a pharmaceutical use thereof.

BACKGROUND ART

Uric acid is a poorly-soluble substance having a molecular weight of 168 and a dissociation constant (pKa value) of 5.75 and is present in the form of uric acid or a conjugate base (urate) thereof, depending on the pH, when it is in the body fluid. In human and many other primates, due to the functional absence of urate oxidase (uricase) in the liver, uric acid is the final metabolite in purine metabolism. About 70% of the uric acid in the body resulted from dietary intake or endogenous production is eliminated through urine via the kidney, and the remaining 30% is eliminated through stools via the intestinal tube.

GLUT9 belongs to the family of glucose transporters encoded by SLC2A9 (Solute carrier family 2, facilitated glucose transporter member 9) genes, which was cloned as a molecule expressed in kidney, liver, placenta and the like in human (Non-Patent Document 1). According to a series of subsequent reports, the genome-wide association analysis confirmed the correlation between mutations in this molecule and blood uric acid levels, and this molecule functioned as a high-affinity, high-capacity uric acid transporter (Non-Patent Documents 2 and 3). It has also been reported that GLUT9 has two isoforms (GLUT9S and GLUT9L) due to N-terminal intracellular portion splice, and both has the same uric acid transport activity (Non-Patent Documents 4 and 5). Moreover, it has become evident that depressed function of this molecule causes severe hypouricemia from the analysis of GLUT9 genetic variation family (Non-Patent Documents 6 and 7).

Uric acid transport kinetics in the kidney have been studied since early times. Thus, uric acid first passes through glomerular, and then undergoes two-way transport via transporter which is either reabsorption or secretion, and eventually about 90% of the amount of the uric acid which has passed through glomerular is reabsorbed. GLUT9 is, from the information mentioned above, considered to play the main role in the uric acid reabsorption in the kidney, and thus an important molecule that controls blood uric acid levels. Therefore, a GLUT9 inhibitor is expected to reduce blood uric acid levels and be effective for hyperuricemia and pathological conditions associated therewith.

In Japan, hyperuricemia is defined as a condition wherein serum uric acid level exceeds 7.0 mg/dL, based on the concentration of uric acid dissolved in blood (Non-Patent Document 8). Persistent hyperuricemia causes gouty arthritis or kidney damage (gouty kidney) resulted from deposition of urate crystals in tissues. A prolonged disease period in gouty arthritis cases results in granuloma formation such as gouty tophus which is primarily due to the urate.

Further, in the recent years, hyperuricemia has been recognized as a lifestyle disease, and there has been many reports suggesting that hyperuricemia is associated with various pathological conditions. Remedy of hyperuricemia can be a potential treatment and prophylaxis for those pathological condition. Pathological conditions listed below are generally known to be associated with hyperuricemia and are particularly suggested to have a relationship with high uric acid.

1) Chronic Kidney Disease (CKD)

Many epidemiological studies have shown that hyperuricemia is a risk factor for development of terminal kidney failure or CKD onset (Non-Patent Documents 9, 10 and 11), and there is a report of intervention trial involving use of uric acid lowering agents which observed a renoprotective effect (Non-Patent Document 12). It is also reported that gene polymorphism of GLUT9 is responsible for CKD onset (Non-Patent Document 13).

2) Hypertension

Many clinical studies have gradually convinced that hyperuricemia is closely associated with the onset of hypertension (Non-Patent Documents 14 and 15). Also, there are clinical results reporting that blood pressure has been decreased by treating hyperuricemia (Non-Patent Document 16).

3) Diabetes

In a meta-analysis which puts together multiple prospective clinical studies, hyperuricemia is reported as an independent risk factor for type 2 diabetes (Non-Patent Document 17). Also studies involving use of mice and cultured cells show that high concentration uric acid suppresses insulin secretion and induces insulin resistance (Non-Patent Documents 18 and 19).

4) Cardiac Disease (Cardiovascular Disease, Cardiac Failure, Atrial Fibrillation)

The blood uric acid level has been reported as an independent risk factor or cardiovascular events (Non-Patent Document 20). Besides the events, a study of correlations between the characteristics of coronary artery and uric acid using intravascular ultrasound (IVUS) shows that hyperuricemia is associated with plaque volume and calcified lesion (Non-Patent Document 21). Hyperuricemia is also observed in many patients with chronic cardiac failure. A Japanese epidemiological study conducted under the Japanese Cardiac Registry of Heart Failure in Cardiology (J-CARE-CARD) test demonstrated that cardiac failure patients with hyperuricemia had a significantly higher rate of all-cause death and cardiac death (Non-Patent Document 22). In the recent years, a complication of hyperuricemia and atrial fibrillation has been attracting attention. It has been reported that prevalence of atrial fibrillation increases according to the serum uric acid level, and prevalence of hyperuricemia with 8 mg/dL or greater is significantly higher than those of 6.9 mg/dL or less (Non-Patent Document 23).

5) Arteriosclerotic Disease

Frequency of hyperuricemia in patients with hypertriglyceridemia is as high as about 30%, which is reported to be closely related with hyperuricemia and hyperlipemia (Non-Patent Documents 24 and 25).

6) Non-Alcoholic Fatty Liver Disease (NAFLD) and Non-Alcoholic Steatohepatitis (NASH)

NAFLD is associated with fatty liver and is a chronic hepatic disease of unknown cause which is commonly diagnosed in people who do not drink alcohol. Further, a pathological condition with a more progressed inflammation and fibrosis is called "NASH" which may cause hepatic cirrhosis and hepatoma. Many NAFLD patients have a complication with hyperuricemia, where the serum uric acid level is an independent risk factor for NAFLD. There is a meta-analysis result reporting that 1 mg/dL increase in the serum uric acid level increases the risk of NAFLD onset by 21% (Non-Patent Document 26).

7) Psoriasis

It has been long known that psoriasis patients generally have a higher uric acid level relative to healthy subjects, as seen in the report that hyperuricemia was observed in about half of psoriasis patients (Non-Patent Document 27). In addition, as it has been reported that risks of cardiovascular disease and kidney damage are significantly higher in psoriasis patients relative to healthy subjects, hyperuricemia may be a factor that plays a role in increasing these risks (Non-Patent Documents 28 and 29).

As described above, a GLUT9 inhibitor is considered to be an agent for the treatment or prophylaxis of pathological conditions that involve high blood uric acid levels; specifically, hyperuricemia, gout (for example, gouty arthritis, gouty kidney, and gouty tophus) and the like. Further, it is considered to have potential to be useful as an agent for the treatment or prophylaxis of pathological conditions which are generally known to have a complication with hyperuricemia and are particularly suggested to have association with high uric acid; specifically, chronic kidney disease (CKD), hypertension, diabetes, cardiac disease (for example, cardiovascular disease, cardiac failure, and atrial fibrillation), arteriosclerotic disease, non-alcoholic fatty liver disease (NAFLD), non-alcoholic steatohepatitis (NASH), psoriasis and the like.

DOCUMENT LIST

Non-Patent Document

[Non-Patent Document 1] Genomics. 2000 Jun. 1; 66(2): 217-20.
[Non-Patent Document 2] PLoS Genet. 2007 November; 3(11):e194.
[Non-Patent Document 3] Nat Genet. 2008 April; 40(4):437-42.
[Non-Patent Document 4] J Biol Chem. 2008 Oct. 3; 283 (40):26834-8.
[Non-Patent Document 5] ADMET & DMPK. 2017; 5(2): 59-74.
[Non-Patent Document 6] Am J Hum Genet. 2008 December; 83(6):744-51.
[Non-Patent Document 7] Nephrol Dial Transplant. 2012 March; 27(3):1035-41.
[Non-Patent Document 8] Japanese guideline for the management of hyperuricemia and gout; second edition, edited by the Guideline Revision Committee, Japanese Society of Gout and Nucleic Acid Metabolism, Osaka, Medical Review Co., Ltd., 2010
[Non-Patent Document 9] Am J Kidney Dis. 2004 October; 44(4):642-50.
[Non-Patent Document 10] J Am Soc Nephrol. 2008 December; 19(12):2407-13.
[Non-Patent Document 11] PLoS One. 2014 Jun. 24; 9(6): e100801.
[Non-Patent Document 12] Am J Kidney Dis. 2015 December; 66(6):945-50.
[Non-Patent Document 13] Clin J Am Soc Nephrol. 2014 Jun. 6; 9(6):1059-65.
[Non-Patent Document 14] Hypertension. 2006 December; 48(6):1031-6.
[Non-Patent Document 15] Ann Rheum Dis. 2013 August; 72(8):1321-7.
[Non-Patent Document 16] JAMA. 2008 Aug. 27; 300(8): 924-32.
[Non-Patent Document 17] PLoS One. 2013; 8(2):e56864.
[Non-Patent Document 18] Mol Cell Endocrinol. 2013 Aug. 15; 375(1-2):89-96.
[Non-Patent Document 19] Biochem Biophys Res Commun. 2014 May 16; 447(4):707-14.
[Non-Patent Document 20] National Health and Nutrition Examination Survey. JAMA. 2000 May 10; 283(18): 2404-10.
[Non-Patent Document 21] Coron Artery Dis. 2014 June; 25(4):343-8.
[Non-Patent Document 22] Int J Cardiol. 2011 Sep. 1; 151(2):143-7.
[Non-Patent Document 23] Hypertens Res. 2014 August; 37(8):785-9.
[Non-Patent Document 24] Br J Rheumatol. 1994 August; 33(8):731-4.
[Non-Patent Document 25] Ther Res 33:1397-1405, 2012
[Non-Patent Document 26] J Clin Endocrinol Metab. 2015 November; 100(11):4198-207.
[Non-Patent Document 27] Am J Dermatopathol. 1981 Winter; 3(4):397-404.
[Non-Patent Document 28] Arch Dermatol. 2008 November; 144(11):1518-9.
[Non-Patent Document 29] BMJ. 2013 Oct. 15; 347:f5961.

SUMMARY OF THE INVENTION

The present invention provides a nitrogen-containing heteroaryl compound having a GLUT9 inhibitory activity, or a pharmaceutically acceptable salt thereof, a pharmaceutical composition containing the same, a pharmaceutical use thereof, and the like. Accordingly, the present invention encompasses the embodiments exemplified below.

[Item 1]

A compound of Formula [I], or a pharmaceutically acceptable salt thereof:

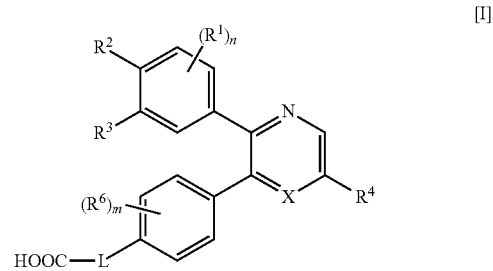

wherein
=X— is =C($R^5$)— or =N—;
-L-COOH is
(1) —COOH,
(2) —C($R^{71}$)($R^{72}$)—COOH,
(3) —C($R^{73}$)($R^{74}$)—C($R^{75}$)($R^{76}$)—COON, or
(4) —O—C($R^{77}$)($R^{78}$)—COOH;
n is 0, 1, or 2;
m is 0, 1, 2, or 3;
$R^1$ is each independently halogen or $C_{1-3}$ alkyl;

$R^2$ is
(1) halogen,
(2) hydroxy,
(3) cyano,
(4) $C_{1-6}$ alkyl optionally substituted with 1 to 3 substituents independently selected from the group consisting of cyano and $C_{1-3}$ alkoxy,
(5) halo $C_{1-6}$ alkyl,
(6) $C_{1-6}$ alkoxy,
(7) halo $C_{1-6}$ alkoxy,
(8) —COOR$^{21}$ wherein $R^{21}$ is hydrogen or $C_{1-3}$ alkyl,
(9) —CON(R$^{22}$)(R$^{23}$) wherein $R^{22}$ and $R^{23}$ are each independently hydrogen or $C_{1-3}$ alkyl,
(10) $C_{3-6}$ cycloalkyl or
(11) a 4- to 6-membered saturated heterocyclic group containing 1 or 2 hetero atom as a ring atom in addition to the carbon atoms, wherein the hetero atom is independently selected from the group consisting of oxygen, nitrogen and sulfur atoms, and
$R^3$ is
(1) hydrogen,
(2) halogen,
(3) cyano,
(4) $C_{1-3}$ alkyl,
(5) halo $C_{1-3}$ alkyl,
(6) $C_{1-3}$ alkoxy, or
(7) —COOR$^{31}$ wherein $R^{31}$ is hydrogen or $C_{1-3}$ alkyl or
$R^2$ and $R^3$, together with the carbon atoms that they are bonded to, form a 4- to 6-membered saturated heterocycle containing 1 or 2 hetero atom as a ring atom in addition to the carbon atoms, wherein the hetero atom is independently selected from the group consisting of oxygen, nitrogen and sulfur atoms;
$R^4$ is
(1) $C_{1-6}$ alkyl optionally substituted with 1 to 3 substituents independently selected from the following Group A,
(2) halo $C_{1-6}$ alkyl,
(3) —CON(R$^{41}$)(R$^{42}$) wherein $R^{41}$ and $R^{42}$ are each independently hydrogen or $C_{1-6}$ alkyl,
(4) $C_{3-6}$ cycloalkyl optionally substituted with 1 to 3 substituents independently selected from $C_{1-3}$ alkoxy, or
(5) a 4- to 6-membered saturated heterocyclic group containing 1 or 2 hetero atom as a ring atom in addition to the carbon atoms, wherein the hetero atom is independently selected from the group consisting of oxygen, nitrogen and sulfur atoms, and wherein the ring atom in the heterocyclic group bonded to

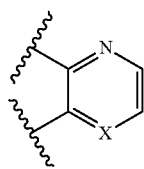

is a carbon atom,
and
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl optionally substituted with one hydroxy, and
(e) phenyl, and
$R^5$ is hydrogen, halogen or $C_{1-3}$ alkyl or $R^4$ and $R^5$, together with the carbon atoms that they are bonded to, form $C_{3-6}$ cycloalkane;
$R^6$ are each independently halogen, hydroxy, $C_{1-3}$ alkyl or $C_{1-3}$ alkoxy; and
$R^{71}$, $R^{72}$, $R^{73}$, $R^{74}$, $R^{75}$, $R^{76}$, $R^{77}$, and $R^{78}$ are each independently hydrogen or $C_{1-3}$ alkyl.

[Item 2]
The compound according to Item 1 or a pharmaceutically acceptable salt thereof, wherein =X— is =C(R$^5$)—.

[Item 3]
The compound according to Item 1 or a pharmaceutically acceptable salt thereof, wherein =X— is =N—.

[Item 4]
The compound according to any one of Items 1 to 3 or a pharmaceutically acceptable salt thereof, wherein -L-COOH is —COOH.

[Item 5]
The compound according to any one of Items 1 to 4 or a pharmaceutically acceptable salt thereof, wherein n is 0 or 1.

[Item 6]
The compound according to any one of Items 1 to 4 or a pharmaceutically acceptable salt thereof, wherein n is 0.

[Item 7]
The compound according to any one of Items 1 to 4 or a pharmaceutically acceptable salt thereof, wherein n is 1.

[Item 8]
The compound according to any one of Items 1 to 7 or a pharmaceutically acceptable salt thereof, wherein m is 0 or 1.

[Item 9]
The compound according to any one of Items 1 to 7 or a pharmaceutically acceptable salt thereof, wherein m is 0.

[Item 10]
The compound according to any one of Items 1 to 7 or a pharmaceutically acceptable salt thereof, wherein m is 1.

[Item 11]
The compound according to any one of Items 1 to 10 or a pharmaceutically acceptable salt thereof, wherein $R^1$ is halogen.

[Item 12]
The compound according to any one of Items 1 to 10 or a pharmaceutically acceptable salt thereof, wherein $R^1$ is $C_{1-3}$ alkyl.

[Item 13]
The compound according to any one of Items 1 to 12 or a pharmaceutically acceptable salt thereof, wherein $R^3$ is
(1) hydrogen, or
(2) halogen.

[Item 14]
The compound according to any one of Items 1 to 12 or a pharmaceutically acceptable salt thereof, wherein $R^3$ is hydrogen.

[Item 15]
The compound according to any one of Items 1 to 12 or a pharmaceutically acceptable salt thereof, wherein $R^3$ is halogen.

[Item 16]
The compound according to any one of Items 1 to 15 or a pharmaceutically acceptable salt thereof, wherein
$R^4$ is
(1) $C_{1-8}$ alkyl optionally substituted with 1 to 3 substituents independently selected from the following Group A,
(2) halo $C_{1-6}$ alkyl, or
(3) —CON(R$^{41}$)(R$^{42}$) wherein $R^{41}$ and $R^{42}$ are each independently hydrogen or $C_{1-6}$ alkyl, and Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl optionally substituted with one hydroxy, and
(e) phenyl.

[Item 17]
The compound according to any one of Items 1 to 15 or a pharmaceutically acceptable salt thereof, wherein
$R^4$ is $C_{1-8}$ alkyl optionally substituted with 1 to 3 substituents independently selected from the following Group A, and
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl, and
(e) phenyl.

[Item 18]
The compound according to any one of Items 1 to 15 or a pharmaceutically acceptable salt thereof, wherein $R^4$ is —CON($R^{41}$)($R^{42}$) wherein $R^{41}$ and $R^{42}$ are each independently hydrogen or $C_{1-6}$ alkyl.

[Item 19]
A compound of the following formula or a pharmaceutically acceptable salt thereof:

(Example 21)

[Item 20]
A compound of the following formula or a pharmaceutically acceptable salt thereof:

(Example 35)

[Item 21]
A compound of the following formula or a pharmaceutically acceptable salt thereof:

(Example 67)

[Item 22]
A compound of the following formula or a pharmaceutically acceptable salt thereof:

(free form of Example 76)

[Item 23]
A compound of the following formula or a pharmaceutically acceptable salt thereof:

(Example 84)

[Item 24]
A compound of the following formula or a pharmaceutically acceptable salt thereof:

(Example 98)

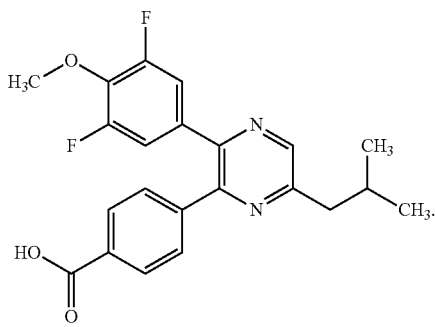

[Item 25]

A compound of the following formula or a pharmaceutically acceptable salt thereof:

(Example 107)

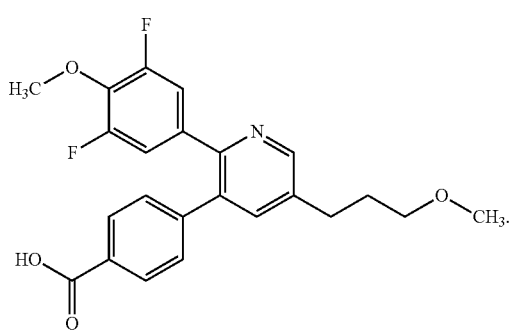

[Item 26]

A compound of the following formula or a pharmaceutically acceptable salt thereof:

(Example 109)

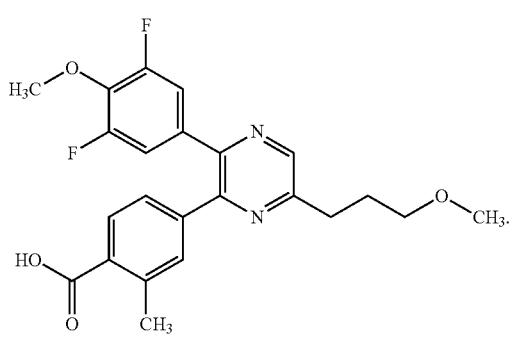

[Item 27]

A compound of the following formula or a pharmaceutically acceptable salt thereof:

(Example 116)

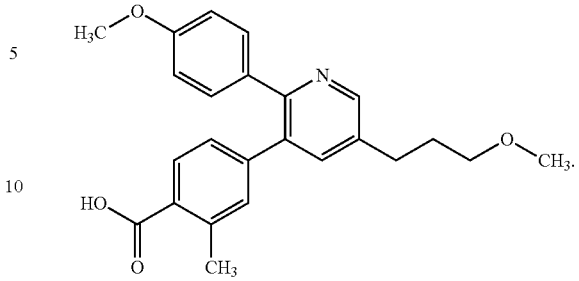

[Item 28]

A compound of the following formula or a pharmaceutically acceptable salt thereof:

(Example 118)

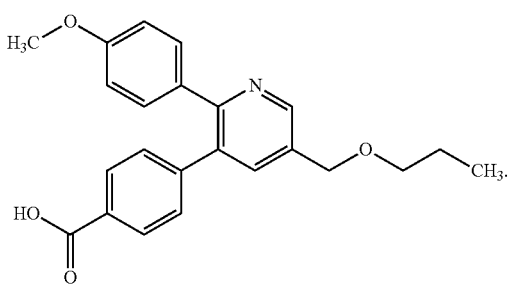

[Item 29]

A compound of the following formula or a pharmaceutically acceptable salt thereof:

(Example 126)

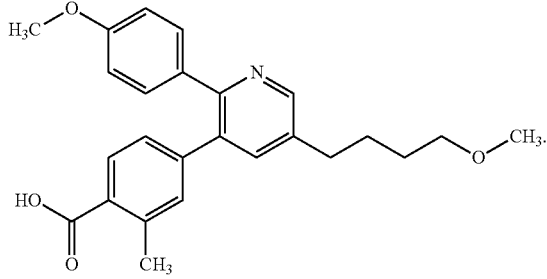

[Item 30]

A pharmaceutical composition comprising the compound according to any one of Items 1 to 29 or a pharmaceutically acceptable salt thereof, and a pharmaceutically acceptable carrier.

[Item 31]

A GLUT9 inhibitor comprising the compound according to any one of Items 1 to 29 or a pharmaceutically acceptable salt thereof.

[Item 32]

An agent for the treatment or prophylaxis of a disease selected from the group consisting of hyperuricemia and gout, which comprises the compound according to any one of Items 1 to 29 or a pharmaceutically acceptable salt thereof.

[Item 33]

A method for the inhibition of GLUT9 in a mammal in need of such inhibition, which comprises administering a pharmaceutically effective amount of the compound according to any one of Items 1 to 29 or a pharmaceutically acceptable salt thereof to the mammal.

[Item 34]

A method for the treatment or prophylaxis of a disease selected from the group consisting of hyperuricemia and gout in a mammal in need of such treatment or prophylaxis, which comprises administering a pharmaceutically effective amount of the compound according to any one of Items 1 to 29 or a pharmaceutically acceptable salt thereof to the mammal.

[Item 35]

Use of the compound according to any one of Items 1 to 29 or a pharmaceutically acceptable salt thereof for the manufacture of a GLUT9 inhibitor.

[Item 36]

Use of the compound according to any one of Items 1 to 29 or a pharmaceutically acceptable salt thereof for the manufacture of an agent for the treatment or prophylaxis of a disease selected from the group consisting of hyperuricemia and gout.

[Item 37]

The compound according to any one of Items 1 to 29 or a pharmaceutically acceptable salt thereof, for use in the inhibition of GLUT9.

[Item 38]

The compound according to any one of Items 1 to 29 or a pharmaceutically acceptable salt thereof, for use in the treatment or prophylaxis of a disease selected from the group consisting of hyperuricemia and gout.

[Item 39]

A commercial package comprising the composition according to Item 30 and a written matter associated therewith, the written matter stating that the composition can or should be used for the treatment or prophylaxis of a disease selected from the group consisting of hyperuricemia and gout.

[Item 40]

A kit comprising the composition according to Item 30 and a written matter associated therewith, the written matter stating that the composition can or should be used for the treatment or prophylaxis of a disease selected from the group consisting of hyperuricemia and gout.

EMBODIMENTS OF THE INVENTION

The definitions of the terms used herein are as follows.
The following wavy line:

in the partial structure means an abbreviation of a bonding partner.

Examples of the "halogen" include fluorine, chlorine, bromine and iodine.

The "$C_{1-3}$ alkyl" means a straight- or branched-chain saturated hydrocarbon group having 1 to 3 carbon atoms. Examples of the "$C_{1-3}$ alkyl" include methyl, ethyl, n-propyl and isopropyl.

The "$C_{1-6}$ alkyl" means a straight- or branched-chain saturated hydrocarbon group having 1 to 6 carbon atoms. Examples of the "$C_{1-6}$ alkyl" include methyl, ethyl, n-propyl, isopropyl, n-butyl, isobutyl, sec-butyl, tert-butyl, n-pentyl, isopentyl and n-hexyl.

The "$C_{1-8}$ alkyl" means a straight- or branched-chain saturated hydrocarbon group having 1 to 8 carbon atoms. Examples of the "$C_{1-8}$ alkyl" include methyl, ethyl, n-propyl, isopropyl, n-butyl, isobutyl, sec-butyl, tert-butyl, n-pentyl, isopentyl, n-hexyl, n-heptyl and n-octyl.

The "halo $C_{1-3}$ alkyl" means the above-mentioned "$C_{1-3}$ alkyl" substituted with 1 to 5 halogen independently selected from the group consisting of the above-mentioned "halogen". Examples of the "halo $C_{1-3}$ alkyl" include monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl and 3,3,3-trifluoropropyl.

The "halo $C_{1-6}$ alkyl" means the above-mentioned "$C_{1-6}$ alkyl" substituted with 1 to 5 halogen independently selected from the group consisting of the above-mentioned "halogen". Examples of the "halo $C_{1-6}$ alkyl" include monofluoromethyl, difluoromethyl, trifluoromethyl, 2-fluoroethyl, 2-chloroethyl, 2-bromoethyl, 1,1-difluoroethyl, 2,2,2-trifluoroethyl, pentafluoroethyl, 3-fluoropropyl, 3-chloropropyl, 1,1-difluoropropyl, 3,3,3-trifluoropropyl, 4,4,4-trifluorobutyl, 5,5,5-trifluoropentyl and 6,6,6-trifluorohexyl.

The "$C_{1-3}$ alkoxy" means a group wherein the above-mentioned "$C_{1-3}$ alkyl" is bonded to an oxygen atom. Examples of the "$C_{1-3}$ alkoxy" include methoxy, ethoxy, n-propoxy and isopropoxy.

The "$C_{1-6}$ alkoxy" means a group wherein the above-mentioned "$C_{1-6}$ alkyl" is bonded to an oxygen atom. Examples of the "$C_{1-6}$ alkoxy" include methoxy, ethoxy, n-propoxy, isopropoxy, n-butoxy, isobutoxy, sec-butoxy, tert-butoxy, n-pentyloxy, isopentyloxy and n-hexyloxy.

The "halo $C_{1-3}$ alkoxy" means the above-mentioned "$C_{1-3}$ alkoxy" substituted with 1 to 5 halogen independently selected from the group consisting of the above-mentioned "halogen". Examples of the "halo $C_{1-3}$ alkoxy" include monofluoromethoxy, difluoromethoxy, trifluoromethoxy, 2-fluoroethoxy, 2-chloroethoxy, 2-bromoethoxy, 1,1-difluoroethoxy, 2,2,2-trifluoroethoxy, pentafluoroethoxy, 3-fluoropropoxy, 3-chloropropoxy, 1,1-difluoropropoxy and 3,3,3-trifluoropropoxy.

The "halo $C_{1-6}$ alkoxy" means the above-mentioned "$C_{1-6}$ alkoxy" substituted with 1 to 5 halogen independently selected from the group consisting of the above-mentioned "halogen". Examples of the "halo $C_{1-6}$ alkoxy" include monofluoromethoxy, difluoromethoxy, trifluoromethoxy, 2-fluoroethoxy, 2-chloroethoxy, 2-bromoethoxy, 1,1-difluoroethoxy, 2,2,2-trifluoroethoxy, pentafluoroethoxy, 3-fluoropropoxy, 3-chloropropoxy, 1,1-difluoropropoxy, 3,3,3-trifluoropropoxy, 4,4,4-trifluorobutoxy, 5,5,5-trifluoropentyloxy and 6,6,6-trifluorohexyloxy.

The "$C_{3-6}$ cycloalkyl" means a monocyclic saturated hydrocarbon group having 3 to 6 carbon atoms. Examples of the "$C_{3-6}$ cycloalkyl" include cyclopropyl, cyclobutyl, cyclopentyl and cyclohexyl.

The "$C_{3-6}$ cycloalkane" means a monocyclic saturated hydrocarbon having 3 to 6 carbon atoms. Examples of the "$C_{3-6}$ cycloalkane" include cyclopropane, cyclobutane, cyclopentane and cyclohexane. Examples of the "$C_{3-6}$ cycloalkane" formed by $R^4$ and $R^5$, together with the carbon atoms that they are bonded to, include the following rings:

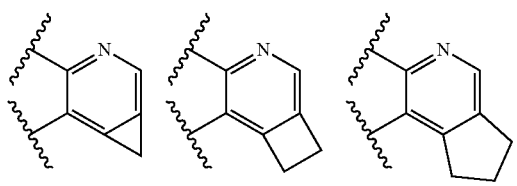

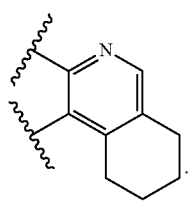

Examples of the "4- to 6-membered saturated heterocyclic group containing 1 or 2 hetero atom as a ring atom in addition to the carbon atoms, wherein the hetero atom is independently selected from the group consisting of oxygen, nitrogen and sulfur atoms" include oxetanyl, tetrahydrofuranyl, tetrahydropyranyl, azetidinyl, pyrrolidinyl and piperidyl.

For example, examples of the "4- to 6-membered saturated heterocyclic group containing 1 or 2 hetero atom as a ring atom in addition to the carbon atoms, wherein the hetero atom is independently selected from the group consisting of oxygen, nitrogen and sulfur atoms, and wherein the ring atom in the heterocyclic group bonded to

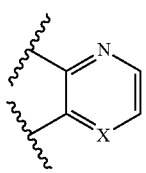

is a carbon atom"
in (5) of $R^4$ include the following groups:

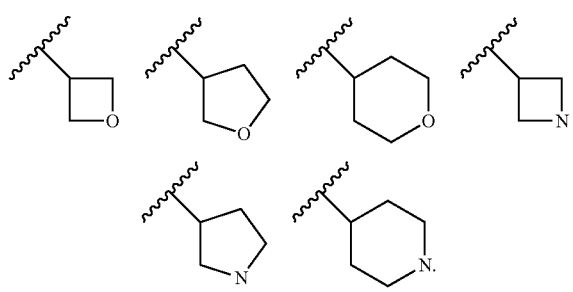

Examples of the "4- to 6-membered saturated heterocycle containing 1 or 2 hetero atom as a ring atom in addition to the carbon atoms, wherein the hetero atom is independently selected from the group consisting of oxygen, nitrogen and sulfur atoms" include oxetane, tetrahydrofuran, tetrahydropyran, 1,4-dioxane, pyrrolidine and piperidine.

For example, examples of the "4- to 6-membered saturated heterocycle containing 1 or 2 hetero atom as a ring atom in addition to the carbon atoms, wherein the hetero atom is independently selected from the group consisting of oxygen, nitrogen and sulfur atoms" formed by $R^2$ and $R^3$, together with the carbon atoms that they are bonded to, include the following rings:

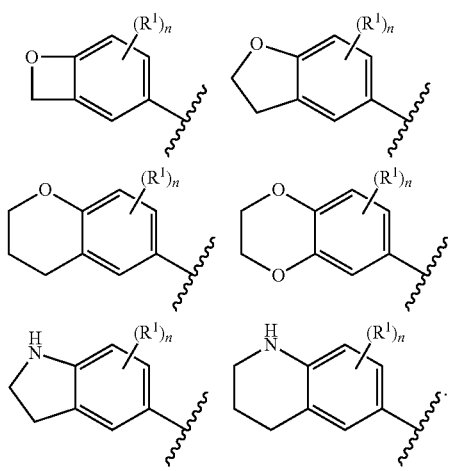

With regard to the term "substituted", for example, $C_{1-6}$ alkyl "optionally substituted with 1 to 3 substituents independently selected from cyano and $C_{1-3}$ alkoxy" in (4) of $R^2$ means unsubstituted $C_{1-6}$ alkyl, or $C_{1-6}$ alkyl substituted with 1 to 3 substituents independently selected from cyano and $C_{1-3}$ alkoxy at any substitutable position.

The "compound of Formula [I]" is hereinafter also referred to as "Compound [I]".

Specific embodiments of each group of Compound [I] are exemplified below, which should not be construed as limitative. Compound [I] also encompasses combinations of two or more embodiments selected appropriately from the specific embodiments of each group.

-L-COOH is preferably
(1) —COOH,
(2) —C($R^{71}$)($R^{72}$)—COOH, or
(3) —C($R^{73}$)($R^{74}$)—C($R^{75}$)($R^{76}$)—COON.

-L-COOH is more preferably —COOH.
n is preferably 0 or 1.
m is preferably 0, 1 or 2.
m is more preferably 0 or 1.
$R^2$ is preferably
(1) halogen,
(2) hydroxy,
(3) cyano,
(4) $C_{1-6}$ alkyl optionally substituted with 1 to 3 substituents independently selected from the group consisting of cyano and $C_{1-3}$ alkoxy,
(5) halo $C_{1-6}$ alkyl,
(6) $C_{1-6}$ alkoxy,
(7) halo $C_{1-6}$ alkoxy,
(8) —COOR$^{21}$ wherein $R^{22}$ is hydrogen or $C_{1-3}$ alkyl, or
(9) —CON($R^{22}$)($R^{23}$) wherein $R^{22}$ and $R^{23}$ are each independently hydrogen or $C_{1-3}$ alkyl.

$R^2$ is more preferably
(2) hydroxy,
(6) $C_{1-6}$ alkoxy, or
(7) halo $C_{1-6}$ alkoxy.

$R^3$ is preferably
(1) hydrogen,
(2) halogen,
(3) cyano,
(4) $C_{1-3}$ alkyl,
(5) halo $C_{1-3}$ alkyl,
(6) $C_{1-3}$ alkoxy, or
(7) —COOR$^{31}$ wherein $R^{31}$ is hydrogen or $C_{1-3}$ alkyl.

R³ is more preferably
(1) hydrogen, or
(2) halogen.
R⁴ is preferably
(1) $C_{1-8}$ alkyl optionally substituted with 1 to 3 substituents independently selected from the following Group A,
(2) halo $C_{1-6}$ alkyl, or
(3) —CON($R^{41}$)($R^{42}$) wherein $R^{41}$ and $R^{42}$ are each independently hydrogen or $C_{1-6}$ alkyl.
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl, and
(e) phenyl.
Group A preferably consists of
(a) hydroxy,
(b) $C_{1-3}$ alkoxy optionally substituted with one hydroxy or one $C_{1-3}$ alkoxy, and
(c) halo $C_{1-3}$ alkoxy.
R⁵ is preferably hydrogen.
A preferable embodiment is Compound [I] wherein
═X— is ═C(R⁵)— or ═N—;
-L-COOH is
(1) —COOH,
(2) —C($R^{71}$)($R^{72}$)—COOH, or
(3) —C($R^{73}$)($R^{74}$)—C($R^{75}$)($R^{76}$)—COON;
n is 0 or 1;
m is 0, 1 or 2;
R¹ is halogen or $C_{1-3}$ alkyl;
R² is
(1) halogen,
(2) hydroxy,
(3) cyano,
(4) $C_{1-6}$ alkyl optionally substituted with 1 to 3 substituents independently selected from the group consisting of cyano and $C_{1-3}$ alkoxy,
(5) halo $C_{1-6}$ alkyl,
(6) $C_{1-6}$ alkoxy,
(7) halo $C_{1-6}$ alkoxy,
(8) —COOR²¹ wherein R²¹ is hydrogen or $C_{1-3}$ alkyl, or
(9) —CON($R^{22}$)($R^{23}$) wherein $R^{22}$ and $R^{23}$ are each independently hydrogen or $C_{1-3}$ alkyl;
R³ is
(1) hydrogen,
(2) halogen,
(3) cyano,
(4) $C_{1-3}$ alkyl,
(5) halo $C_{1-3}$ alkyl,
(6) $C_{1-3}$ alkoxy, or
(7) —COOR³¹ wherein R³¹ is hydrogen or $C_{1-3}$ alkyl;
R⁴ is
(1) $C_{1-8}$ alkyl optionally substituted with 1 to 3 substituents independently selected from the following Group A,
(2) halo $C_{1-6}$ alkyl, or
(3) —CON($R^{41}$)($R^{42}$) wherein $R^{41}$ and $R^{42}$ are each independently hydrogen or $C_{1-6}$ alkyl, and
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl, and
(e) phenyl;

R⁵ is hydrogen;
R⁶ are each independently halogen, hydroxy, $C_{1-3}$ alkyl or $C_{1-3}$ alkoxy; and
$R^{71}$, $R^{72}$, $R^{73}$, $R^{74}$, $R^{75}$, $R^{76}$, $R^{77}$, and $R^{78}$ are each independently hydrogen or $C_{1-3}$ alkyl.
A more preferable embodiment is Compound [I] wherein
═X— is ═C(R⁵)— or ═N—;
-L-COOH is —COOH;
n is 0 or 1;
m is 0 or 1;
R¹ is halogen or $C_{1-3}$ alkyl;
R² is
(2) hydroxy,
(6) $C_{1-6}$ alkoxy, or
(7) halo $C_{1-6}$ alkoxy;
R³ is
(1) hydrogen, or
(2) halogen;
R⁴ is
(1) $C_{1-8}$ alkyl optionally substituted with 1 to 3 substituents independently selected from the following Group A,
(2) halo $C_{1-6}$ alkyl, or
(3) —CON($R^{41}$)($R^{42}$) wherein $R^{41}$ and $R^{42}$ are each independently hydrogen or $C_{1-6}$ alkyl, and
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl, and
(e) phenyl;
R⁵ is hydrogen; and
R⁶ is halogen, hydroxy, $C_{1-3}$ alkyl or $C_{1-3}$ alkoxy.
Another preferable embodiment is a compound of Formula [II], or a pharmaceutically acceptable salt thereof:

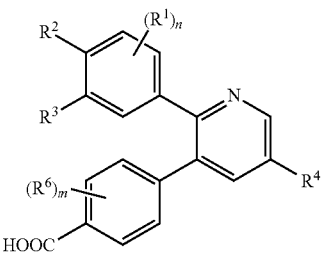

[II]

wherein
n is 0 or 1;
m is 0 or 1;
R¹ is halogen or $C_{1-3}$ alkyl;
R² is hydroxy, $C_{1-6}$ alkoxy or halo $C_{1-6}$ alkoxy;
R³ is hydrogen or halogen;
R⁴ is
(1) $C_{1-8}$ alkyl optionally substituted with 1 to 3 substituents independently selected from the following Group A,
(2) halo $C_{1-6}$ alkyl, or
(3) —CON($R^{41}$)($R^{42}$) wherein $R^{41}$ and $R^{42}$ are each independently hydrogen or $C_{1-6}$ alkyl, and
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl, and
(e) phenyl; and
R⁶ is halogen, hydroxy, $C_{1-3}$ alkyl or $C_{1-3}$ alkoxy.

Another preferable embodiment is a compound of Formula [III], or a pharmaceutically acceptable salt thereof:

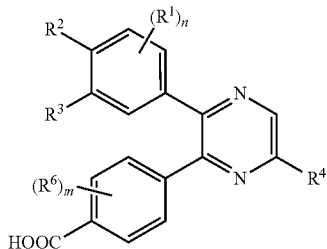

wherein
n is 0 or 1;
m is 0 or 1;
$R^1$ is halogen or $C_{1-3}$ alkyl;
$R^2$ is hydroxy, $C_{1-6}$ alkoxy or halo $C_{1-6}$ alkoxy;
$R^3$ is hydrogen or halogen;
$R^4$ is
(1) $C_{1-8}$ alkyl optionally substituted with 1 to 3 substituents independently selected from the following Group A,
(2) halo $C_{1-6}$ alkyl, or
(3) —CON($R^{41}$)($R^{42}$) wherein $R^{41}$ and $R^{42}$ are each independently hydrogen or $C_{1-6}$ alkyl, and
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl, and
(e) phenyl; and
$R^6$ is halogen, hydroxy, $C_{1-3}$ alkyl or $C_{1-3}$ alkoxy.

The "pharmaceutically acceptable salt" may be any salt known in the art as long as it is not associated with undue toxicity. Specific examples thereof include salts with inorganic acid, salts with organic acid, salts with inorganic base, and salts with organic base. Various forms of pharmaceutically acceptable salts are well known in the art and, for example, they are described in the following documents.
(a) Berge et al., J. Pharm. Sci., 66, p 1-19 (1977),
(b) Stahl et al., "Handbook of Pharmaceutical Salt: Properties, Selection, and Use" (Wiley-VCH, Weinheim, Germany, 2002),
(c) Paulekuhn et al., J. Med. Chem., 50, p 6665-6672 (2007)

The pharmaceutically acceptable salt of Compound [I] can be obtained by reacting Compound [I] with an inorganic acid, an organic acid, an inorganic base or an organic base, according to a known method.

Examples of the salt with inorganic acid include salts with hydrofluoric acid, hydrochloric acid, hydrobromic acid, hydriodic acid, nitric acid, phosphoric acid and sulfuric acid.

Examples of the salt with organic acid include salts with acetic acid, adipic acid, alginic acid, 4-aminosalicylic acid, anhydromethylenecitric acid, benzoic acid, benzenesulfonic acid, camphoric acid, camphor-10-sulfonic acid, carbonic acid, citric acid, edetic acid, ethane-1,2-disulfonic acid, dodecylsulfuric acid, ethanesulfonic acid, fumaric acid, glucoheptonic acid, gluconic acid, glucuronic acid, glycollylarsanilic acid, hydroxynaphthoic acid, 2-hydroxy-1-ethanesulfonic acid, lactic acid, lactobionic acid, malic acid, maleic acid, mandelic acid, methanesulfonic acid, methylsulfuric acid, methylnitric acid, methylenebis(salicylic acid), galactaric acid, naphthalene-2-sulfonic acid, 2-naphthoic acid, 1,5-naphthalenedisulfonic acid, oleic acid, oxalic acid, pamoic acid, pantothenic acid, pectic acid, picric acid, propionic acid, polygalacturonic acid, salicylic acid, stearic acid, succinic acid, tannic acid, tartaric acid, teoclic acid, thiocyanic acid, trifluoroacetic acid, p-toluenesulfonic acid, undecanoic acid, aspartic acid and glutamic acid.

Examples of the salt with inorganic base include salts with lithium, sodium, potassium, magnesium, calcium, barium, aluminium, zinc, bismass and ammonium.

Examples of the salt with organic base include salts with arecoline, betaine, choline, clemizole, ethylene diamine, N-methylglucamine, N-benzylphenethylamine, tris(hydroxymethyl)methylamine, arginine and lysine.

Preferable embodiments of the "pharmaceutically acceptable salt" are as follows.

Examples of the salt with inorganic acid include salts with hydrochloric acid, nitric acid, sulfuric acid, phosphoric acid and hydrobromic acid.

Examples of the salt with organic acid include salts with oxalic acid, maleic acid, citric acid, fumaric acid, lactic acid, malic acid, succinic acid, tartaric acid, acetic acid, trifluoroacetic acid, benzoic acid, glucuronic acid, oleic acid, pamoic acid, methanesulfonic acid, benzenesulfonic acid, p-toluenesulfonic acid and 2-hydroxy-1-ethanesulfonic acid.

Examples of the salt with inorganic base include salts with sodium, potassium, calcium, magnesium and zinc.

Examples of the salt with organic base include salts with tris(hydroxymethyl)methylamine, N-methylglucamine and lysine.

Compound [I] or a pharmaceutically acceptable salt thereof may be present as a solvate.

The "solvate" is Compound [I] or a pharmaceutically acceptable salt thereof which is coordinated with a solvent molecule, and also encompasses hydrates. The solvate is preferably a pharmaceutically acceptable solvate, and examples thereof include a hydrate, an ethanolate and a dimethyl sulfoxidate of Compound [I] or a pharmaceutically acceptable salt thereof.

Specific examples include semihydrate, monohydrate, dihydrate and monoethanolate of Compound [I], monohydrate of hydrochloride of Compound [I], and ⅔ ethanolate of dihydrochloride of Compound [I]. These solvates can be obtained according to a known method.

Compound [I] or a pharmaceutically acceptable salt thereof may be present as a tautomer. In this case, Compound [I] or a pharmaceutically acceptable salt thereof can be a single tautomer or a mixture thereof.

Compound [I] or a pharmaceutically acceptable salt thereof may have a carbon-carbon double bond. In this case, Compound [I] or a pharmaceutically acceptable salt thereof can be present as an E form, a Z form, or a mixture thereof.

Compound [I] or a pharmaceutically acceptable salt thereof may contain a stereoisomer that should be recognized as a cis/trans isomer. In this case, Compound [I] or a pharmaceutically acceptable salt thereof can be present as a cis form, a trans form, or a mixture thereof.

Compound [I] or a pharmaceutically acceptable salt thereof may contain one or more asymmetric carbons. In this case, Compound [I] or a pharmaceutically acceptable salt thereof may be present as a single enantiomer, a single diastereomer, a mixture of enantiomers or a mixture of diastereomers.

Compound [I] or a pharmaceutically acceptable salt thereof may be present as an atropisomer. In this case, Compound [I] or a pharmaceutically acceptable salt thereof may be present as a single atropisomer or a mixture thereof.

Compound [I] or a pharmaceutically acceptable salt thereof may simultaneously contain plural structural characteristics derived from the above-mentioned isomers. Moreover, Compound [I] or a pharmaceutically acceptable salt thereof may contain the above-mentioned isomers at any ratio.

The formulae, chemical structures and compound names indicated herein without specifying the stereochemistry thereof encompass all the above-mentioned isomers that may be present unless a particular note to the stereochemistry is made herein.

A diastereomeric mixture can be separated into each diastereomer by conventional methods such as chromatography and crystallization. Alternatively, each diastereomer can also be produced by using a stereochemically single starting material, or by a synthesis method employing a stereoselective reaction.

An enantiomeric mixture can be separated into each single enantiomer by a method well known in the art.

For example, first, a diastereomeric mixture can be prepared by reacting an enantiomeric mixture with a substantially pure enantiomer compound known as a chiral auxiliary. Next, the obtained diastereomeric mixture can be separated into a single diastereomer having high isomer ratio or a substantially pure single diastereomer by a conventional method such as fractional crystallization and chromatography. Finally, the separated diastereomer can be converted to a desired enantiomer by removing the added chiral auxiliary by cleavage.

Moreover, an enantiomeric mixture can also be directly separated into each enantiomer by a chromatography method using a chiral solid phase well known in the art. Alternatively, one of enantiomers can also be obtained by using a substantially pure optically active starting material or by employing stereoselective synthesis (asymmetric induction) of a prochiral intermediate using a chiral auxiliary and an asymmetric catalyst.

The absolute steric configuration can be determined by the X-ray crystal analysis of the crystalline product or intermediate. In this case, a crystalline product or intermediate derivatized with a reagent having an asymmetric center with a known steric configuration may be used if necessary.

Compound [I] or a pharmaceutically acceptable salt thereof may be labeled with isotope (e.g., $^2$H, $^3$H, $^{14}$C, and $^{35}$S).

Compound [I] or a pharmaceutically acceptable salt thereof is preferably substantially pure, more preferably has a purity of 80% or more.

As used herein, the pharmaceutical composition may be produced according to a method known per se in the art of pharmaceutical preparations, by mixing Compound [I] or a pharmaceutically acceptable salt thereof with a suitable amount of at least one type of pharmaceutically acceptable carrier and the like as appropriate. The content of Compound [I] or a pharmaceutically acceptable salt thereof in the pharmaceutical composition varies depending on the dosage form, dose and the like, and is, for example, 0.1 to 100 wt % of the whole composition.

Examples of the dosage form of Compound [I] or a pharmaceutically acceptable salt thereof include oral preparations such as tablet, capsule, granule, powder, troche, syrup, emulsion, and suspension, and parenteral preparations such as external preparation, suppository, injection, eye drop, nasal preparations, and pulmonary preparation.

Examples of the "pharmaceutically acceptable carrier" include various organic or inorganic carrier substances conventionally used as preparation materials, and specifically include excipient, disintegrant, binder, glidant, and lubricant for solid preparations; solvent, solubilizing agent, suspending agent, isotonicity agent, buffering agent, and soothing agent for liquid preparations; and base, emulsifier, moistening agent, stabilizer, stabilizing agent, dispersant, plasticizer, pH adjuster, absorption enhancer, gelling agent, preservative, filler, solvent, solubilizing agent, and suspending agent for semi-solid preparations. Where necessary, additives such as preservative, antioxidant, colorant, and sweetening agent may be used.

Examples of the "excipient" include lactose, sucrose, D-mannitol, D-sorbitol, corn starch, dextrin, microcrystalline cellulose, crystalline cellulose, carmellose, carmellose calcium, sodium carboxymethyl starch, low-substituted hydroxypropylcellulose and gum arabic.

Examples of the "disintegrant" include carmellose, carmellose calcium, carmellose sodium, sodium carboxymethyl starch, croscarmellose sodium, crospovidone, low-substituted hydroxypropylcellulose, hydroxypropylmethylcellulose and crystalline cellulose.

Examples of the "binder" include hydroxypropylcellulose, hydroxypropylmethylcellulose, povidone, crystalline cellulose, sucrose, dextrin, starch, gelatin, carmellose sodium and gum arabic.

Examples of the "glidant" include light anhydrous silicic acid and magnesium stearate.

Examples of the "lubricant" include magnesium stearate, calcium stearate and talc.

Examples of the "solvent" include purified water, ethanol, propylene glycol, macrogol, sesame oil, corn oil and olive oil.

Examples of the "solubilizing agent" include propylene glycol, D-mannitol, benzyl benzoate, ethanol, triethanolamine, sodium carbonate and sodium citrate.

Examples of the "suspending agent" include benzalkonium chloride, carmellose, hydroxypropylcellulose, propylene glycol, povidone, methylcellulose and glycerol monostearate.

Examples of the "isotonic agent" include glucose, D-sorbitol, sodium chloride and D-mannitol.

Examples of the "buffering agent" include sodium hydrogenphosphate, sodium acetate, sodium carbonate and sodium citrate.

Examples of the "soothing agent" include benzyl alcohol.

Examples of the "base" include water, animal and vegetable oils (e.g., olive oil, corn oil, arachis oil, sesame oil, and castor oil), lower alcohols (e.g., ethanol, propanol, propylene glycol, 1,3-butylene glycol, and phenol), higher fatty acids and esters thereof, wax, higher alcohols, polyalcohols, hydrocarbons (e.g., white vaseline, liquid paraffin, and paraffin), hydrophilic vaseline, purified lanolin, absorptive ointment, hydrous lanolin, hydrophilic ointment, starch, pullulan, gum arabic, tragacanth gum, gelatin, dextran, cellulose derivatives (e.g., methyl cellulose, carboxymethyl cellulose, hydroxyethyl cellulose, and hydroxypropyl cellulose), synthetic polymers (e.g., carboxyvinyl polymer, sodium polyacrylate, polyvinyl alcohol, and polyvinyl pyrrolidone), propylene glycol, Macrogol (e.g., Macrogol 200 to 600), and combinations of two or more types thereof.

Examples of the "preservative" include ethyl parahydroxybenzoate, chlorobutanol, benzyl alcohol, sodium dehydroacetate and sorbic acid.

Examples of the "antioxidant" include sodium sulfite and ascorbic acid.

Examples of the "colorant" include food colors (e.g., Food Color Red No. 2 or 3, and Food Color Yellow No. 4 or 5) and β-carotene.

Examples of the "sweetening agent" include saccharin sodium, dipotassium glycyrrhizinate and aspartame.

As used herein, the pharmaceutical composition can be administered orally or parenterally (e.g., topical, rectal, intravenous, intramuscular, and subcutaneous administration) to human as well as mammals other than human (e.g., mouse, rat, hamster, guinea pig, rabbit, cat, dog, swine, bovine, horse, sheep, and monkey). The dose varies depending on the subject of administration, disease, symptom, dosage form, administration route and the like. For example, the daily dose for oral administration to an adult patient is generally within the range of about 0.01 mg to 1 g based on the active ingredient (i.e., Compound [I]). This amount can be administered in one to several portions.

Since Compound [I] or a pharmaceutically acceptable salt thereof has a GLUT9 inhibitory action, it is useful as a GLUT9 inhibitor.

The expression "have GLUT9 inhibitory action" or "inhibit GLUT9" means elimination or attenuation of GLUT9 activity by inhibiting a GLUT9 function, for example, it means specific inhibition of GLUT9 function under the below-mentioned condition of Test Example 1.

The "GLUT9 inhibitor" means a substance which inhibits a GLUT9 function.

The "GLUT9" is preferably "human GLUT9".

In one embodiment, since Compound [I] or a pharmaceutically acceptable salt thereof has a GLUT9 inhibitory action, it is expected to be effective for diseases that involve GLUT9.

That is, Compound [I] or a pharmaceutically acceptable salt thereof is expected to be useful for the treatment or prophylaxis of a disease selected from the group consisting of hyperuricemia and gout.

Examples of the "gout" include gouty arthritis, gouty kidney and gouty tophus.

In another embodiment, Compound [I] or a pharmaceutically acceptable salt thereof is expected to be useful for the treatment or prophylaxis of diseases selected from the group consisting of chronic kidney disease (CKD), hypertension, diabetes, cardiac disease, arteriosclerotic disease, non-alcoholic fatty liver disease (NAFLD), non-alcoholic steatohepatitis (NASH) and psoriasis.

Examples of the "cardiac disease" include cardiovascular disease, cardiac failure and atrial fibrillation.

As used herein, the "treatment" encompasses improving symptoms, preventing the aggravation of symptoms, maintaining the remission of symptoms, preventing the exacerbation of symptoms, and preventing the relapse of symptoms.

As used herein, the "prophylaxis" means suppressing the onset of symptoms.

Compound [I] or a pharmaceutically acceptable salt thereof can be used in combination with one or a plurality of other medicaments (hereinafter to be also referred to as a concomitant drug) according to a method generally employed in the medical field (hereinafter to be referred to as combined use).

The timing of administering Compound [I] or a pharmaceutically acceptable salt thereof and the concomitant drug is not limited, and they may be administered to the subject as a combination preparation, or the both preparations may be administered simultaneously or separately at certain intervals. In addition, the pharmaceutical composition containing Compound [I] or a pharmaceutically acceptable salt thereof and the concomitant drug may be used in the form of a kit. The dose of the concomitant drug is similar to the clinically-employed dose and can be appropriately selected according to the administration subject, disease, symptom, dosage form, administration route, administration time, combination and the like. The administration form of the concomitant drug is not particularly limited as long as it is combined with Compound [I] or a pharmaceutically acceptable salt thereof.

Examples of the concomitant drug include
(1) an agent for the treatment and/or prophylaxis of hyperuricemia, and
(2) an agent for the treatment and/or prophylaxis of gout, and at least one of these agents can be used in combination with Compound [I] or a pharmaceutically acceptable salt thereof.

As long as the embodiment disclosed herein does not contradict other embodiments disclosed herein, any combination of any of two or more such embodiments is intended to be encompassed by the technical scope of the present invention.

The production methods of Compound [I] or a pharmaceutically acceptable salt thereof are explained in the following, which should not be construed as limitative. Unless otherwise referred, the salt of each compound in general production methods can be selected appropriately from the above-mentioned "pharmaceutically acceptable salt".

The compound obtained in each step can be, if necessary, isolated or purified according to a method known per se such as distillation, recrystallization and column chromatography, or directly used in the next step without isolation or purification.

[General Production Method]
Production Method A1: Production Method of Compound [IA] or a Salt Thereof

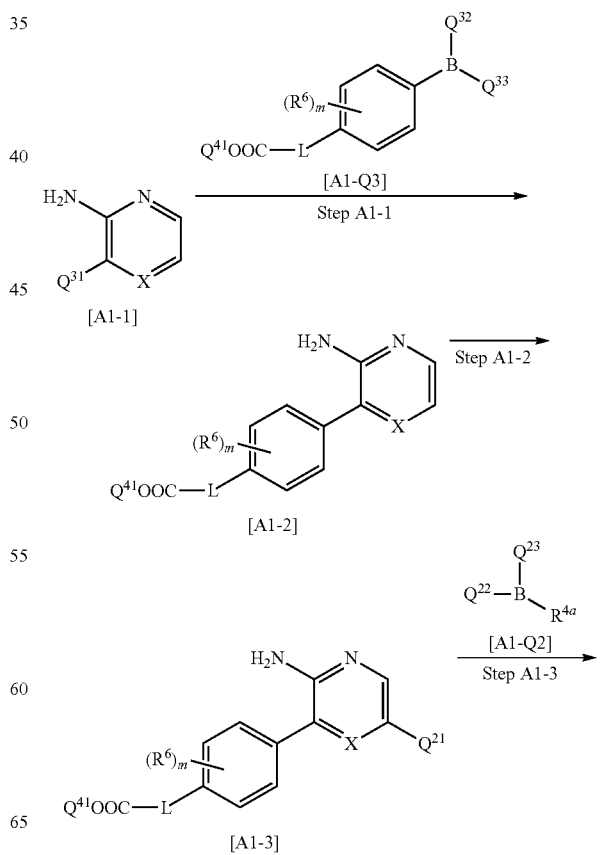

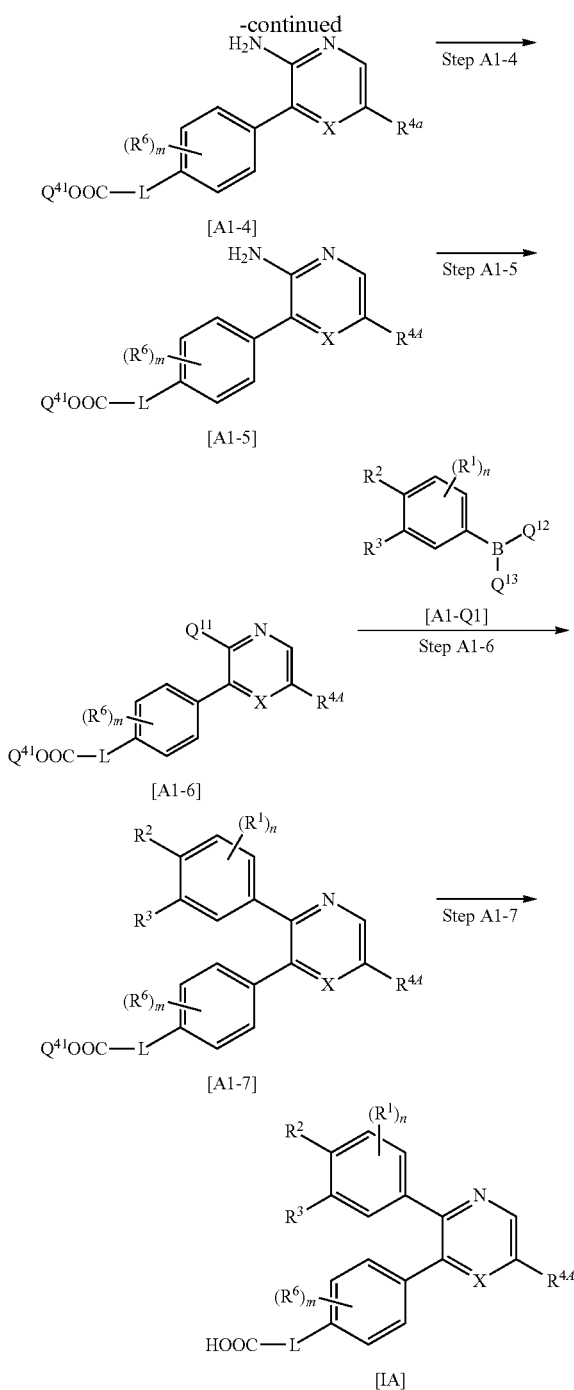

[A1-4]

[A1-5]

[A1-Q1]
Step A1-6

[A1-6]

Step A1-7

[A1-7]

[IA]

wherein
R^{4a} is
(1) $C_{1-8}$ alkenyl optionally substituted with 1 to 3 substituents independently selected from Group A,
(2) halo $C_{1-6}$ alkenyl,
(4) $C_{3-6}$ cycloalkenyl optionally substituted with 1 to 3 substituents independently selected from $C_{1-3}$ alkoxy, or
(5) a 4- to 6-membered unsaturated heterocyclic group containing one carbon-carbon double bond, and containing 1 or 2 hetero atom as a ring atom in addition to the carbon atoms, wherein the hetero atom is independently selected from the group consisting of oxygen, nitrogen and sulfur atoms, and wherein the ring atom in the heterocyclic group of Compound [A1-Q2] bonded to the boron is a carbon atom, and the ring atom in the heterocyclic group of Compound [A1-4] bonded to

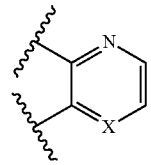

is a carbon atom,
$R^{4A}$ is
(1) $C_{1-8}$ alkyl optionally substituted with 1 to 3 substituents independently selected from Group A,
(2) halo $C_{1-6}$ alkyl,
(4) $C_{3-6}$ cycloalkyl optionally substituted with 1 to 3 substituents independently selected from $C_{1-3}$ alkoxy, or
(5) a 4- to 6-membered saturated heterocyclic group containing 1 or 2 hetero atom as a ring atom in addition to the carbon atoms, wherein the hetero atom is independently selected from the group consisting of oxygen, nitrogen and sulfur atoms, and wherein the ring atom in the heterocyclic group bonded to

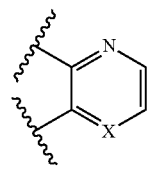

is a carbon atom,
Group A is as defined above,
$Q^{11}$ and $Q^{21}$ are each independently halogen,
$Q^{31}$ is a leaving group (e.g., halogen and sulfonyloxy (e.g., methanesulfonyloxy, trifluoromethanesulfonyloxy, benzenesulfonyloxy, and toluenesulfonyloxy)),
$Q^{12}$, $Q^{13}$, $Q^{22}$, $Q^{23}$, $Q^{32}$ and $Q^{33}$ are hydroxy, or $Q^{12}$ and $Q^{13}$, $Q^{22}$ and $Q^{23}$, and $Q^{32}$ and $Q^{33}$, together with the boron atom that they are bonded to, each independently optionally form a borate,
$Q^{41}$ is a protecting group for a carboxy group (e.g., methyl, benzyl, and tert-butyl), and
the other symbols are as defined above.
(Step A1-1)
Compound [A1-2] or a salt thereof can be obtained by subjecting Compound [A1-1] or a salt thereof and Compound [A1-Q3] to Suzuki coupling reaction. For example, Compound [A1-2] or a salt thereof can be obtained by reacting Compound [A1-1] or a salt thereof with Compound [A1-Q3] under heating in the presence of a base and a palladium catalyst, in a solvent.
Examples of the solvent include ether solvents such as 1,4-dioxane, tetrahydrofuran, and 1,2-dimethoxyethane; alcohol solvents such as methanol, and ethanol; hydrocarbon solvents such as benzene, toluene, and xylene; polar solvents such as N,N-dimethylformamide, dimethyl sulfoxide, and acetonitrile; mixed solvents thereof, and mixed solvents of the above-mentioned solvent and water. A preferable solvent is a mixed solvent of 1,4-dioxane and water, a mixed solvent of tetrahydrofuran and water, a mixed solvent of 1,2-dimethoxyethane and water, a mixed solvent of toluene and water, or a mixed solvent of the above-mentioned mixed solvent and an alcohol solvent such as ethanol.

Examples of the base include potassium phosphate, potassium carbonate, sodium carbonate, cesium carbonate and cesium fluoride. A preferable base is potassium phosphate, potassium carbonate or sodium carbonate.

Examples of the palladium catalyst include palladium complexes such as tetrakis(triphenylphosphine)palladium (0), bis(triphenylphosphine)palladium(II) dichloride, and [1,1'-bis(diphenylphosphino)-ferrocene]palladium(II) dichloride; and palladium complexes prepared in reaction system from a palladium compound (e.g., palladium(II) acetate, and tris(dibenzylideneacetone)dipalladium(0)), and a phosphine ligand (e.g., 2-dicyclohexylphosphino-2',6'-dimethoxybiphenyl, and 2-dicyclohexylphosphino-2',4',6'-triisopropylbiphenyl). A preferable palladium catalyst is tetrakis(triphenylphosphine)palladium(0) or [1,1'-bis (diphenylphosphino)-ferrocene]palladium(II) dichloride. When $Q^{31}$ is chlorine, a method using palladium(II) acetate and 2-dicyclohexylphosphino-2',6'-dimethoxybiphenyl is preferably employed.

The reaction temperature under heating is, for example, 40° C. to 140° C., preferably 70° C. to 110° C.

Compound [A1-1] or a salt thereof is a commercially available product, or can be obtained by a known method.

Compound [A1-Q3] is a commercially available product, or can be obtained by a known method.

(Step A1-2)

Compound [A1-3] or a salt thereof can be obtained by subjecting Compound [A1-2] or a salt thereof to a halogenation reaction. For example, Compound [A1-3] or a salt thereof can be obtained by reacting Compound [A1-2] or a salt thereof with a halogenating agent in a solvent.

Examples of the solvent include polar solvents such as N,N-dimethylformamide, dimethyl sulfoxide, acetonitrile, and acetic acid; and halogen solvents such as dichloromethane, and chloroform. A preferable solvent is N,N-dimethylformamide or acetonitrile.

Examples of the halogenating agent include N-bromosuccinimide, N-iodosuccinimide, N-chlorosuccinimide and bromine. A preferable halogenating agent is N-bromosuccinimide or N-iodosuccinimide.

The reaction temperature is, for example, 0° C. to 120° C., preferably 0° C. to room temperature (about 25° C.)

(Step A1-3)

Compound [A1-4] or a salt thereof can be obtained by reacting Compound [A1-3] or a salt thereof and Compound [A1-Q2] according to Step A1-1.

Compound [A1-Q2] is a commercially available product, or can be obtained by a known method.

(Step A1-4)

Compound [A1-5] or a salt thereof can be obtained by subjecting Compound [A1-4] or a salt thereof to a hydrogenation reaction. For example, Compound [A1-5] or a salt thereof can be obtained by reacting Compound [A1-4] or a salt thereof under hydrogen gas atmosphere in the presence of a palladium catalyst, in a solvent.

Examples of the solvent include ether solvents such as 1,4-dioxane, tetrahydrofuran, and 1,2-dimethoxyethane; alcohol solvents such as methanol, and ethanol; ester solvents such as ethyl acetate, and acetic acid isobutyl, and mixed solvents thereof. A preferable solvent is methanol, ethyl acetate, or a mixed solvent of methanol or ethyl acetate and tetrahydrofuran.

Examples of the palladium catalyst include 5% or 10% palladium on carbon (dry product, wet product). A preferable palladium catalyst is 10% palladium on carbon (wet product).

The reaction temperature is, for example, room temperature (about 25° C.) to 50° C., preferably room temperature (about 25° C.)

The pressure is, for example, 1 atm to 4 atm, preferably 1 atm.

(Step A1-5)

Compound [A1-6] or a salt thereof can be obtained by subjecting Compound [A1-5] or a salt thereof to Sandmeyer reaction. For example, Compound [A1-6] or a salt thereof can be obtained by subjecting Compound [A1-5] or a salt thereof to a diazotization in a solvent, and then reacting the resulting compound with a halogenating agent.

Examples of the solvent include dibromomethane, acetonitrile, tetrahydrofuran, N,N-dimethylformamide, and water. A preferable solvent is dibromomethane.

Examples of the diazotizing agent include nitrites such as isobutyl nitrite, t-butyl nitrite and isopentyl nitrite, and sodium nitrite. A preferable diazotizing agent is isobutyl nitrite, t-butyl nitrite, isopentyl nitrite or sodium nitrite.

Examples of the halogenating agent include bromotrimethylsilane, and copper(II) bromide. A preferable halogenating agent is bromotrimethylsilane.

The reaction temperature is, for example, 0° C. to 80° C., preferably 0° C. to room temperature (about 25° C.)

(Step A1-6)

Compound [A1-7] or a salt thereof can be obtained by reacting Compound [A1-6] or a salt thereof with Compound [A1-Q1] according to Step A1-1.

Compound [A1-Q1] is a commercially available product, or can be obtained by a known method.

(Step A1-7)

Compound [IA] or a salt thereof can be obtained by subjecting Compound [A1-7] or a salt thereof to a deprotection reaction to remove $Q^{41}$. The deprotection reaction can be carried out in a suitable condition depending on the type of $Q^{41}$.

For example, when $Q^{41}$ is methyl, Compound [IA] or a salt thereof can be obtained by subjecting Compound [A1-7] or a salt thereof to a hydrolysis reaction in the presence of a base, in a solvent.

Examples of the solvent include a mixed solvent of water and an alcohol solvent such as methanol and ethanol, and a mixed solvent of an alcohol solvent, water and tetrahydrofuran. A preferable solvent is a mixed solvent of methanol and water.

Examples of the base include lithium hydroxide, sodium hydroxide, and potassium hydroxide. A preferable base is sodium hydroxide.

The reaction temperature is, for example, room temperature (about 25° C.) to 80° C., preferably room temperature (about 25° C.) to 50° C.

Production Method A2: Alternative Step of Step A1-3 and Step A1-4

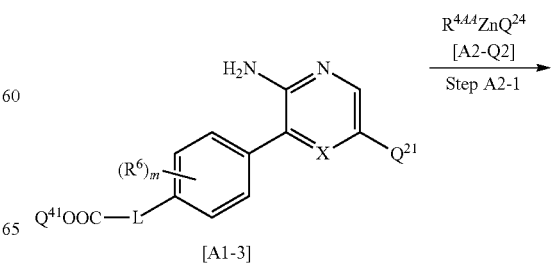

-continued

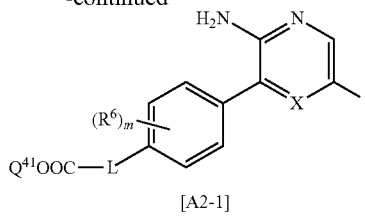

[A2-1]

wherein
R[4A] is
(1) C_{1-8} alkyl optionally substituted with 1 to 3 substituents independently selected from Group A, or
(2) halo C_{1-6} alkyl,
Group A is as defined above,
Q[24] is halogen, and
the other symbols are as defined above.
(Step A2-1)
Compound [A2-1] or a salt thereof can be obtained by subjecting Compound [A1-3] or a salt thereof and Compound [A2-Q2] to Negishi coupling reaction. For example, Compound [A2-1] or a salt thereof can be obtained by reacting Compound [A1-3] or a salt thereof with Compound [A2-Q2] in the presence of a palladium catalyst and a ligand, in a solvent.

Examples of the solvent include ether solvents such as 1,4-dioxane, tetrahydrofuran, and 1,2-dimethoxyethane; and hydrocarbon solvents such as benzene, toluene, and xylene. A preferable solvent is tetrahydrofuran or toluene.

Examples of the palladium catalyst include palladium(II) acetate, and tris(dibenzylideneacetone)dipalladium(0). A preferable palladium catalyst is palladium(II) acetate.

Examples of the ligand include 2-dicyclohexylphosphino-2',6'-dimethoxybiphenyl, 2-dicyclohexylphosphino-2',6'-diisopropyloxybiphenyl, and 2-dicyclohexylphosphino-2',6'-bis(N,N-dimethylamino)biphenyl. A preferable ligand is 2-dicyclohexylphosphino-2',6'-bis(N,N-dimethylamino)biphenyl.

The reaction temperature is, for example, 0° C. to 50° C., preferably 0° C. to room temperature (about 25° C.)

Compound [A2-Q2] is a commercially available product, or can be obtained by a known method.

Production Method A3: Alternative Production Method of Compound [IA] or a Salt Thereof

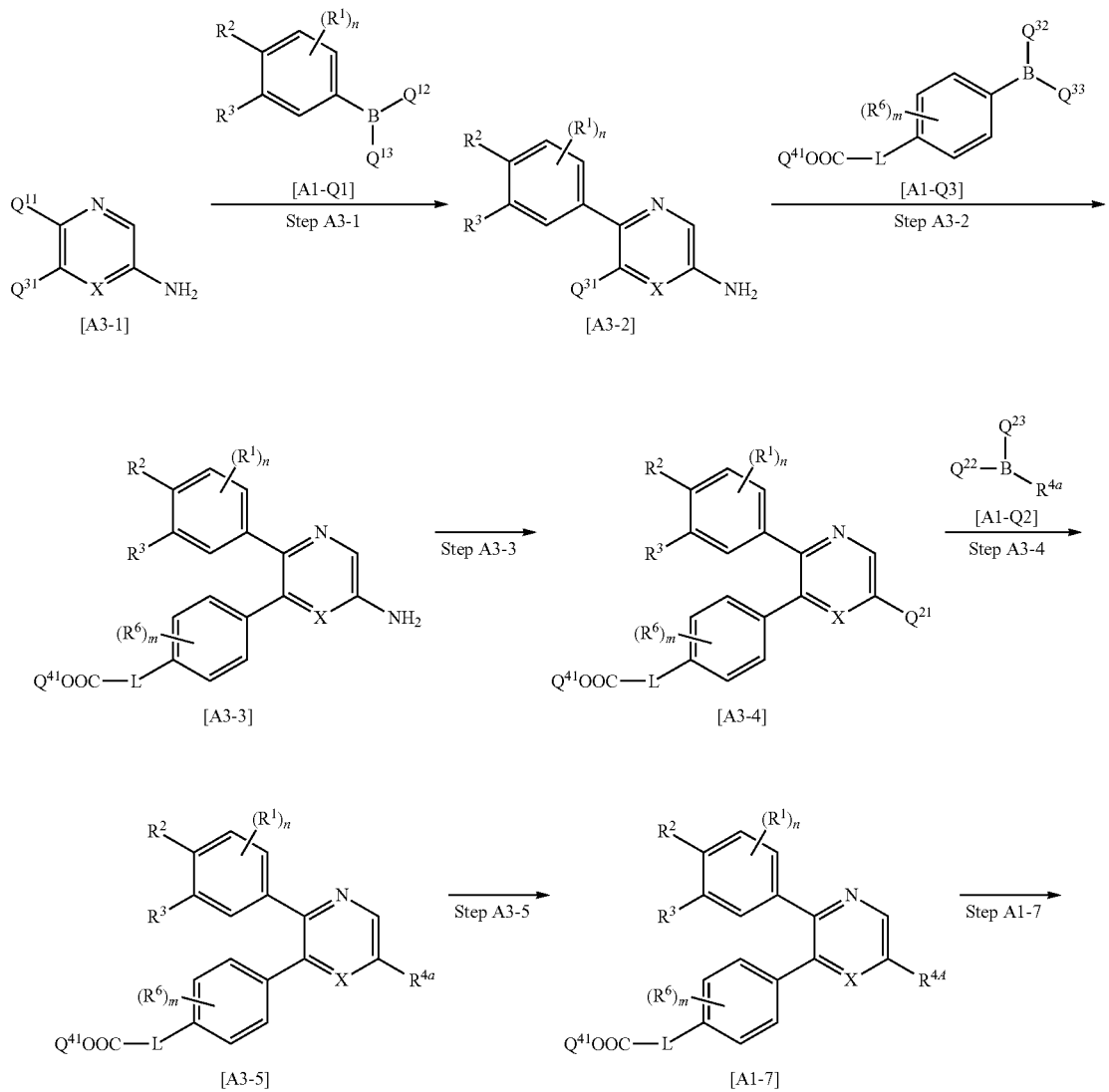

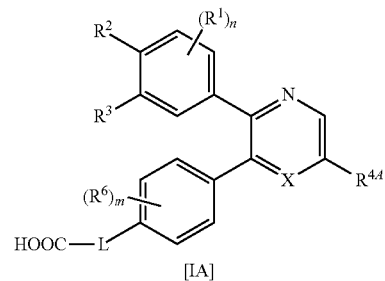

[IA]

wherein each symbol is as defined above, provided that $Q^{31}$ is preferably a group having reactivity equal to or lower than (for example, when $Q^{11}$ is chlorine, $Q^{31}$ is chlorine), and those skilled in the art can easily select such a group.

(Step A3-1)

Compound [A3-2] or a salt thereof can be obtained by reacting Compound [A3-1] or a salt thereof with Compound [A1-Q1] according to Step A1-1.

Compound [A3-1] or a salt thereof is a commercially available product, or can be obtained by a known method.

(Step A3-2)

Compound [A3-3] or a salt thereof can be obtained by reacting Compound [A3-2] or a salt thereof with Compound [A1-Q3] according to Step A1-1.

(Step A3-3)

Compound [A3-4] or a salt thereof can be obtained by reacting Compound [A3-3] or a salt thereof according to Step A1-5.

(Step A3-4)

Compound [A3-5] or a salt thereof can be obtained by reacting Compound [A3-4] or a salt thereof with Compound [A1-Q2] according to Step A1-1.

(Step A3-5)

Compound [A1-7] or a salt thereof can be obtained by reacting Compound [A3-5] or a salt thereof according to Step A1-4.

Production Method A4: Alternative Step of Step A3-4 and Step A3-5

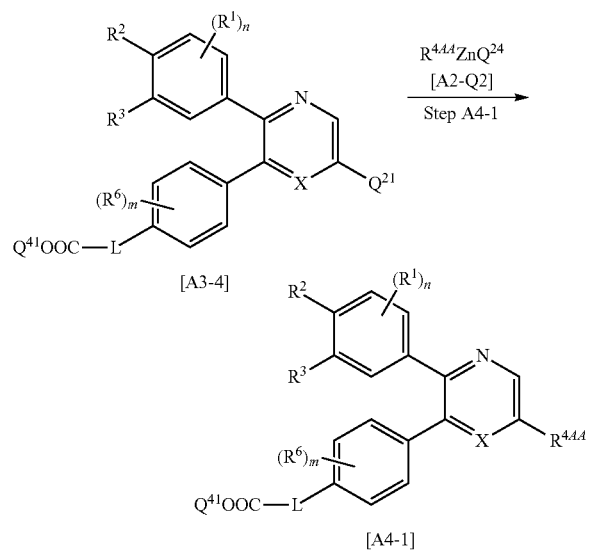

wherein each symbol is as defined above.

(Step A4-1)

Compound [A4-1] or a salt thereof can be obtained by reacting Compound [A3-4] or a salt thereof with Compound [A2-Q2] according to Step A2-1.

Production Method A5: Production Method of Compound [IAA] or a Salt Thereof

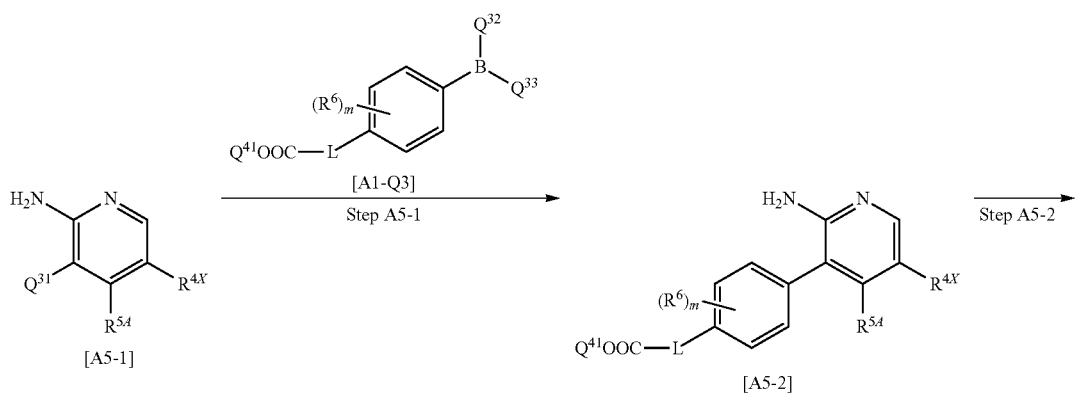

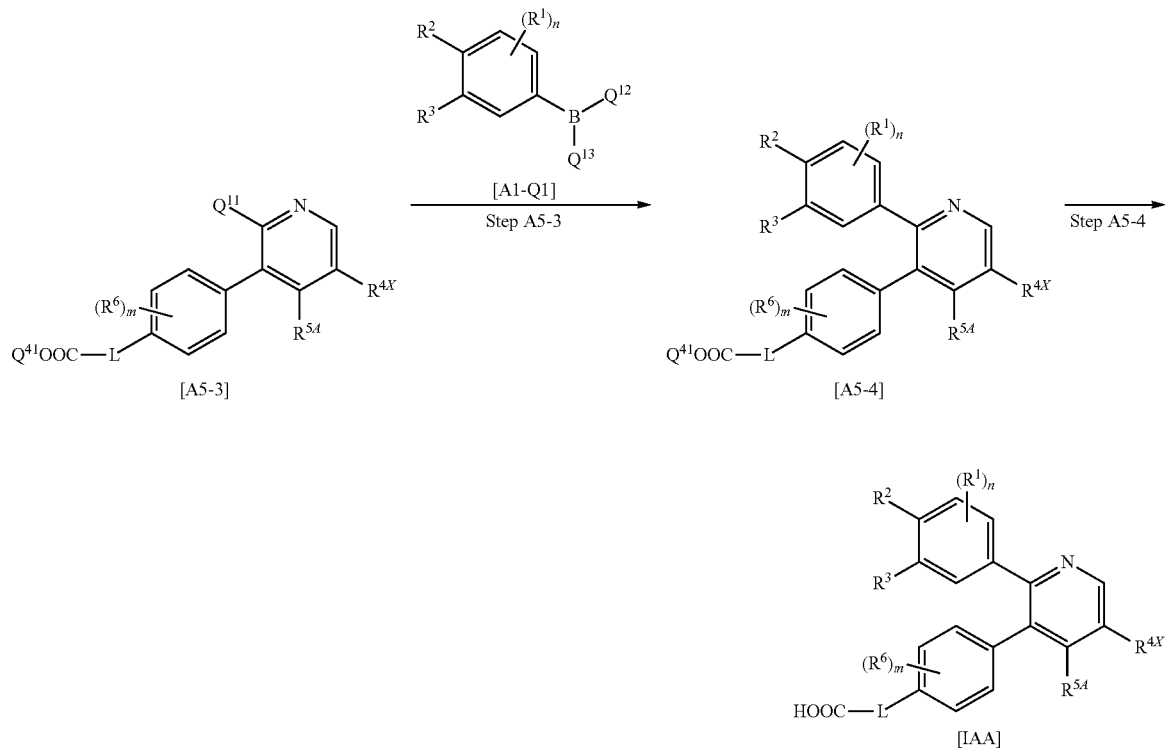

wherein
$R^{4X}$ and $R^{5A}$, together with the carbon atoms that they are bonded to, form $C_{3-6}$ cycloalkane, and
the other symbols are as defined above.

(Step A5-1)
Compound [A5-2] or a salt thereof can be obtained by reacting Compound [A5-1] or a salt thereof with Compound [A1-Q3] according to Step A1-1.
Compound [A5-1] or a salt thereof is a commercially available product, or can be obtained by a known method.

(Step A5-2)
Compound [A5-3] or a salt thereof can be obtained by reacting Compound [A5-2] or a salt thereof according to Step A1-5.

(Step A5-3)
Compound [A5-4] or a salt thereof can be obtained by reacting Compound [A5-3] or a salt thereof with Compound [A1-Q1] according to Step A1-1.

(Step A5-4)
Compound [IAA] or a salt thereof can be obtained by reacting Compound [A5-4] or a salt thereof according to Step A1-7.

Production Method A6: Production Method of Compound [IAAA] or a Salt Thereof

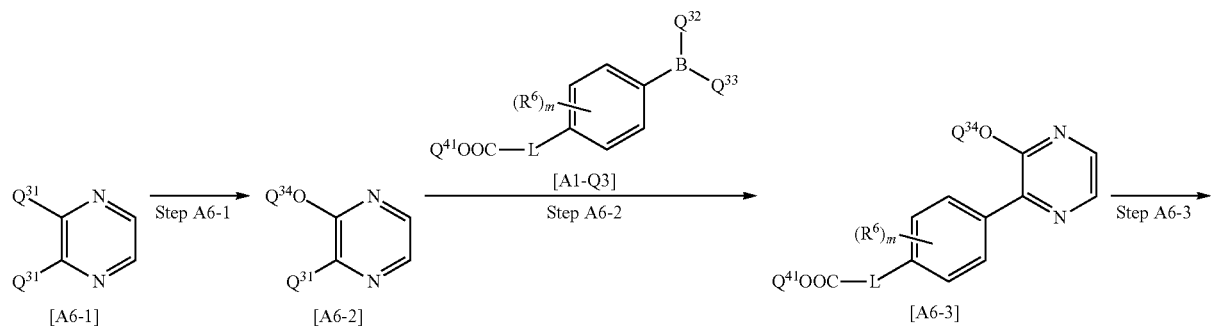

-continued
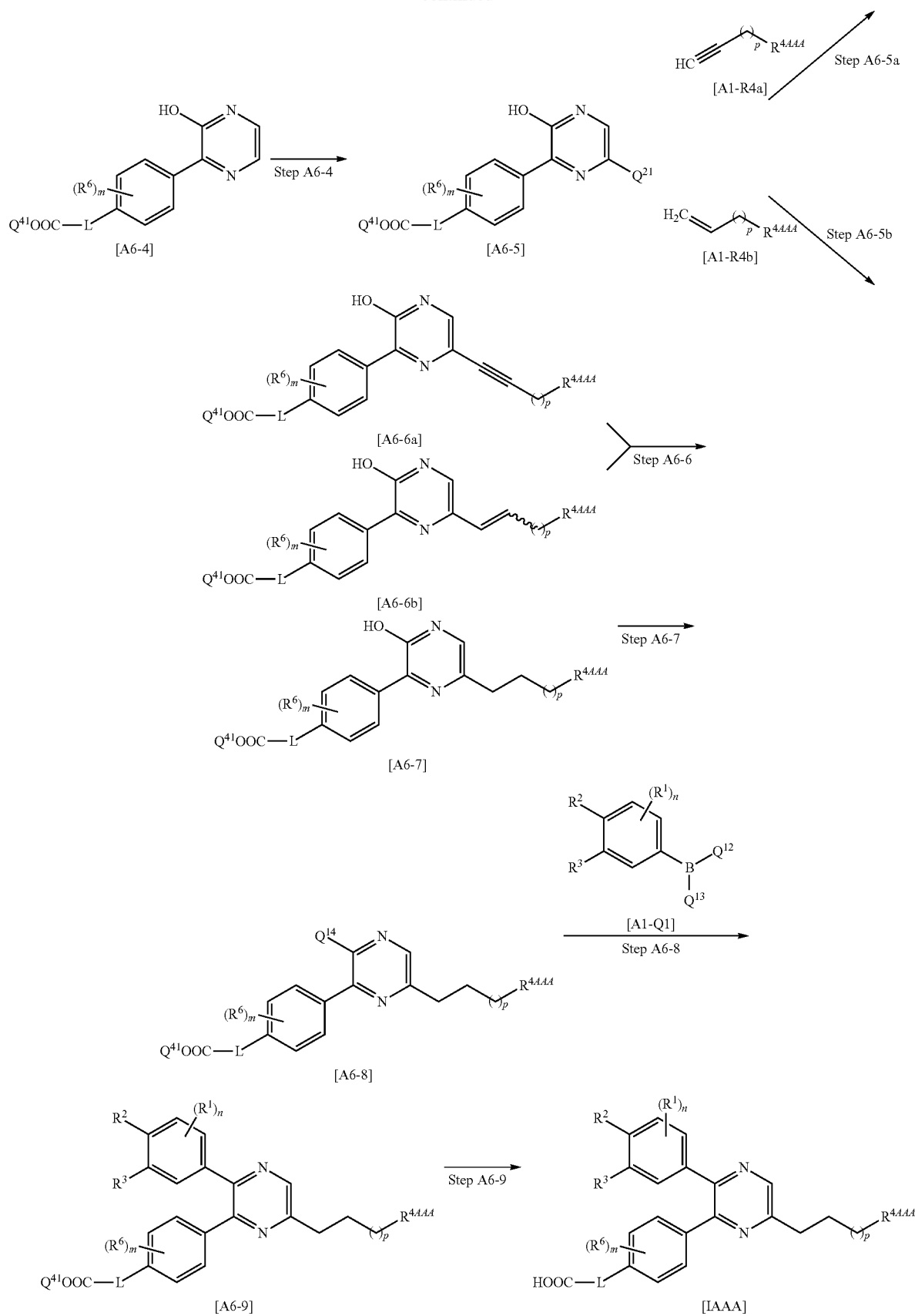

wherein p is 1, 2, 3, 4, 5 or 6, $Q^{34}$ is methyl, ethyl or tert-butyl, $Q^{14}$ is sulfonyloxy (e.g., methanesulfonyloxy, trifluoromethanesulfonyloxy, benzenesulfonyloxy, and toluenesulfonyloxy)), $R^{4AA4}$ is selected from Group A, and the other symbols are as defined above.

(Step A6-1)

Compound [A6-2] or a salt thereof can be obtained by reacting Compound [A6-1] or a salt thereof with a metal alkoxide, in a solvent.

Examples of a combination of the solvent and metal alkoxide include a combination of methanol and sodium methoxide, a combination of ethanol and sodium ethoxide, a combination of benzyl alcohol and sodium benzyloxide, a combination of tert-butanol and potassium tert-butoxide, and a combination of tetrahydrofuran or N,N-dimethylformamide, and sodium methoxide, sodium ethoxide, sodium benzyloxide or potassium tert-butoxide. A preferable combination of the solvent and metal alkoxide is a combination of tetrahydrofuran and potassium tert-butoxide.

The reaction temperature is, for example, −5° C. to 30° C., preferably 0° C. to 15° C.

Compound [A6-1] or a salt thereof is a commercially available product, or can be obtained by a known method.

(Step A6-2)

Compound [A6-3] or a salt thereof can be obtained by reacting Compound [A6-2] or a salt thereof with Compound [A1-Q3] according to Step A1-1.

(Step A6-3)

Compound [A6-4] or a salt thereof can be obtained by subjecting Compound [A6-3] or a salt thereof to a deprotection reaction to remove $Q^{34}$. The deprotection reaction can be carried out in a suitable condition depending on the type of $Q^{34}$.

For example, when $Q^{34}$ is tert-butyl, Compound [A6-4] or a salt thereof can be obtained by reacting Compound [A6-3] or a salt thereof with an acid, in a solvent.

Examples of the solvent include methanol, ethanol, 2-propanol, tetrahydrofuran, toluene, and mixed solvent thereof. A preferable solvent is a mixed solvent of ethanol and tetrahydrofuran.

Examples of the acid include hydrochloric acid, hydrobromic acid, sulfuric acid, and trifluoroacetic acid. A preferable acid is hydrochloric acid.

The reaction temperature is, for example, 15° C. to 60° C., preferably 30° C. to 40° C.

(Step A6-4)

Compound [A6-5] or a salt thereof can be obtained by subjecting Compound [A6-4] or a salt thereof to a halogenation reaction according to Step A1-2.

(Step A6-5a)

Compound [A6-6a] or a salt thereof can be obtained by subjecting Compound [A6-5] or a salt thereof and Compound [A1-R4a] to Sonogashira coupling reaction. For example, Compound [A6-6a] or a salt thereof can be obtained by reacting Compound [A6-5] or a salt thereof with Compound [A1-R4a] in the presence of a base, a palladium catalyst and a copper catalyst, in a solvent.

Examples of the solvent include N,N-dimethylformamide, acetonitrile, and tetrahydrofuran. A preferable solvent is acetonitrile.

Examples of the base include triethylamine, diisopropylethylamine, and diisopropylamine. A preferable base is triethylamine.

Examples of the palladium catalyst include tetrakis(triphenylphosphine)palladium(0), and bis(triphenylphosphine)palladium(II) dichloride. A preferable palladium catalyst is bis(triphenylphosphine)palladium(II) dichloride.

Examples of the copper catalyst include copper(I) iodide, and copper(I) bromide. A preferable copper catalyst is copper(I) iodide.

The reaction temperature is, for example, 15° C. to 50° C., preferably 25° C. to 40° C.

(Step A6-5b)

Compound [A6-6b] or a salt thereof can be obtained by subjecting Compound [A6-5] or a salt thereof and Compound [A1-R4b] to Heck reaction. For example, Compound [A6-6b] or a salt thereof can be obtained by reacting Compound [A6-5] or a salt thereof with Compound [A1-R4b] in the presence of a base and a palladium catalyst, in a solvent.

(Step A6-6)

Compound [A6-7] or a salt thereof can be obtained by subjecting Compound [A6-6a] or a salt thereof or Compound [A6-6b] or a salt thereof to a hydrogenation reaction according to Step A1-4.

(Step A6-7)

Compound [A6-8] or a salt thereof can be obtained by subjecting Compound [A6-7] or a salt thereof to a sulfonylation reaction of hydroxy. The sulfonylation reaction can be carried out in a suitable condition depending on the type of For example, when $Q^{14}$ is trifluoromethanesulfonyloxy, Compound [A6-8] or a salt thereof can be obtained by reacting Compound [A6-7] or a salt thereof with trifluoromethanesulfonic anhydride in the presence of a base, in a solvent.

Examples of the solvent include toluene, dichloromethane, pyridine, and mixed solvents of the above-mentioned solvent and water. A preferable solvent is a mixed solvent of toluene and water.

Examples of the base include inorganic bases such as dipotassium hydrogenphosphate, tripotassium phosphate, and potassium carbonate, and organic bases such as pyridine, 4-dimethylaminopyridine, 2,6-lutidine, triethylamine, and diisopropylethylamine. A preferable base is dipotassium hydrogenphosphate.

The reaction temperature is, for example, 0° C. to 30° C., preferably 5° C. to 10° C.

(Step A6-8)

Compound [A6-9] or a salt thereof can be obtained by reacting Compound [A6-8] or a salt thereof with Compound [A1-Q1] according to Step A1-6.

(Step A6-9)

Compound [IAAA] or a salt thereof can be obtained by subjecting Compound [A6-9] or a salt thereof to a hydrolysis reaction according to Step A1-7.

Production Method B1: Production Method of Compound [IB] or a Salt Thereof

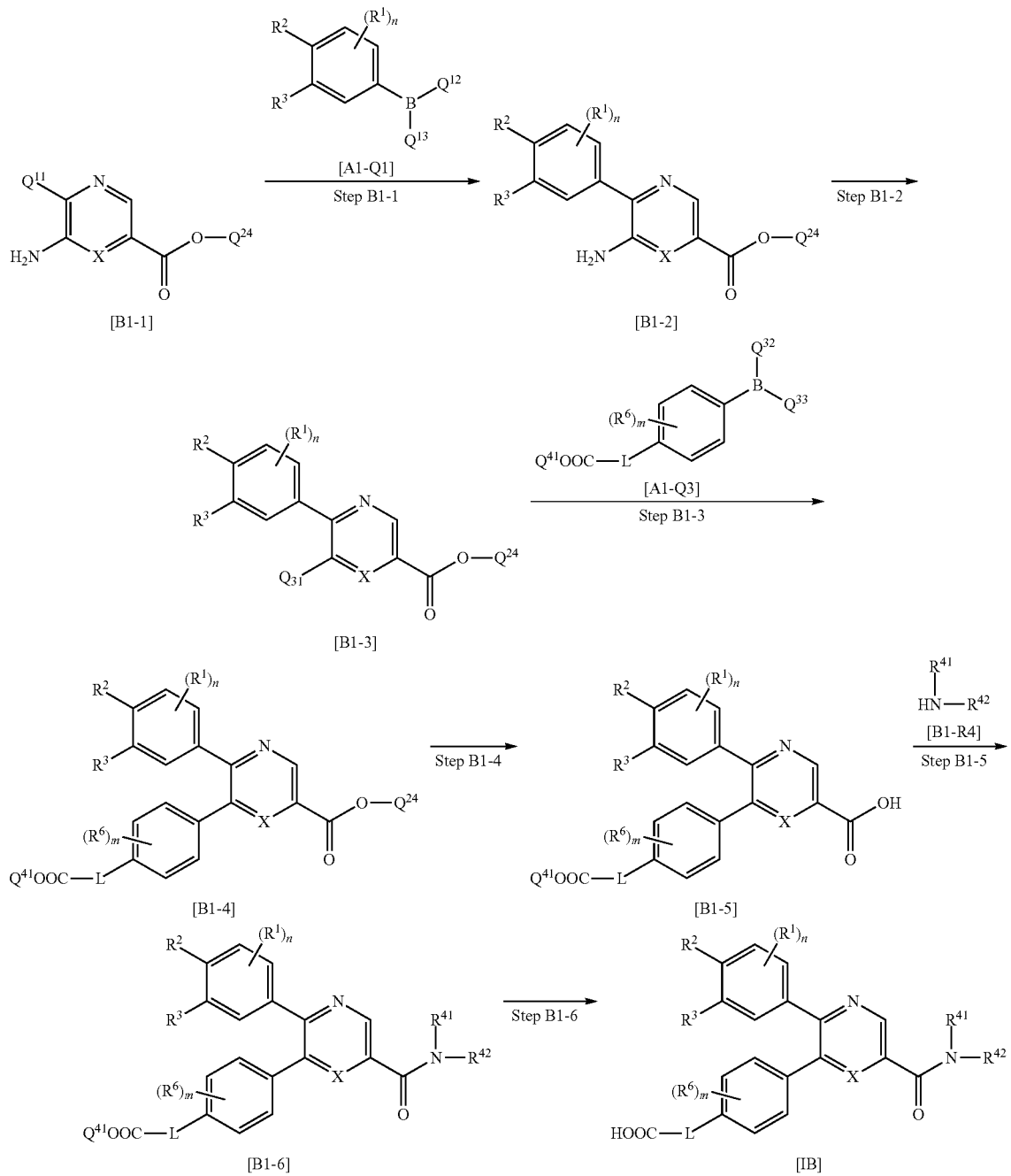

wherein each symbol is as defined above.

(Step B1-1)

Compound [B1-2] or a salt thereof can be obtained by reacting Compound [B1-1] or a salt thereof with Compound [A1-Q1] according to Step A1-1.

Compound [B1-1] or a salt thereof is a commercially available product, or can be obtained by a known method.

(Step B1-2)

Compound [B1-3] or a salt thereof can be obtained by reacting Compound [B1-2] or a salt thereof according to Step A1-5.

(Step B1-3)

Compound [B1-4] or a salt thereof can be obtained by reacting Compound [B1-3] or a salt thereof with Compound [A1-Q3] according to Step A1-1.

(Step B1-4)

Compound [B1-5] or a salt thereof can be obtained by reacting Compound [B1-4] or a salt thereof at room temperature (about 25° C.) according to Step A1-7.

(Step B1-5)

Compound [B1-6] or a salt thereof can be obtained by subjecting Compound [B1-5] or a salt thereof and Compound [B1-R4] or a salt thereof to an amidation reaction. For example, Compound [B1-6] or a salt thereof can be obtained by reacting Compound [B1-5] or a salt thereof with Compound [B1-R4] or a salt thereof in the presence of a condensing agent and an optional base, in a solvent.

Examples of the solvent include ether solvents such as 1,4-dioxane, tetrahydrofuran, and 1,2-dimethoxyethane; halogen solvents such as dichloromethane, and chloroform; and polar solvents such as N,N-dimethylformamide, and acetonitrile. A preferable solvent is N,N-dimethylformamide or acetonitrile.

Examples of the condensing agent include N,N'-dicyclohexylcarbodiimide, 1-(3-dimethylaminopropyl)-3-ethylcarbodiimide, and HATU [O-(7-azabenzotriazol-1-yl)-N,N,N',N'-tetramethyluronium hexafluorophosphate] [alias: 2-(7-aza-1H-benzotriazol-1-yl)-1,1,3,3-tetramethyluronium hexafluorophosphate]. A preferable condensing agent is HATU.

Examples of the optional base include triethylamine, and N,N-diisopropylethylamine. A preferable base is triethylamine.

The reaction temperature is, for example, room temperature (about 25° C.) to 60° C., preferably room temperature (about 25° C.)

Compound [B1-R4] or a salt thereof is a commercially available product, or can be obtained by a known method.

(Step B1-6)
Compound [IB] or a salt thereof can be obtained by reacting Compound [B1-6] or a salt thereof according to Step A1-7.

Production Method C1: Production Method of Compound [IC] or a Salt Thereof

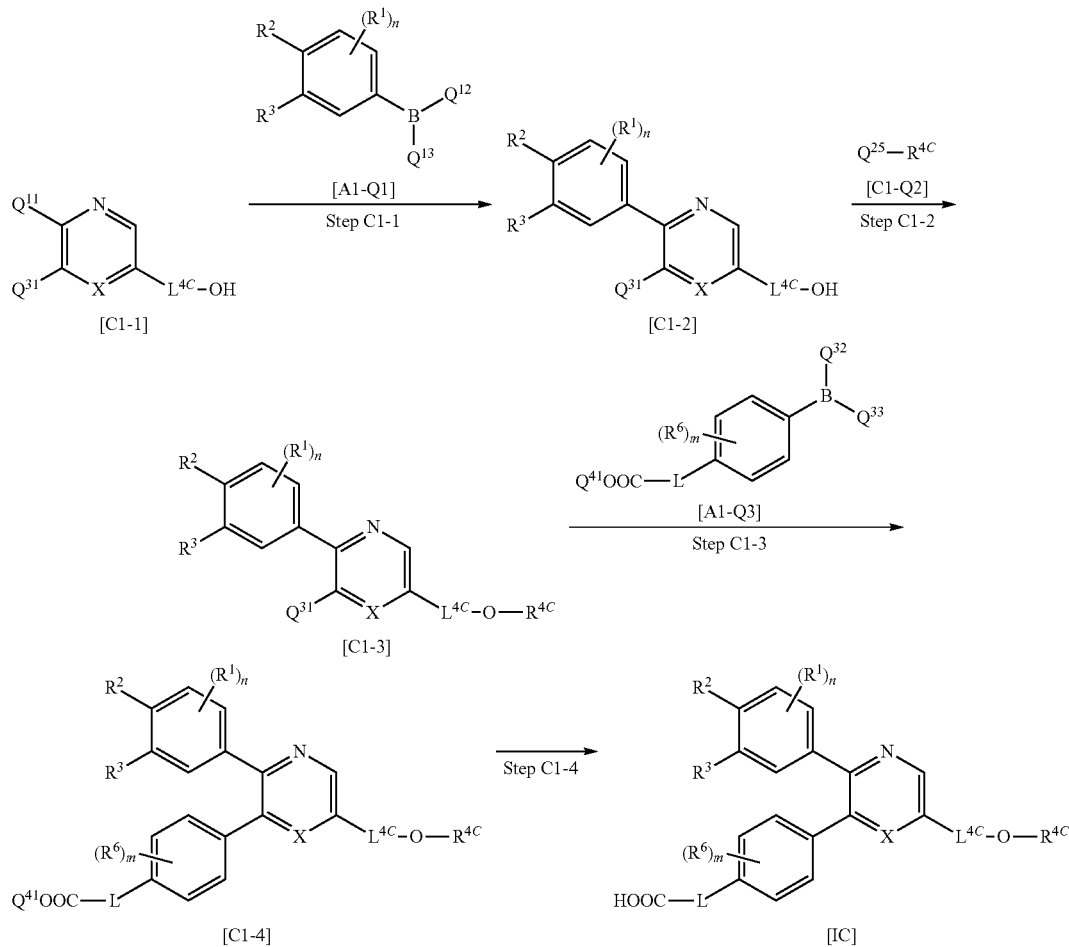

wherein
$L^{4C}$ is $C_{1-8}$ alkylene or $C_{3-6}$ cycloalkylene,
$R^{4C}$ is $C_{1-3}$ alkyl optionally substituted with one hydroxy or one $C_{1-3}$ alkoxy, or halo $C_{1-3}$ alkyl,
$Q^{25}$ is halogen, and
the other symbols are as defined above.

(Step C1-1)
Compound [C1-2] or a salt thereof can be obtained by reacting Compound [C1-1] or a salt thereof with Compound [A1-Q1] according to Step A1-1.

Compound [C1-1] or a salt thereof is a commercially available product, or can be obtained by a known method.

(Step C1-2)
Compound $[C_{1-3}]$ or a salt thereof can be obtained by subjecting Compound [C1-2] or a salt thereof and Compound [C1-Q2] to an alkylation reaction. For example, Compound $[C_{1-3}]$ or a salt thereof can be obtained by reacting Compound [C1-2] or a salt thereof with Compound [C1-Q2] in the presence of a base, in a solvent.

Examples of the solvent include ether solvents such as 1,4-dioxane, tetrahydrofuran and 1,2-dimethoxyethane, and N,N-dimethylformamide. A preferable solvent is tetrahydrofuran or N,N-dimethylformamide.

Examples of the base include sodium hydride, potassium t-butoxide, and sodium t-butoxide. A preferable base is sodium hydride.

The reaction temperature is, for example, 0° C. to 70° C., preferably 0° C. to room temperature (about 25° C.)

Compound [C1-Q2] is a commercially available product, or can be obtained by a known method.

(Step C$_{1-3}$)

Compound [C1-4] or a salt thereof can be obtained by reacting Compound [C$_{1-3}$] or a salt thereof with Compound [A1-Q3] according to Step A1-1.

(Step C1-4)

Compound [IC] or a salt thereof can be obtained by reacting Compound [C1-4] or a salt thereof according to Step A1-7.

EXAMPLES

Next, the production method of Compound [I] or a pharmaceutically acceptable salt thereof is concretely explained by referring to Examples, which should not be construed as limitative.

In the following Examples, the following abbreviation is used.

HATU: O-(7-azabenzotriazol-1-yl)-N,N,N',N'-tetramethyluronium hexafluorophosphate [alias: 2-(7-aza-1H-benzotriazol-1-yl)-1,1,3,3-tetramethyluronium hexafluorophosphate]

Production Example 1

Synthesis of 4-(3-(3,5-difluoro-4-methoxyphenyl)-6-(3-methoxypropyl)pyrazin-2-yl)benzoic Acid (Example 67)

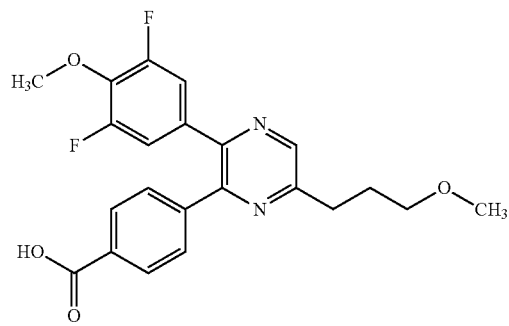

Step 1-1: Methyl 4-(3-aminopyrazin-2-yl)benzoate

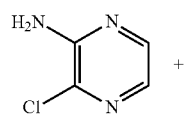

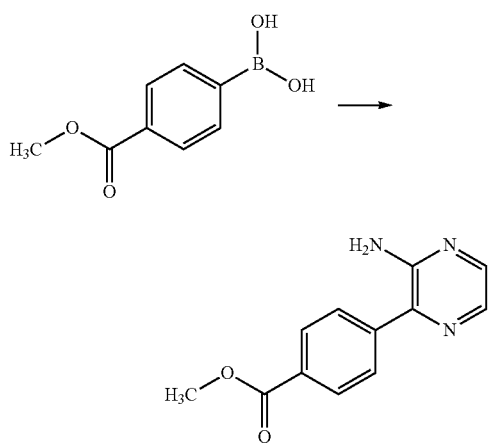

Under inert gas atmosphere, to a solution of 3-chloropyrazin-2-amine (3.00 g, 23.2 mmol), (4-(methoxycarbonyl)phenyl)boric acid (5.00 g, 27.8 mmol) and [1,1'-bis(diphenylphosphino)-ferrocene]palladium(II) dichloride dichloromethane adduct (0.378 g, 0.463 mmol) in tetrahydrofuran (100 mL) was added 2M-aqueous potassium phosphate solution (23.2 mL, 46.3 mmol), and the mixture was stirred at 70° C. for 1 hr. The reaction solution was diluted with water and ethyl acetate, and separated, and the organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=2:1 to 1:2) to give methyl 4-(3-aminopyrazin-2-yl)benzoate (2.56 g, yield 48%).

1H-NMR (DMSO-D6) δ: 3.87 (3H, s), 6.27 (2H, br s), 7.84 (2H, dt, J=8.4, 1.8 Hz), 7.89 (1H, d, J=2.5 Hz), 7.97 (1H, d, J=2.5 Hz), 8.04 (2H, dt, J=8.6, 1.8 Hz).

Step 1-2: Methyl 4-(3-amino-6-bromopyrazin-2-yl)benzoate

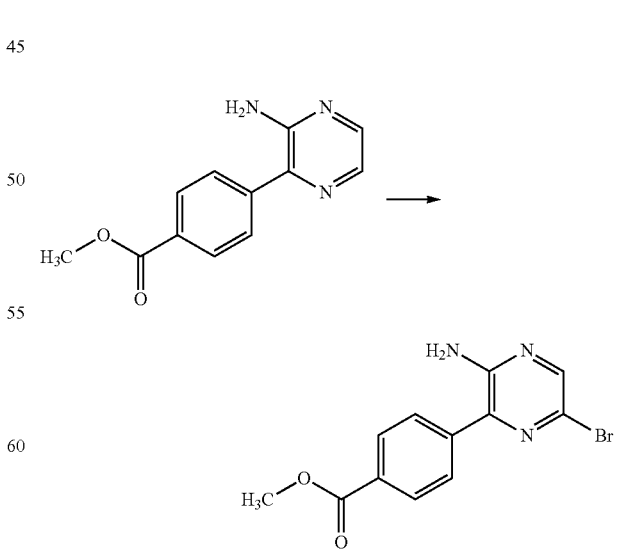

Under ice cooling, to a suspension of methyl 4-(3-aminopyrazin-2-yl)benzoate (3.15 g, 13.7 mmol) in acetonitrile (80 mL) was added N-bromosuccinimide (2.56 g, 14.4 mmol), and the mixture was stirred for 30 min. To the reaction solution was added water (160 mL), and the mixture was stirred at room temperature for 1 hr. The precipitated solid was collected by filtration, and dried under reduced pressure to give methyl 4-(3-amino-6-bromopyrazin-2-yl)benzoate (3.93 g, yield 92%). 1H-NMR (DMSO-D6) δ: 3.88 (3H, s), 6.57 (2H, br s), 7.82 (2H, dt, J=8.5, 1.8 Hz), 8.05 (2H, dt, J=8.6, 1.8 Hz), 8.12 (1H, s).

Step 1-3: Methyl (E)-4-(3-amino-6-(3-methoxy-prop-1-en-1-yl)pyrazin-2-yl)benzoate

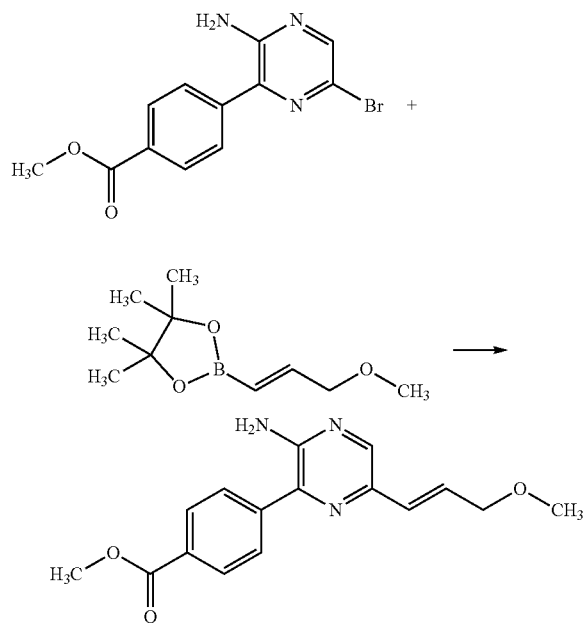

Under inert gas atmosphere, to a suspension of methyl 4-(3-amino-6-bromopyrazin-2-yl)benzoate (2.00 g, 6.49 mmol), (E)-2-(3-methoxyprop-1-en-1-yl)-4,4,5,5-tetramethyl-1,3,2-dioxaborolane (1.54 g, 7.79 mmol) and [1,1'-bis(diphenylphosphino)-ferrocene]palladium(II) dichloride dichloromethane adduct (0.106 g, 0.130 mmol) in toluene (20 mL) was added 2M-aqueous potassium phosphate solution (4.87 mL, 9.74 mmol), and the mixture was stirred at 100° C. for 2 hr. The mixture was allowed to cool to room temperature, and diluted with ethyl acetate (50 mL), and the insoluble substance was removed by filtration through Celite. The organic layer was washed successively with water and saturated brine, and dried over magnesium sulfate. The magnesium sulfate was removed by filtration, and the filtrate was concentrated under reduced pressure. The obtained residue was purified by silica gel chromatography (hexane:ethyl acetate=2:1 to 1:4) to give methyl (E)-4-(3-amino-6-(3-methoxyprop-1-en-1-yl)pyrazin-2-yl)benzoate (1.78 g, yield 91%).

1H-NMR (DMSO-D6) δ: 3.27 (3H, s), 3.88 (3H, s), 4.04 (2H, dd, J=5.4, 1.3 Hz), 6.37 (2H, br s), 6.46-6.53 (1H, m), 6.59 (1H, dt, J=15.7, 1.2 Hz), 7.86 (2H, dt, J=8.5, 1.8 Hz), 8.03-8.06 (3H, m).

Step 1-4: Methyl 4-(3-amino-6-(3-methoxypropyl)pyrazin-2-yl)benzoate

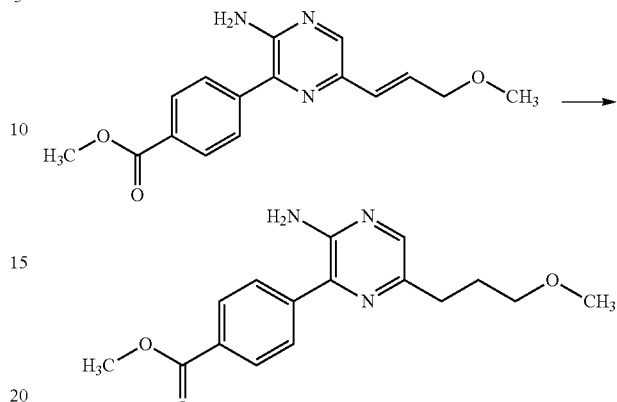

To methyl (E)-4-(3-amino-6-(3-methoxyprop-1-en-1-yl)pyrazin-2-yl)benzoate (777 mg, 2.60 mmol) were added methanol (13 mL) and 10% palladium on carbon catalyst (50% wet, 155 mg), and the mixture was stirred under hydrogen gas atmosphere for 24 hr. The palladium on carbon catalyst was removed from the reaction solution by filtration, and the filtrate was concentrated under reduced pressure. The residue was purified by silica gel chromatography (hexane:ethyl acetate=1:4) to give methyl 4-(3-amino-6-(3-methoxypropyl)pyrazin-2-yl)benzoate (772 mg, yield 98%).

1H-NMR (DMSO-D6) δ: 1.80-1.88 (2H, m), 2.64 (2H, t, J=7.6 Hz), 3.21 (3H, s), 3.34 (2H, t, J=6.4 Hz), 3.87 (3H, s), 6.02 (2H, br s), 7.84-7.87 (3H, m), 8.03 (2H, dt, J=8.6, 1.8 Hz).

Step 1-5: Methyl 4-(3-bromo-6-(3-methoxypropyl)pyrazin-2-yl)benzoate

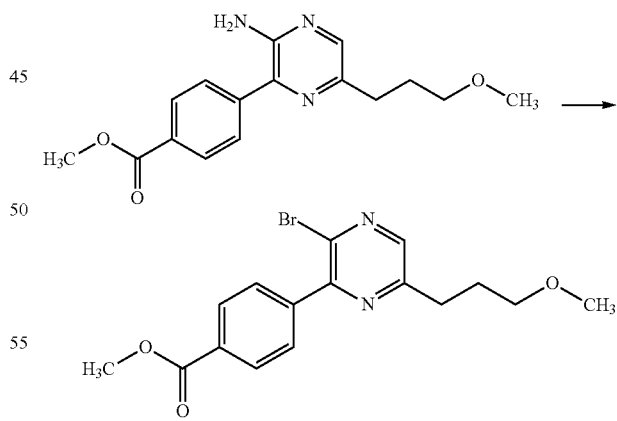

A solution of methyl 4-(3-amino-6-(3-methoxypropyl)pyrazin-2-yl)benzoate (5.00 g, 16.6 mmol) in dibromomethane (140 mL) was stirred at room temperature, and isopentyl nitrite (2.40 mL, 18.3 mmol) was added thereto. To the reaction solution was added dropwise a solution of bromotrimethylsilane (2.41 mL, 18.3 mmol) in dibromomethane (20 mL) over 10 min, and the reaction solution was stirred at room temperature for 24 hr. To the reaction solution was added saturated aqueous sodium hydrogencarbonate solution (50 mL), and the mixture was extracted with ethyl acetate (100 mL). The organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=7:1 to 2:1) to give methyl 4-(3-bromo-6-(3-methoxypropyl)pyrazin-2-yl)benzoate (4.31 g, yield 71%).

1H-NMR (DMSO-D6) δ: 1.89-1.96 (2H, m), 2.82-2.87 (2H, m), 3.21 (3H, s), 3.36 (2H, t, J=6.2 Hz), 3.89 (3H, s), 7.85 (2H, dt, J=8.5, 1.8 Hz), 8.08 (2H, dt, J=8.4, 1.8 Hz), 8.43 (1H, s).

Step 1-6: Methyl 4-(3-(3,5-difluoro-4-methoxyphenyl)-6-(3-methoxypropyl)pyrazin-2-yl)benzoate

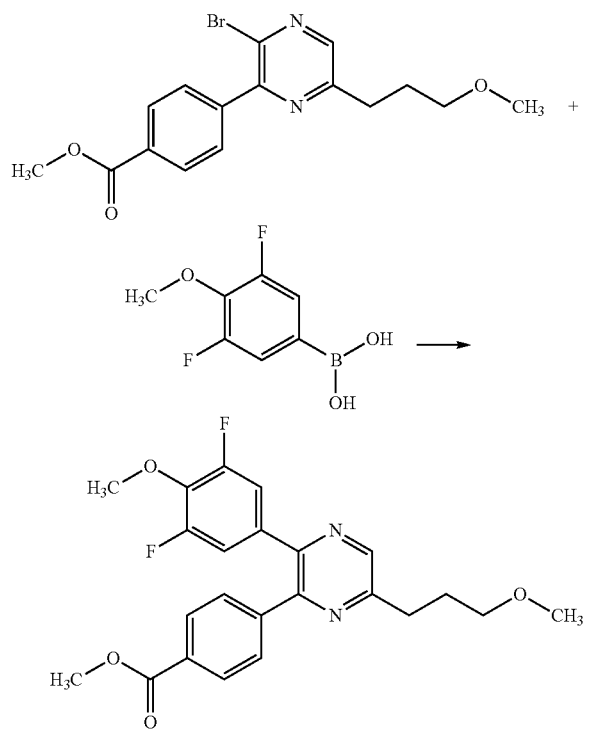

Under inert gas atmosphere, to a solution of methyl 4-(3-bromo-6-(3-methoxypropyl)pyrazin-2-yl)benzoate (4.30 g, 11.8 mmol) and (3,5-difluoro-4-methoxyphenyl)boric acid (2.66 g, 14.1 mmol) in toluene (44 mL) were added [1,1'-bis(diphenylphosphino)-ferrocene]palladium(II) dichloride dichloromethane adduct (0.192 g, 0.235 mmol) and 2M-aqueous potassium phosphate solution (8.83 mL, 17.7 mmol), and the mixture was stirred at 100° C. for 4 hr. The mixture was allowed to cool to room temperature, water (100 mL) was added thereto, and the mixture was extracted with ethyl acetate (200 mL). The organic layer was washed successively with water and saturated brine, and dried over sodium sulfate. The sodium sulfate was removed by filtration, and the filtrate was concentrated under reduced pressure. The obtained residue was purified by silica gel chromatography (hexane:ethyl acetate=4:1 to 2:1) to give methyl 4-(3-(3,5-difluoro-4-methoxyphenyl)-6-(3-methoxypropyl)pyrazin-2-yl)benzoate (4.86 g, yield 96%).

1H-NMR (DMSO-D6) δ: 1.94-2.01 (2H, m), 2.90-2.94 (2H, m), 3.23 (3H, s), 3.40 (2H, t, J=6.2 Hz), 3.85 (3H, s), 3.93 (3H, s), 7.05-7.12 (2H, m), 7.56 (2H, dt, J=8.5, 1.8 Hz), 7.95 (2H, dt, J=8.4, 1.8 Hz), 8.65 (1H, s).

Step 1-7: 4-(3-(3,5-Difluoro-4-methoxyphenyl)-6-(3-methoxypropyl)pyrazin-2-yl)benzoic Acid

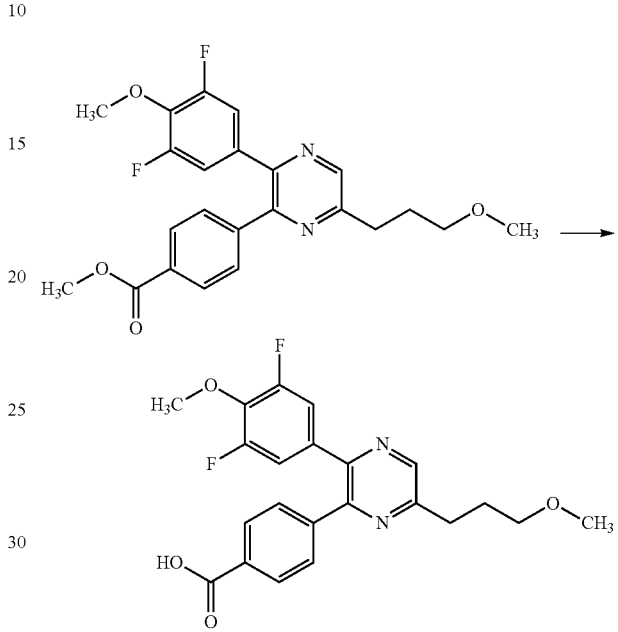

To a solution of methyl 4-(3-(3,5-difluoro-4-methoxyphenyl)-6-(3-methoxypropyl)pyrazin-2-yl)benzoate (1.00 g, 2.33 mmol) in methanol (14 mL) was added 4N-aqueous sodium hydroxide solution (3.50 mL, 14.0 mmol), and the mixture was stirred at 50° C. for 2 hr. The mixture was allowed to cool to room temperature, 10 wt %-aqueous citric acid solution (10.5 mL) and water (15 mL) were added thereto, and the mixture was stirred at room temperature for 2 hr. The precipitated solid was collected by filtration, and dried under reduced pressure to give 4-(3-(3,5-difluoro-4-methoxyphenyl)-6-(3-methoxypropyl)pyrazin-2-yl)benzoic acid (824 mg, yield 85%).

1H-NMR (DMSO-D6) δ: 1.92-2.02 (2H, m), 2.91 (2H, t, J=7.7 Hz), 3.24 (3H, s), 3.40 (2H, t, J=6.4 Hz), 3.93 (3H, s), 7.09 (2H, d, J=9.5 Hz), 7.53 (2H, d, J=8.6 Hz), 7.92 (2H, d, J=8.6 Hz), 8.64 (1H, s), 13.10 (1H, s).

Step 1-8: Crystals of 4-(3-(3,5-difluoro-4-methoxyphenyl)-6-(3-methoxypropyl)pyrazin-2-yl)benzoic Acid To 4-(3-(3,5-difluoro-4-methoxyphenyl)-6-(3-methoxypropyl)pyrazin-2-yl)benzoic acid (50 mg) were added 2-propanol (0.075 mL) and n-heptane (0.025 mL), and the mixture was stirred at 100° C. to give a solution. The stirring was stopped, and the mixture was allowed to cool to room temperature. The precipitated solid was collected by filtration, and dried under reduced pressure to give crystals of 4-(3-(3,5-difluoro-4-methoxyphenyl)-6-(3-methoxypropyl)pyrazin-2-yl)benzoic acid (31 mg, yield 62%).

Production Example 2

Synthesis of 4-(5-(butylcarbamoyl)-2-(4-methoxyphenyl)pyridin-3-yl)benzoic Acid Hydrochloride (Example 76)

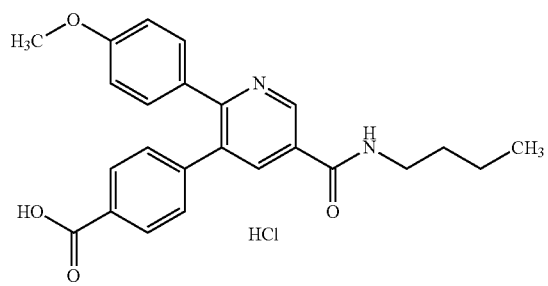 [SMILES: CCCCNC(=O)c1cnc(-c2ccc(OC)cc2)c(-c2ccc(C(=O)O)cc2)c1 ; Cl]

Step 2-1: Methyl 5-amino-6-(4-methoxyphenyl)nicotinate

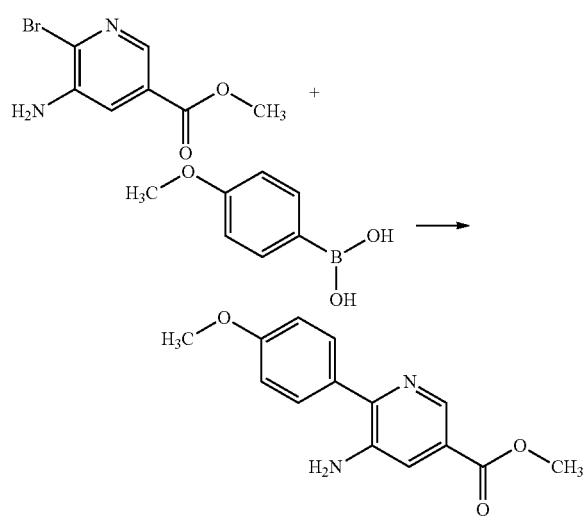

To a mixture of methyl 5-amino-6-bromonicotinate (0.500 g, 2.16 mmol), (4-methoxyphenyl)boric acid (0.660 g, 4.34 mmol) and potassium phosphate (1.43 g, 6.73 mmol) were added 1,2-dimethoxyethane (12 mL) and water (4 mL). Under inert gas atmosphere, [1,1'-bis(diphenylphosphino)-ferrocene]palladium(II) dichloride dichloromethane adduct (0.180 g, 0.220 mmol) was added thereto, and the mixture was stirred at 100° C. for 3.5 hr. The reaction solution was diluted with water and ethyl acetate, and the insoluble substance was removed by filtration. The organic layer was washed with saturated brine, and dried over sodium sulfate. The sodium sulfate was removed by filtration, and the filtrate was concentrated under reduced pressure. The residue was dissolved in ethyl acetate (10 mL), and 4N-hydrogen chloride ethyl acetate solution (2 mL) was added thereto. The precipitated solid was collected by filtration, and dissolved in water (20 mL). To this solution was added saturated aqueous sodium hydrogencarbonate solution, and the resulting solid was collected by filtration, and dried under reduced pressure to give methyl 5-amino-6-(4-methoxyphenyl)nicotinate (0.448 g, yield 80%).

1H-NMR (DMSO-D6) δ: 3.80 (3H, s), 3.84 (3H, s), 5.36 (2H, br s), 7.02 (2H, dt, J=9.5, 2.4 Hz), 7.63-7.68 (3H, m), 8.37 (1H, d, J=1.8 Hz).

Step 2-2: Methyl 5-bromo-6-(4-methoxyphenyl)nicotinate

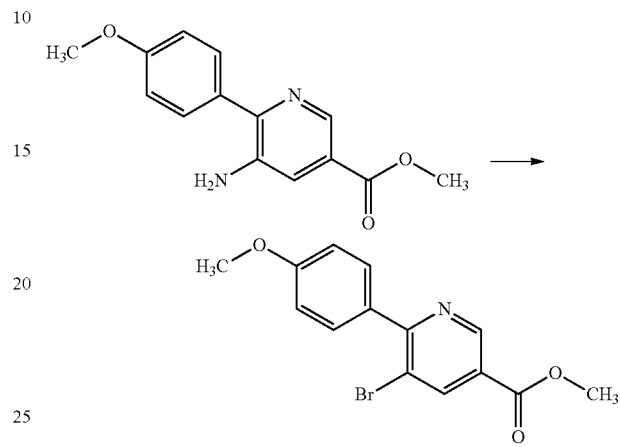

Under inert gas atmosphere, a solution of methyl 5-amino-6-(4-methoxyphenyl)nicotinate (0.448 g, 1.74 mmol) in dibromomethane was stirred at room temperature, and isopentyl nitrite (0.256 mL, 1.91 mmol) was added thereto. To the reaction solution was added dropwise a solution of bromotrimethylsilane (0.249 mL, 1.91 mmol) in dibromomethane, and the mixture was stirred at room temperature for 2 hr. To the reaction solution was added saturated aqueous sodium hydrogencarbonate solution (10 mL), and the mixture was extracted with chloroform. The organic layer was washed with saturated brine, and dried over sodium sulfate. The sodium sulfate was removed by filtration, and the filtrate was concentrated under reduced pressure. The residue was purified by silica gel chromatography (hexane:ethyl acetate=6:1 to 4:1) to give methyl 5-bromo-6-(4-methoxyphenyl)nicotinate (0.308 g, yield 55%).

Step 2-3: Methyl 5-(4-(tert-butoxycarbonyl)phenyl)-6-(4-methoxyphenyl)nicotinate

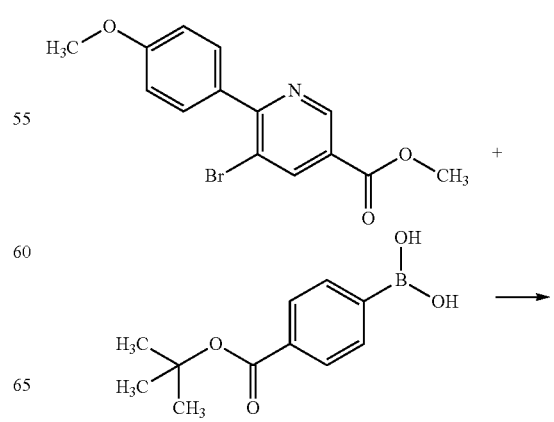

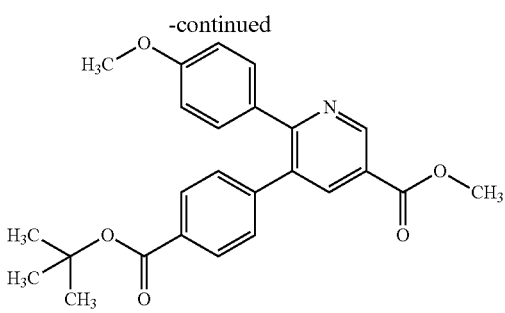

To a mixture of methyl 5-bromo-6-(4-methoxyphenyl)nicotinate (0.308 g, 0.956 mmol), (4-(tert-butoxycarbonyl)phenyl)boric acid (0.425 g, 1.91 mmol) and potassium phosphate (0.609 g, 2.87 mmol) were added toluene (4.5 mL) and water (1.5 mL). Under inert gas atmosphere, [1,1'-bis(diphenylphosphino)-ferrocene]palladium(II) dichloride dichloromethane adduct (0.078 g, 0.096 mmol) was added thereto, and the mixture was stirred at 100° C. for 4 hr. The reaction solution was diluted with water and ethyl acetate, and the insoluble substance was removed by filtration. The organic layer was washed with saturated brine, and dried over sodium sulfate. The sodium sulfate was removed by filtration, and the filtrate was concentrated under reduced pressure. The residue was purified by silica gel chromatography (hexane:ethyl acetate=5:1 to 3:1), ethyl acetate (1 mL) and hexane (10 mL) were added thereto, and the obtained suspension was stirred. The insoluble substance was collected by filtration, and dried under reduced pressure to give methyl 5-(4-(tert-butoxycarbonyl)phenyl)-6-(4-methoxyphenyl)nicotinate (0.149 mg, yield 37%).

1H-NMR (DMSO-D6) δ: 1.53 (9H, s), 3.73 (3H, s), 3.91 (3H, s), 6.85 (2H, dt, J=9.4, 2.5 Hz), 7.29 (2H, dt, J=9.4, 2.5 Hz), 7.37 (2H, dt, J=8.4, 1.8 Hz), 7.86 (2H, dt, J=8.3, 1.8 Hz), 8.17 (1H, d, J=2.1 Hz), 9.14 (1H, d, J=2.1 Hz).

Step 2-4: 5-(4-(tert-Butoxycarbonyl)phenyl)-6-(4-methoxyphenyl)nicotinic Acid

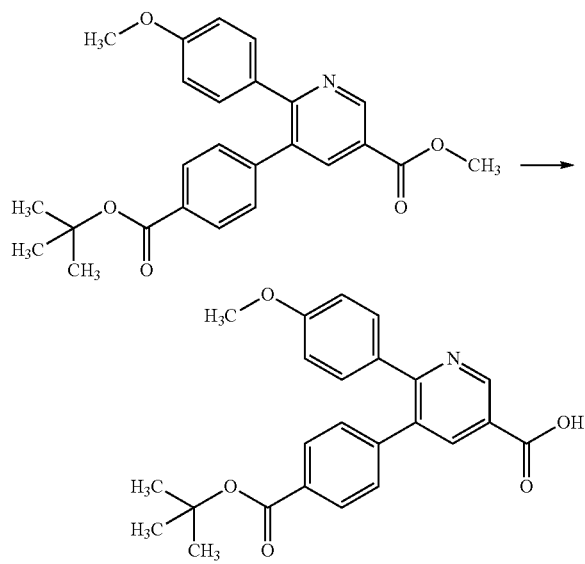

Methyl 5-(4-(tert-butoxycarbonyl)phenyl)-6-(4-methoxyphenyl)nicotinate (137 mg, 0.327 mmol) was dissolved in methanol (2 mL) and tetrahydrofuran (2 mL). To this solution was added 4M-aqueous lithium hydroxide solution (0.50 mL, 2.00 mmol), and the mixture was stirred at room temperature for 16 hr. To the reaction solution was added 1M-hydrochloric acid (2.0 mL), the methanol and tetrahydrofuran were evaporated under reduced pressure, and the residue was diluted with water (1 mL). The precipitated solid was collected by filtration, and dried under reduced pressure to give 5-(4-(tert-butoxycarbonyl)phenyl)-6-(4-methoxyphenyl)nicotinic acid (56 mg).

Step 2-5: tert-Butyl 4-(5-(butylcarbamoyl)-2-(4-methoxyphenyl)pyridin-3-yl)benzoate

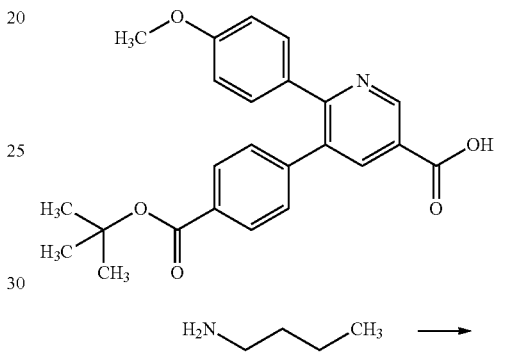

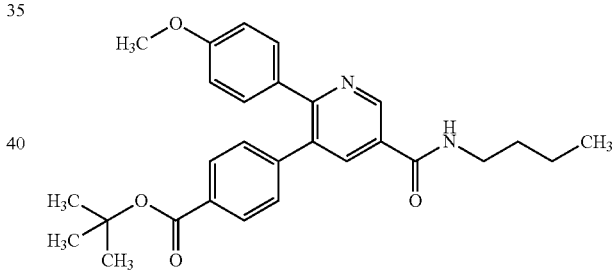

To a solution of 5-(4-(tert-butoxycarbonyl)phenyl)-6-(4-methoxyphenyl)nicotinic acid (56 mg, 0.138 mmol) obtained in the previous step in N,N-dimethylformamide were added successively butan-1-amine (0.050 mL, 0.51 mmol), triethylamine (0.060 mL, 0.43 mmol) and HATU (80 mg, 0.21 mmol), and the mixture was stirred at room temperature for 23 hr. The reaction solution was diluted with saturated aqueous sodium hydrogencarbonate solution and water, and extracted with ethyl acetate. The organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=3:1 to 1:1) to give tert-butyl 4-(5-(butylcarbamoyl)-2-(4-methoxyphenyl)pyridin-3-yl)benzoate (19 mg, yield 29%).

Step 2-6: 4-(5-(Butylcarbamoyl)-2-(4-methoxyphenyl)pyridin-3-yl)benzoic Acid Hydrochloride

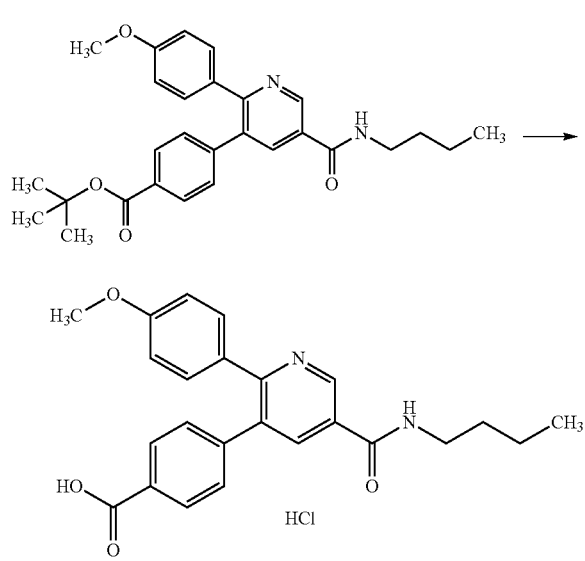

tert-Butyl 4-(5-(butylcarbamoyl)-2-(4-methoxyphenyl)pyridin-3-yl)benzoate (18 mg, 0.039 mmol) was dissolved in trifluoroacetic acid (1.0 mL), and the solution was stirred at room temperature for 1.5 hr. The reaction solution was concentrated under reduced pressure, and to the obtained residue was added 4N-hydrogen chloride ethyl acetate solution. The resulting precipitate was collected by filtration, and dried under reduced pressure to give 4-(5-(butylcarbamoyl)-2-(4-methoxyphenyl)pyridin-3-yl)benzoic acid hydrochloride (7.9 mg, yield 45%).

1H-NMR (DMSO-D6) δ: 0.91 (3H, t, J=7.4 Hz), 1.32-1.40 (2H, m), 1.50-1.57 (2H, m), 3.31 (2H, dd, J=12.8, 6.8 Hz), 3.74 (3H, d, J=0.7 Hz), 6.86 (2H, dd, J=8.9, 2.9 Hz), 7.28 (2H, dd, J=8.8, 1.6 Hz), 7.39 (2H, d, J=8.1 Hz), 7.91 (2H, d, J=8.1 Hz), 8.25 (1H, br s), 8.74 (1H, br s), 9.07 (1H, s).

Production Example 3

Synthesis of 4-(2-(4-methoxyphenyl)-5-(3-methoxypropyl)pyridin-3-yl)benzoic Acid (Example 84)

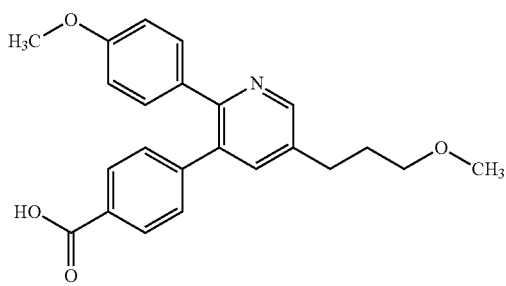

Step 3-1: 3-(Benzyloxy)-5-bromo-2-chloropyridine

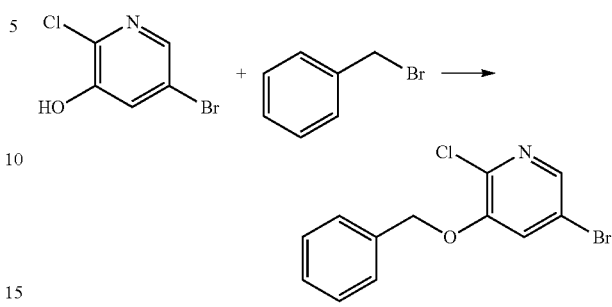

To a solution of 5-bromo-2-chloropyridin-3-ol (50.2 g, 241 mmol) in N,N-dimethylformamide (200 mL) were added successively benzyl bromide (33.0 mL, 278 mmol) and potassium carbonate (48.6 g, 352 mmol), and the mixture was stirred at room temperature for 4 hr. To the reaction solution was added water (600 mL), and the mixture was stirred for 2 hr. The precipitate was collected by filtration, and dried under reduced pressure to give 3-(benzyloxy)-5-bromo-2-chloropyridine (69.7 g, yield 96%).

1H-NMR (DMSO-D6) δ: 5.29 (2H, s), 7.33-7.47 (5H, m), 7.98 (1H, d, J=2.1 Hz), 8.14 (1H, d, J=1.8 Hz).

Step 3-2: (E)-3-(Benzyloxy)-2-chloro-5-(3-methoxyprop-1-en-1-yl)pyridine

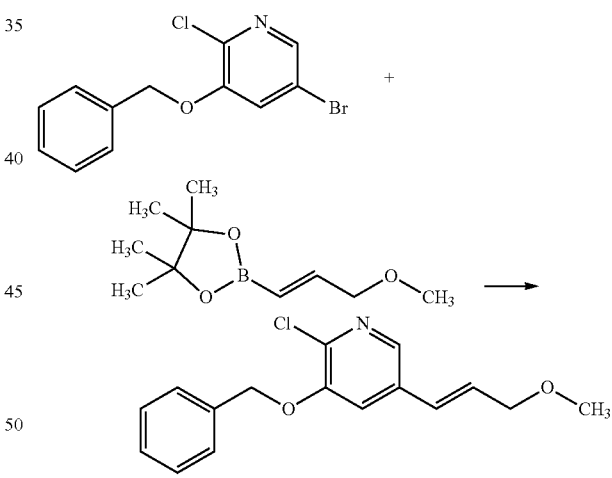

To a suspension of 3-(benzyloxy)-5-bromo-2-chloropyridine (25.7 mg, 86.0 mmol) and potassium phosphate (54.9 g, 259 mmol) in tetrahydrofuran (180 mL) were added successively water (130 mL), (E)-2-(3-methoxyprop-1-en-1-yl)-4,4,5,5-tetramethyl-1,3,2-dioxaborolane (20.1 mL, 95.0 mmol) and [1,1'-bis(diphenylphosphino)-ferrocene] palladium(II) dichloride dichloromethane adduct (3.54 g, 4.33 mmol), and the mixture was stirred at room temperature for 2 hr. [1,1'-Bis(diphenylphosphino)-ferrocene]palladium (II) dichloride dichloromethane adduct (1.70 g, 2.04 mmol) was added again thereto, and the mixture was stirred at room temperature for 3 hr, warmed to 33° C., and stirred for 1 hr. The reaction solution was diluted with ethyl acetate (180 mL), and the insoluble substance was removed by filtration.

The organic layer of the filtrate was washed with water and saturated brine, silica gel (50 g) was added thereto, and the mixture was stirred at room temperature for 1 hr. The silica gel was removed by filtration, and the filtrate was concentrated under reduced pressure. The residue was purified by silica gel chromatography (hexane:ethyl acetate=15:1 to 4:3) to give (E)-3-(benzyloxy)-2-chloro-5-(3-methoxyprop-1-en-1-yl)pyridine (20.9 g, yield 83%).

1H-NMR (DMSO-D6) δ: 3.29 (3H, s), 4.06-4.07 (2H, m), 5.29 (2H, s), 6.59-6.60 (2H, m), 7.32-7.49 (5H, m), 7.81 (1H, d, J=1.8 Hz), 8.02 (1H, d, J=2.1 Hz).

Step 3-3: (E)-3-(Benzyloxy)-2-(4-methoxyphenyl)-5-(3-methoxyprop-1-en-1-yl)pyridine

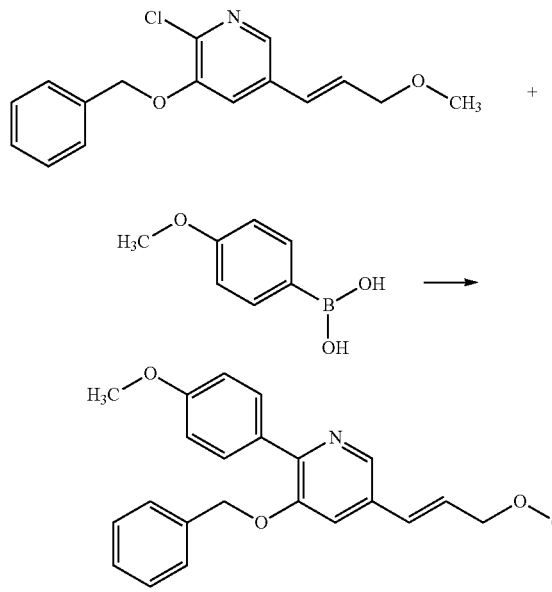

To a solution of (E)-3-(benzyloxy)-2-chloro-5-(3-methoxyprop-1-en-1-yl)pyridine (17.8 g, 61.4 mmol), 4-methoxyphenylboric acid (11.2 g, 73.7 mmol), palladium (II) acetate (0.276 g, 1.13 mmol) and 2-dicyclohexylphosphino-2',6'-dimethoxybiphenyl (1.01 g, 2.46 mmol) in 1,2-dimethoxyethane (138 mL) was added 2M-aqueous potassium phosphate solution (46.1 mL, 92.2 mmol), and the mixture was stirred at 50° C. for 5 hr. The reaction solution was allowed to cool to room temperature, water (100 mL) was added thereto, and the mixture was extracted with ethyl acetate (200 mL). The organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=3:1 to 1:1) to give (E)-3-(benzyloxy)-2-(4-methoxyphenyl)-5-(3-methoxyprop-1-en-1-yl)pyridine (23.1 g, yield 104%).

1H-NMR (DMSO-D6) δ: 3.30 (3H, s), 3.77 (3H, s), 4.07-4.09 (2H, m), 5.26 (2H, s), 6.52-6.66 (2H, m), 6.95 (2H, dt, J=9.6, 2.5 Hz), 7.30-7.46 (5H, m), 7.72 (1H, d, J=1.6 Hz), 7.93 (2H, dt, J=9.6, 2.5 Hz), 8.27 (1H, d, J=1.6 Hz).

Step 3-4: 2-(4-Methoxyphenyl)-5-(3-methoxypropyl)pyridin-3-ol

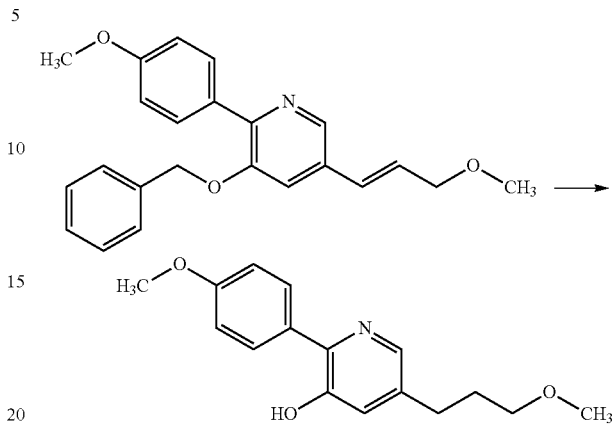

To (E)-3-(benzyloxy)-2-(4-methoxyphenyl)-5-(3-methoxyprop-1-en-1-yl)pyridine (23.1 g) obtained in the previous step were added methanol (230 mL) and 10% palladium on carbon catalyst (50% wet, 4.62 g), and the mixture was stirred under hydrogen gas atmosphere for 24 hr. The palladium on carbon catalyst was removed from the reaction solution by filtration, and the filtrate was concentrated under reduced pressure. To the obtained crude crystals was added ethyl acetate (50 mL), the mixture was stirred at 80° C. for 20 min, and hexane (150 mL) was added thereto. The mixture was stirred for additional 2 hr while allowed to cool to room temperature. The precipitate was collected by filtration, and dried under reduced pressure to give 2-(4-methoxyphenyl)-5-(3-methoxypropyl)pyridin-3-ol (13.6 g, yield in two step 81%).

1H-NMR (DMSO-D6) δ: 1.74-1.81 (2H, m), 2.54-2.58 (2H, m), 3.23 (3H, s), 3.32 (2H, t, J=6.4 Hz), 3.77 (3H, s), 6.95 (2H, dt, J=9.5, 2.5 Hz), 7.09 (1H, d, J=1.8 Hz), 7.95-7.99 (3H, m), 9.94 (1H, br s).

Step 3-5: 2-(4-Methoxyphenyl)-5-(3-methoxypropyl)pyridin-3-yl Trifluoromethanesulfonate

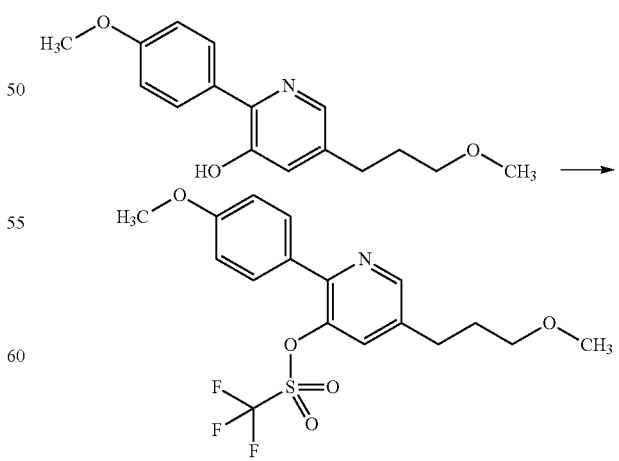

To a solution of 2-(4-methoxyphenyl)-5-(3-methoxypropyl)pyridin-3-ol (13.7 g, 50.0 mmol) in N,N-dimethylformamide (100 mL) was added potassium carbonate (15.2 g, 110 mmol). The reaction solution was ice-cooled, N-(5-chloropyridin-2-yl)-1,1,1-trifluoro-N-((trifluoromethyl)sulfonyl)methanesulfonamide (21.6 g, 55.0 mmol) was added thereto, and the mixture was stirred at room temperature for 2 hr. The reaction solution was diluted with water, and extracted with ethyl acetate. The organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=4:1 to 1:1) to give 2-(4-methoxyphenyl)-5-(3-methoxypropyl)pyridin-3-yl trifluoromethanesulfonate (18.9 g, yield 93%).

1H-NMR (DMSO-D6) δ: 1.82-1.89 (2H, m), 2.73-2.77 (2H, m), 3.23 (3H, s), 3.34 (2H, t, J=6.4 Hz), 3.81 (3H, s), 7.06 (2H, dt, J=9.5, 2.5 Hz), 7.68 (2H, dt, J=9.6, 2.5 Hz), 7.90 (1H, d, J=1.6 Hz), 8.59 (1H, d, J=1.6 Hz).

Step 3-6: Methyl 4-(2-(4-methoxyphenyl)-5-(3-methoxypropyl)pyridin-3-yl)benzoate

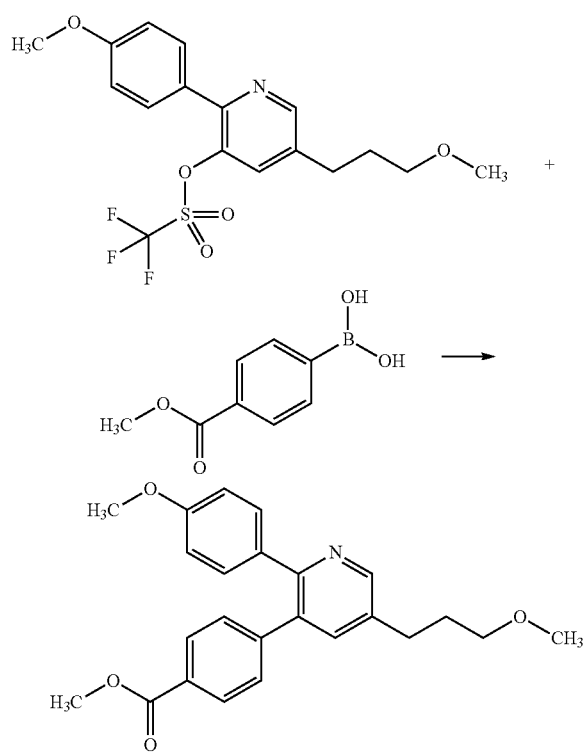

To a solution of 2-(4-methoxyphenyl)-5-(3-methoxypropyl)pyridin-3-yl trifluoromethanesulfonate (18.9 g, 46.7 mmol) and (4-(methoxycarbonyl)phenyl)boric acid (10.1 g, 56.1 mmol) in 1,2-dimethoxyethane (105 mL) were added successively 2M-aqueous potassium phosphate solution (35.0 mL, 70.0 mmol) and [1,1'-bis(diphenylphosphino)-ferrocene]palladium(II) dichloride dichloromethane adduct (0.763 g, 0.934 mmol), and the mixture was stirred at 80° C. for 1 hr. The reaction solution was allowed to cool to room temperature, and water was added thereto. The mixture was extracted with ethyl acetate, and the organic layer was dried over sodium sulfate. The sodium sulfate was removed by filtration, and the filtrate was concentrated under reduced pressure. To the obtained residue were added ethyl acetate (50 mL) and hexane (150 mL), the mixture was stirred at room temperature for 30 min, and the insoluble substance was removed by filtration. The filtrate was concentrated under reduced pressure, and the obtained residue was purified by silica gel chromatography (hexane:ethyl acetate=3:1 to 1:1) to give methyl 4-(2-(4-methoxyphenyl)-5-(3-methoxypropyl)pyridin-3-yl)benzoate (16.9 g, 43.4 mmol).

1H-NMR (DMSO-D6) δ: 1.83-1.90 (2H, m), 2.68-2.73 (2H, m), 3.24 (3H, s), 3.36 (2H, t, J=6.4 Hz), 3.71 (3H, s), 3.83 (3H, s), 6.79 (2H, dt, J=9.4, 2.5 Hz), 7.18 (2H, dt, J=9.4, 2.5 Hz), 7.33 (2H, dt, J=8.4, 1.8 Hz), 7.64 (1H, d, J=2.1 Hz), 7.88 (2H, dt, J=8.5, 1.9 Hz), 8.51 (1H, d, J=2.1 Hz).

Step 3-7: 4-(2-(4-Methoxyphenyl)-5-(3-methoxypropyl)pyridin-3-yl)benzoic Acid

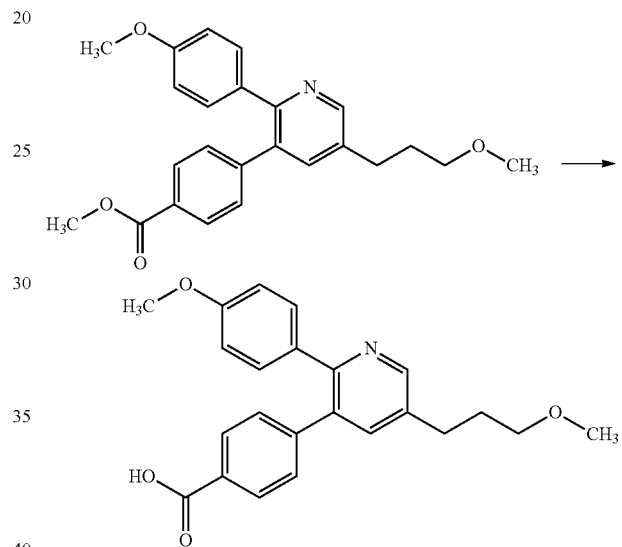

To a solution of methyl 4-(2-(4-methoxyphenyl)-5-(3-methoxypropyl)pyridin-3-yl)benzoate (2.00 g, 5.11 mmol) in methanol (30.6 mL) was added 4N-aqueous sodium hydroxide solution (7.66 mL, 30.6 mmol), and the mixture was stirred at 50° C. for 2 hr. The mixture was allowed to cool to room temperature, 10 wt %-aqueous citric acid solution (23.0 mL) and water (46 mL) were added thereto, and the mixture was stirred at room temperature for 2 hr. The precipitated solid was collected by filtration, and dried under reduced pressure to give 4-(2-(4-methoxyphenyl)-5-(3-methoxypropyl)pyridin-3-yl)benzoic acid (1.66 g, yield 86%).

1H-NMR (DMSO-D6) δ: 1.84-1.93 (2H, m), 2.72 (2H, t, J=7.8 Hz), 3.25 (3H, s), 3.38 (2H, t, J=6.4 Hz), 3.72 (3H, s), 6.81 (2H, d, J=8.8 Hz), 7.20 (2H, d, J=8.8 Hz), 7.32 (2H, d, J=8.3 Hz), 7.65 (1H, d, J=2.2 Hz), 7.87 (2H, d, J=8.6 Hz), 8.52 (1H, d, J=2.2 Hz), 12.99 (1H, br s).

Step 3-8: Crystals (Form II) of 4-(2-(4-methoxyphenyl)-5-(3-methoxypropyl)pyridin-3-yl)benzoic Acid To 4-(2-(4-methoxyphenyl)-5-(3-methoxypropyl)pyridin-3-yl)benzoic acid (300 mg) was added methyl t-butyl ether (3 mL), and the mixture was stirred at 70° C. to give a solution. While stirring, the mixture was allowed to cool to room temperature, and then for 3 days. The precipitated solid was collected by filtration, and dried under reduced pressure to give crystals (Form II) of 4-(2-(4-methoxyphenyl)-5-(3-methoxypropyl)pyridin-3-yl)benzoic acid (191 mg, yield 64%).

Step 3-9: Crystals (Form X) of 4-(2-(4-methoxyphenyl)-5-(3-methoxypropyl)pyridin-3-yl)benzoic acid 4-(2-(4-Methoxyphenyl)-5-(3-methoxypropyl)pyridin-3-yl)benzoic acid (20 mg) was suspended in methanol (0.12 mL), and the suspension was stirred at room temperature for 2 weeks. The resulting solid was collected by filtration, and dried under reduced pressure to give crystals (Form X) of 4-(2-(4-methoxyphenyl)-5-(3-methoxypropyl)pyridin-3-yl)benzoic acid (8.3 mg, yield 42%).

Step 3-10: Crystals (Form VIII) of 4-(2-(4-methoxyphenyl)-5-(3-methoxypropyl)pyridin-3-yl)benzoic Acid To 4-(2-(4-methoxyphenyl)-5-(3-methoxypropyl)pyridin-3-yl)benzoic acid (600 mg) was added methanol (3.6 mL), and the mixture was stirred at room temperature for 4 days. To this mixture was added a trace amount of Form X, and the mixture was stirred for additional 3 days. The resulting solid was collected by filtration, and dried under reduced pressure to give crystals (Form VIII) of 4-(2-(4-methoxyphenyl)-5-(3-methoxypropyl)pyridin-3-yl)benzoic acid.

Step 3-11: Crystals (Form XV) of 4-(2-(4-methoxyphenyl)-5-(3-methoxypropyl)pyridin-3-yl)benzoic Acid Form II (15 mg) and Form VIII (15 mg) of 4-(2-(4-methoxyphenyl)-5-(3-methoxypropyl)pyridin-3-yl)benzoic acid were suspended in a mixed solvent of 1-propanol (0.24 mL) and water (0.24 mL), and the suspension was stirred at room temperature for 11 days. The resulting solid was collected by filtration, and dried under reduced pressure to give crystals (Form XV) of 4-(2-(4-methoxyphenyl)-5-(3-methoxypropyl)pyridin-3-yl)benzoic acid.

Production Example 4

Synthesis of 4-(2-(4-methoxyphenyl)-5-(3-methoxypropyl)pyridin-3-yl)-2-methylbenzoic Acid (Example 116)

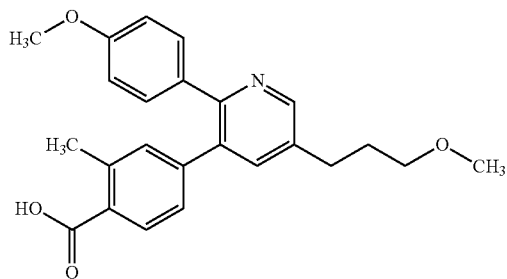

Step 4-1: Methyl 4-(2-(4-methoxyphenyl)-5-(3-methoxypropyl)pyridin-3-yl)-2-methylbenzoate

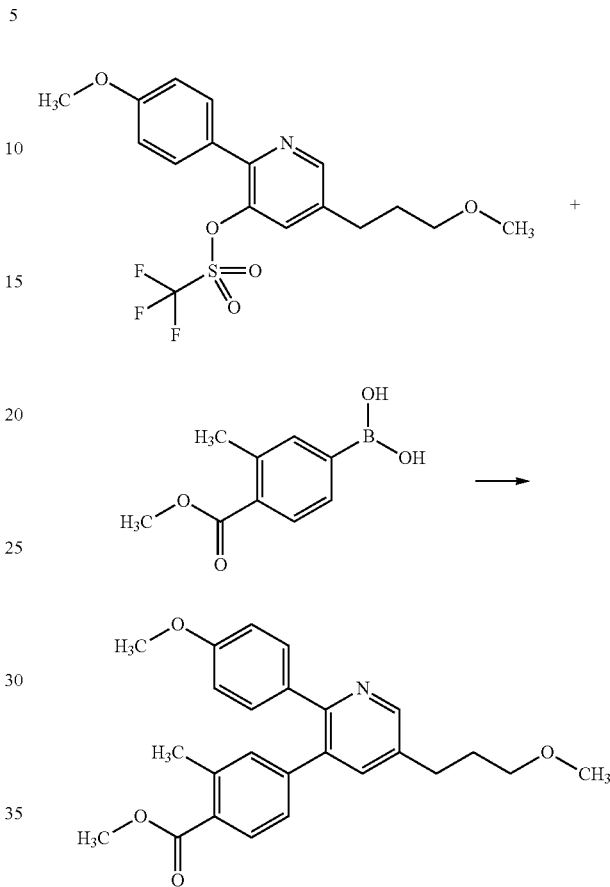

To a solution of 2-(4-methoxyphenyl)-5-(3-methoxypropyl)pyridin-3-yl trifluoromethanesulfonate (2.00 g, 4.93 mmol), which was synthesized by a method similar to that of Step 3-5 in Production Example 3, and (4-(methoxycarbonyl)-3-methylphenyl)boric acid (1.05 g, 5.43 mmol) in 1,2-dimethoxyethane (11.1 mL) were added successively 2M-aqueous potassium phosphate solution (3.70 mL, 7.40 mmol) and [1,1'-bis(diphenylphosphino)-ferrocene]palladium(II) dichloride dichloromethane adduct (0.081 g, 0.099 mmol), and the mixture was stirred at 80° C. for 2 hr. The reaction solution was allowed to cool to room temperature, and water was added thereto. The mixture was extracted with ethyl acetate, and the organic layer was dried over sodium sulfate. The sodium sulfate was removed by filtration, and the filtrate was concentrated under reduced pressure. The residue was purified by silica gel chromatography (hexane:ethyl acetate=3:1 to 1:1) to give methyl 4-(2-(4-methoxyphenyl)-5-(3-methoxypropyl)pyridin-3-yl)-2-methylbenzoate (1.85 g, yield 92%).

1H-NMR (DMSO-D6) δ: 1.83-1.90 (2H, m), 2.47 (3H, s), 2.68-2.72 (2H, m), 3.24 (3H, s), 3.36 (2H, t, J=6.4 Hz), 3.71 (3H, s), 3.80 (3H, s), 6.80 (2H, dt, J=9.4, 2.5 Hz), 7.01 (1H, dd, J=8.1, 1.4 Hz), 7.20 (2H, dt, J=9.4, 2.5 Hz), 7.26 (1H, d, J=1.4 Hz), 7.63 (1H, d, J=2.1 Hz), 7.69 (1H, d, J=8.1 Hz), 8.49 (1H, d, J=2.1 Hz).

Step 4-2: 4-(2-(4-Methoxyphenyl)-5-(3-methoxypropyl)pyridin-3-yl)-2-methylbenzoic Acid

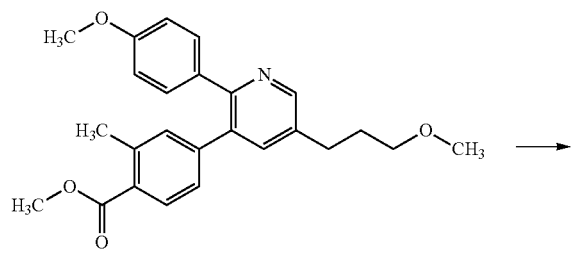

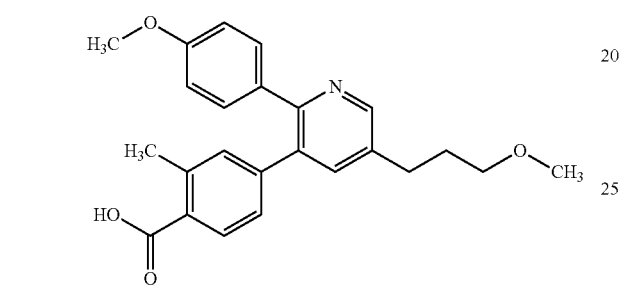

To a solution of methyl 4-(2-(4-methoxyphenyl)-5-(3-methoxypropyl)pyridin-3-yl)-2-methylbenzoate (2.30 g, 5.67 mmol) in methanol (34 mL) was added 4N-aqueous sodium hydroxide solution (8.51 mL, 34.0 mmol), and the mixture was stirred at 50° C. for 2 hr. The mixture was allowed to cool to room temperature, 10 wt %-aqueous citric acid solution (25.5 mL) and water (55 mL) were added thereto, and the mixture was stirred at room temperature for 1 hr. The precipitated solid was collected by filtration, and dried under reduced pressure to give 4-(2-(4-methoxyphenyl)-5-(3-methoxypropyl)pyridin-3-yl)-2-methylbenzoic acid (2.05 g, yield 92%).

1H-NMR (DMSO-D6) δ: 1.81-1.91 (2H, m), 2.47 (3H, s), 2.70 (2H, t, J=7.7 Hz), 3.24 (3H, s), 3.36 (2H, t, J=6.2 Hz), 3.71 (3H, s), 6.81 (2H, d, J=8.8 Hz), 6.98 (1H, dd, J=8.1, 1.4 Hz), 7.18-7.24 (3H, m), 7.62 (1H, d, J=2.3 Hz), 7.69 (1H, d, J=8.1 Hz), 8.49 (1H, d, J=2.3 Hz), 12.81 (1H, br s).

Step 4-3: Crystals of 4-(2-(4-methoxyphenyl)-5-(3-methoxypropyl)pyridin-3-yl)-2-methylbenzoic Acid To 4-(2-(4-methoxyphenyl)-5-(3-methoxypropyl)pyridin-3-yl)-2-methylbenzoic acid (50 mg) was added 2-propanol (0.300 mL), and the mixture was stirred at 100° C. to give a solution. The stirring was stopped, and the mixture was allowed to cool to room temperature. The precipitated solid was collected by filtration, and dried under reduced pressure to give crystals of 4-(2-(4-methoxyphenyl)-5-(3-methoxypropyl)pyridin-3-yl)-2-methylbenzoic acid (36 mg, yield 72%).

Production Example 5

Synthesis of 4-(2-(4-methoxyphenyl)-5-(propoxymethyl)pyridin-3-yl)benzoic Acid (Example 118)

Step 5-1: (5-Chloro-6-(4-methoxyphenyl)pyridin-3-yl)methanol

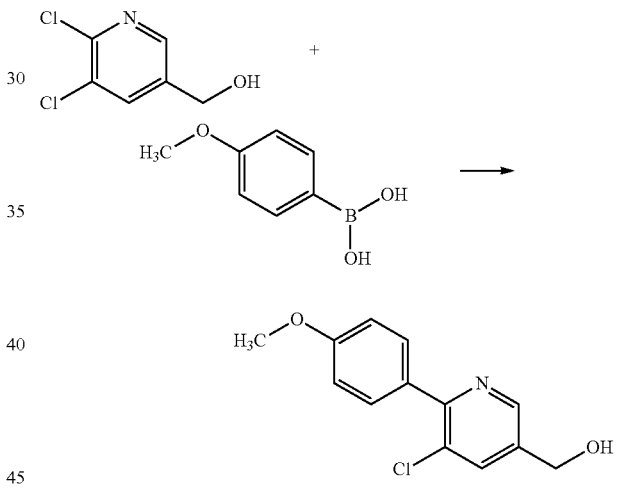

To a mixture of (5,6-dichloropyridin-3-yl)methanol (200 mg, 1.12 mmol) and (4-methoxyphenyl)boric acid (188 mg, 1.24 mmol) was added toluene (5 mL). Under inert gas atmosphere, [1,1'-bis(diphenylphosphino)-ferrocene]palladium(II) dichloride dichloromethane adduct (45.9 mg, 0.056 mmol) and 2M-aqueous potassium phosphate solution (1.12 mL, 2.24 mmol) were added successively thereto, and the mixture was stirred at 70° C. for 1 hr. The mixture was allowed to cool to room temperature, and the reaction solution was diluted with water and ethyl acetate, and separated. The organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=2:1 to 1:2) to give (5-chloro-6-(4-methoxyphenyl)pyridin-3-yl)methanol (250 mg, yield 89%).

Step 5-2: 3-Chloro-2-(4-methoxyphenyl)-5-(propoxymethyl)pyridine

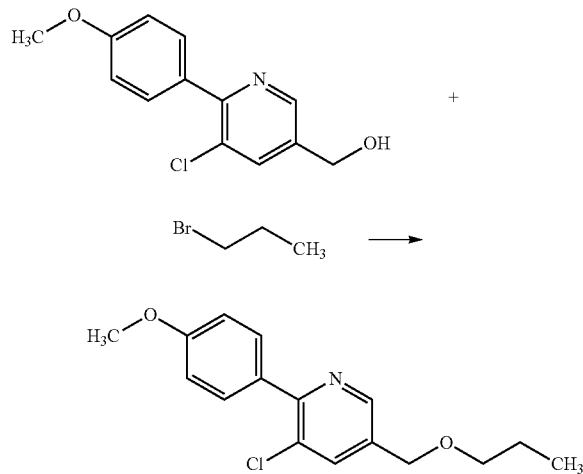

Under inert gas atmosphere, to a suspension of sodium hydride (44.0 mg, 1.10 mmol) in tetrahydrofuran (5 mL) were added successively 1-bromopropane (0.455 mL, 5.01 mmol) and a solution of (5-chloro-6-(4-methoxyphenyl) pyridin-3-yl)methanol (250 mg, 1.00 mmol) in tetrahydrofuran (3 mL), and the mixture was stirred at 100° C. for 24 hr. The reaction solution was allowed to cool to room temperature, diluted with water (20 mL), and extracted with ethyl acetate (20 mL). The organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=3:1 to 1:1) to give 3-chloro-2-(4-methoxyphenyl)-5-(propoxymethyl)pyridine (123 mg, yield 42%).

Step 5-3: Methyl 4-(2-(4-methoxyphenyl)-5-(propoxymethyl)pyridin-3-yl)benzoate

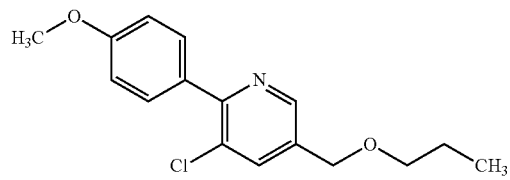

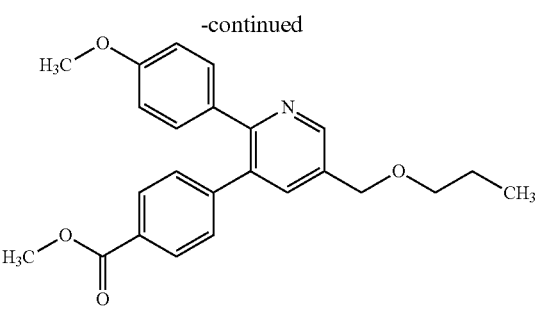

Under inert gas atmosphere, to a mixture of 3-chloro-2-(4-methoxyphenyl)-5-(propoxymethyl)pyridine (50.0 mg, 0.171 mmol), palladium(II) acetate (3.9 mg, 0.017 mmol), 2-dicyclohexylphosphino-2',6'-dimethoxybiphenyl (14.1 mg, 0.034 mmol) and (4-(methoxycarbonyl)phenyl)boric acid (93.0 mg, 0.514 mmol) were added successively toluene (2 mL) and 2M-aqueous potassium phosphate solution (0.343 mL, 0.685 mmol), and the mixture was stirred at 100° C. for 2 hr. The reaction solution was allowed to cool to room temperature, diluted with water (10 mL), and extracted with ethyl acetate (50 mL). The organic layer was washed successively with water and saturated brine, and dried over sodium sulfate. The sodium sulfate was removed by filtration, and the filtrate was concentrated under reduced pressure. The residue was purified by silica gel chromatography (hexane:ethyl acetate=2:1 to 1:2) to give methyl 4-(2-(4-methoxyphenyl)-5-(propoxymethyl)pyridin-3-yl)benzoate (47.4 mg, yield 70%).

Step 5-4: 4-(2-(4-Methoxyphenyl)-5-(propoxymethyl)pyridin-3-yl)benzoic Acid

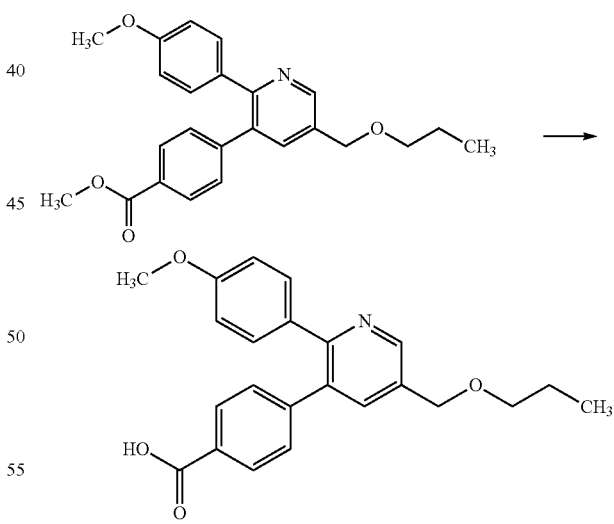

To a solution of methyl 4-(2-(4-methoxyphenyl)-5-(propoxymethyl)pyridin-3-yl)benzoate (47.4 mg, 0.121 mmol) in methanol (0.90 mL) was added 4N-aqueous sodium hydroxide solution (0.182 mL, 0.726 mmol), and the mixture was stirred at 50° C. for 2 hr. The reaction solution was allowed to cool to room temperature, 10 wt %-aqueous citric acid solution (0.546 mL) and water (2 mL) were added thereto, and the mixture was stirred. The precipitated solid was collected by filtration, and dried under reduced pressure to give 4-(2-(4-methoxyphenyl)-5-(propoxymethyl)pyridin-3-yl)benzoic acid (43.5 mg, yield 95%).

1H-NMR (DMSO-D6) δ: 0.88 (3H, t, J=7.4 Hz), 1.51-1.62 (2H, m), 3.45 (2H, t, J=6.6 Hz), 3.71 (3H, s), 4.57 (2H, s), 6.81 (2H, d, J=8.8 Hz), 7.21 (2H, d, J=8.8 Hz), 7.30 (2H, d, J=8.3 Hz), 7.71 (1H, d, J=2.1 Hz), 7.86 (2H, d, J=8.6 Hz), 8.60 (1H, d, J=2.1 Hz), 13.01 (1H, br s).

Production Example 6

Alternative Production Method of 4-(3-(3,5-difluoro-4-methoxyphenyl)-6-(3-methoxypropyl)pyrazin-2-yl)benzoic Acid (Example 67)

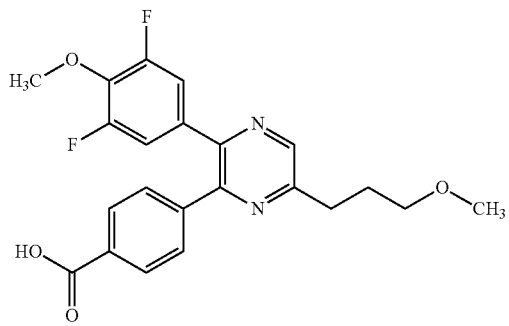

Step 6-1: 2-(tert-Butoxy)-3-chloropyrazine

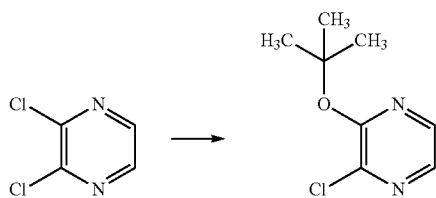

Under nitrogen atmosphere, 2,3-dichloropyrazine (150.0 g, 1007 mmol) was dissolved in tetrahydrofuran (450 mL), and a solution of potassium tert-butoxide (129.9 g, 1158 mmol) in tetrahydrofuran (600 mL) was added dropwise thereto under ice-cooling from a dropping funnel. The dropping funnel was washed with tetrahydrofuran (150 mL), and the wash solution was added dropwise to the reaction mixture. The reaction mixture was stirred under ice-cooling for 1 hr, water (450 mL) was added thereto, and the mixture was separated. The organic layer was washed with 10% brine to give a solution of 2-(tert-butoxy)-3-chloropyrazine in tetrahydrofuran. The obtained solution of 2-(tert-butoxy)-3-chloropyrazine in tetrahydrofuran was used in the next step, regarded as yield 100%.

The solution of 2-(tert-butoxy)-3-chloropyrazine in tetrahydrofuran was synthesized by the same production method, and concentrated, and the NMR was measured.

1H-NMR (DMSO-D6) δ: 1.60 (9H, s), 8.01 (1H, d, J=2.8 Hz), 8.19 (1H, d, J=2.8 Hz).

Step 6-2: Ethyl 4-(3-(tert-butoxy)pyrazin-2-yl)benzoate

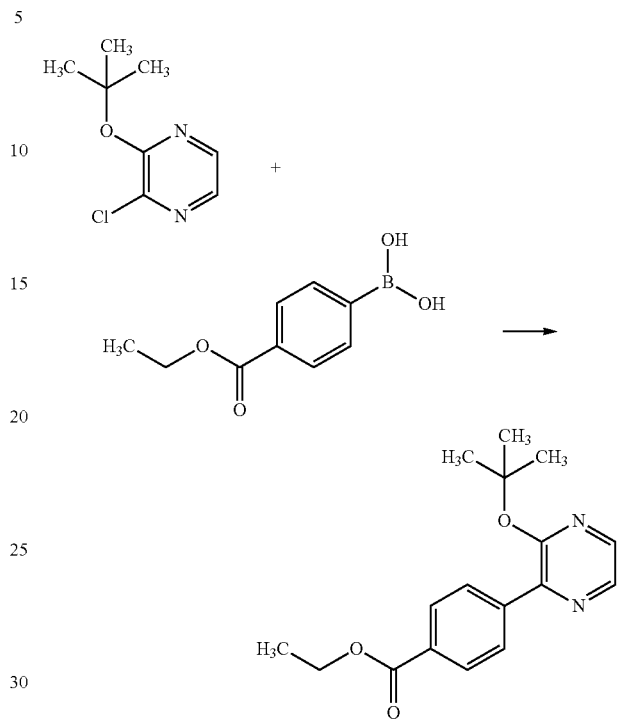

Under nitrogen atmosphere, to 2-(tert-butoxy)-3-chloropyrazine in tetrahydrofuran solution (corresponding to 1007 mmol) were added (4-(ethoxycarbonyl)phenyl)boric acid (195.3 g, 1007 mmol) and tetrahydrofuran (150 mL). Then, 2-dicyclohexylphosphino-2',6'-dimethoxybiphenyl (8.27 g, 20.1 mmol) and palladium(II) acetate (2.26 g, 10.1 mmol) were added thereto. The reaction system was degassed under reduced pressure, and replaced with nitrogen. The procedure was repeated three times in total. To this mixture was added dropwise a solution of tripotassium phosphate (363.3 g, 1712 mmol) in water (600 mL) over about 30 min at 40° C. The reaction mixture was stirred at the same temperature for about 1 hr, allowed to cool, and separated. The organic layer was washed twice with 10% brine (600 mL). To the organic layer was added activated carbon (15.00 g), and the mixture was stirred at room temperature for 2 hr. The activated carbon was removed by filtration, and washed with tetrahydrofuran (450 mL). The combined filtrate was concentrated under reduced pressure until the volume became 400 mL to give a solution of ethyl 4-(3-(tert-butoxy)pyrazin-2-yl)benzoate in tetrahydrofuran. The obtained solution of ethyl 4-(3-(tert-butoxy)pyrazin-2-yl)benzoate in tetrahydrofuran was used in the next step, regarded as yield 100%.

The solution of ethyl 4-(3-(tert-butoxy)pyrazin-2-yl)benzoate in tetrahydrofuran was synthesized by the same production method, and concentrated to dryness, and the solid was collected by filtration with a mixed solvent of ethanol/water (2/1), and the NMR was measured.

1H-NMR (DMSO-D6) δ: 1.35 (3H, t, J=7.1 Hz), 1.62 (9H, s), 4.35 (2H, q, J=7.1 Hz), 8.05 (2H, dt, J=6.8, 2.0 Hz), 8.14 (2H, dt, J=6.8, 2.0 Hz), 8.22 (1H, d, J=2.5 Hz), 8.31 (1H, d, J=2.5 Hz).

Step 6-3: Ethyl 4-(3-hydroxypyrazin-2-yl)benzoate

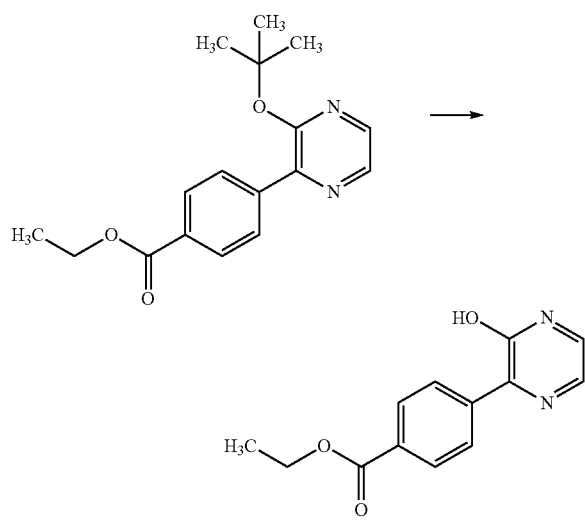

Under nitrogen atmosphere, to ethyl 4-(3-(tert-butoxy)pyrazin-2-yl)benzoate in tetrahydrofuran solution (corresponding to 1007 mmol) was added ethanol (300 mL), and then 4N hydrochloric acid (300 mL, 1200 mmol) was added dropwise thereto at room temperature, and the mixture was stirred for about 1 hr. To the reaction suspension was added water (750 mL), and the mixture was stirred at room temperature for 1 hr. Water (750 mL) was added again thereto, and the mixture was stirred at room temperature for 2 hr. The precipitated solid was collected by filtration, and the obtained solid was washed twice with a mixed solvent of water/ethanol (4/1, 300 mL), and dried under reduced pressure at 60° C. to give ethyl 4-(3-hydroxypyrazin-2-yl)benzoate (232.1 g, 950.6 mmol, yield 94.4% from 2,3-dichloropyrazine).

1H-NMR (DMSO-D6) δ: 1.34 (3H, t, J=7.1 Hz), 4.34 (2H, q, J=7.1 Hz), 7.53 (1H, d, J=3.7 Hz), 7.55 (1H, d, J=3.7 Hz), 8.02 (2H, dt, J=8.6, 1.8 Hz), 8.46 (2H, dt, J=8.6, 1.8 Hz), 12.67 (1H, s).

Step 6-4: Ethyl 4-(3-hydroxy-6-iodopyrazin-2-yl)benzoate

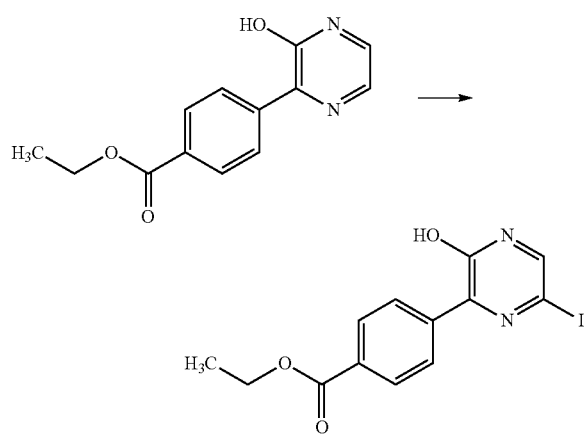

Under nitrogen atmosphere, to ethyl 4-(3-hydroxypyrazin-2-yl)benzoate (100 g, 409 mmol) was added acetonitrile (500 mL), and then, 1,8-diazabicyclo[5.4.0]undec-7-ene (31.2 g, 205 mmol) was added thereto. To this mixture was added dropwise a solution of N-iodosuccinimide (101 g, 450 mmol) in acetonitrile (750 mL) over about 1 hr at room temperature from a dropping funnel. The dropping funnel was washed with acetonitrile (50 mL), the wash solution was added dropwise to the reaction mixture, and the mixture was stirred at room temperature for about 2 hr. To the reaction suspension was added dropwise a solution of sodium sulfite (12.4 g, 123 mmol) in water (600 mL), and the mixture was stirred for 20 min. Then, a solution of conc. hydrochloric acid (21.3 g, 205 mmol) in water (600 mL) was added dropwise thereto, and the mixture was stirred at 45 to 55° C. for 30 min, and then at room temperature for about 30 min. The precipitated solid was collected by filtration, and the obtained solid was washed twice with a mixed solvent of acetonitrile/water (1/2, 300 mL), and dried under reduced pressure at 50° C. to give ethyl 4-(3-hydroxy-6-iodopyrazin-2-yl)benzoate (135 g, yield 89.3%).

1H-NMR (DMSO-D6) δ: 1.34 (3H, t, J=7.1 Hz), 4.35 (2H, q, J=7.1 Hz), 7.98 (1H, br s), 8.03 (2H, d, J=8.6 Hz), 8.35 (2H, d, J=8.6 Hz), 12.85 (1H, s).

Step 6-5: Ethyl 4-(3-hydroxy-6-(3-methoxyprop-1-yn-1-yl)pyrazin-2-yl)benzoate

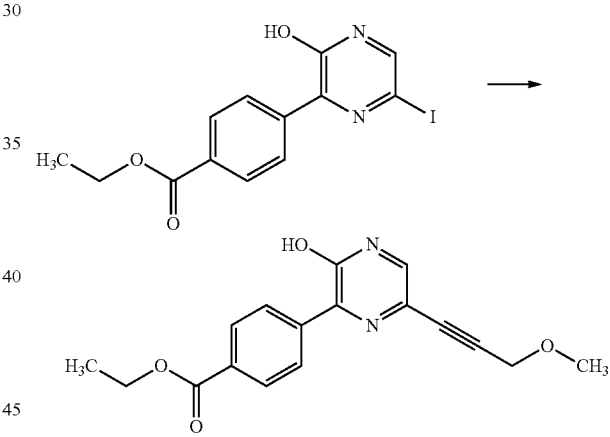

Under nitrogen atmosphere, to ethyl 4-(3-hydroxy-6-iodopyrazin-2-yl)benzoate (200 g, 540 mmol) was added acetonitrile (1200 mL), and triethylamine (164 g, 1621 mmol) was added thereto, and then, copper(I) iodide (4.12 g, 21.6 mmol), triphenylphosphine (2.83 g, 10.8 mmol) and bis(triphenylphosphine)palladium(II) dichloride (3.79 g, 5.40 mmol) were added thereto. The reaction system was degassed under reduced pressure, and replaced with nitrogen. The procedure was repeated three times in total. To this mixture was added dropwise a solution of methylpropargyl ether (56.8 g, 810 mmol) in acetonitrile (200 mL) over about 1 hr at 40° C., and the mixture was stirred at the same temperature for about 2 hr. To the reaction mixture was added acetonitrile (600 mL), and the mixture was concentrated under reduced pressure until the volume became 1000 mL. To the residue was added dropwise acetic acid (64.89 g, 1081 mmol) at 40° C., and the mixture was stirred at the same temperature for 1 hr, and then at room temperature for an additional 1 hr. The precipitated solid was collected by filtration, and washed with acetonitrile (400 mL). The obtained solid was suspended in acetonitrile (1600 mL), and the suspension was stirred at 70° C. for 1 hr, and then at room temperature for 10 hr. The resulting solid was collected by filtration, washed twice with acetonitrile (400 mL), and dried under reduced pressure at 50° C. to give ethyl 4-(3-hydroxy-6-(3-methoxyprop-1-yn-1-yl)pyrazin-2-yl)benzoate (121 g, yield 71.7%).

1H-NMR (DMSO-D6) δ: 1.34 (3H, t, J=7.2 Hz), 3.34 (3H, s), 4.35 (4H, q, J=7.2 Hz), 7.85 (1H, s), 8.03 (2H, d, J=8.6 Hz), 8.40 (2H, d, J=8.6 Hz), 12.96 (1H, s).

Step 6-6: Ethyl 4-(3-hydroxy-6-(3-methoxypropyl)pyrazin-2-yl)benzoate

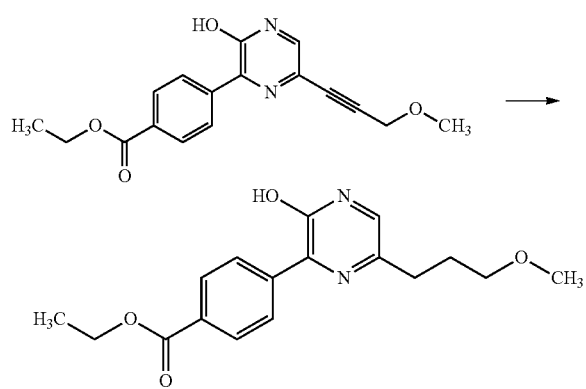

Under nitrogen atmosphere, to ethyl 4-(3-hydroxy-6-(3-methoxyprop-1-yn-1-yl)pyrazin-2-yl)benzoate (30.0 g, 96.1 mmol) was added tetrahydrofuran (360 mL), and 5% palladium on carbon catalyst (50% wet, 1.50 g) was added thereto. The reaction system was replaced with hydrogen, and the mixture was stirred under 0.2 MPa of hydrogen pressure for 4 hr. The 5% palladium on carbon catalyst was removed by filtration, and washed with tetrahydrofuran (120 mL), and the combined filtrate was concentrated under reduced pressure until the volume became 150 mL. To the residue was added dropwise heptane (120 mL) at 40° C., and the mixture was stirred at the same temperature for 10 min. Heptane (480 mL) was added dropwise thereto at 45° C., and the mixture was stirred at the same temperature for 30 min, and then at room temperature for 30 min. The precipitated solid was collected by filtration, and the obtained solid was washed with heptane (150 mL), and dried under reduced pressure at 50° C. to give ethyl 4-(3-hydroxy-6-(3-methoxypropyl)pyrazin-2-yl)benzoate (28.0 g, yield 92.1%).

1H-NMR (DMSO-D6) δ: 1.34 (3H, t, J=6.9 Hz), 1.84-1.91 (2H, m), 2.61 (2H, t, J=7.6 Hz), 3.24 (3H, s), 3.38 (2H, t, J=6.4 Hz), 4.34 (2H, q, J=6.9 Hz), 7.37 (1H, s), 8.02 (2H, d, J=8.6 Hz), 8.47 (2H, d, J=8.6 Hz), 12.49 (1H, s).

Step 6-7: Ethyl 4-(6-(3-methoxypropyl)-3-(((trifluoromethyl)sulfonyl)oxy)pyrazin-2-yl)benzoate

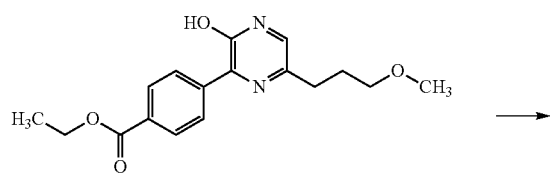

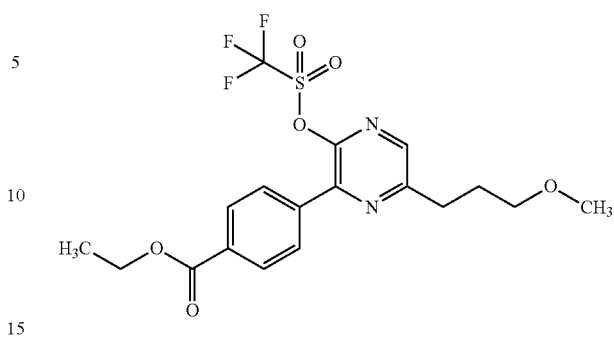

Under nitrogen atmosphere, to a solution of dipotassium hydrogenphosphate (42.1 g, 242 mmol) in water (85 mL) was added toluene (153 mL), and ethyl 4-(3-hydroxy-6-(3-methoxypropyl)pyrazin-2-yl)benzoate (17.0 g, 53.7 mmol) was added thereto. To this mixture was added dropwise trifluoromethanesulfonic anhydride (22.7 g, 80.5 mmol) over 1 hr at 5 to 10° C., and the mixture was stirred at the same temperature for 1 hr. The reaction mixture was separated, and the organic layer was washed with 20% brine (68 g) to give a solution of ethyl 4-(6-(3-methoxypropyl)-3-(((trifluoromethyl)sulfonyl)oxy)pyrazin-2-yl)benzoate in toluene. The obtained solution of ethyl 4-(6-(3-methoxypropyl)-3-(((trifluoromethyl)sulfonyl)oxy)pyrazin-2-yl)benzoate in toluene was used in the next step, regarded as yield 100%.

The solution of ethyl 4-(6-(3-methoxypropyl)-3-(((trifluoromethyl)sulfonyl)oxy)pyrazin-2-yl)benzoate in toluene was synthesized by the same production method, and concentrated to dryness, and the residue was purified by silica gel chromatography (hexane:ethyl acetate=4:1), and the NMR was measured.

1H-NMR (DMSO-D6) δ: 1.36 (3H, t, J=7.2 Hz), 1.97-2.04 (2H, m), 3.00 (2H, t, J=7.7 Hz), 3.23 (3H, s), 3.41 (2H, t, J=6.2 Hz), 4.37 (2H, q, J=7.2 Hz), 8.00 (2H, dt, J=8.6, 1.8 Hz), 8.15 (2H, dt, J=8.6, 1.8 Hz), 8.53 (1H, s).

Step 6-8: Ethyl 4-(3-(3,5-difluoro-4-methoxyphenyl)-6-(3-methoxypropyl)pyrazin-2-yl)benzoate

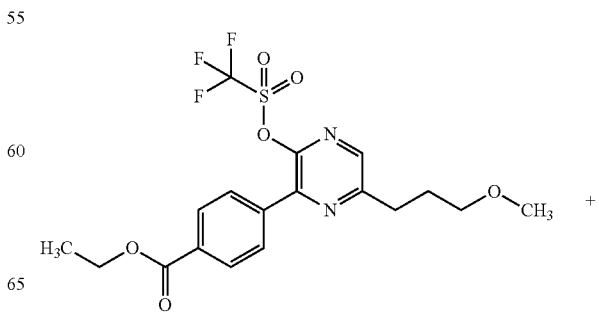 +

-continued

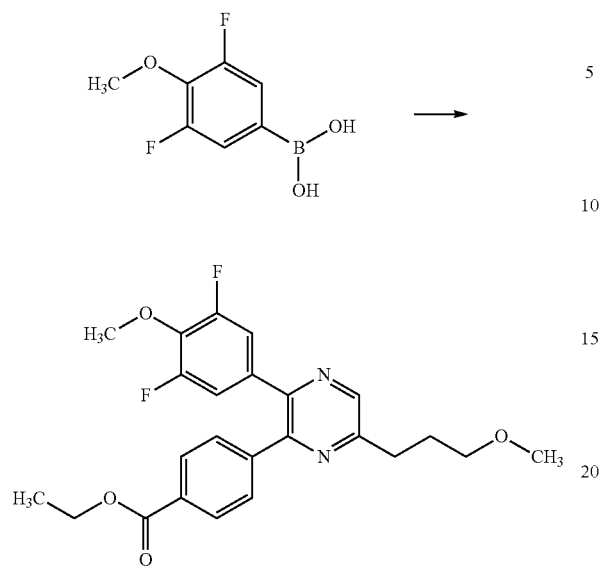

Under nitrogen atmosphere, to a solution of ethyl 4-(6-(3-methoxypropyl)-3-(((trifluoromethyl)sulfonyl)oxy) pyrazin-2-yl)benzoate in toluene (corresponding to 53.7 mmol) was added tetrahydrofuran (34 mL), and (3,5-difluoro-4-methoxyphenyl)boric acid (12.1 g, 64.5 mmol) was added thereto, and the used container was washed with tetrahydrofuran (17 mL). Bis(triphenylphosphine)palladium (II) dichloride (0.377 g, 0.537 mmol) was added thereto, and the reaction system was degassed under reduced pressure, and replaced with nitrogen. To this mixture was added dropwise a solution of tripotassium phosphate (13.7 g, 64.5 mmol) in water (65 mL) over 2 hr at 70° C., and the mixture was stirred at the same temperature for 2 hr. The reaction mixture was separated, and the organic layer was washed twice with 20% brine (68 g), and concentrated under reduced pressure until the volume became 68 mL. To the residue was added toluene until the volume became 136 mL, activated carbon (3.4 g) and metal scavenger (Fuji Silysia Chemical Ltd, SCAVENGER SH SILICA, 1.0 g) were added thereto, and the mixture was stirred at room temperature for 2 hr. The activated carbon and metal scavenger were removed by filtration, and washed with toluene (51 mL). The combined filtrate was concentrated under reduced pressure, to the residue was added 2-propanol (102 mL), and the mixture was concentrated under reduced pressure. The procedure was repeated twice in total. To the residue was added 2-propanol until the volume became 85 mL, and the mixture was stirred at room temperature for 1 hr, and then under ice-cooling for 2 hr. The precipitated solid was collected by filtration, washed with cooled 2-propanol (51 mL), and dried under reduced pressure at 50° C. to give ethyl 4-(3-(3,5-difluoro-4-methoxyphenyl)-6-(3-methoxypropyl)pyrazin-2-yl)benzoate (21.9 g, yield 92.1%).

1H-NMR (DMSO-D6) δ: 1.33 (3H, t, J=7.1 Hz), 1.96-2.03 (2H, m), 2.91-2.95 (2H, m), 3.25 (3H, s), 3.42 (2H, t, J=6.4 Hz), 3.95 (3H, s), 4.33 (2H, q, J=7.1 Hz), 7.08-7.14 (2H, m), 7.57 (2H, dt, J=8.5, 1.8 Hz), 7.96 (2H, dt, J=8.5, 1.8 Hz), 8.66 (1H, s).

Step 6-9: 4-(3-(3,5-Difluoro-4-methoxyphenyl)-6-(3-methoxypropyl)pyrazin-2-yl)benzoic Acid

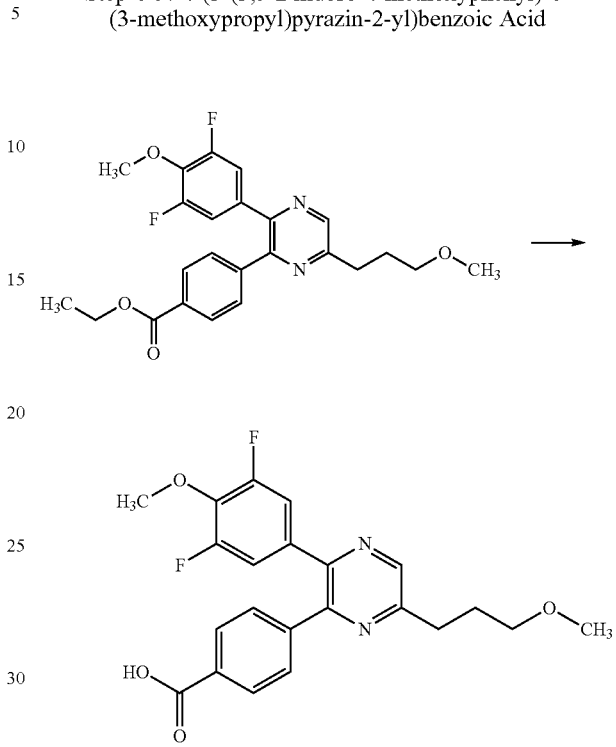

Under nitrogen atmosphere, to ethyl 4-(3-(3,5-difluoro-4-methoxyphenyl)-6-(3-methoxypropyl)pyrazin-2-yl)benzoate (5.0 g, 11.3 mmol) was added ethanol (15 mL), and 2N aqueous sodium hydroxide solution (7.5 mL, 15.0 mmol) was added thereto, and the mixture was stirred at 40° C. for 1.5 hr. The reaction mixture was filtered through 0.45 μM membrane filter, and washed with a mixed solvent of ethanol/water (3/1.4, 22 mL). To the combined filtrate was added dropwise 3N hydrochloric acid (5.5 mL, 16.5 mmol) at room temperature, and the mixture was stirred at room temperature for 0.5 hr. To this mixture was added dropwise water (10 mL) at 35° C., and the mixture was stirred at the same temperature for 30 min, and then at room temperature for about 2 hr. The precipitated solid was collected by filtration, and the obtained solid was washed successively with a mixed solvent of ethanol/water (1/2, 22.5 mL) and water (30 mL), and dried under reduced pressure at 50° C. to give 4-(3-(3,5-difluoro-4-methoxyphenyl)-6-(3-methoxypropyl) pyrazin-2-yl)benzoic acid (4.45 g, yield 95.1%).

1H-NMR (DMSO-D6) δ: 1.96-2.03 (2H, m), 2.93 (2H, t, J=7.7 Hz), 3.25 (3H, s), 3.42 (2H, t, J=6.4 Hz), 3.95 (3H, s), 7.07-7.14 (2H, m), 7.54 (2H, d, J=8.3 Hz), 7.94 (2H, d, J=8.3 Hz), 8.66 (1H, s), 13.11 (1H, s).

The compounds of the other Examples were obtained according to the above-mentioned general production methods or by a method similar to that of the Production Example, using the other known methods as necessary. The structural formulas and property data of the compounds of Examples 1 to 153 are shown in the following Table 1-1 to Table 1-20. The MS value marked with "—COOH" in the tables means a value of fragment after decarboxylation.

TABLE 1-1

| Ex. | Structure | NMR | MS (M + H) | MS (M − H) |
|---|---|---|---|---|
| 1 | 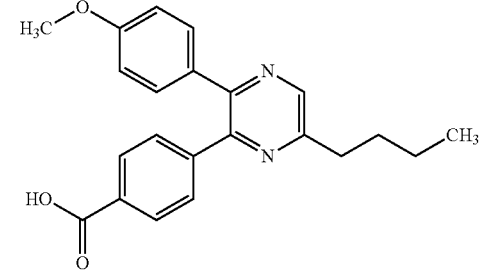 [SMILES: CCCCc1cnc(-c2ccc(OC)cc2)c(-c2ccc(C(=O)O)cc2)n1] | 1H-NMR (DMSO-D6) δ: 0.92 (3H, t, J = 7.4 Hz), 1.38 (2H, td, J = 14.8, 7.5 Hz), 1.68-1.77 (2H, m), 2.85 (2H, t, J = 7.7 Hz), 3.74 (3H, s), 6.87 (2H, dt, J = 9.4, 2.5 Hz), 7.29 (2H, dt, J = 9.4, 2.5 Hz), 7.49 (2H, dt, J = 8.4, 1.8 Hz), 7.88 (2H, dt, J = 8.5, 1.8 Hz), 8.59 (1H, t, J = 4.9 Hz), 13.01 (1H, br s). | 363 | 361 |
| 2 | 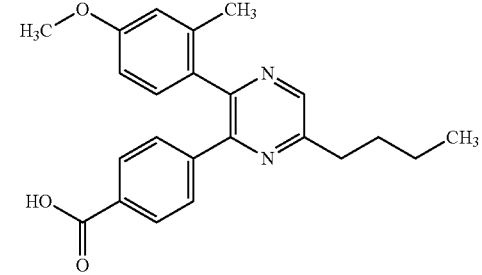 [SMILES: CCCCc1cnc(-c2ccc(OC)cc2C)c(-c2ccc(C(=O)O)cc2)n1] | 1H-NMR (DMSO-D6) δ: 0.93 (3H, t, J = 7.3 Hz), 1.35-1.44 (2H, m), 1.71-1.79 (2H, m), 1.92 (3H, s), 2.88 (2H, t, J = 7.7 Hz), 3.73 (3H, s), 6.72 (1H, dd, J = 8.3, 2.5 Hz), 6.76 (1H, d, J = 2.5 Hz), 7.04 (1H, d, J = 8.6 Hz), 7.42 (2H, dd, J = 6.7, 1.8 Hz), 7.81 (2H, dd, J = 6.7, 1.8 Hz), 8.61 (1H, s), 13.00 (1H, br s). | 377 | 375 |
| 3 | 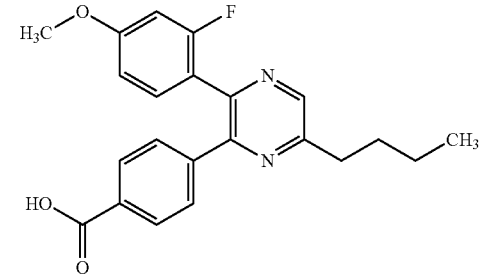 [SMILES: CCCCc1cnc(-c2ccc(OC)cc2F)c(-c2ccc(C(=O)O)cc2)n1] | 1H-NMR (DMSO-D6) δ: 0.93 (3H, t, J = 7.3 Hz), 1.34-1.43 (2H, m), 1.70-1.78 (2H, m), 2.88 (2H, t, J = 7.7 Hz), 3.76 (3H, s), 6.71 (1H, dd, J = 12.3, 2.5 Hz), 6.87 (1H, dd, J = 8.7, 2.4 Hz), 7.43-7.51 (3H, m), 7.84 (2H, dd, J = 6.7, 1.8 Hz), 8.64 (1H, s), 13.04 (1H, br s). | 381 | 379 |
| 4 | 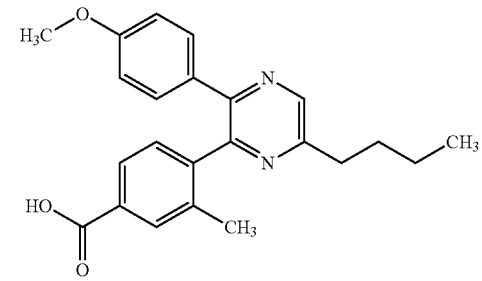 [SMILES: CCCCc1cnc(-c2ccc(OC)cc2)c(-c2ccc(C(=O)O)cc2C)n1] | 1H-NMR (DMSO-D6) δ: 0.90 (3H, t, J = 7.3 Hz), 1.35 (2H, td, J = 14.9, 7.4 Hz), 1.70 (2H, dt, J = 15.8, 7.0 Hz), 1.98 (3H, s), 2.84 (2H, t, J = 7.6 Hz), 3.70 (3H, s), 6.78-6.84 (2H, m), 7.21-7.29 (3H, m), 7.74 (1H, dd, J = 7.9, 1.2 Hz), 7.78 (1H, s), 8.62 (1H, s), 12.97 (1H, br s). | 377 | 375 |
| 5 | 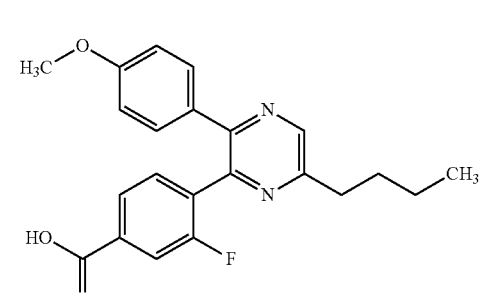 | 1H-NMR (DMSO-D6) δ: 0.91 (3H, t, J = 7.4 Hz), 1.31-1.43 (2H, m), 1.65-1.76 (2H, m), 2.85 (2H, t, J = 7.7 Hz), 3.72 (3H, s), 6.85 (2H, d, J = 8.6 Hz), 7.29 (2H, d, J = 8.6 Hz), 7.56 (1H, dd, J = 10.4, 1.4 Hz), 7.68 (1H, t, J = 7.6 Hz), 7.85 (1H, dd, J = 7.9, 1.2 Hz), 8.66 (1H, s), 13.37 (1H, br s). | 381 | 379 |

TABLE 1-1-continued
| Ex. | Structure | NMR | MS (M + H) | MS (M − H) |
|---|---|---|---|---|
| 6 | 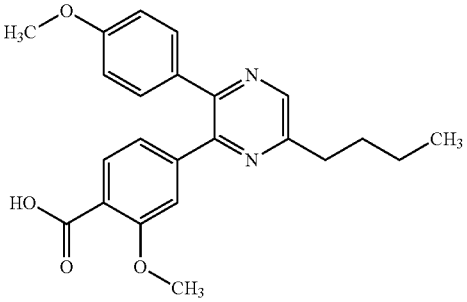 [SMILES: CCCCc1cnc(-c2ccc(OC)cc2)c(-c2ccc(C(=O)O)c(OC)c2)n1] | 1H-NMR (DMSO-D6) δ: 0.93 (3H, t, J = 7.3 Hz), 1.32-1.45 (2H, m), 1.67-1.79 (2H, m), 2.85 (2H, t, J = 7.6 Hz), 3.58 (3H, s), 3.74 (3H, s), 6.90 (2H, dt, J = 9.4, 2.5 Hz), 7.00-7.06 (2H, m), 7.32 (2H, dt, J = 9.3, 2.5 Hz), 7.57 (1H, d, J = 7.9 Hz), 8.58 (1H, s), 12.66 (1H, br s). | 393 | 391 |
| 7 | 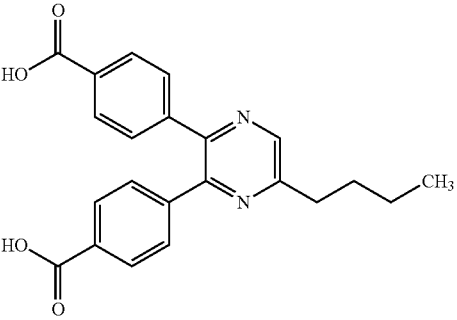 [SMILES: CCCCc1cnc(-c2ccc(C(=O)O)cc2)c(-c2ccc(C(=O)O)cc2)n1] | 1H-NMR (DMSO-D6) δ: 0.93 (3H, t, J = 7.4 Hz), 1.34-1.45 (2H, m), 1.69-1.80 (2H, m), 2.89 (2H, t, J = 7.6 Hz), 7.45-7.50 (4H, m), 7.84-7.89 (4H, m), 8.67 (1H, s), 13.03 (2H, br s). | 377 | 375 |
| 8 | 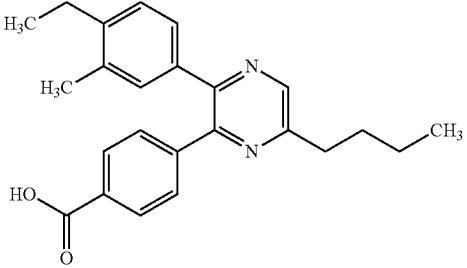 [SMILES: CCCCc1cnc(-c2ccc(CC)c(C)c2)c(-c2ccc(C(=O)O)cc2)n1] | 1H-NMR (DMSO-D6) δ: 0.92 (3H, t, J = 7.4 Hz), 1.32-1.43 (2H, m), 1.67-1.77 (2H, m), 2.07 (3H, s), 2.84 (2H, t, J = 7.7 Hz), 3.75 (3H, s), 6.81 (1H, d, J = 8.6 Hz), 6.99-7.07 (1H, m), 7.28 (1H, dd, J = 2.3, 0.7 Hz), 7.49 (2H, dt, J = 8.4, 1.8 Hz), 7.88 (2H, dt, J = 8.4, 1.7 Hz), 8.57 (1H, s), 13.02 (1H, br s). | 377 | 375 |
TABLE 1-2
| Ex. | Structure | NMR | MS (M + H) | MS (M − H) |
|---|---|---|---|---|
| 9 | 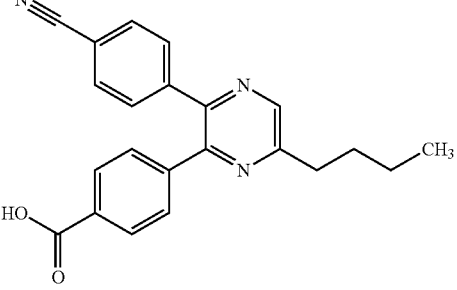 | 1H-NMR (DMSO-D6) δ: 0.92 (3H, t, J = 7.4 Hz), 1.33-1.45 (2H, m), 1.69-1.79 (2H, m), 2.89 (2H, t, J = 7.7 Hz), 7.48 (2H, d, J = 8.6 Hz), 7.54 (2H, d, J = 8.1 Hz), 7.80 (2H, d, J = 8.1 Hz), 7.88 (2H, d, J = 8.6 Hz), 8.69 (1H, s), 13.08 (1H, s). | 358 | 356 |

TABLE 1-2-continued

| Ex. | Structure | NMR | MS (M + H) | MS (M − H) |
|---|---|---|---|---|
| 10 | 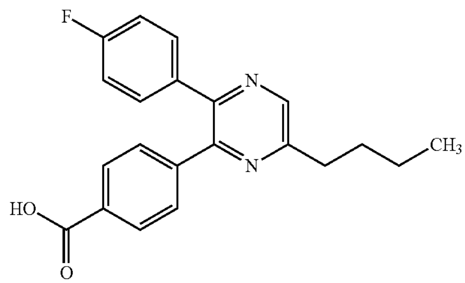 [SMILES: CCCCc1cnc(-c2ccc(F)cc2)c(-c2ccc(C(=O)O)cc2)n1] | 1H-NMR (DMSO-D6) δ: 0.92 (3H, t, J = 7.3 Hz), 1.33-1.44 (2H, m), 1.68-1.78 (2H, m), 2.87 (2H, t, J = 7.7 Hz), 7.16 (2H, t, J = 8.9 Hz), 7.39 (2H, dd, J = 8.8, 5.5 Hz), 7.48 (2H, d, J = 8.6 Hz), 7.88 (2H, d, J = 8.6 Hz), 8.63 (1H, s), 13.05 (1H, br s). | 351 | 349 |
| 11 | 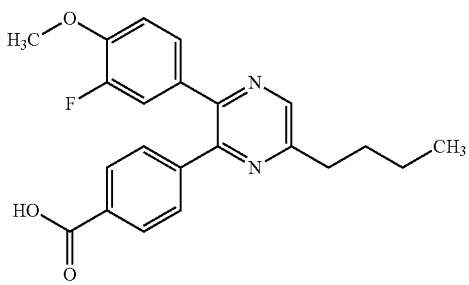 [SMILES: CCCCc1cnc(-c2ccc(OC)c(F)c2)c(-c2ccc(C(=O)O)cc2)n1] | 1H-NMR (DMSO-D6) δ: 0.92 (3H, t, J = 7.3 Hz), 1.31-1.44 (2H, m), 1.66-1.78 (2H, m), 2.86 (2H, t, J = 7.7 Hz), 3.82 (3H, s), 7.03-7.12 (2H, m), 7.19-7.26 (1H, m), 7.51 (2H, d, J = 8.6 Hz), 7.90 (2H, d, J = 8.6 Hz), 8.61 (1H, s), 13.05 (1H, br s). | 381 | 379 |
| 12 | 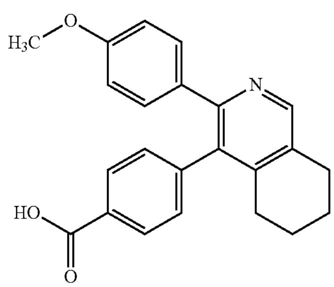 [SMILES: COc1ccc(-c2ncc3c(c2-c2ccc(C(=O)O)cc2)CCCC3)cc1] | 1H-NMR (DMSO-D6) δ: 1.61-1.68 (2H, m), 1.69-1.76 (2H, m), 2.31 (2H, t, J = 6.2 Hz), 2.80 (2H, t, J = 6.1 Hz), 3.66 (3H, s), 6.70 (2H, dt, J = 9.4, 2.5 Hz), 7.09 (2H, dt, J = 9.5, 2.5 Hz), 7.21 (2H, dt, J = 8.2, 1.8 Hz), 7.86 (2H, dt, J = 8.3, 1.8 Hz), 8.36 (1H, s), 12.97 (1H, br s). | 360 | 358 |
| 13 | 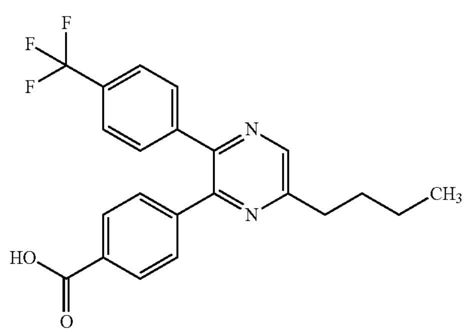 [SMILES: CCCCc1cnc(-c2ccc(C(F)(F)F)cc2)c(-c2ccc(C(=O)O)cc2)n1] | 1H-NMR (DMSO-D6) δ: 0.93 (3H, t, J = 7.3 Hz), 1.34-1.45 (2H, m), 1.69-1.80 (2H, m), 2.89 (2H, t, J = 7.7 Hz), 7.49 (2H, d, J = 8.6 Hz), 7.58 (2H, d, J = 8.1 Hz), 7.69 (2H, d, J = 8.8 Hz), 7.89 (2H, d, J = 8.6 Hz), 8.69 (1H, s), 13.09 (1H, br s). | 401 | 399 |
| 14 | 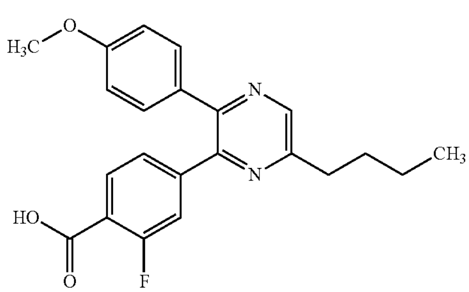 [SMILES: CCCCc1cnc(-c2ccc(OC)cc2)c(-c2ccc(C(=O)O)c(F)c2)n1] | 1H-NMR (DMSO-D6) δ: 0.92 (3H, t, J = 7.3 Hz), 1.32-1.44 (2H, m), 1.67-1.77 (2H, m), 2.85 (2H, t, J = 7.6 Hz), 3.75 (3H, s), 6.90 (2H, d, J = 8.8 Hz), 7.22-7.35 (4H, m), 7.78 (1H, t, J = 7.9 Hz), 8.61 (1H, s), 13.32 (1H, br s). | 381 | 379 |

TABLE 1-2-continued

| Ex. | Structure | NMR | MS (M + H) | MS (M − H) |
|---|---|---|---|---|
| 15 | 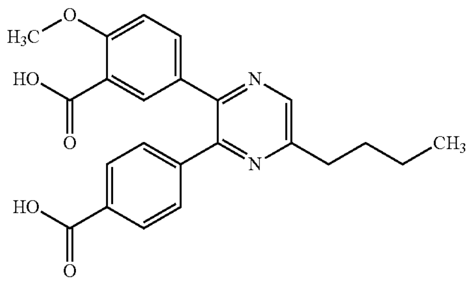 [SMILES: CCCCc1cnc(-c2ccc(OC)c(C(=O)O)c2)c(-c2ccc(C(=O)O)cc2)n1] | 1H-NMR (DMSO-D6) δ: 0.92 (3H, t, J = 7.4 Hz), 1.33-1.44 (2H, m), 1.67-1.78 (2H, m), 2.86 (2H, t, J = 7.7 Hz), 3.79 (3H, s), 7.02 (1H, d, J = 9.0 Hz), 7.37 (1H, dd, J = 8.7, 2.4 Hz), 7.51 (2H, d, J = 8.6 Hz), 7.78 (1H, d, J = 2.5 Hz), 7.89 (2H, d, J = 8.6 Hz), 8.61 (1H, s), 12.81 (1H, br s). | 407 | 405 |
| 16 | 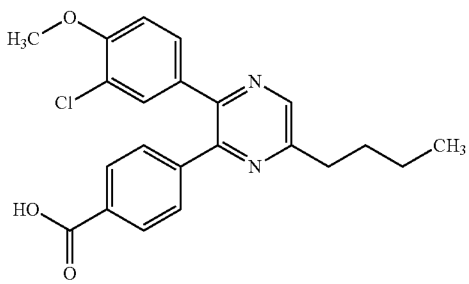 [SMILES: CCCCc1cnc(-c2ccc(OC)c(Cl)c2)c(-c2ccc(C(=O)O)cc2)n1] | 1H-NMR (DMSO-D6) δ: 0.92 (3H, t, J = 7.4 Hz), 1.31-1.45 (2H, m), 1.66-1.78 (2H, m), 2.86 (2H, t, J = 7.7 Hz), 3.83 (3H, s), 7.05 (1H, d, J = 8.8 Hz), 7.19 (1H, dd, J = 8.6, 2.1 Hz), 7.45-7.54 (3H, m), 7.90 (2H, d, J = 8.6 Hz), 8.61 (1H, s), 13.09 (1H, br s). | 397 | 395 |

TABLE 1-3

| Ex. | Structure | NMR | MS (M + H) | MS (M − H) |
|---|---|---|---|---|
| 17 | 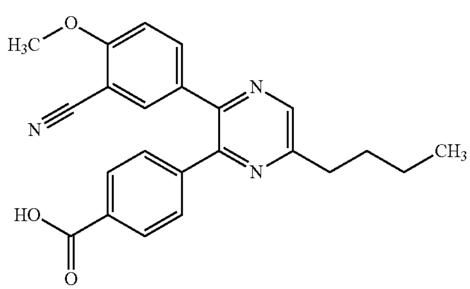 [SMILES: CCCCc1cnc(-c2ccc(OC)c(C#N)c2)c(-c2ccc(C(=O)O)cc2)n1] | 1H-NMR (DMSO-D6) δ: 0.92 (3H, t, J = 7.4 Hz), 1.33-1.44 (2H, m), 1.68-1.77 (2H, m), 2.87 (2H, t, J = 7.7 Hz), 3.90 (3H, s), 7.18 (1H, d, J = 9.0 Hz), 7.50 (2H, d, J = 8.6 Hz), 7.56 (1H, dd, J = 8.8, 2.3 Hz), 7.73 (1H, d, J = 2.1 Hz), 7.91 (2H, d, J = 6.7 Hz), 8.63 (1H, s), 13.09 (1H, br s). | 388 | 386 |
| 18 | 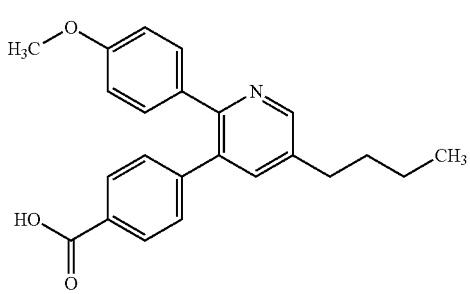 [SMILES: CCCCc1cnc(-c2ccc(OC)cc2)c(-c2ccc(C(=O)O)cc2)c1] | 1H-NMR (DMSO-D6) δ: 0.91 (3H, t, J = 7.3 Hz), 1.30-1.40 (2H, m), 1.58-1.66 (2H, m), 2.67 (2H, t, J = 7.7 Hz), 3.71 (3H, s), 6.79 (2H, dt, J = 9.4, 2.5 Hz), 7.19 (2H, dt, J = 9.5, 2.5 Hz), 7.30 (2H, dt, J = 8.4, 1.8 Hz), 7.62 (1H, d, J = 2.3 Hz), 7.85 (2H, dt, J = 8.6, 1.8 Hz), 8.50 (1H, d, J = 2.1 Hz), 12.93 (1H, br s). | 362 | 360 |

TABLE 1-3-continued

| Ex. | Structure | NMR | MS (M + H) | MS (M − H) |
|---|---|---|---|---|
| 19 | 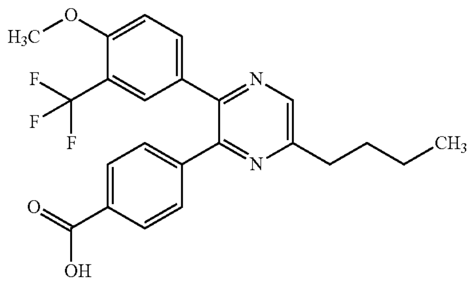 [SMILES: CCCCc1cnc(-c2ccc(OC)c(C(F)(F)F)c2)c(-c2ccc(C(=O)O)cc2)n1] | 1H-NMR (DMSO-D6) δ: 0.92 (3H, t, J = 7.3 Hz), 1.32-1.44 (2H, m), 1.66-1.79 (2H, m), 2.87 (2H, t, J = 7.6 Hz), 3.87 (3H, s), 7.18 (1H, d, J = 8.8 Hz), 7.48-7.53 (3H, m), 7.66 (1H, d, J = 2.3 Hz), 7.91 (2H, d, J = 8.6 Hz), 8.63 (1H, s), 13.06 (1H, br s). | 431 | 429 |
| 20 | 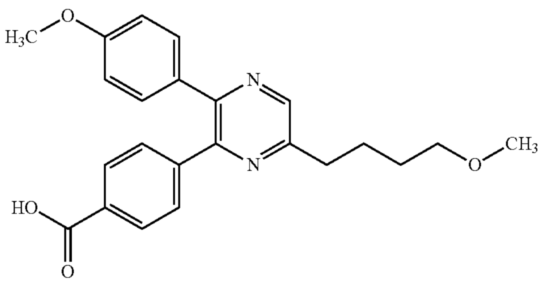 [SMILES: COCCCCc1cnc(-c2ccc(OC)cc2)c(-c2ccc(C(=O)O)cc2)n1] | 1H-NMR (DMSO-D6) δ: 1.56-1.63 (2H, m), 1.75-1.83 (2H, m), 2.87 (2H, t, J = 7.6 Hz), 3.22 (3H, s), 3.36 (2H, t, J = 6.3 Hz), 3.75 (3H, s), 6.88 (2H, d, J = 8.7 Hz), 7.31 (2H, d, J = 8.7 Hz), 7.51 (2H, d, J = 7.8 Hz), 7.90 (2H, d, J = 8.1 Hz), 8.60 (1H, s), 13.05 (1H, b rs). | 393 | 391 |
| 21 | 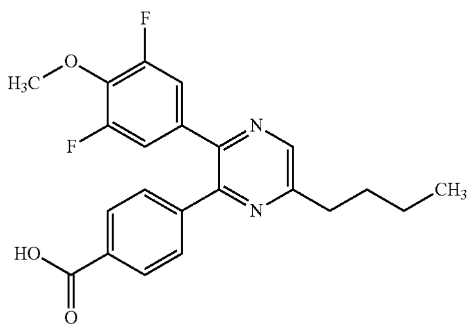 [SMILES: CCCCc1cnc(-c2cc(F)c(OC)c(F)c2)c(-c2ccc(C(=O)O)cc2)n1] | 1H-NMR (DMSO-D6) δ: 0.92 (3H, t, J = 7.4 Hz), 1.31-1.44 (2H, m), 1.66-1.78 (2H, m), 2.87 (2H, t, J = 7.7 Hz), 3.93 (3H, s), 7.08 (2H, d, J = 9.2 Hz), 7.51 (2H, d, J = 8.3 Hz), 7.92 (2H, d, J = 8.3 Hz), 8.64 (1H, s), 13.11 (1H, br s). | 399 | 397 |
| 22 | 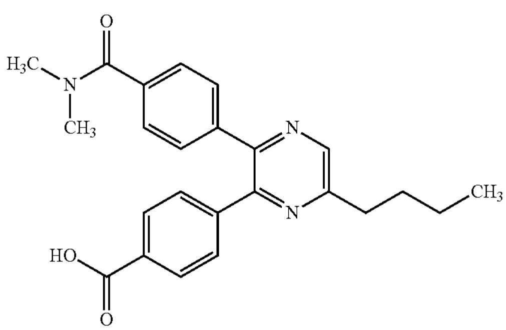 [SMILES: CCCCc1cnc(-c2ccc(C(=O)N(C)C)cc2)c(-c2ccc(C(=O)O)cc2)n1] | 1H-NMR (DMSO-D6) δ: 0.93 (3H, t, J = 7.4 Hz), 1.33-1.45 (2H, m), 1.68-1.79 (2H, m), 2.80-3.00 (8H, m), 7.33 (2H, d, J = 8.3 Hz), 7.41 (2H, d, J = 8.3 Hz), 7.49 (2H, d, J = 8.3 Hz), 7.87 (2H, d, J = 8.3 Hz), 8.66 (1H, s), 13.04 (1H, br s). | 404 | 402 |
| 23 | 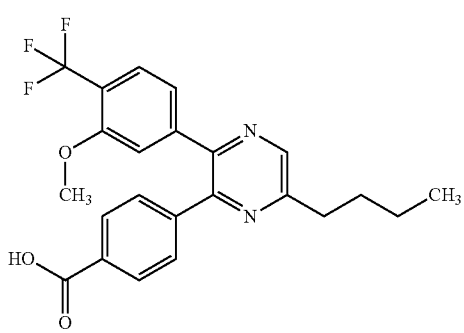 [SMILES: CCCCc1cnc(-c2ccc(C(F)(F)F)c(OC)c2)c(-c2ccc(C(=O)O)cc2)n1] | 1H-NMR (DMSO-D6) δ: 0.93 (3H, t, J = 7.4 Hz), 1.32-1.46 (2H, m), 1.68-1.80 (2H, m), 2.90 (2H, t, J = 7.6 Hz), 3.67 (3H, s), 7.03 (1H, d, J = 8.1 Hz), 7.24 (1H, s), 7.50 (2H, d, J = 8.3 Hz), 7.54 (1H, d, J = 8.1 Hz), 7.90 (2H, d, J = 8.3 Hz), 8.69 (1H, s), 13.11 (1H, br s). | 431 | 429 |

TABLE 1-3-continued

| Ex. | Structure | NMR | MS (M + H) | MS (M − H) |
|---|---|---|---|---|
| 24 | 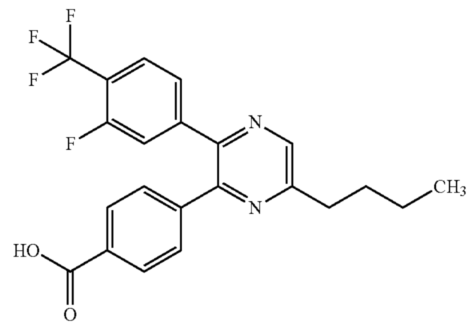 [SMILES: CCCCc1cnc(-c2ccc(C(F)(F)F)c(F)c2)c(-c2ccc(C(=O)O)cc2)n1] | 1H-NMR (DMSO-D6) δ: 0.93 (3H, t, J = 7.4 Hz), 1.33-1.45 (2H, m), 1.68-1.80 (2H, m), 2.90 (2H, t, J = 7.6 Hz), 7.31 (1H, d, J = 8.1 Hz), 7.47-7.57 (3H, m), 7.72 (1H, t, J = 7.9 Hz), 7.91 (2H, d, J = 8.3 Hz), 8.70 (1H, s), 13.08 (1H, br s). | 419 | 417 |

TABLE 1-4

| Ex. | Structure | NMR | MS (M + H) | MS (M − H) |
|---|---|---|---|---|
| 25 | 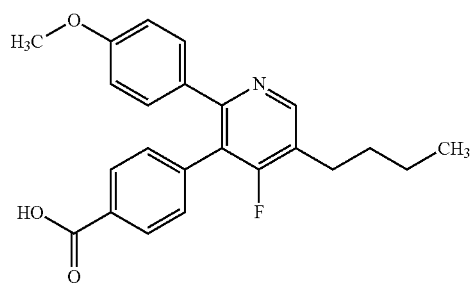 [SMILES: CCCCc1cnc(-c2ccc(OC)cc2)c(-c2ccc(C(=O)O)cc2)c1F] | 1H-NMR (DMSO-D6) δ: 0.91 (3H, t, J = 7.3 Hz), 1.31-1.39 (2H, m), 1.57-1.64 (2H, m), 2.68 (2H, t, J = 7.6 Hz), 3.69 (3H, s), 6.76-6.79 (2H, m), 7.16 (2H, dt, J = 9.4, 2.5 Hz), 7.32 (2H, d, J = 8.1 Hz), 7.89 (2H, d, J = 8.1 Hz), 8.57 (1H, d, J = 9.9 Hz), 13.03 (1H, br s). | 378 | 380 |
| 26 | 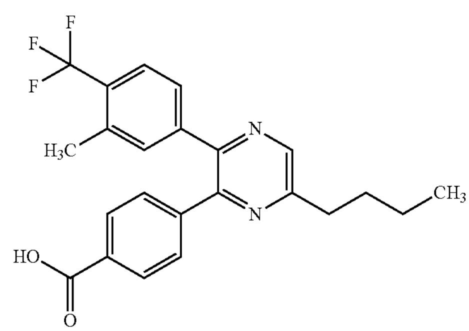 [SMILES: CCCCc1cnc(-c2ccc(C(F)(F)F)c(C)c2)c(-c2ccc(C(=O)O)cc2)n1] | 1H-NMR (DMSO-D6) δ: 0.93 (3H, t, J = 7.3 Hz), 1.33-1.44 (2H, m), 1.69-1.79 (2H, m), 2.38 (3H, s), 2.89 (2H, t, J = 7.7 Hz), 7.23 (1H, d, J = 8.3 Hz), 7.50 (2H, d, J = 8.3 Hz), 7.56 (2H, d, J = 8.3 Hz), 7.89 (2H, d, J = 8.3 Hz), 8.68 (1H, S), 13.07 (1H, br s). | 415 | 413 |
| 27 | 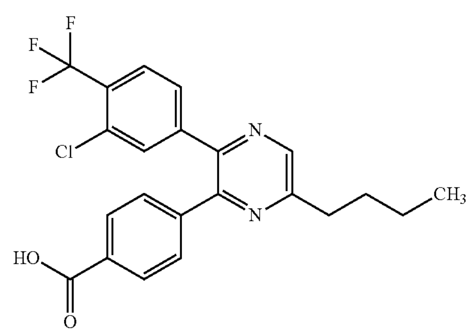 [SMILES: CCCCc1cnc(-c2ccc(C(F)(F)F)c(Cl)c2)c(-c2ccc(C(=O)O)cc2)n1] | 1H-NMR (DMSO-D6) δ: 0.93 (3H, t, J = 7.4 Hz), 1.33-1.44 (2H, m), 1.69-1.80 (2H, m), 2.90 (2H, t, J = 7.6 Hz), 7.42 (1H, d, J = 8.3 Hz), 7.51 (2H, d, J = 8.3 Hz), 7.75 (1H, s), 7.78 (1H, d, J = 8.3 Hz), 7.91 (2H, d, J = 8.1 Hz), 8.70 (1H, s), 13.13 (1H, br s). | 435 | 433 |

TABLE 1-4-continued

| Ex. | Structure | NMR | MS (M + H) | MS (M − H) |
|---|---|---|---|---|
| 28 | 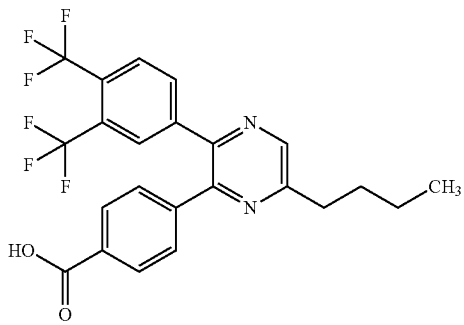 [SMILES: CCCCc1cnc(-c2ccc(C(F)(F)F)c(C(F)(F)F)c2)c(-c2ccc(C(=O)O)cc2)n1] | 1H-NMR (DMSO-D6) δ: 0.93 (3H, t, J = 7.4 Hz), 1.34-1.46 (2H, m), 1.69-1.80 (2H, m), 2.92 (2H, t, J = 7.7 Hz), 7.53 (2H, d, J = 8.6 Hz), 7.83 (1H, d, J = 8.6 Hz), 7.92 (2H, d, J = 8.6 Hz), 7.96-8.03 (2H, m), 8.74 (1H, s), 13.09 (1H, br s). | 469 | 467 |
| 29 | 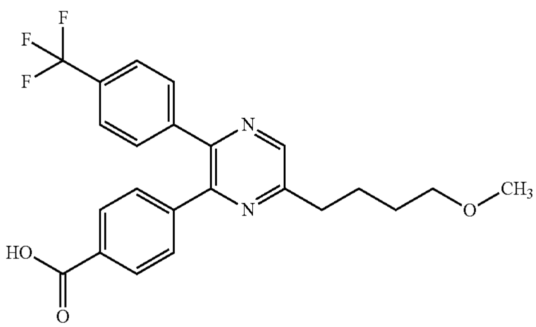 [SMILES: COCCCCc1cnc(-c2ccc(C(F)(F)F)cc2)c(-c2ccc(C(=O)O)cc2)n1] | 1H-NMR (DMSO-D6) δ: 1.56-1.63 (2H, m), 1.76-1.84 (2H, m), 2.91 (2H, t, J = 7.6 Hz), 3.20 (3H, s), 3.35 (2H, t, J = 6.4 Hz), 7.50 (2H, dd, J = 6.7, 1.8 Hz), 7.58 (2H, d, J = 8.1 Hz), 7.70 (2H, d, J = 8.1 Hz), 7.89 (2H, dd, J = 6.7, 1.8 Hz), 8.69 (1H, s), 13.07 (1H, br s). | 429 | 431 |
| 30 | 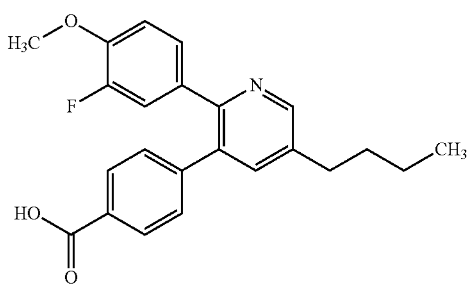 | 1H-NMR (DMSO-D6) δ: 0.91 (3H, t, J = 7.4 Hz), 1.30-1.40 (2H, m), 1.58-1.66 (2H, m), 2.67 (2H, t, J = 7.7 Hz), 3.79 (3H, s), 6.93-6.96 (1H, m), 7.01 (1H, t, J = 8.7 Hz), 7.11 (1H, dd, J = 12.7, 2.1 Hz), 7.32 (2H, dt, J = 8.4, 1.8 Hz), 7.65 (1H, d, J = 2.3 Hz), 7.88 (2H, dt, J = 8.5, 1.8 Hz), 8.51 (1H, d, J = 2.1 Hz), 13.00 (1H, br s). | 378 | 380 |
| 31 | 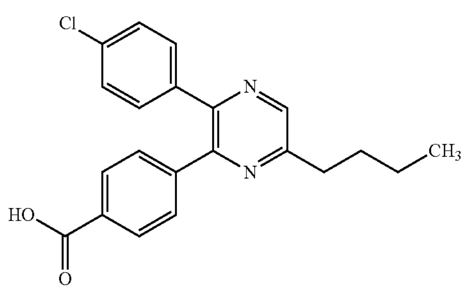 [SMILES: CCCCc1cnc(-c2ccc(Cl)cc2)c(-c2ccc(C(=O)O)cc2)n1] | 1H-NMR (DMSO-D6) δ: 0.94 (3H, t, J = 7.4 Hz), 1.35-1.45 (2H, m), 1.79-1.71 (2H, m), 2.89 (2H, t, J = 7.7 Hz), 7.37-7.42 (4H, m), 7.50 (2H, dt, J = 8.4, 1.8 Hz), 7.91 (2H, dt, J = 8.4, 1.8 Hz), 8.66 (1H, s), 13.07 (1H, br s). | 367 | 365 |
| 32 | 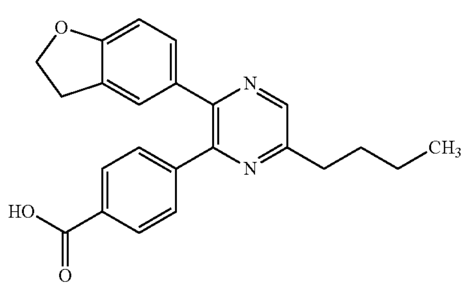 [SMILES: CCCCc1cnc(-c2ccc3c(c2)CCO3)c(-c2ccc(C(=O)O)cc2)n1] | 1H-NMR (DMSO-D6) δ: 0.93 (3H, t, J = 7.3 Hz), 1.35-1.44 (2H, m), 1.77-1.70 (2H, m), 2.85 (2H, t, J = 7.7 Hz), 3.13 (2H, t, J = 8.7 Hz), 4.54 (2H, t, J = 8.7 Hz), 6.65 (1H, d, J = 8.3 Hz), 6.99 (1H, dd, J = 8.3, 2.0 Hz), 7.35 (1H, d, J = 1.4 Hz), 7.52 (2H, dt, J = 8.4, 1.8 Hz), 7.90 (2H, dt, J = 8.5, 1.8 Hz), 8.58 (1H, s), 13.02 (1H, s). | 375 | 373 |

TABLE 1-5

| Ex. | Structure | NMR | MS (M + H) | MS (M − H) |
|---|---|---|---|---|
| 33 | 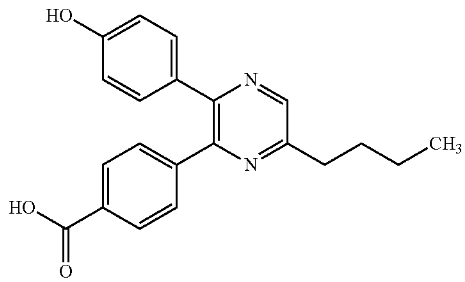 [SMILES: CCCCc1cnc(-c2ccc(O)cc2)c(-c2ccc(C(=O)O)cc2)n1] | 1H-NMR (DMSO-D6) δ: 0.93 (3H, t, J = 7.4 Hz), 1.34-1.44 (2H, m), 1.69-1.77 (2H, m), 2.85 (2H, t, J = 7.6 Hz), 6.69 (2H, dt, J = 9.2, 2.4 Hz), 7.19 (2H, dt, J = 9.2, 2.4 Hz), 7.50 (2H, dt, J = 8.4, 1.7 Hz), 7.89 (2H, dt, J = 8.4, 1.7 Hz), 8.57 (1H, s), 9.69 (1H, s), 13.03 (1H, br s). | 349 | 347 |
| 34 | 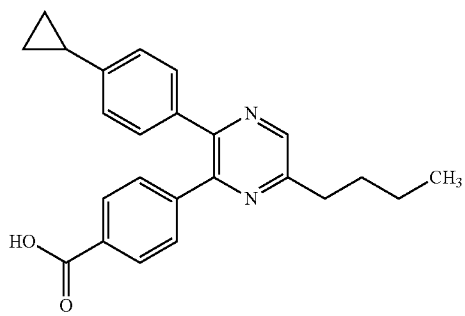 [SMILES: CCCCc1cnc(-c2ccc(C3CC3)cc2)c(-c2ccc(C(=O)O)cc2)n1] | 1H-NMR (DMSO-D6) δ: 0.66-0.69 (2H, m), 0.92-0.98 (5H, m), 1.44-1.35 (2H, m), 1.70-1.78 (2H, m), 1.87-1.92 (1H, m), 2.87 (2H, t, J = 7.6 Hz), 7.02 (2H, dt, J = 8.5, 1.8 Hz), 7.25 (2H, dt, J = 8.4, 1.8 Hz), 7.50 (2H, dt, J = 8.4, 1.8 Hz), 7.89 (2H, dt, J = 8.5, 1.8 Hz), 8.62 (1H, s), 13.04 (1H, s). | 373 | 371 |
| 35 | 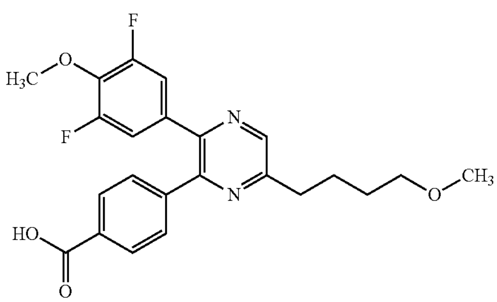 [SMILES: COCCCCc1cnc(-c2cc(F)c(OC)c(F)c2)c(-c2ccc(C(=O)O)cc2)n1] | 1H-NMR (DMSO-D6) δ: 1.54-1.63 (2H, m), 1.72-1.83 (2H, m), 2.88 (2H, t, J = 7.6 Hz), 3.20 (3H, s), 3.34 (2H, t, J = 6.5 Hz), 3.93 (3H, s), 7.09 (2H, d, J = 9.5 Hz), 7.52 (2H, d, J = 8.6 Hz), 7.92 (2H, d, J = 8.6 Hz), 8.64 (1H, s), 13.10 (1H, br s). | 429 | 427 |
| 36 | 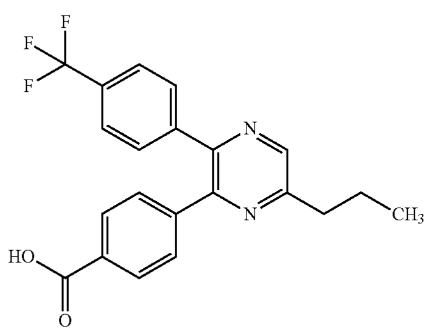 [SMILES: CCCc1cnc(-c2ccc(C(F)(F)F)cc2)c(-c2ccc(C(=O)O)cc2)n1] | 1H-NMR (DMSO-D6) δ: 0.98 (3H, t, J = 7.4 Hz), 1.73-1.85 (2H, m), 2.87 (2H, t, J = 7.5 Hz), 7.49 (2H, d, J = 8.6 Hz), 7.58 (2H, d, J = 8.1 Hz), 7.70 (2H, d, J = 8.3 Hz), 7.89 (2H, d, J = 8.6 Hz), 8.69 (1H, s), 13.08 (1H, br s). | 387 | 385 |
| 37 | 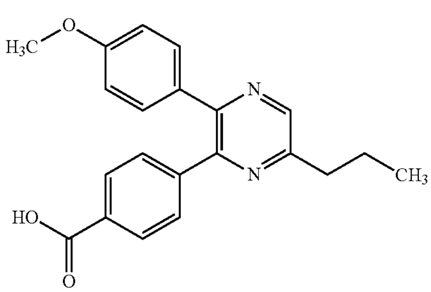 | 1H-NMR (DMSO-D6) δ: 0.96 (3H, t, J = 7.3 Hz), 1.70-1.82 (2H, m), 2.82 (2H, t, J = 7.6 Hz), 3.74 (3H, s), 6.87 (2H, d, J = 8.8 Hz), 7.30 (2H, d, J = 8.8 Hz), 7.49 (2H, d, J = 8.6 Hz), 7.88 (2H, d, J = 8.8 Hz), 8.58 (1H, s), 13.04 (1H, br s). | 349 | 347 |

TABLE 1-5-continued

| Ex. | Structure | NMR | MS (M + H) | MS (M − H) |
|---|---|---|---|---|
| 38 | (structure) | 1H-NMR (DMSO-D6) δ: 0.93 (3H, t, J = 7.2 Hz), 1.34-1.44 (2H, m), 1.70-1.77 (2H, m), 2.84 (2H, t, J = 7.5 Hz), 3.58 (2H, s), 3.75 (3H, s), 6.88 (2H, d, J = 8.7 Hz), 7.22 (2H, d, J = 7.8 Hz), 7.31-7.36 (4H, m), 8.54 (1H, s), 12.35 (1H, s). | 377 | 331 (—COOH) |
| 39 | (structure) | 1H-NMR (DMSO-D6) δ: 0.95 (3H, t, J = 7.3 Hz), 1.36-1.46 (2H, m), 1.53-1.61 (2H, m), 2.02 (3H, s), 2.68 (2H, t, J = 7.6 Hz), 3.68 (3H, s), 6.71 (2H, d, J = 8.7 Hz), 7.09 (2H, d, J = 8.7 Hz), 7.23 (2H, d, J = 8.1 Hz), 7.88 (2H, d, J = 8.1 Hz), 8.41 (1H, s), 12.98 (1H, br s). | 376 | 374 |
| 40 | (structure) | 1H-NMR (DMSO-D6) δ: 0.94 (3H, t, J = 7.4 Hz), 1.35-1.44 (2H, m), 1.70-1.78 (2H, m), 2.30 (3H, s), 2.87 (2H, t, J = 7.7 Hz), 7.13 (2H, d, J = 8.1 Hz), 7.26 (2H, d, J = 8.1 Hz), 7.49 (2H, d, J = 8.6 Hz), 7.88 (2H, dt, J = 8.6, 1.7 Hz), 8.63 (1H, s), 13.04 (1H, s). | 347 | 345 |

TABLE 1-6

| Ex. | Structure | NMR | MS (M + H) | MS (M − H) |
|---|---|---|---|---|
| 41 | (structure) | 1H-NMR (DMSO-D6) δ: 0.93 (3H, t, J = 7.3 Hz), 1.61-1.71 (2H, m), 2.64 (2H, t, J = 9.7 Hz), 3.71 (3H, s), 6.79 (2H, dd, J = 6.7, 2.1 Hz), 7.19 (2H, dd, J = 6.8, 2.2 Hz), 7.30 (2H, dd, J = 6.7, 1.8 Hz), 7.62 (1H, d, J = 2.3 Hz), 7.85 (2H, dd, J = 6.7, 1.8 Hz), 8.50 (1H, d, J = 2.3 Hz), 12.97 (1H, br s). | 346 | 348 |

TABLE 1-6-continued

| Ex. | Structure | NMR | MS (M + H) | MS (M − H) |
|---|---|---|---|---|
| 42 | 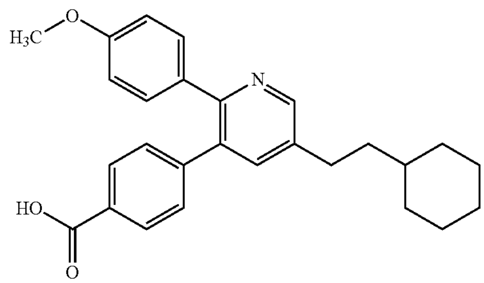 [SMILES: COc1ccc(-c2ncc(CCC3CCCCC3)cc2-c2ccc(C(=O)O)cc2)cc1] | 1H-NMR (DMSO-D6) δ: 0.86-1.00 (2H, m), 1.08-1.35 (4H, m), 1.47-1.81 (7H, m), 2.67 (2H, t, J = 8.0 Hz), 3.71 (3H, s), 6.79 (2H, d, J = 9.0 Hz), 7.18 (2H, d, J = 8.8 Hz), 7.29 (2H, d, J = 8.6 Hz), 7.62 (1H, d, J = 2.1 Hz), 7.85 (2H, d, J = 8.6 Hz), 8.49 (1H, d, J = 2.1 Hz), 13.00 (1H, br s). | 416 | 414 |
| 43 | 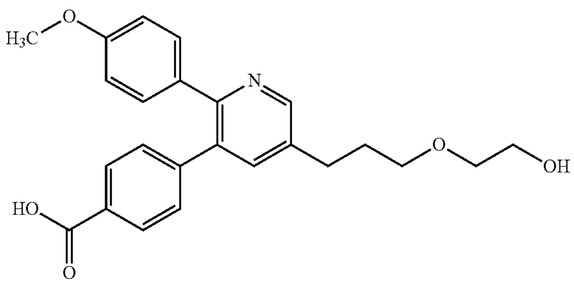 [SMILES: COc1ccc(-c2ncc(CCCOCCO)cc2-c2ccc(C(=O)O)cc2)cc1] | 1H-NMR (DMSO-D6) δ: 1.81-1.92 (2H, m), 2.72 (2H, t, J = 7.6 Hz), 3.36-3.53 (6H, m), 3.71 (3H, s), 4.56 (1H, t, J = 5.3 Hz), 6.80 (2H, d, J = 9.0 Hz), 7.19 (2H, d, J = 8.8 Hz), 7.30 (2H, d, J = 8.3 Hz), 7.64 (1H, d, J = 2.1 Hz), 7.85 (2H, d, J = 8.6 Hz), 8.51 (1H, d, J = 2.1 Hz), 12.97 (1H, br s). | 408 | 406 |
| 44 | 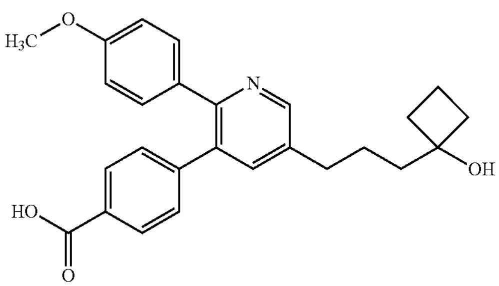 [SMILES: COc1ccc(-c2ncc(CCCC3(O)CCC3)cc2-c2ccc(C(=O)O)cc2)cc1] | 1H-NMR (DMSO-D6) δ: 1.32-1.47 (1H, m), 1.49-1.74 (5H, m), 1.89 (4H, dd, J = 8.8, 6.5 Hz), 2.68 (2H, t, J = 7.5 Hz), 3.71 (3H, s), 4.75 (1H, s), 6.80 (2H, d, J = 9.0 Hz), 7.19 (2H, d, J = 8.8 Hz), 7.30 (2H, d, J = 8.6 Hz), 7.63 (1H, d, J = 2.3 Hz), 7.85 (2H, d, J = 8.6 Hz), 8.51 (1H, d, J = 2.1 Hz), 12.96 (1H, br s). | 418 | 416 |
| 45 | 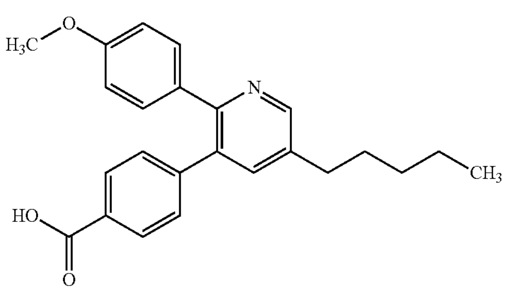 [SMILES: CCCCCc1cnc(-c2ccc(OC)cc2)c(-c2ccc(C(=O)O)cc2)c1] | 1H-NMR (DMSO-D6) δ: 0.87 (3H, t, J = 6.9 Hz), 1.28-1.36 (4H, m), 1.60-1.68 (2H, m), 2.66 (2H, t, J = 7.7 Hz), 3.71 (3H, s), 6.79 (2H, dt, J = 9.4, 2.5 Hz), 7.19 (2H, dt, J = 9.3, 2.5 Hz), 7.30 (2H, dd, J = 6.6, 1.7 Hz), 7.62 (1H, d, J = 2.1 Hz), 7.85 (2H, dd, J = 6.7, 1.8 Hz), 8.50 (1H, d, J = 2.1 Hz), 12.97 (1H, br s). | 374 | 376 |
| 46 | 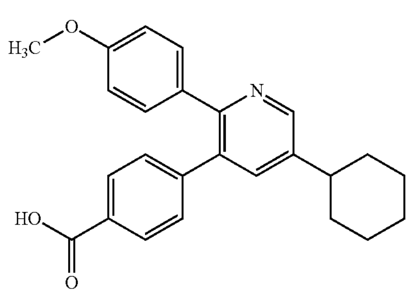 [SMILES: COc1ccc(-c2ncc(C3CCCCC3)cc2-c2ccc(C(=O)O)cc2)cc1] | 1H-NMR (DMSO-D6) δ: 1.17-1.58 (5H, m), 1.65-1.90 (5H, m), 2.58-2.70 (1H, m), 3.71 (3H, s), 6.79 (2H, d, J = 8.8 Hz), 7.18 (2H, d, J = 8.8 Hz), 7.30 (2H, d, J = 8.6 Hz), 7.62 (1H, d, J = 2.3 Hz), 7.85 (2H, d, J = 8.6 Hz), 8.53 (1H, d, J = 2.1 Hz), 13.00 (1H, s). | 388 | 386 |

TABLE 1-6-continued

| Ex. | Structure | NMR | MS (M + H) | MS (M − H) |
|---|---|---|---|---|
| 47 | 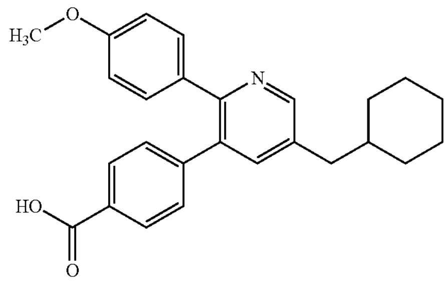 [SMILES: COc1ccc(-c2ncc(CC3CCCCC3)cc2-c2ccc(C(=O)O)cc2)cc1] | 1H-NMR (DMSO-D6) δ: 0.92-1.22 (5H, m), 1.55-1.67 (6H, m), 2.55 (2H, d, J = 6.9 Hz), 3.71 (3H, s), 6.79 (2H, dt, J = 9.5, 2.4 Hz), 7.19 (2H, dt, J = 9.4, 2.5 Hz), 7.26 (2H, d, J = 8.3 Hz), 7.57 (1H, d, J = 2.1 Hz), 7.84 (2H, d, J = 8.3 Hz), 8.44 (1H, d, J = 2.1 Hz), 13.13 (1H, br s). | 400 | 402 |
| 48 | 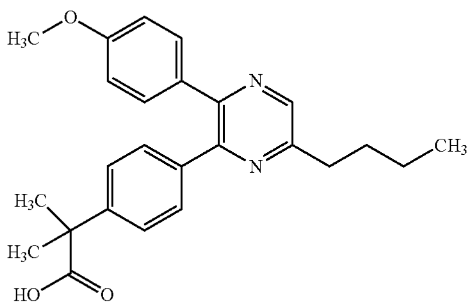 [SMILES: CCCCc1cnc(-c2ccc(OC)cc2)c(-c2ccc(C(C)(C)C(=O)O)cc2)n1] | 1H-NMR (DMSO-D6) δ: 0.93 (3H, t, J = 7.9 Hz), 1.34-1.44 (2H, m), 1.47 (6H, s), 1.69-1.77 (2H, m), 2.83 (2H, t, J = 7.6 Hz), 3.76 (3H, s), 6.88 (2H, d, J = 9.0 Hz), 7.30-7.38 (6H, m), 8.53 (1H, s), 12.36 (1H, s). | 405 | 359 (—COOH) |

TABLE 1-7

| Ex. | Structure | NMR | MS (M + H) | MS (M − H) |
|---|---|---|---|---|
| 49 | 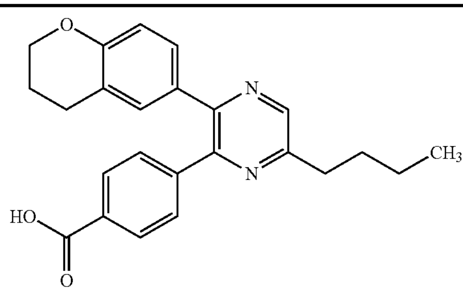 | 1H-NMR (DMSO-D6) δ: 0.93 (3H, t, J = 7.5 Hz), 1.34-1.44 (2H, m), 1.69-1.77 (2H, m), 1.86-1.93 (2H, m), 2.66 (2H, t, J = 6.3 Hz), 2.85 (2H, t, J = 7.6 Hz), 4.14 (2H, t, J = 4.9 Hz), 6.60 (1H, d, J = 8.4 Hz), 6.92 (1H, dd, J = 8.5, 1.9 Hz), 7.23 (1H, d, J = 1.9 Hz), 7.52 (2H, d, J = 8.6 Hz), 7.91 (2H, d, J = 8.6 Hz), 8.58 (1H, s), 13.05 (1H, br s). | 389 | 387 |
| 50 | 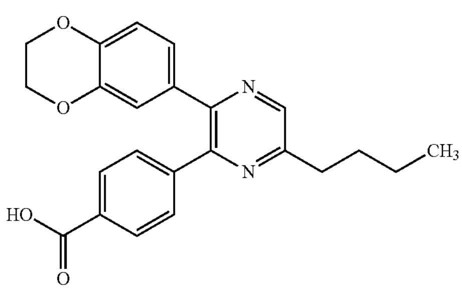 [SMILES: CCCCc1cnc(-c2ccc3c(c2)OCCO3)c(-c2ccc(C(=O)O)cc2)n1] | 1H-NMR (DMSO-D6) δ: 0.93 (3H, t, J = 7.3 Hz), 1.34-1.44 (2H, m), 1.69-1.77 (2H, m), 2.85 (2H, t, J = 7.8 Hz), 4.19-4.26 (4H, m), 6.74-6.79 (2H, m), 6.92 (1H, br s), 7.52 (2H, d, J = 8.1 Hz), 7.91 (2H, d, J = 8.1 Hz), 8.59 (1H, s), 13.07 (1H, br s). | 391 | 389 |
| 51 | 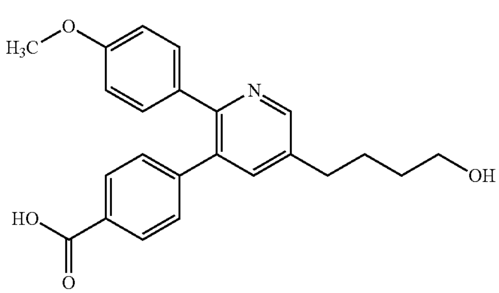 [SMILES: COc1ccc(-c2ncc(CCCCO)cc2-c2ccc(C(=O)O)cc2)cc1] | 1H-NMR (DMSO-D6) δ: 1.42-1.53 (2H, m), 1.60-1.72 (2H, m), 2.67 (2H, t, J = 7.6 Hz), 3.38-3.46 (2H, m), 3.71 (3H, s), 4.38 (1H, br s), 6.79 (2H, d, J = 8.8 Hz), 7.19 (2H, d, J = 8.8 Hz), 7.30 (2H, d, J = 8.6 Hz), 7.63 (1H, d, J = 2.1 Hz), 7.85 (2H, d, J = 8.6 Hz), 8.50 (1H, d, J = 2.1 Hz), 12.97 (1H, br s). | 378 | 376 |

TABLE 1-7-continued

| Ex. | Structure | NMR | MS (M + H) | MS (M − H) |
|---|---|---|---|---|
| 52 | 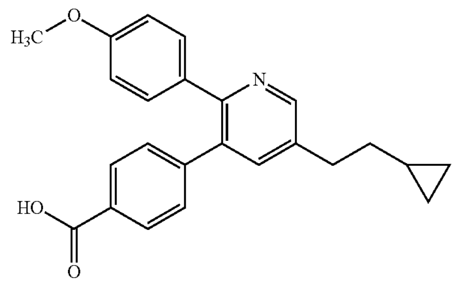 [SMILES: COc1ccc(-c2ncc(CCC3CC3)cc2-c2ccc(C(=O)O)cc2)cc1] | 1H-NMR (DMSO-D6) δ: 0.03-0.11 (2H, m), 0.37-0.45 (2H, m), 0.66-0.80 (1H, m), 1.54 (2H, dd, J = 15.4, 7.1 Hz), 2.74 (2H, dd, J = 14.4, 6.6 Hz), 3.71 (3H, s), 6.79 (2H, d, J = 8.8 Hz), 7.18 (2H, d, J = 8.8 Hz), 7.29 (2H, d, J = 8.6 Hz), 7.64 (1H, d, J = 2.1 Hz), 7.85 (2H, d, J = 8.6 Hz), 8.51 (1H, d, J = 2.3 Hz), 12.99 (1H, br s). | 374 | 372 |
| 53 | 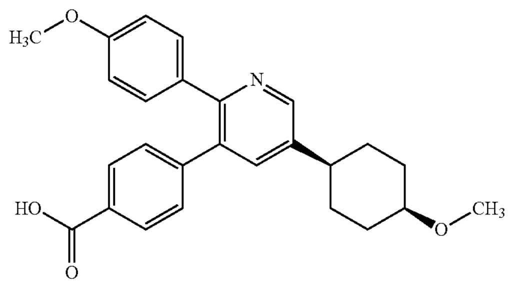 | 1H-NMR (DMSO-D6) δ: 1.50-1.57 (2H, m), 1.61-1.67 (2H, m), 1.71-1.82 (2H, m), 1.95-2.02 (2H, m), 2.67-2.76 (1H, m), 3.25 (3H, s), 3.49 (1H, br s), 3.72 (3H, s), 6.81 (2H, d, J = 8.4 Hz), 7.20 (2H, d, J = 8.4 Hz), 7.32 (2H, d, J = 8.1 Hz), 7.58 (1H, d, J = 1.7 Hz), 7.87 (2H, d, J = 8.1 Hz), 8.54 (1H, d, J = 1.7 Hz), 13.00 (1H, br s). | 418 | 416 |
| 54 | 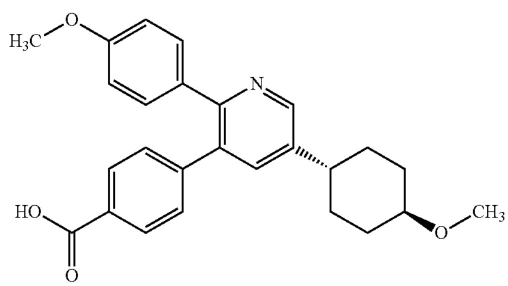 | 1H-NMR (DMSO-D6) δ: 1.20-1.32 (2H, m), 1.55-1.67 (2H, m), 1.87-1.95 (2H, m), 2.09-2.16 (2H, m), 2.61-2.70 (1H, m), 3.15-3.25 (1H, m), 3.27 (3H, s), 3.72 (3H, s), 6.81 (2H, d, J = 8.4 Hz), 7.20 (2H, d, J = 8.4 Hz), 7.31 (2H, d, J = 8.0 Hz), 7.65 (1H, d, J = 1.5 Hz), 7.86 (2H, d, J = 8.0 Hz), 8.56 (1H, d, J = 1.5 Hz), 13.00 (1H, br s). | 418 | 416 |
| 55 | 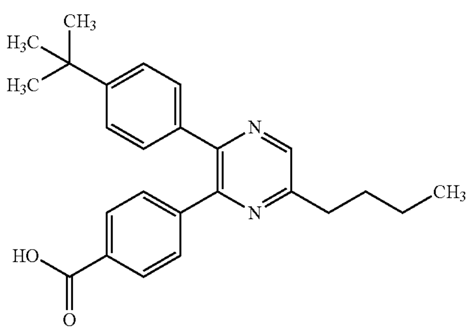 [SMILES: CCCCc1cnc(-c2ccc(C(C)(C)C)cc2)c(-c2ccc(C(=O)O)cc2)n1] | 1H-NMR (DMSO-D6) δ: 0.92 (3H, t, J = 7.3 Hz), 1.25 (9H, s), 1.33-1.43 (2H, m), 1.68-1.77 (2H, m), 2.86 (2H, t, J = 7.7 Hz), 7.30 (2H, d, J = 8.8 Hz), 7.33 (2H, d, J = 8.8 Hz), 7.49 (2H, d, J = 8.3 Hz), 7.87 (2H, d, J = 8.3 Hz), 8.62 (1H, s), 13.08 (1H, br s). | 389 | 387 |
| 56 | 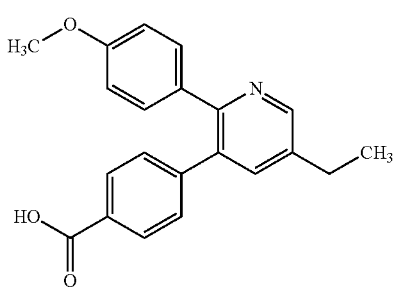 [SMILES: CCc1cnc(-c2ccc(OC)cc2)c(-c2ccc(C(=O)O)cc2)c1] | 1H-NMR (DMSO-D6) δ: 1.26 (3H, t, J = 7.7 Hz), 2.71 (2H, q, J = 7.7 Hz), 3.72 (3H, s), 6.81 (2H, d, J = 9.0 Hz), 7.20 (2H, d, J = 9.0 Hz), 7.32 (2H, d, J = 8.6 Hz), 7.66 (1H, d, J = 2.1 Hz), 7.87 (2H, d, J = 8.6 Hz), 8.54 (1H, d, J = 2.1 Hz), 12.99 (1H, br s). | 334 | 332 |

TABLE 1-8

| Ex. | Structure | NMR | MS (M + H) | MS (M − H) |
|---|---|---|---|---|
| 57 | 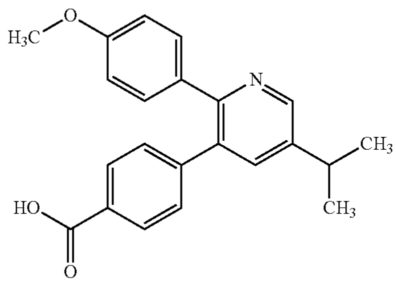 [SMILES: COc1ccc(-c2ncc(C(C)C)cc2-c2ccc(C(=O)O)cc2)cc1] | 1H-NMR (DMSO-D6) δ: 1.30 (6H, d, J = 6.9 Hz), 2.99-3.10 (1H, m), 3.72 (3H, s), 6.81 (2H, d, J = 8.9 Hz), 7.20 (2H, d, J = 8.9 Hz), 7.33 (2H, d, J = 8.1 Hz), 7.67 (1H, d, J = 2.1 Hz), 7.87 (2H, d, J = 8.1 Hz), 8.58 (1H, d, J = 2.1 Hz), 12.99 (1H, br s). | 348 | 346 |
| 58 | 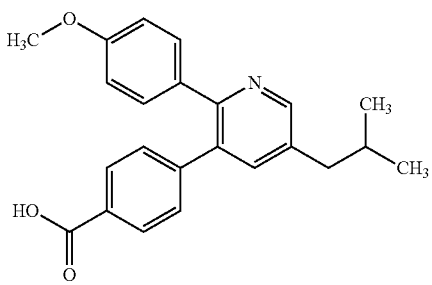 [SMILES: COc1ccc(-c2ncc(CC(C)C)cc2-c2ccc(C(=O)O)cc2)cc1] | 1H-NMR (DMSO-D6) δ: 0.93 (6H, d, J = 6.6 Hz), 1.87-1.99 (1H, m), 2.56 (2H, d, J = 7.2 Hz), 3.72 (3H, s), 6.81 (2H, d, J = 8.9 Hz), 7.21 (2H, d, J = 8.9 Hz), 7.32 (2H, d, J = 8.7 Hz), 7.61 (1H, d, J = 2.1 Hz), 7.87 (2H, d, J = 8.7 Hz), 8.48 (1H, d, J = 2.1 Hz), 12.99 (1H, br s). | 362 | 360 |
| 59 | 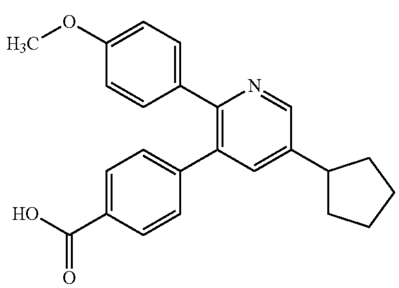 [SMILES: COc1ccc(-c2ncc(C3CCCC3)cc2-c2ccc(C(=O)O)cc2)cc1] | 1H-NMR (DMSO-D6) δ: 1.58-1.87 (6H, m), 2.04-2.15 (2H, m), 3.04-3.15 (1H, m), 3.72 (3H, s), 6.81 (2H, d, J = 9.0 Hz), 7.20 (2H, d, J = 9.0 Hz), 7.32 (2H, d, J = 8.6 Hz), 7.65 (1H, d, J = 2.1 Hz), 7.87 (2H, d, J = 8.6 Hz), 8.57 (1H, d, J = 2.1 Hz), 12.99 (1H, br s). | 374 | 372 |
| 60 | 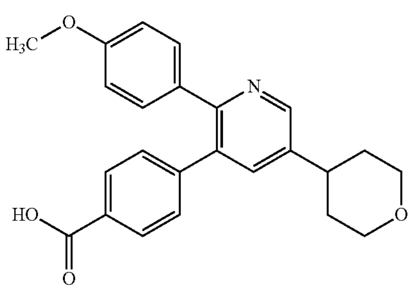 [SMILES: COc1ccc(-c2ncc(C3CCOCC3)cc2-c2ccc(C(=O)O)cc2)cc1] | 1H-NMR (DMSO-D6) δ: 1.74-1.83 (4H, m), 2.88-2.99 (1H, m), 3.41-3.52 (2H, m), 3.72 (3H, s), 3.94-4.01 (2H, m), 6.81 (2H, d, J = 9.0 Hz), 7.20 (2H, d, J = 9.0 Hz), 7.33 (2H, d, J = 8.2 Hz), 7.67 (1H, br s), 7.87 (2H, d, J = 8.2 Hz), 8.59 (1H, br s), 12.91 (1H, br s). | 390 | 388 |
| 61 | 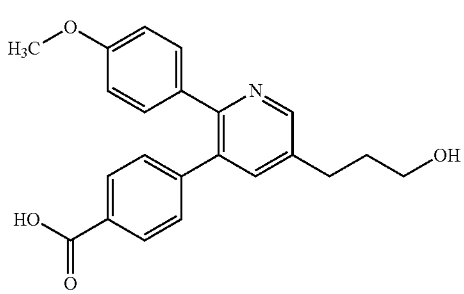 [SMILES: COc1ccc(-c2ncc(CCCO)cc2-c2ccc(C(=O)O)cc2)cc1] | 1H-NMR (DMSO-D6) δ: 1.75-1.84 (2H, m), 2.68-2.75 (2H, m), 3.42-3.49 (2H, m), 3.72 (3H, s), 4.51-4.56 (1H, m), 6.81 (2H, d, J = 9.0 Hz), 7.20 (2H, d, J = 9.0 Hz), 7.32 (2H, d, J = 8.1 Hz), 7.64 (1H, br s), 7.87 (2H, d, J = 8.1 Hz), 8.52 (1H, br s), 12.99 (1H, br s). | 364 | 362 |

TABLE 1-8-continued

| Ex. | Structure | NMR | MS (M + H) | MS (M − H) |
|---|---|---|---|---|
| 62 | 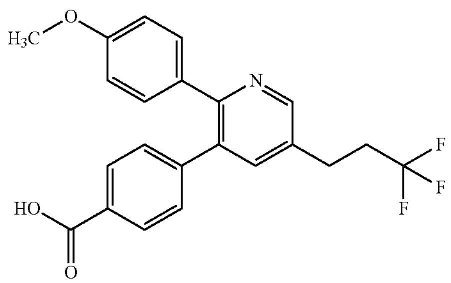 [SMILES: COc1ccc(-c2ncc(CCC(F)(F)F)cc2-c2ccc(C(=O)O)cc2)cc1] | 1H-NMR (DMSO-D6) δ: 2.66-2.79 (2H, m), 2.93 (2H, dd, J = 9.8, 6.4 Hz), 3.71 (3H, s), 6.80 (2H, d, J = 8.8 Hz), 7.19 (2H, d, J = 8.8 Hz), 7.31 (2H, d, J = 8.6 Hz), 7.79 (1H, d, J = 2.1 Hz), 7.86 (2H, d, J = 8.3 Hz), 8.59 (1H, d, J = 2.3 Hz), 13.01 (1H, br s). | 402 | 400 |
| 63 | 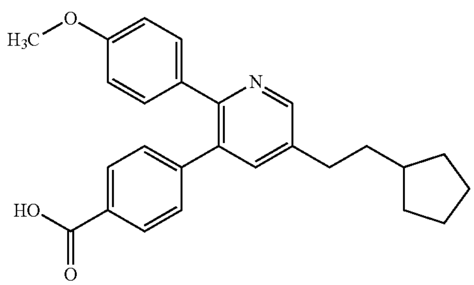 [SMILES: COc1ccc(-c2ncc(CCC3CCCC3)cc2-c2ccc(C(=O)O)cc2)cc1] | 1H-NMR (DMSO-D6) δ: 1.06-1.22 (2H, m), 1.40-1.70 (6H, m), 1.70-1.85 (3H, m), 2.67 (2H, t, J = 7.9 Hz), 3.71 (3H, s), 6.79 (2H, d, J = 9.0 Hz), 7.18 (2H, d, J = 9.0 Hz), 7.29 (2H, d, J = 8.6 Hz), 7.63 (1H, d, J = 2.1 Hz), 7.85 (2H, d, J = 8.3 Hz), 8.50 (1H, d, J = 2.1 Hz), 13.01 (1H, br s). | 402 | 400 |
| 64 | 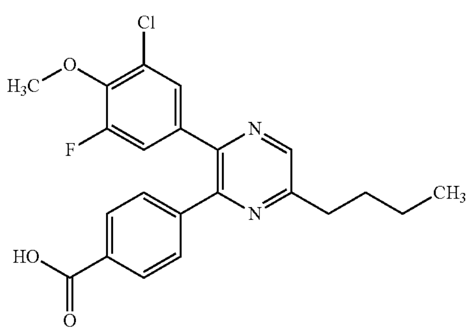 | 1H-NMR (DMSO-D6) δ: 0.92 (3H, t, J = 7.3 Hz), 1.32-1.44 (2H, m), 1.68-1.78 (2H, m), 2.87 (2H, t, J = 7.7 Hz), 3.90 (3H, d, J = 1.6 Hz), 7.21 (1H, dd, J = 11.9, 2.0 Hz), 7.29 (1H, t, J = 1.7 Hz), 7.53 (2H, d, J = 8.3 Hz), 7.93 (2H, d, J = 8.6 Hz), 8.65 (1H, s), 13.09 (1H, br s). | 415 | 413 |

TABLE 1-9

| Ex. | Structure | NMR | MS (M + H) | MS (M − H) |
|---|---|---|---|---|
| 65 | 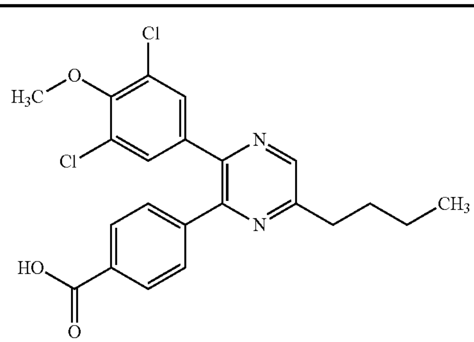 | 1H-NMR (DMSO-D6) δ: 0.92 (3H, t, J = 7.4 Hz), 1.32-1.44 (2H, m), 1.68-1.78 (2H, m), 2.88 (2H, t, J = 7.7 Hz), 3.82 (3H, s), 7.42 (2H, s), 7.53 (2H, d, J = 8.6 Hz), 7.93 (2H, d, J = 8.6 Hz), 8.65 (1H, s), 13.13 (1H, br s). | 431 | 429 |

TABLE 1-9-continued

| Ex. | Structure | NMR | MS (M + H) | MS (M − H) |
|---|---|---|---|---|
| 66 | 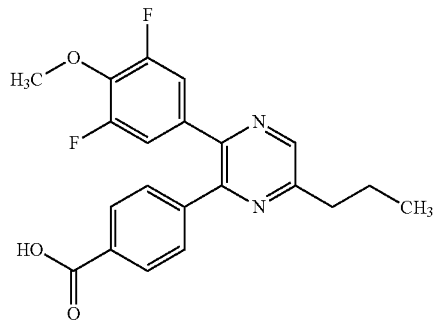 [SMILES: CCCc1cnc(-c2cc(F)c(OC)c(F)c2)c(-c2ccc(C(=O)O)cc2)n1] | 1H-NMR (DMSO-D6) δ: 0.96 (3H, t, J = 7.4 Hz), 1.71-1.83 (2H, m), 2.85 (2H, t, J = 7.6 Hz), 3.93 (3H, s), 7.09 (2H, d, J = 9.5 Hz), 7.52 (2H, d, J = 8.6 Hz), 7.92 (2H, d, J = 8.6 Hz), 8.64 (1H, s), 13.11 (1H, br s). | 385 | 383 |
| 67 | 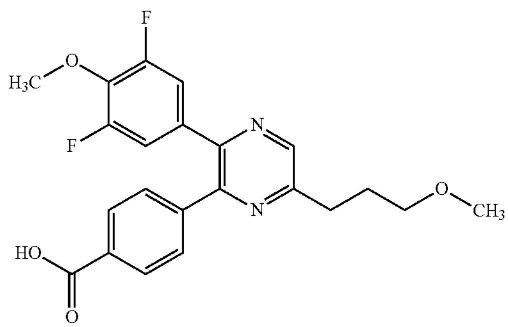 | 1H-NMR (DMSO-D6) δ: 1.92-2.02 (2H, m), 2.91 (2H, t, J = 7.7 Hz), 3.24 (3H, s), 3.40 (2H, t, J = 6.4 Hz), 3.93 (3H, s), 7.09 (2H, d, J = 9.5 Hz), 7.53 (2H, d, J = 8.6 Hz), 7.92 (2H, d, J = 8.6 Hz), 8.64 (1H, s), 13.10 (1H, s). | 415 | 413 |
| 68 | 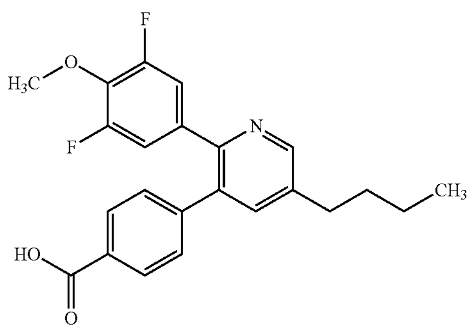 [SMILES: CCCCc1cnc(-c2cc(F)c(OC)c(F)c2)c(-c2ccc(C(=O)O)cc2)c1] | 1H-NMR (DMSO-D6) δ: 0.91 (3H, t, J = 7.4 Hz), 1.29-1.39 (2H, m), 1.58-1.66 (2H, m), 2.65-2.71 (2H, m), 3.90 (3H, s), 6.95 (2H, d, J = 9.7 Hz), 7.34 (2H, dd, J = 6.7, 1.8 Hz), 7.70 (1H, d, J = 2.3 Hz), 7.90 (2H, dd, J = 6.5, 1.8 Hz), 8.54 (1H, d, J = 2.1 Hz), 13.04 (1H, br s). | 396 | 398 |
| 69 | 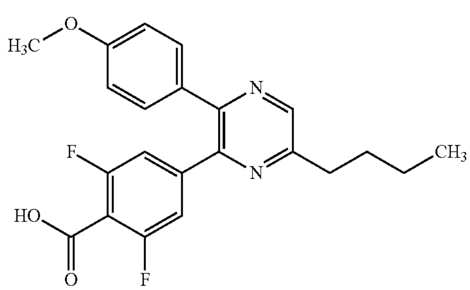 [SMILES: CCCCc1cnc(-c2ccc(OC)cc2)c(-c2cc(F)c(C(=O)O)c(F)c2)n1] | 1H-NMR (DMSO-D6) δ: 0.94 (3H, t, J = 7.4 Hz), 1.35-1.44 (2H, m), 1.70-1.78 (2H, m), 2.87 (2H, t, J = 7.7 Hz), 3.78 (3H, s), 6.95 (2H, dt, J = 9.4, 2.5 Hz), 7.18 (2H, d, J = 9.0 Hz), 7.36 (2H, dt, J = 9.4, 2.5 Hz), 8.65 (1H, s), 14.03 (1H, s). | 399 | 353 (—COOH) |
| 70 | 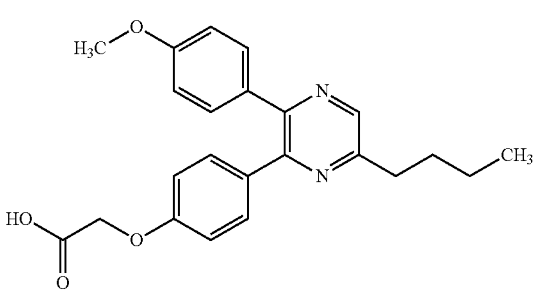 [SMILES: CCCCc1cnc(-c2ccc(OC)cc2)c(-c2ccc(OCC(=O)O)cc2)n1] | 1H-NMR (DMSO-D6) δ: 0.93 (3H, t, J = 7.4 Hz), 1.34-1.43 (2H, m), 1.69-1.77 (2H, m), 2.82 (2H, t, J = 7.6 Hz), 3.76 (3H, s), 4.69 (2H, s), 6.86-6.91 (4H, m), 7.35-7.31 (4H, m), 8.49 (1H, s), 13.02 (1H, s). | 393 | 391 |

TABLE 1-9-continued

| Ex. | Structure | NMR | MS (M + H) | MS (M − H) |
|---|---|---|---|---|
| 71 | 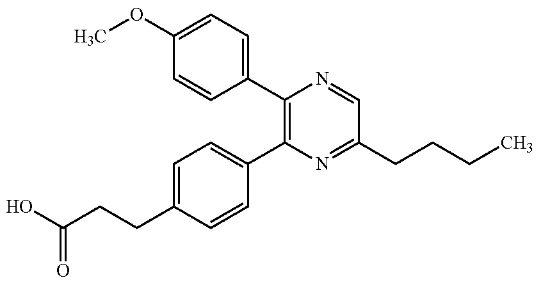 [SMILES: CCCCc1cnc(-c2ccc(OC)cc2)c(-c2ccc(CCC(=O)O)cc2)n1] | 1H-NMR (DMSO-D6) δ: 0.93 (3H, t, J = 7.3 Hz), 1.33-1.43 (2H, m), 1.68-1.76 (2H, m), 2.23 (2H, t, J = 7.7 Hz), 2.76 (2H, t, J = 7.7 Hz), 2.82 (2H, t, J = 7.7 Hz), 3.75 (3H, s), 6.87 (2H, dt, J = 9.5, 2.5 Hz), 7.15 (2H, d, J = 8.1 Hz), 7.27 (2H, d, J = 8.1 Hz), 7.31 (2H, dt, J = 9.4, 2.5 Hz), 8.50 (1H, s). | 391 | 389 |
| 72 | 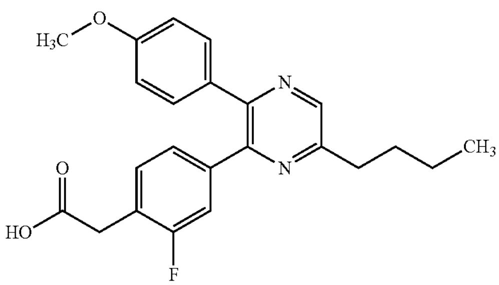 [SMILES: CCCCc1cnc(-c2ccc(OC)cc2)c(-c2ccc(CC(=O)O)c(F)c2)n1] | 1H-NMR (DMSO-D6) δ: 0.93 (3H, t, J = 7.4 Hz), 1.34-1.42 (2H, m), 1.70-1.77 (2H, m), 2.84 (2H, t, J = 7.6 Hz), 3.22 (2H, br s), 3.76 (3H, s), 6.91 (2H, dt, J = 9.4, 2.5 Hz), 7.03-7.10 (2H, m), 7.20 (1H, t, J = 7.7 Hz), 7.35 (2H, dt, J = 9.4, 2.5 Hz), 8.53 (1H, s). | 395 | 349 (—COOH) |

TABLE 1-10

| Ex. | Structure | NMR | MS (M + H) | MS (M − H) |
|---|---|---|---|---|
| 73 | 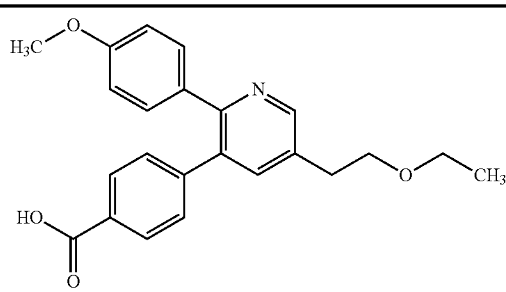 | 1H-NMR (DMSO-D6) δ: 1.10 (3H, t, J = 7.0 Hz), 2.91 (2H, t, J = 6.7 Hz), 3.46 (2H, q, J = 7.0 Hz), 3.66 (2H, t, J = 6.7 Hz), 3.72 (3H, s), 6.81 (2H, d, J = 8.8 Hz), 7.20 (2H, d, J = 8.8 Hz), 7.31 (2H, d, J = 8.5 Hz), 7.70 (1H, d, J = 2.2 Hz), 7.87 (2H, d, J = 8.5 Hz), 8.54 (1H, d, J = 2.2 Hz), 12.99 (1H, br s). | 378 | 376 |
| 74 | 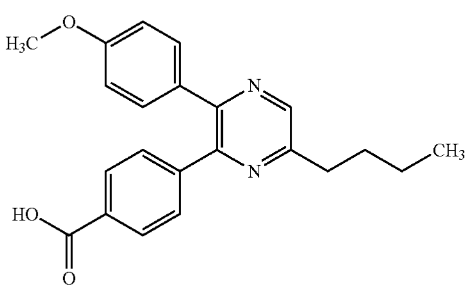 [SMILES: CCCCc1cnc(-c2ccc(OC)cc2)c(-c2ccc(C(=O)O)cc2)n1] | 1H-NMR (DMSO-D6) δ: 0.94 (3H, t, J = 7.3 Hz), 1.17 (3H, t, J = 7.6 Hz), 1.33-1.46 (2H, m), 1.69-1.79 (2H, m), 2.60 (2H, q, J = 7.6 Hz), 2.87 (2H, t, J = 7.8 Hz), 7.17 (2H, d, J = 8.1 Hz), 7.29 (2H, d, J = 8.1 Hz), 7.50 (2H, d, J = 8.1 Hz), 7.88 (2H, d, J = 8.1 Hz), 8.63 (1H, s), 13.09 (1H, br s). | 361 | 359 |
| 75 | 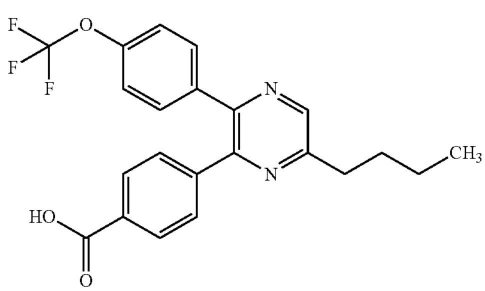 [SMILES: CCCCc1cnc(-c2ccc(OC(F)(F)F)cc2)c(-c2ccc(C(=O)O)cc2)n1] | 1H-NMR (DMSO-D6) δ: 0.94 (3H, t, J = 7.3 Hz), 1.34-1.46 (2H, m), 1.69-1.81 (2H, m), 2.90 (2H, t, J = 7.6 Hz), 7.34 (2H, d, J = 8.4 Hz), 7.46-7.53 (4H, m), 7.90 (2H, d, J = 8.1 Hz), 8.67 (1H, s), 13.11 (1H, br s). | 417 | 415 |

TABLE 1-10-continued

| Ex. | Structure | NMR | MS (M + H) | MS (M − H) |
|---|---|---|---|---|
| 76 | 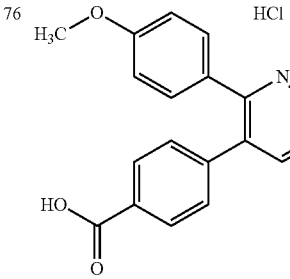 | 1H-NMR (DMSO-D6) δ: 0.91 (3H, t, J = 7.4 Hz), 1.32-1.40 (2H, m), 1.50-1.57 (2H, m), 3.31 (2H, dd, J = 12.8, 6.8 Hz), 3.74 (3H, d, J = 0.7 Hz), 6.86 (2H, dd, J = 8.9, 2.9 Hz), 7.28 (2H, dd, J = 8.8, 1.6 Hz), 7.39 (2H, d, J = 8.1 Hz), 7.91 (2H, d, J = 8.1 Hz), 8.25 (1H, br s), 8.74 (1H, br s), 9.07 (1H, s). | 405 | 403 |
| 77 | 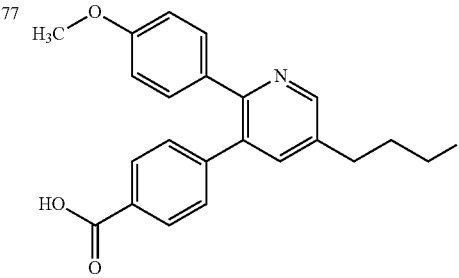 | 1H-NMR (DMSO-D6) δ: 1.11 (3H, t, J = 7.0 Hz), 1.83-1.92 (2H, m), 2.70-2.76 (2H, m), 3.38-3.46 (4H, m), 3.72 (3H, s), 6.81 (2H, d, J = 8.8 Hz), 7.20 (2H, d, J = 8.8 Hz), 7.32 (2H, d, J = 8.6 Hz), 7.65 (1H, d, J = 2.2 Hz), 7.87 (2H, d, J = 8.6 Hz), 8.52 (1H, d, J = 2.2 Hz), 12.98 (1H, br s). | 392 | 390 |
| 78 | 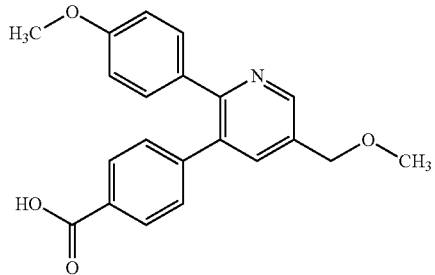 | 1H-NMR (DMSO-D6) δ: 3.36 (3H, s), 3.73 (3H, s), 4.55 (2H, s), 6.82 (2H, d, J = 8.8 Hz), 7.23 (2H, d, J = 8.8 Hz), 7.33 (2H, d, J = 8.6 Hz), 7.74 (1H, d, J = 2.1 Hz), 7.88 (2H, d, J = 8.6 Hz), 8.62 (1H, d, J = 2.1 Hz), 13.01 (1H, br s). | 350 | 348 |
| 79 | 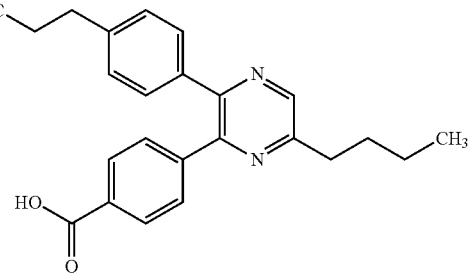 | 1H-NMR (DMSO-D6) δ: 0.86 (3H, t, J = 7.3 Hz), 0.92 (3H, t, J = 7.3 Hz), 1.33-1.43 (2H, m), 1.50-1.62 (2H, m), 1.68-1.78 (2H, m), 2.53 (2H, t, J = 7.6 Hz), 2.86 (2H, t, J = 7.7 Hz), 7.13 (2H, d, J = 8.3 Hz), 7.26 (2H, d, J = 8.1 Hz), 7.47 (2H, d, J = 8.6 Hz), 7.85 (2H, d, J = 8.3 Hz), 8.61 (1H, s), 13.04 (1H, s). | 375 | 373 |
| 80 | 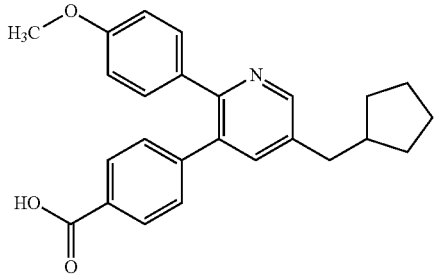 [SMILES: COc1ccc(-c2ncc(CC3CCCC3)cc2-c2ccc(C(=O)O)cc2)cc1] | 1H-NMR (DMSO-D6) δ: 1.16-1.26 (2H, m), 1.45-1.55 (2H, m), 1.58-1.73 (4H, m), 2.10-2.17 (1H, m), 2.67 (2H, d, J = 7.4 Hz), 3.71 (3H, s), 6.79 (2H, dt, J = 9.5,2.5 Hz), 7.19 (2H, dt, J = 9.4, 2.5 Hz), 7.30 (2H, dt, J = 8.4, 1.8 Hz), 7.62 (1H, d, J = 2.1 Hz), 7.85 (2H, dt, J = 8.5, 1.8 Hz), 8.49 (1H, d, J = 2.1 Hz), 12.97 (1H, br s). | 386 | 388 |

TABLE 1-11

| Ex. | Structure | NMR | MS (M + H) | MS (M − H) |
|---|---|---|---|---|
| 81 | 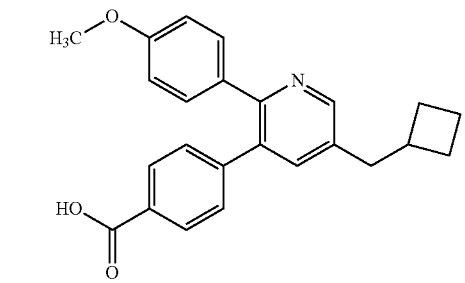 [SMILES: COc1ccc(-c2ncc(CC3CCC3)cc2-c2ccc(C(=O)O)cc2)cc1] | 1H-NMR (DMSO-D6) δ: 1.70-1.86 (4H, m), 1.96-2.05 (2H, m), 2.57-2.66 (1H, m), 2.76 (2H, d, J = 7.4 Hz), 3.71 (3H, s), 6.79 (2H, dt, J = 9.5, 2.4 Hz), 7.18 (2H, dt, J = 9.4, 2.5 Hz), 7.29 (2H, dt, J = 8.4, 1.7 Hz), 7.58 (1H, d, J = 2.1 Hz), 7.85 (2H, dt, J = 8.4, 1.8 Hz), 8.47 (1H, d, J = 2.1 Hz), 12.97 (1H, br s). | 372 | 374 |
| 82 | 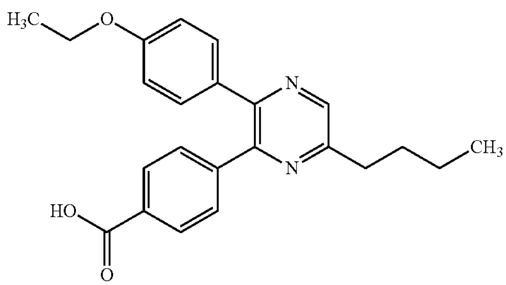 | 1H-NMR (DMSO-D6) δ: 0.92 (3H, t, J = 7.4 Hz), 1.29 (3H, t, J = 7.1 Hz), 1.32-1.43 (2H, m), 1.66-1.77 (2H, m), 2.84 (2H, t, J = 7.6 Hz), 4.00 (2H, q, J = 6.9 Hz), 6.85 (2H, d, J = 8.8 Hz), 7.28 (2H, d, J = 8.8 Hz), 7.47 (2H, d, J = 8.6 Hz), 7.87 (2H, d, J = 8.6 Hz), 8.58 (1H, s), 13.13 (1H, br s). | 377 | 375 |
| 83 | 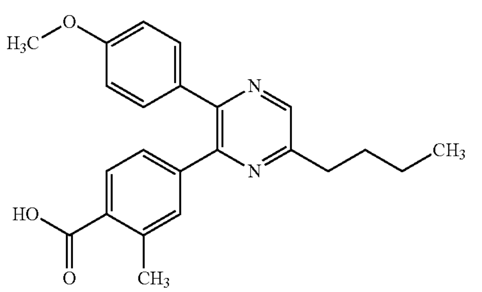 [SMILES: CCCCc1cnc(-c2ccc(OC)cc2)c(-c2ccc(C(=O)O)c(C)c2)n1] | 1H-NMR (DMSO-D6) δ: 0.94 (3H, t, J = 7.4 Hz), 1.35-1.42 (2H, m), 1.69-1.77 (2H, m), 2.48 (3H, s), 2.85 (2H, t, J = 7.7 Hz), 3.75 (3H, s), 6.89 (2H, dt, J = 9.4, 2.5 Hz), 7.18 (1H, dd, J = 8.1, 1.6 Hz), 7.32 (2H, dt, J = 9.4, 2.5 Hz), 7.41 (1H, d, J = 1.6 Hz), 7.72 (1H, d, J = 8.1 Hz), 8.59 (1H, s), 12.92 (1H, br s). | 377 | 375 |
| 84 | 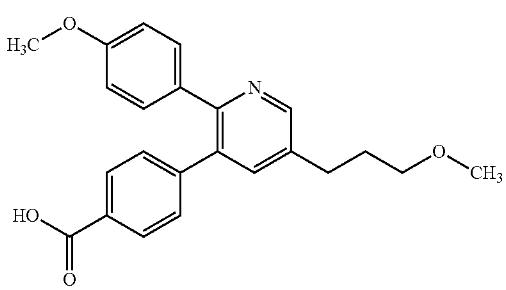 | 1H-NMR (DMSO-D6) δ: 1.84-1.93 (2H, m), 2.72 (2H, t, J = 7.8 Hz), 3.25 (3H, s), 3.38 (2H, t, J = 6.4 Hz), 3.72 (3H, s), 6.81 (2H, d, J = 8.8 Hz), 7.20 (2H, d, J = 8.8 Hz), 7.32 (2H, d, J = 8.3 Hz), 7.65 (1H, d, J = 2.2 Hz), 7.87 (2H, d, J = 8.6 Hz), 8.52 (1H, d, J = 2.2 Hz), 12.99 (1H, br s). | 378 | 376 |
| 85 | 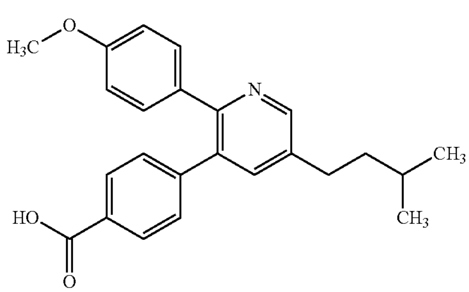 [SMILES: COc1ccc(-c2ncc(CCC(C)C)cc2-c2ccc(C(=O)O)cc2)cc1] | 1H-NMR (DMSO-D6) δ: 0.94 (6H, d, J = 6.4 Hz), 1.50-1.65 (3H, m), 2.68 (2H, t, J = 7.8 Hz), 3.72 (3H, s), 6.81 (2H, d, J = 8.9 Hz), 7.20 (2H, d, J = 8.9 Hz), 7.31 (2H, d, J = 8.3 Hz), 7.65 (1H, d, J = 2.1 Hz), 7.87 (2H, d, J = 8.3 Hz), 8.52 (1H, d, J = 2.1 Hz), 12.99 (1H, br s). | 376 | 374 |

TABLE 1-11-continued

| Ex. | Structure | NMR | MS (M + H) | MS (M − H) |
|---|---|---|---|---|
| 86 | 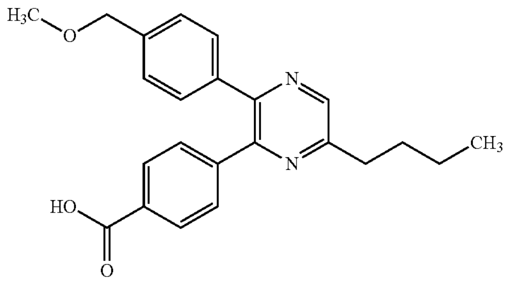 [SMILES: CCCCc1cnc(-c2ccc(COC)cc2)c(-c2ccc(C(=O)O)cc2)n1] | 1H-NMR (DMSO-D6) δ: 0.92 (3H, t, J = 7.3 Hz), 1.32-1.44 (2H, m), 1.68-1.79 (2H, m), 2.87 (2H, t, J = 7.7 Hz), 3.27 (3H, s), 4.39 (2H, s), 7.25 (2H, d, J = 8.6 Hz), 7.33 (2H, d, J = 8.3 Hz), 7.47 (2H, d, J = 8.6 Hz), 7.86 (2H, d, J = 8.6 Hz), 8.63 (1H, s), 13.02 (1H, br s). | 377 | 375 |
| 87 | 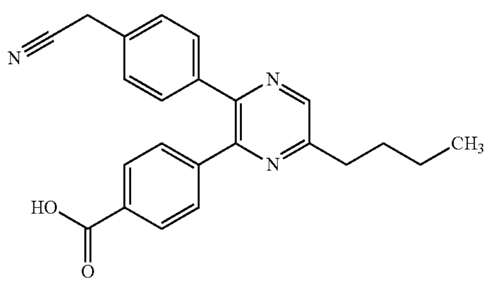 [SMILES: CCCCc1cnc(-c2ccc(CC#N)cc2)c(-c2ccc(C(=O)O)cc2)n1] | 1H-NMR (DMSO-D6) δ: 0.92 (3H, t, J = 7.4 Hz), 1.33-1.45 (2H, m), 1.67-1.79 (2H, m), 2.87 (2H, t, J = 7.7 Hz), 4.04 (2H, s), 7.29 (2H, d, J = 8.6 Hz), 7.38 (2H, d, J = 8.6 Hz), 7.48 (2H, d, J = 8.6 Hz), 7.87 (2H, d, J = 8.6 Hz), 8.64 (1H, s), 13.06 (1H, br s). | 372 | 370 |
| 88 | 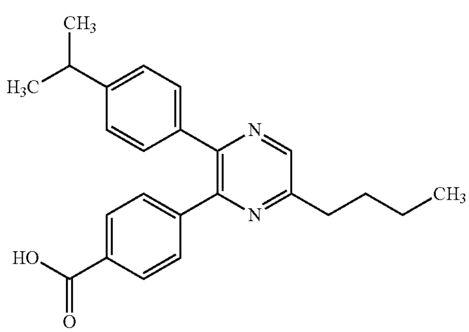 [SMILES: CCCCc1cnc(-c2ccc(C(C)C)cc2)c(-c2ccc(C(=O)O)cc2)n1] | 1H-NMR (DMSO-D6) δ: 0.92 (3H, t, J = 7.4 Hz), 1.17 (6H, d, J = 6.9 Hz), 1.32-1.44 (2H, m), 1.67-1.78 (2H, m), 2.81-2.91 (3H, m), 7.18 (2H, d, J = 8.1 Hz), 7.28 (2H, d, J = 8.3 Hz), 7.49 (2H, d, J = 8.6 Hz), 7.87 (2H, d, J = 8.6 Hz), 8.61 (1H, s), 13.04 (1H, br s). | 375 | 373 |

TABLE 1-12

| Ex. | Structure | NMR | MS (M + H) | MS (M − H) |
|---|---|---|---|---|
| 89 | 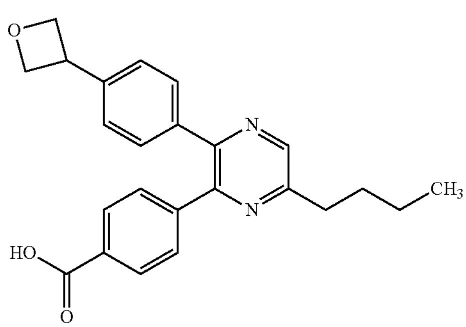 [SMILES: CCCCc1cnc(-c2ccc(C3COC3)cc2)c(-c2ccc(C(=O)O)cc2)n1] | 1H-NMR (DMSO-D6) δ: 0.92 (3H, t, J = 7.3 Hz), 1.33-1.44 (2H, m), 1.67-1.80 (2H, m), 2.87 (2H, t, J = 7.6 Hz), 4.19-4.28 (1H, m), 4.59 (2H, t, J = 6.4 Hz), 4.90 (2H, dd, J = 8.4, 5.9 Hz), 7.34 (2H, d, J = 8.8 Hz), 7.37 (2H, d, J = 8.6 Hz), 7.49 (2H, d, J = 8.6 Hz), 7.87 (2H, d, J = 8.6 Hz), 8.63 (1H, s), 13.05 (1H, br s). | 389 | 387 |

TABLE 1-12-continued

| Ex. | Structure | NMR | MS (M + H) | MS (M − H) |
|---|---|---|---|---|
| 90 | 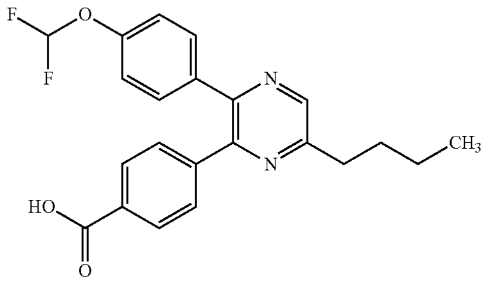 [SMILES: CCCCc1cnc(-c2ccc(OC(F)F)cc2)c(-c2ccc(C(=O)O)cc2)n1] | 1H-NMR (DMSO-D6) δ: 0.94 (3H, t, J = 7.4 Hz), 1.35-1.45 (2H, m), 1.71-1.78 (2H, m), 2.88 (2H, t, J = 7.7 Hz), 7.10-7.15 (2H, m), 7.29 (1H, t, J = 73.5 Hz), 7.42 (2H, dt, J = 9.2, 2.4 Hz), 7.51 (2H, dt, J = 8.4, 1.8 Hz), 7.90 (2H, dt, J = 8.4, 1.8 Hz), 8.65 (1H, s), 13.07 (1H, s). | 399 | 397 |
| 91 | 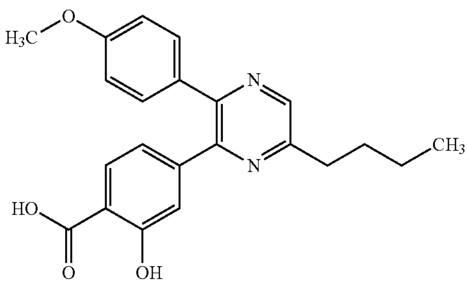 [SMILES: CCCCc1cnc(-c2ccc(OC)cc2)c(-c2ccc(C(=O)O)c(O)c2)n1] | 1H-NMR (DMSO-D6) δ: 0.92 (3H, t, J = 7.3 Hz), 1.31-1.44 (2H, m), 1.66-1.78 (2H, m), 2.84 (2H, t, J = 7.6 Hz), 3.74 (3H, d' (2H, J = 3.7 Hz), 6.83-6.92 (3H, m), 6.97 (1H, d, J = 1.6 Hz), 7.33 (2H, d, J = 9.0 Hz), 7.70 (1H, d, J = 8.1 Hz), 8.58 (1H, s). | 379 | 377 |
| 92 | 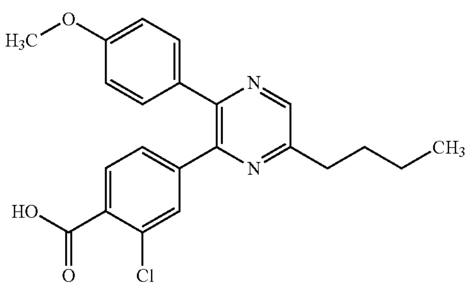 [SMILES: CCCCc1cnc(-c2ccc(OC)cc2)c(-c2ccc(C(=O)O)c(Cl)c2)n1] | 1H-NMR (DMSO-D6) δ: 0.92 (3H, t, J = 7.4 Hz), 1.33-1.44 (2H, m), 1.67-1.77 (2H, m), 2.85 (2H, t, J = 7.6 Hz), 3.75 (3H, s), 6.91 (2H, d, J = 8.8 Hz), 7.29-7.37 (3H, m), 7.57 (1H, d, J = 1.6 Hz), 7.70 (1H, d, J = 7.9 Hz), 8.61 (1H, s), 13.47 (1H, br s). | 397 | 395 |
| 93 | 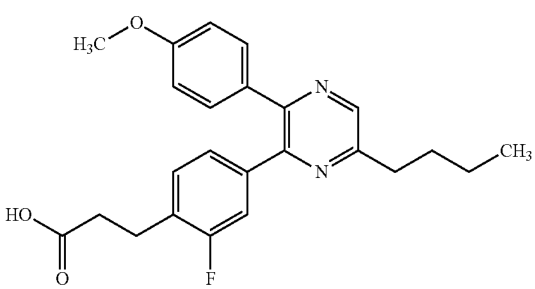 [SMILES: CCCCc1cnc(-c2ccc(OC)cc2)c(-c2ccc(CCC(=O)O)c(F)c2)n1] | 1H-NMR (DMSO-D6) δ: 0.92 (3H, t, J = 7.3 Hz), 1.31-1.44 (2H, m), 1.66-1.77 (2H, m), 2.49-2.54 (2H, m), 2.82 (4H, t, J = 7.6 Hz), 3.75 (3H, s), 6.88 (2H, d, J = 8.8 Hz), 7.09 (1H, dd, J = 7.9, 1.6 Hz), 7.15 (1H, dd, J = 11.1, 1.6 Hz), 7.25 (1H, t, J = 7.9 Hz), 7.31 (2H, d, J = 9.0 Hz), 8.55 (1H, s), 12.23 (1H, br s). | 409 | 407 |
| 94 | 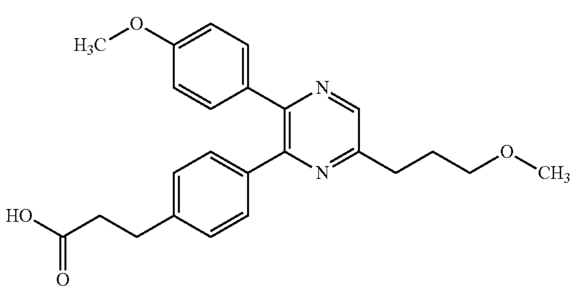 [SMILES: COCCCc1cnc(-c2ccc(OC)cc2)c(-c2ccc(CCC(=O)O)cc2)n1] | 1H-NMR (DMSO-D6) δ: 1.83-1.90 (2H, m), 2.51-2.55 (2H, m), 2.69 (2H, t, J = 7.6 Hz), 2.81 (2H, t, J = 7.6 Hz), 3.25 (3H, s), 3.37 (2H, t, J = 6.3 Hz), 3.72 (3H, s), 6.79 (2H, d, J = 8.4 Hz), 7.10 (2H, d, J = 7.8 Hz), 7.17-7.20 (4H, m), 7.57 (1H, d, J = 1.8 Hz), 8.45 (1H, d, J = 1.5 Hz), 12.12 (1H, br s). | 406 | 404 |

TABLE 1-12-continued

| Ex. | Structure | NMR | MS (M + H) | MS (M − H) |
|---|---|---|---|---|
| 95 | 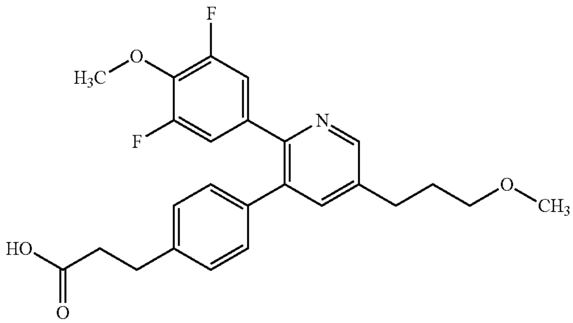 [SMILES: COCCCc1cnc(-c2cc(F)c(OC)c(F)c2)c(-c2ccc(CCC(=O)O)cc2)c1] | 1H-NMR (DMSO-D6) δ: 1.83-1.92 (2H, m), 2.50-2.57 (2H, m), 2.72 (2H, t, J = 7.7 Hz), 2.84 (2H, t, J = 7.7 Hz), 3.25 (3H, s), 3.37 (2H, t, J = 6.3 Hz), 3.91 (3H, s), 6.91-6.99 (2H, m), 7.14 (2H, d, J = 8.0 Hz), 7.24 (2H, d, J = 8.0 Hz), 7.65 (1H, d, J = 1.8 Hz), 8.50 (1H, d, J = 1.8 Hz), 12.13 (1H, s). | 442 | 440 |
| 96 | 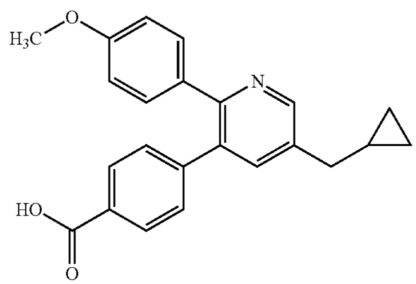 [SMILES: COc1ccc(-c2ncc(CC3CC3)cc2-c2ccc(C(=O)O)cc2)cc1] | 1H-NMR (DMSO-D6) δ: 0.24-0.30 (2H, m), 0.47-0.54 (2H, m), 1.00-1.11 (1H, m), 2.60 (2H, d, J = 6.9 Hz), 3.73 (3H, s), 6.81 (2H, d, J = 8.7 Hz), 7.21 (2H, d, J = 8.4 Hz), 7.32 (2H, d, J = 8.1 Hz), 7.71 (1H, d, J = 1.5 Hz), 7.88 (2H, d, J = 8.1 Hz), 8.57 (1H, d, J = 1.8 Hz), 12.99 (1H, br s). | 360 | 358 |

TABLE 1-13

| Ex. | Structure | NMR | MS (M + H) | MS (M − H) |
|---|---|---|---|---|
| 97 | 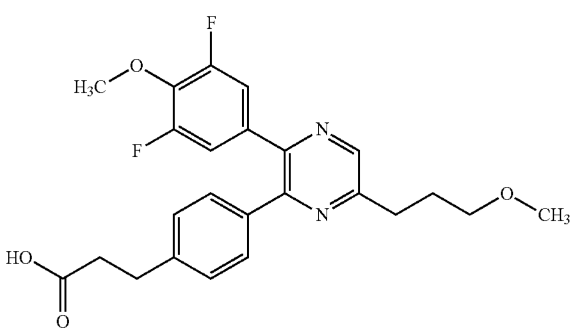 | 1H-NMR (DMSO-D6) δ: 1.95-2.02 (2H, m), 2.54 (2H, t, J = 7.7 Hz), 2.85 (2H, t, J = 7.6 Hz), 2.90 (2H, t, J = 7.6 Hz), 3.25 (3H, s), 3.41 (2H, t, J = 6.2 Hz), 3.94 (3H, s), 7.09 (2H, d, J = 9.9 Hz), 7.25 (2H, d, J = 8.1 Hz), 7.34 (2H, d, J = 8.1 Hz), 8.58 (1H, s), 12.14 (1H, s). | 443 | 441 |
| 98 | 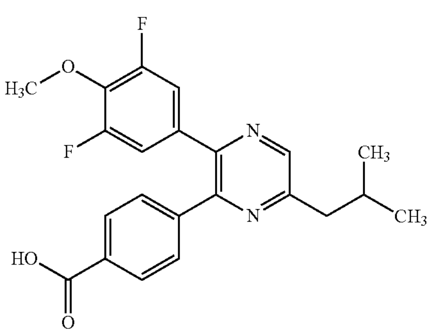 [SMILES: COc1c(F)cc(-c2ncc(CC(C)C)nc2-c2ccc(C(=O)O)cc2)cc1F] | 1H-NMR (DMSO-D6) δ: 0.94 (6H, d, J = 6.7 Hz), 2.06-2.19 (1H, m), 2.75 (2H, d, J = 7.2 Hz), 3.93 (3H, s), 7.10 (2H, d, J = 9.5 Hz), 7.52 (2H, d, J = 8.3 Hz), 7.92 (2H, d, J = 8.3 Hz), 8.61 (1H, s), 13.07 (1H, br s). | 399 | 397 |

TABLE 1-13-continued

| Ex. | Structure | NMR | MS (M + H) | MS (M − H) |
|---|---|---|---|---|
| 99 | 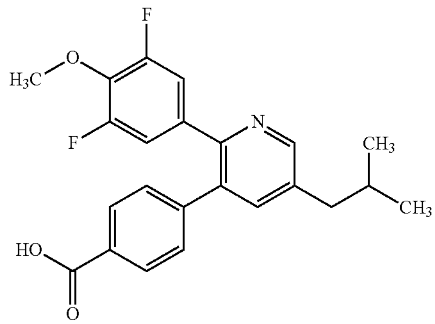 [SMILES: COc1c(F)cc(-c2ncc(CC(C)C)cc2-c2ccc(C(=O)O)cc2)cc1F] | 1H-NMR (DMSO-D6) δ: 0.91 (6H, t, J = 5.4 Hz), 1.86-1.99 (1H, m), 2.57 (2H, d, J = 7.2 Hz), 3.90 (3H, s), 6.96 (2H, d, J = 9.7 Hz), 7.34 (2H, d, J = 8.6 Hz), 7.67 (1H, d, J = 2.3 Hz), 7.90 (2H, d, J = 8.6 Hz), 8.51 (1H, d, J = 2.1 Hz), 12.97 (1H, br s). | 398 | 396 |
| 100 | 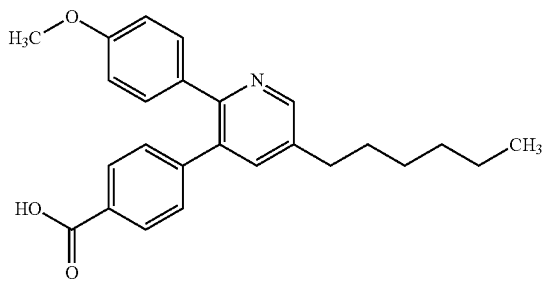 [SMILES: CCCCCCc1cnc(-c2ccc(OC)cc2)c(-c2ccc(C(=O)O)cc2)c1] | 1H-NMR (DMSO-D6) δ: 0.85 (3H, t, J = 7.1 Hz), 1.19-1.41 (6H, m), 1.56-1.69 (2H, m), 2.66 (2H, t, J = 7.7 Hz), 3.71 (3H, s), 6.79 (2H, d, J = 9.0 Hz), 7.19 (2H, d, J = 8.8 Hz), 7.27 (2H, d, J = 8.3 Hz), 7.62 (1H, d, J = 2.1 Hz), 7.84 (2H, d, J = 8.6 Hz), 8.49 (1H, d, J = 2.1 Hz). | 390 | 388 |
| 101 | 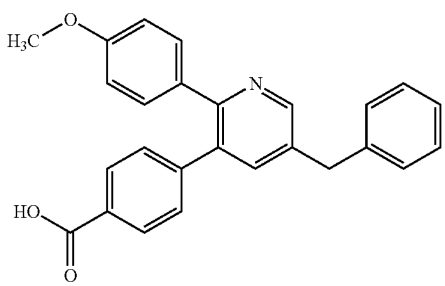 [SMILES: COc1ccc(-c2ncc(Cc3ccccc3)cc2-c2ccc(C(=O)O)cc2)cc1] | 1H-NMR (DMSO-D6) δ: 3.70 (3H, s), 4.04 (2H, s), 6.79 (2H, d, J = 8.8 Hz), 7.14-7.23 (3H, m), 7.23-7.36 (6H, m), 7.65 (1H, d, J = 2.1 Hz), 7.84 (2H, d, J = 8.6 Hz), 8.57 (1H, d, J = 2.3 Hz), 13.01 (1H, br s). | 396 | 394 |
| 102 | 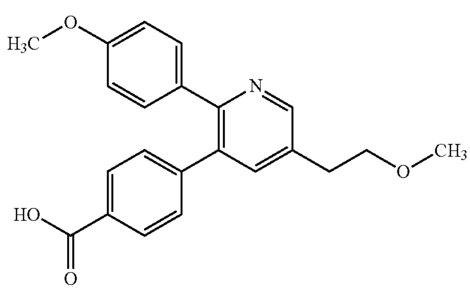 | 1H-NMR (DMSO-D6) δ: 2.91 (2H, t, J = 6.6 Hz), 3.27 (3H, s), 3.63 (2H, t, J = 6.6 Hz), 3.72 (3H, s), 6.81 (2H, d, J = 8.8 Hz), 7.20 (2H, d, J = 8.8 Hz), 7.31 (2H, d, J = 8.3 Hz), 7.69 (1H, d, J = 2.2 Hz), 7.87 (2H, d, J = 8.3 Hz), 8.54 (1H, d, J = 2.2 Hz), 12.99 (1H, br s). | 364 | 362 |
| 103 | 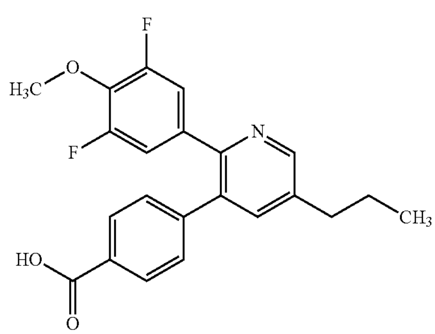 [SMILES: CCCc1cnc(-c2cc(F)c(OC)c(F)c2)c(-c2ccc(C(=O)O)cc2)c1] | 1H-NMR (DMSO-D6) δ: 0.93 (3H, t, J = 7.3 Hz), 1.61-1.71 (2H, m), 2.66 (2H, t, J = 7.5 Hz), 3.90 (3H, s), 6.95 (2H, d, J = 9.7 Hz), 7.34 (2H, dt, J = 8.5, 1.8 Hz), 7.70 (1H, d, J = 2.1 Hz), 7.90 (2H, dt, J = 8.3, 1.8 Hz), 8.54 (1H, d, J = 2.1 Hz), 13.04 (1H, br s). | 382 | 384 |

TABLE 1-13-continued

| Ex. | Structure | NMR | MS (M + H) | MS (M − H) |
|---|---|---|---|---|
| 104 | 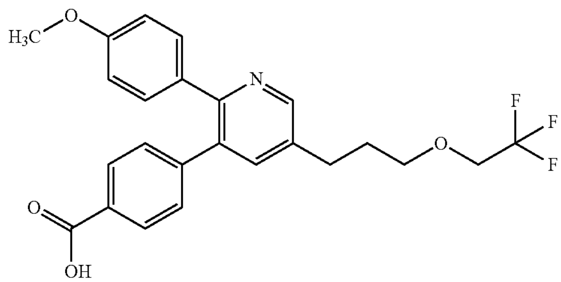 [SMILES: COc1ccc(-c2ncc(CCCOCC(F)(F)F)cc2-c2ccc(C(=O)O)cc2)cc1] | 1H-NMR (DMSO-D6) δ: 1.88-2.00 (2H, m), 2.73 (2H, t, J = 7.6 Hz), 3.64 (2H, t, J = 6.3 Hz), 3.72 (3H, s), 4.06 (2H, q, J = 9.5 Hz), 6.81 (2H, d, J = 8.7 Hz), 7.20 (2H, d, J = 8.4 Hz), 7.32 (2H, d, J = 8.1 Hz), 7.67 (1H, d, J = 1.8 Hz), 7.87 (2H, d, J = 8.1 Hz), 8.53 (1H, d, J = 1.8 Hz), 13.04 (1H, br s). | 446 | 444 |

TABLE 1-14

| Ex. | Structure | NMR | MS (M + H) | MS (M − H) |
|---|---|---|---|---|
| 105 | 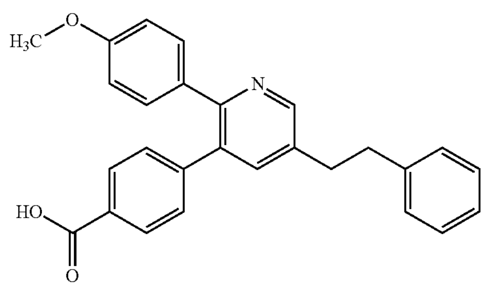 [SMILES: COc1ccc(-c2ncc(CCc3ccccc3)cc2-c2ccc(C(=O)O)cc2)cc1] | 1H-NMR (DMSO-D6) δ: 2.98 (4H, s), 3.72 (3H, s), 6.81 (2H, d, J = 8.7 Hz), 7.17-7.23 (3H, m), 7.25-7.34 (6H, m), 7.66 (1H, s), 7.87 (2H, d, J = 8.1 Hz), 8.52 (1H, s), 13.05 (1H, br s). | 410 | 408 |
| 106 | 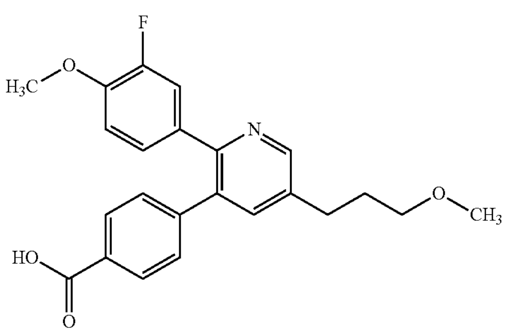 | 1H-NMR (DMSO-D6) δ: 1.83-1.94 (2H, m), 2.73 (2H, t, J = 7.8 Hz), 3.26 (3H, s), 3.38 (2H, t, J = 6.3 Hz), 3.80 (3H, s), 6.93-7.07 (2H, m), 7.13 (1H, d, J = 12.9 Hz), 7.34 (2H, d, J = 8.1 Hz), 7.68 (1H, s), 7.89 (2H, d, J = 8.1 Hz), 8.54 (1H, s), 13.04 (1H, br s). | 396 | 394 |
| 107 | 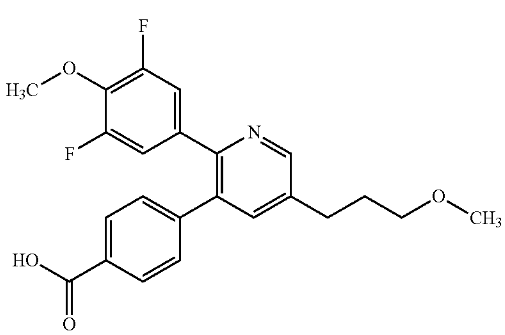 | 1H-NMR (DMSO-D6) δ: 1.83-1.94 (2H, m), 2.74 (2H, t, J = 7.8 Hz), 3.25 (3H, s), 3.38 (2H, t, J = 6.3 Hz), 3.91 (3H, s), 6.96 (2H, d, J = 9.6 Hz), 7.35 (2H, d, J = 8.4 Hz), 7.72 (1H, d, J = 1.8 Hz), 7.91 (2H, d, J = 8.4 Hz), 8.56 (1H, d, J = 1.8 Hz), 13.09 (1H, br s). | 414 | 412 |

TABLE 1-14-continued

| Ex. | Structure | NMR | MS (M + H) | MS (M − H) |
|---|---|---|---|---|
| 108 | 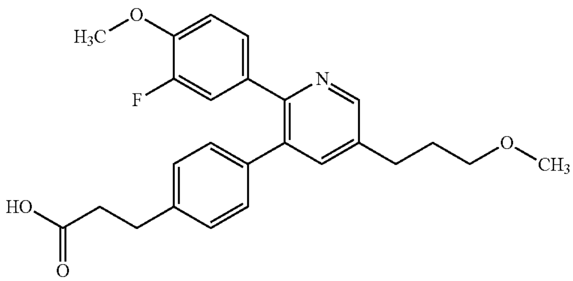 [SMILES: COCCCc1cnc(-c2ccc(OC)c(F)c2)c(-c2ccc(CCC(=O)O)cc2)c1] | 1H-NMR (DMSO-D6) δ: 1.82-1.92 (2H, m), 2.51-2.56 (2H, m), 2.70 (2H, t, J = 7.7 Hz), 2.83 (2H, t, J = 7.6 Hz), 3.25 (3H, s), 3.37 (2H, t, J = 6.2 Hz), 3.81 (3H, s), 7.00-7.14 (5H, m), 7.20 (2H, d, J = 8.1 Hz), 7.60 (1H, d, J = 2.2 Hz), 8.47 (1H, d, J = 2.2 Hz), 12.13 (1H, br s). | 424 | 422 |
| 109 | 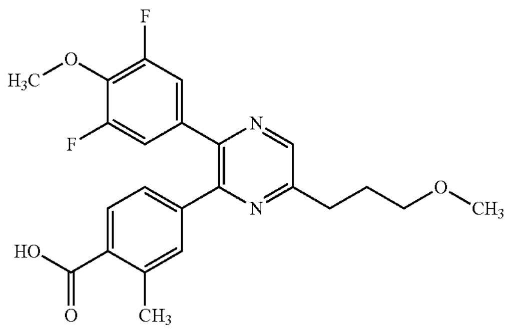 | 1H-NMR (DMSO-D6) δ: 1.95-2.02 (2H, m), 2.51 (3H, s), 2.92 (2H, t, J = 8.4 Hz), 3.25 (3H, s), 3.42 (2H, t, J = 6.2 Hz), 3.95 (3H, s), 7.12 (2H, d, J = 9.7 Hz), 7.23 (1H, dd, J = 8.1, 1.4 Hz), 7.43 (1H, d, J = 1.4 Hz), 7.77 (1H, d, J = 8.1 Hz), 8.64 (1H, s), 12.96 (1H, s). | 429 | 427 |
| 110 | 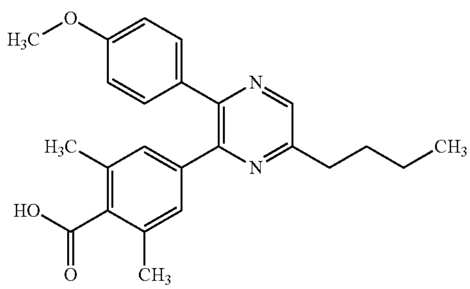 [SMILES: CCCCc1cnc(-c2ccc(OC)cc2)c(-c2cc(C)c(C(=O)O)c(C)c2)n1] | 1H-NMR (DMSO-D6) δ: 0.91 (3H, t, J = 7.4 Hz), 1.31-1.42 (2H, m), 1.65-1.76 (2H, m), 2.14 (6H, s), 2.81 (2H, t, J = 7.7 Hz), 3.74 (3H, s), 6.88 (2H, d, J = 9.0 Hz), 7.03 (2H, s), 7.33 (2H, d, J = 8.8 Hz), 8.52 (1H, s). | 391 | 389 |
| 111 | 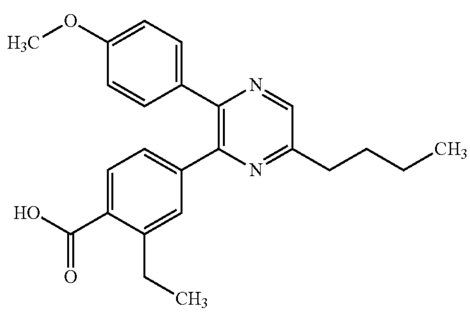 [SMILES: CCCCc1cnc(-c2ccc(OC)cc2)c(-c2ccc(C(=O)O)c(CC)c2)n1] | 1H-NMR (DMSO-D6) δ: 0.92 (3H, t, J = 7.4 Hz), 0.97 (3H, t, J = 7.5 Hz), 1.32-1.44 (2H, m), 1.67-1.77 (2H, m), 2.78 (2H, q, J = 7.5 Hz), 2.84 (2H, t, J = 7.6 Hz), 3.73 (3H, s), 6.88 (2H, d, J = 9.0 Hz), 7.23 (1H, d, J = 1.6 Hz), 7.29 (2H, d, J = 9.0 Hz), 7.35 (1H, dd, J = 8.1, 1.8 Hz), 7.73 (1H, d, J = 8.1 Hz), 8.57 (1H, s), 12.92 (1H, br s). | 391 | 389 |
| 112 | 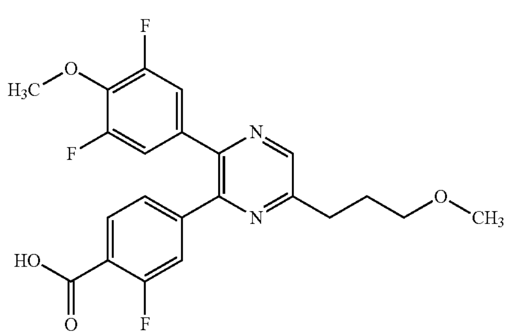 | 1H-NMR (DMSO-D6) δ: 1.93-2.03 (2H, m), 2.92 (2H, t, J = 7.7 Hz), 3.24 (3H, s), 3.41 (2H, t, J = 6.2 Hz), 3.94 (3H, s), 7.13 (2H, d, J = 9.5 Hz), 7.26 (1H, dd, J = 8.1, 1.6 Hz), 7.37 (1H, dd, J = 11.7, 1.5 Hz), 7.82 (1H, t, J = 7.9 Hz), 8.67 (1H, s), 13.38 (1H, br s). | 433 | 431 |

TABLE 1-15

| Ex. | Structure | NMR | MS (M + H) | MS (M − H) |
|---|---|---|---|---|
| 113 | 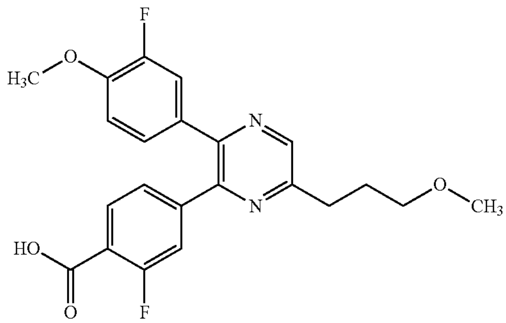 | 1H-NMR (DMSO-D6) δ: 1.93-2.02 (2H, m), 2.90 (2H, t, J = 7.7 Hz), 3.24 (3H, s), 3.40 (2H, t, J = 6.4 Hz), 3.83 (3H, s), 7.07-7.15 (2H, m), 7.24-7.28 (2H, m), 7.32 (1H, dt, J = 15.0, 5.5 Hz), 7.80 (1H, t, J = 7.9 Hz), 8.63 (1H, s), 13.37 (1H, br s). | 415 | 413 |
| 114 | 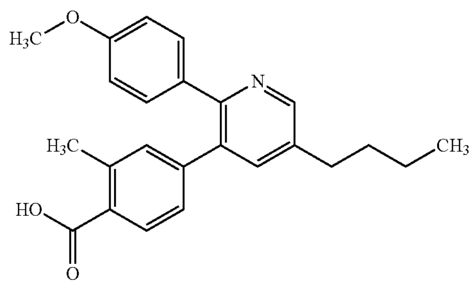 [SMILES: CCCCc1cnc(-c2ccc(OC)cc2)c(-c2ccc(C(=O)O)c(C)c2)c1] | 1H-NMR (DMSO-D6) δ: 0.93 (3H, t, J = 7.3 Hz), 1.31-1.42 (2H, m), 1.58-1.68 (2H, m), 2.49 (3H, s), 2.67 (2H, t, J = 7.6 Hz), 3.73 (3H, s), 6.82 (2H, d, J = 9.0 Hz), 7.00 (1H, dd, J = 8.0, 1.5 Hz), 7.21-7.23 (3H, m), 7.62 (1H, d, J = 2.0 Hz), 7.70 (1H, d, J = 8.0 Hz), 8.50 (1H, d, J = 2.0 Hz), 12.84 (1H, br s). | 376 | 374 |
| 115 | 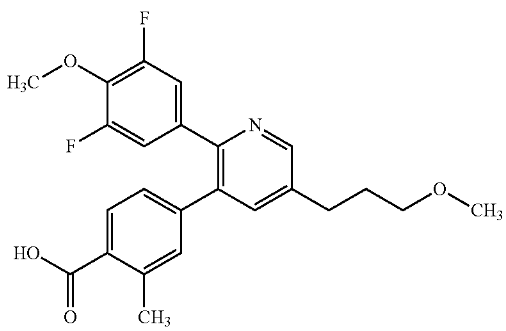 | 1H-NMR (DMSO-D6) δ: 1.82-1.91 (2H, m), 2.49 (3H, s), 2.72 (2H, t, J = 7.7 Hz), 3.24 (3H, s), 3.36 (2H, t, J = 6.2 Hz), 3.90 (3H, s), 6.97 (2H, d, J = 9.5 Hz), 7.04 (1H, dd, J = 8.1, 1.6 Hz), 7.23 (1H, s), 7.69 (1H, d, J = 2.1 Hz), 7.74 (1H, d, J = 8.1 Hz), 8.53 (1H, d, J = 2.3 Hz), 12.90 (1H, br s). | 428 | 426 |
| 116 | 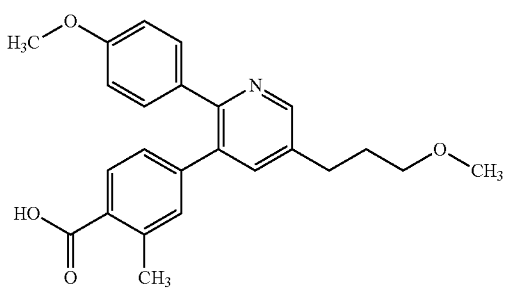 | 1H-NMR (DMSO-D6) δ: 1.81-1.91 (2H, m), 2.47 (3H, s), 2.70 (2H, t, J = 7.7 Hz), 3.24 (3H, s), 3.36 (2H, t, J = 6.2 Hz), 3.71 (3H, s), 6.81 (2H, d, J = 8.8 Hz), 6.98 (1H, dd, J = 8.1, 1.4 Hz), 7.18-7.24 (3H, m), 7.62 (1H, d, J = 2.3 Hz), 7.69 (1H, d, J = 8.1 Hz), 8.49 (1H, d, J = 2.3 Hz), 12.81 (1H, br s). | 392 | 390 |
| 117 | 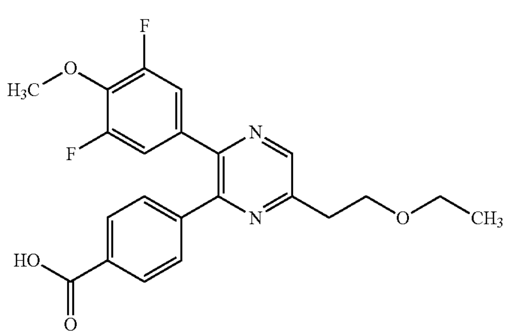 [SMILES: CCOCCc1cnc(-c2cc(F)c(OC)c(F)c2)c(-c2ccc(C(=O)O)cc2)n1] | 1H-NMR (DMSO-D6) δ: 1.08 (3H, t, J = 7.1 Hz), 3.11 (2H, t, J = 6.5 Hz), 3.46 (2H, q, J = 7.0 Hz), 3.80 (2H, t, J = 6.5 Hz), 3.93 (3H, s), 7.10 (2H, d, J = 9.7 Hz), 7.52 (2H, d, J = 8.6 Hz), 7.92 (2H, d, J = 8.6 Hz), 8.65 (1H, s), 13.10 (1H, s). | 415 | 413 |

TABLE 1-15-continued

| Ex. | Structure | NMR | MS (M + H) | MS (M − H) |
|---|---|---|---|---|
| 118 | 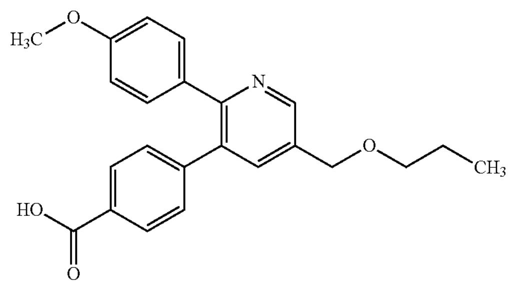 [SMILES: CCCOCc1cnc(-c2ccc(OC)cc2)c(-c2ccc(C(=O)O)cc2)c1] | 1H-NMR (DMSO-D6) δ: 0.88 (3H, t, J = 7.4 Hz), 1.51-1.62 (2H, m), 3.45 (2H, t, J = 6.6 Hz), 3.71 (3H, s), 4.57 (2H, s), 6.81 (2H, d, J = 8.8 Hz), 7.21 (2H, d, J = 8.8 Hz), 7.30 (2H, d, J = 8.3 Hz), 7.71 (1H, d, J = 2.1 Hz), 7.86 (2H, d, J = 8.6 Hz), 8.60 (1H, d, J = 2.1 Hz), 13.01 (1H, br s). | 378 | 376 |
| 119 | 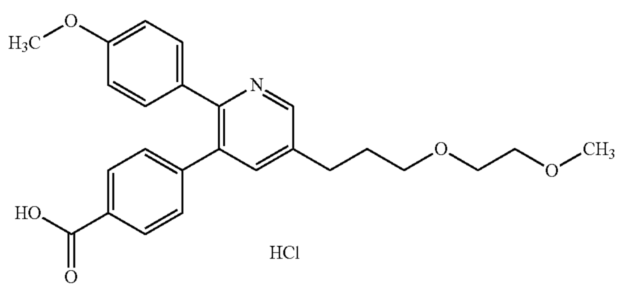 | 1H-NMR (DMSO-D6) δ: 1.86-1.97 (2H, m), 2.83 (2H, t, J = 7.6 Hz), 3.21 (3H, s), 3.39-3.51 (6H, m), 3.75 (3H, s), 6.91 (2H, d, J = 9.0 Hz), 7.26 (2H, d, J = 9.0 Hz), 7.34 (2H, d, J = 8.6 Hz), 7.89 (2H, d, J = 8.6 Hz), 8.15 (1H, br s), 8.68 (1H, d, J = 1.8 Hz), 13.04 (1H, br s). | 422 | 420 |
| 120 | 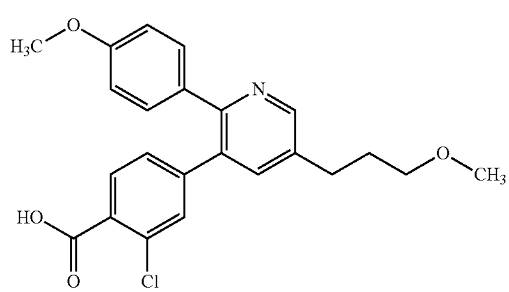 | 1H-NMR (DMSO-D6) δ: 1.82-1.92 (2H, m), 2.70 (2H, t, J = 7.7 Hz), 3.24 (3H, s), 3.36 (2H, t, J = 6.4 Hz), 3.72 (3H, s), 6.84 (2H, d, J = 8.8 Hz), 7.14 (1H, dd, J = 8.1, 1.6 Hz), 7.22 (2H, d, J = 8.8 Hz), 7.42 (1H, d, J = 1.6 Hz), 7.64-7.70 (2H, m), 8.51 (1H, d, J = 2.1 Hz), 13.39 (1H, br s). | 412 | 410 |

TABLE 1-16

| Ex. | Structure | NMR | MS (M + H) | MS (M − H) |
|---|---|---|---|---|
| 121 | 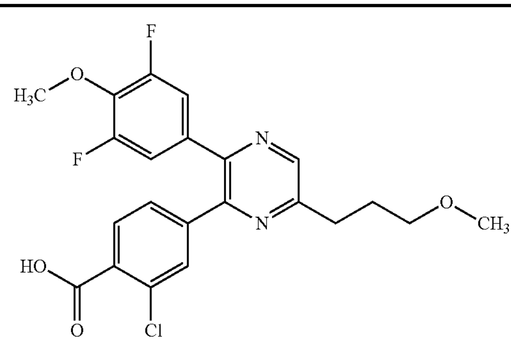 | 1H-NMR (DMSO-D6) δ: 1.96-2.03 (2H, m), 2.93 (2H, t, J = 7.7 Hz), 3.25 (3H, s), 3.42 (2H, t, J = 6.4 Hz), 3.96 (3H, s), 7.17 (2H, d, J = 9.2 Hz), 7.36 (1H, dd, J = 8.1, 1.6 Hz), 7.64 (1H, d, J = 1.6 Hz), 7.75 (1H, d, J = 8.1 Hz), 8.68 (1H, s), 13.52 (1H, s). | 449 | 447 |

TABLE 1-16-continued

| Ex. | Structure | NMR | MS (M + H) | MS (M − H) |
|---|---|---|---|---|
| 122 | 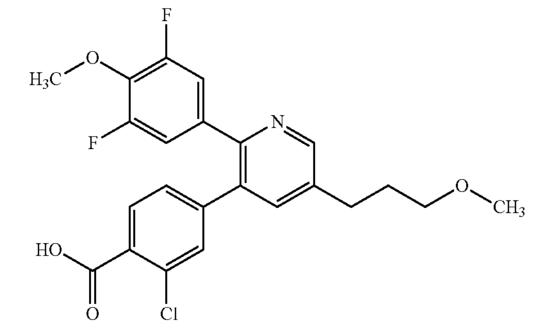 | 1H-NMR (DMSO-D6) δ: 1.82-1.92 (2H, m), 2.72 (2H, t, J = 7.7 Hz), 3.24 (3H, s), 3.36 (2H, t, J = 6.2 Hz), 3.91 (3H, s), 7.00 (2H, d, J = 9.7 Hz), 7.18 (1H, dd, J = 8.0, 1.7 Hz), 7.47 (1H, d, J = 1.6 Hz), 7.71 (1H, d, J = 7.9 Hz), 7.76 (1H, d, J = 2.1 Hz), 8.55 (1H, d, J = 2.1 Hz), 13.42 (1H, br s). | 446 | 448 |
| 123 | 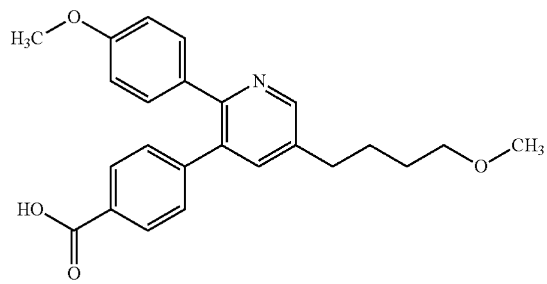 | 1H-NMR (DMSO-D6) δ: 1.51-1.74 (4H, m), 2.69 (2H, t, J = 7.5 Hz), 3.22 (3H, s), 3.35 (2H, t, J = 6.3 Hz), 3.72 (3H, s), 6.81 (2H, d, J = 8.9 Hz), 7.20 (2H, d, J = 8.9 Hz), 7.32 (2H, d, J = 8.1 Hz), 7.64 (1H, d, J = 1.5 Hz), 7.87 (2H, d, J = 8.1 Hz), 8.52 (1H, d, J = 1.5 Hz), 12.99 (1H, br s). | 392 | 390 |
| 124 | 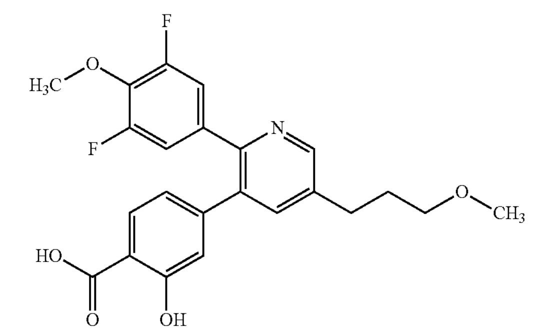 | 1H-NMR (DMSO-D6) δ: 1.82-1.91 (2H, m), 2.72 (2H, t, J = 7.7 Hz), 3.24 (3H, s), 3.36 (2H, t, J = 6.2 Hz), 3.91 (3H, s), 6.70 (1H, dd, J = 8.1, 1.6 Hz), 6.87 (1H, d, J = 1.6 Hz), 7.00 (2H, d, J = 9.7 Hz), 7.70 (1H, d, J = 2.1 Hz), 7.71 (1H, d, J = 8.1 Hz), 8.54 (1H, d, J = 2.1 Hz), 11.37 (1H, br s), 14.00 (1H, br s). | 430 | 428 |
| 125 | 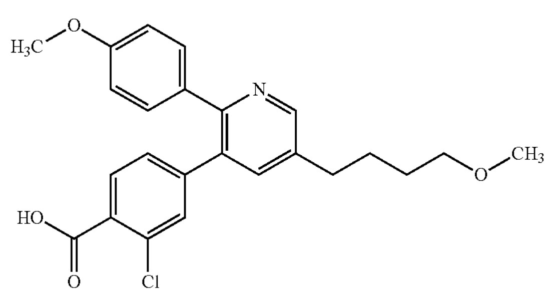 | 1H-NMR (DMSO-D6) δ: 1.50-1.59 (2H, m), 1.62-1.72 (2H, m), 2.67 (2H, t, J = 7.6 Hz), 3.20 (3H, s), 3.34 (2H, t, J = 6.4 Hz), 3.72 (3H, s), 6.84 (2H, d, J = 9.0 Hz), 7.14 (1H, dd, J = 8.0, 1.7 Hz), 7.22 (2H, d, J = 8.8 Hz), 7.41 (1H, d, J = 1.8 Hz), 7.65-7.69 (2H, m), 8.51 (1H, d, J = 2.1 Hz), 13.39 (1H, br s). | 426 | 424 |
| 126 | 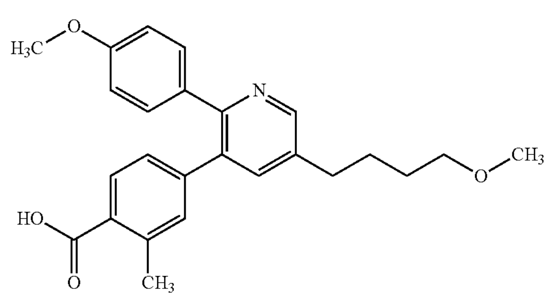 | 1H-NMR (DMSO-D6) δ: 1.50-1.59 (2H, m), 1.62-1.71 (2H, m), 2.47 (3H, s), 2.67 (2H, t, J = 7.5 Hz), 3.20 (3H, s), 3.33 (2H, t, J = 6.4 Hz), 3.71 (3H, s), 6.81 (2H, d, J = 9.0 Hz), 6.98 (1H, dd, J = 8.0, 1.5 Hz), 7.19-7.23 (3H, m), 7.61 (1H, d, J = 2.1 Hz), 7.68 (1H, d, J = 8.1 Hz), 8.48 (1H, d, J = 2.1 Hz), 12.81 (1H, br s). | 406 | 404 |

TABLE 1-16-continued

| Ex. | Structure | NMR | MS (M + H) | MS (M − H) |
|---|---|---|---|---|
| 127 | 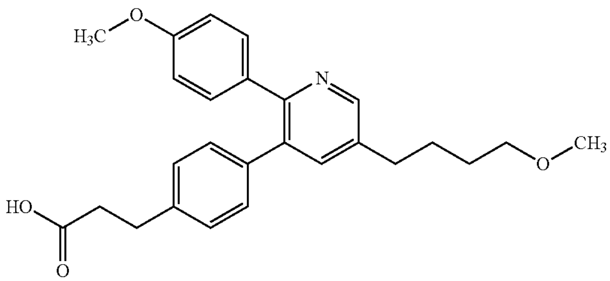 [SMILES: COCCCCc1cnc(-c2ccc(OC)cc2)c(-c2ccc(CCC(=O)O)cc2)c1] | 1H-NMR (DMSO-D6) δ: 1.49-1.58 (2H, m), 1.60-1.71 (2H, m), 2.47-2.53 (2H, m), 2.65 (2H, t, J = 7.5 Hz), 2.80 (2H, t, J = 7.6 Hz), 3.20 (3H, s), 3.33 (2H, t, J = 6.4 Hz), 3.71 (3H, s), 6.77 (2H, d, J = 9.0 Hz), 7.08 (2H, d, J = 8.3 Hz), 7.16 (2H, d, J = 8.3 Hz), 7.19 (2H, d, J = 8.8 Hz), 7.55 (1H, d, J = 2.3 Hz), 8.44 (1H, d, J = 2.1 Hz), 12.15 (1H, br s). | 420 | 418 |
| 128 | 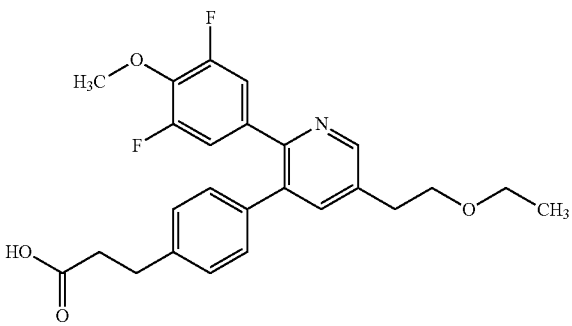 [SMILES: CCOCCc1cnc(-c2cc(F)c(OC)c(F)c2)c(-c2ccc(CCC(=O)O)cc2)c1] | 1H-NMR (DMSO-D6) δ: 1.08 (3H, t, J = 7.1 Hz), 2.49-2.55 (2H, m), 2.82 (2H, t, J = 7.6 Hz), 2.89 (2H, t, J = 6.6 Hz), 3.44 (2H, q, J = 6.9 Hz), 3.64 (2H, t, J = 6.7 Hz), 3.90 (3H, s), 6.94 (2H, d, J = 9.7 Hz), 7.11 (2H, d, J = 8.3 Hz), 7.22 (2H, d, J = 8.3 Hz), 7.67 (1H, d, J = 2.1 Hz), 8.51 (1H, d, J = 2.1 Hz), 12.15 (1H, br s). | 442 | 420 |

TABLE 1-17

| Ex. | Structure | NMR | MS (M + H) | MS (M − H) |
|---|---|---|---|---|
| 129 | 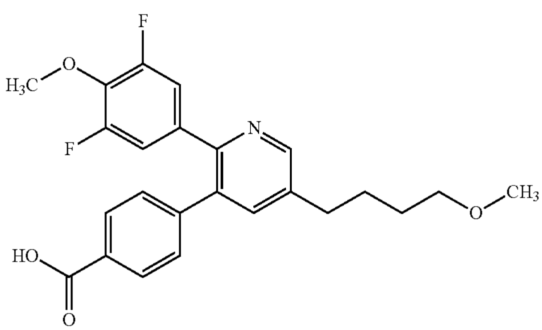 | 1H-NMR (DMSO-D6) δ: 1.52-1.72 (4H, m), 2.71 (2H, t, J = 7.6 Hz), 3.21 (3H, s), 3.35 (2H, t, J = 6.3 Hz), 3.91 (3H, s), 6.94-6.99 (2H, m), 7.36 (2H, d, J = 8.1 Hz), 7.71 (1H, d, J = 1.8 Hz), 7.92 (2H, d, J = 8.1 Hz), 8.56 (1H, d, J = 1.8 Hz), 13.06 (1H, br s). | 428 | 426 |
| 130 | 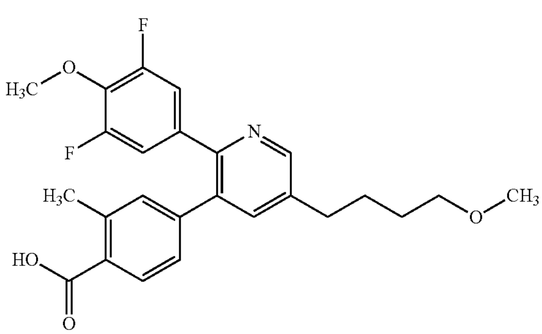 | 1H-NMR (DMSO-D6) δ: 1.50-1.73 (4H, m), 2.51 (3H, s), 2.71 (2H, t, J = 7.3 Hz), 3.22 (3H, s), 3.35 (2H, t, J = 6.4 Hz), 3.91 (3H, s), 6.94-7.01 (2H, m), 7.06 (1H, d, J = 8.1 Hz), 7.25 (1H, br s), 7.70 (1H, br s), 7.76 (1H, d, J = 8.1 Hz), 8.54 (1H, br s), 12.90 (1H, br s). | 442 | 440 |

TABLE 1-17-continued

| Ex. | Structure | NMR | MS (M + H) | MS (M − H) |
|---|---|---|---|---|
| 131 | 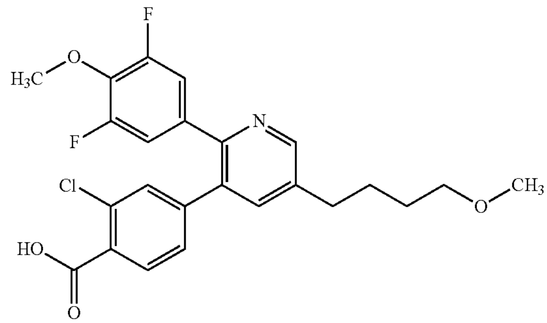 | 1H-NMR (DMSO-D6) δ: 1.50-1.75 (4H, m), 2.71 (2H, t, J = 7.6 Hz), 3.22 (3H, s), 3.32-3.38 (2H, m), 3.93 (3H, s), 6.97-7.06 (2H, m), 7.20 (1H, d, J = 8.1 Hz), 7.48 (1H, br s), 7.71-7.77 (2H, m), 8.56 (1H, br s), 13.46 (1H, br s). | 462 | 460 |
| 132 | 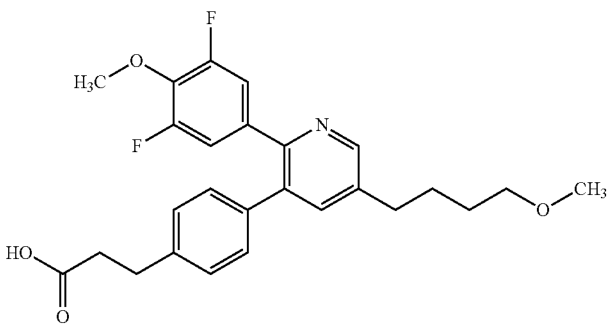 [SMILES: COCCCCc1cnc(-c2cc(F)c(OC)c(F)c2)c(-c2ccc(CCC(=O)O)cc2)c1] | 1H-NMR (DMSO-D6) δ: 1.50-1.73 (4H, m), 2.50-2.56 (2H, m), 2.69 (2H, t, J = 7.5 Hz), 2.84 (2H, t, J = 7.6 Hz), 3.21 (3H, s), 3.31-3.37 (2H, m), 3.91 (3H, s), 6.91-7.00 (2H, m), 7.13 (2H, d, J = 8.0 Hz), 7.24 (2H, d, J = 8.0 Hz), 7.64 (1H, d, J = 1.7 Hz), 8.50 (1H, d, J = 1.7 Hz), 12.13 (1H, br s). | 456 | 454 |
| 133 | 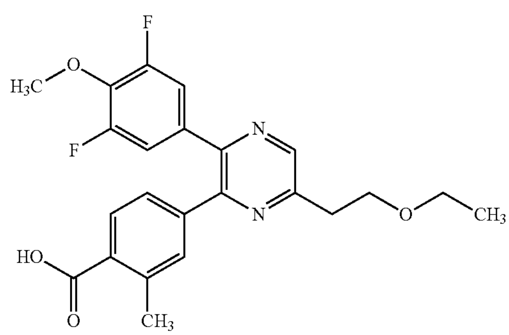 | 1H-NMR (DMSO-D6) δ: 1.08 (3H, t, J = 7.1 Hz), 2.49 (3H, s), 3.10 (2H, t, J = 6.5 Hz), 3.46 (2H, q, J = 7.0 Hz), 3.79 (2H, t, J = 6.5 Hz), 3.93 (3H, s), 7.11 (2H, d, J = 9.5 Hz), 7.21 (1H, dd, J = 8.1, 1.4 Hz), 7.41 (1H, d, J = 1.6 Hz), 7.75 (1H, d, J = 8.1 Hz), 8.64 (1H, s), 12.96 (1H, br s). | 429 | 427 |
| 134 | 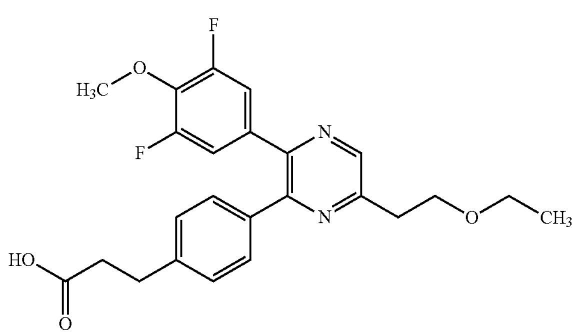 [SMILES: CCOCCc1cnc(-c2cc(F)c(OC)c(F)c2)c(-c2ccc(CCC(=O)O)cc2)n1] | 1H-NMR (DMSO-D6) δ: 1.08 (3H, t, J = 7.1 Hz), 2.53 (2H, t, J = 7.6 Hz), 2.83 (2H, t, J = 7.5 Hz), 3.08 (2H, t, J = 6.6 Hz), 3.45 (2H, q, J = 7.0 Hz), 3.79 (2H, t, J = 6.5 Hz), 3.93 (3H, s), 7.08 (2H, d, J = 9.7 Hz), 7.24 (2H, d, J = 8.3 Hz), 7.32 (2H, d, J = 8.3 Hz), 8.58 (1H, s), 12.07 (1H, br s). | 443 | 441 |

TABLE 1-17-continued

| Ex. | Structure | NMR | MS (M + H) | MS (M − H) |
|---|---|---|---|---|
| 135 | 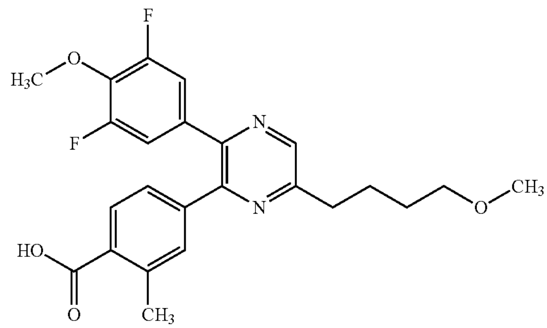 | 1H-NMR (DMSO-D6) δ: 1.56-1.63 (2H, m), 1.75-1.82 (2H, m), 2.51 (3H, s), 2.89 (2H, t, J = 7.6 Hz), 3.22 (3H, s), 3.36 (2H, t, J = 6.5 Hz), 3.94 (3H, s), 7.11 (2H, d, J = 9.2 Hz), 7.23 (1H, dd, J = 8.1, 1.4 Hz), 7.42 (1H, d, J = 1.4 Hz), 7.77 (1H, d, J = 8.1 Hz), 8.64 (1H, s), 12.96 (1H, s). | 443 | 441 |
| 136 | 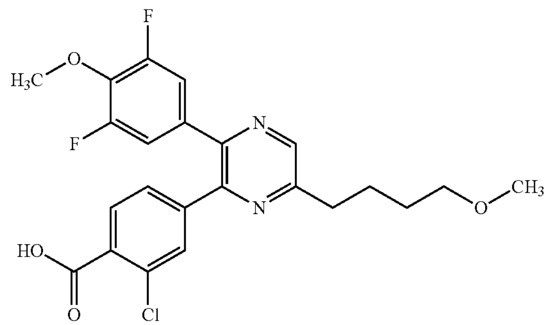 | 1H-NMR (DMSO-D6) δ: 1.56-1.63 (2H, m), 1.75-1.83 (2H, m), 2.89 (2H, t, J = 7.6 Hz), 3.22 (3H, s), 3.36 (2H, t, J = 6.5 Hz), 3.94 (3H, s), 7.11 (2H, d, J = 9.2 Hz), 7.23 (1H, dd, J = 8.1, 1.5 Hz), 7.42 (1H, d, J = 1.5 Hz), 7.77 (1H, d, J = 8.1 Hz), 8.64 (1H, s), 12.96 (1H, s). | 463 | 461 |

TABLE 1-18

| Ex. | Structure | NMR | MS (M + H) | MS (M − H) |
|---|---|---|---|---|
| 137 | 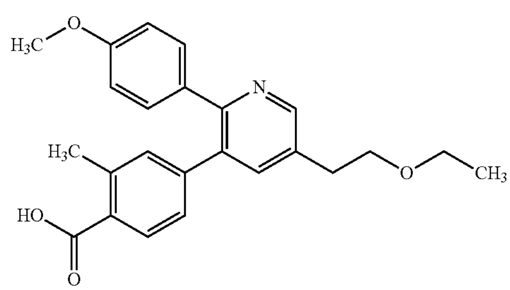 | 1H-NMR (DMSO-D6) δ: 1.11 (3H, t, J = 7.0 Hz), 2.49 (3H, s), 2.90 (2H, t, J = 6.7 Hz), 3.46 (2H, q, J = 7.0 Hz), 3.65 (2H, t, J = 6.7 Hz), 3.73 (3H, s), 6.83 (2H, d, J = 8.7 Hz), 7.00 (1H, d, J = 8.1 Hz), 7.23 (2H, d, J = 8.7 Hz), 7.23 (1H, brs), 7.68 (1H, d, J = 1.8 Hz), 7.71 (1H, d, J = 8.1 Hz), 8.53 (1H, d, J = 1.8 Hz), 12.84 (1H, s). | 392 | 390 |
| 138 | 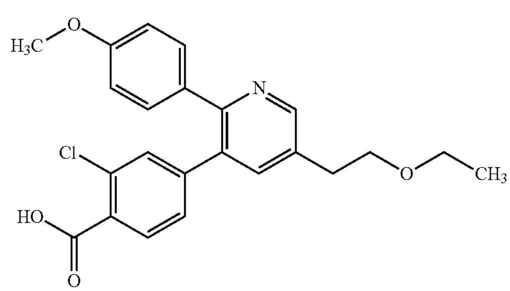 [SMILES: CCOCCc1cnc(-c2ccc(OC)cc2)c(-c2ccc(C(=O)O)c(Cl)c2)c1] | 1H-NMR (DMSO-D6) δ: 1.11 (3H, t, J = 7.0 Hz), 2.91 (2H, t, J = 6.7 Hz), 3.47 (2H, q, J = 7.0 Hz), 3.66 (2H, t, J = 6.7 Hz), 3.74 (3H, s), 6.86 (2H, d, J = 9.0 Hz), 7.16 (1H, dd, J = 8.1, 1.5 Hz), 7.23 (2H, d, J = 9.0 Hz), 7.43 (1H, d, J = 1.5 Hz), 7.71 (1H, d, J = 8.1 Hz), 7.74 (1H, d, J = 2.1 Hz), 8.55 (1H, d, J = 1.8 Hz), 13.41 (1H, s). | 412 | 410 |

TABLE 1-18-continued

| Ex. | Structure | NMR | MS (M + H) | MS (M − H) |
|---|---|---|---|---|
| 139 | 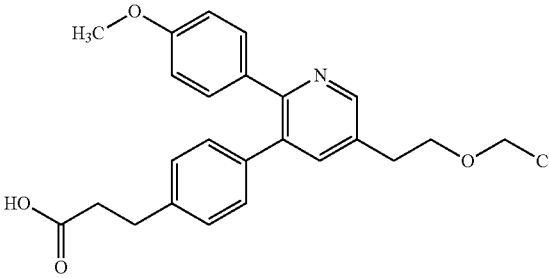 | 1H-NMR (DMSO-D6) δ: 1.10 (3H, t, J = 7.0 Hz), 2.51 (2H, t, J = 7.6 Hz), 2.81 (2H, t, J = 7.6 Hz), 2.88 (2H, t, J = 6.7 Hz), 3.46 (2H, q, J = 7.0 Hz), 3.65 (2H, t, J = 6.7 Hz), 3.73 (3H, s), 6.79 (2H, d, J = 9.0 Hz), 7.09 (2H, d, J = 8.1 Hz), 7.18 (2H, d, J = 8.1 Hz), 7.21 (2H, d, J = 9.0 Hz), 7.62 (1H, d, J = 1.8 Hz), 8.48 (1H, d, J = 1.8 Hz), 12.18 (1H, s). | 406 | 404 |
| 140 | 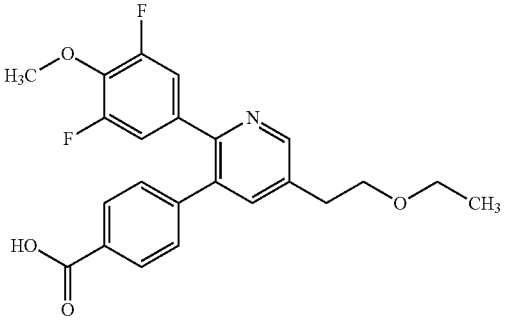 [SMILES: CCOCCc1cnc(-c2cc(F)c(OC)c(F)c2)c(-c2ccc(C(=O)O)cc2)c1] | 1H-NMR (DMSO-D6) δ: 1.10 (3H, t, J = 7.0 Hz), 2.93 (2H, t, J = 6.6 Hz), 3.46 (2H, q, J = 7.1 Hz), 3.66 (2H, t, J = 6.6 Hz), 3.91 (3H, s), 6.97 (2H, d, J = 9.3 Hz), 7.35 (2H, d, J = 8.1 Hz), 7.76 (1H, d, J = 1.8 Hz), 7.92 (2H, d, J = 8.1 Hz), 8.59 (1H, d, J = 2.1 Hz), 13.06 (1H, s). | 414 | 412 |
| 141 | 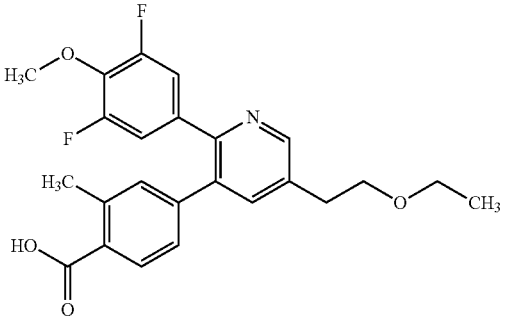 [SMILES: CCOCCc1cnc(-c2cc(F)c(OC)c(F)c2)c(-c2ccc(C(=O)O)c(C)c2)c1] | 1H-NMR (DMSO-D6) δ: 1.10 (3H, t, J = 7.0 Hz), 2.51 (3H, s), 2.92 (2H, t, J = 6.4 Hz), 3.43-3.49 (2H, m), 3.66 (2H, t, J = 6.7 Hz), 3.92 (3H, s), 6.96-7.07 (3H, m), 7.22-7.25 (1H, m), 7.73-7.77 (2H, m), 8.57 (1H, d, J = 1.8 Hz), 12.91 (1H, br s). | 428 | 426 |
| 142 | 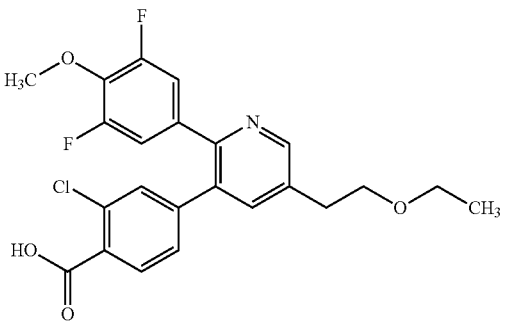 [SMILES: CCOCCc1cnc(-c2cc(F)c(OC)c(F)c2)c(-c2ccc(C(=O)O)c(Cl)c2)c1] | 1H-NMR (DMSO-D6) δ: 1.10 (3H, t, J = 6.9 Hz), 2.93 (2H, t, J = 6.6 Hz), 3.46 (2H, q, J = 6.9 Hz), 3.66 (2H, t, J = 6.6 Hz), 3.93 (3H, s), 7.02 (2H, d, J = 9.3 Hz), 7.19 (1H, d, J = 7.8 Hz), 7.47 (1H, s), 7.73 (1H, d, J = 7.8 Hz), 7.81 (1H, s), 8.59 (1H, s), 13.47 (1H, s). | 448 | 446 |
| 143 | 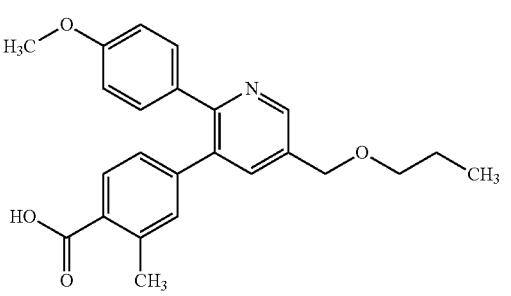 [SMILES: CCCOCc1cnc(-c2ccc(OC)cc2)c(-c2ccc(C(=O)O)c(C)c2)c1] | 1H-NMR (DMSO-D6) δ: 0.88 (3H, t, J = 7.5 Hz), 1.50-1.61 (2H, m), 2.47 (3H, s), 3.45 (2H, t, J = 6.6 Hz), 3.72 (3H, s), 4.56 (2H, s), 6.82 (2H, d, J = 8.8 Hz), 6.99 (1H, dd, J = 8.0, 1.5 Hz), 7.20-7.26 (3H, m), 7.70 (2H, dd, J = 5.1, 3.0 Hz), 8.59 (1H, d, J = 2.1 Hz), 12.82 (1H, br s). | 392 | 390 |

TABLE 1-18-continued

| Ex. | Structure | NMR | MS (M + H) | MS (M − H) |
|---|---|---|---|---|
| 144 | 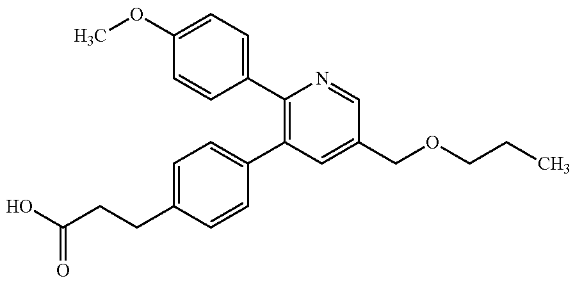 [SMILES: CCCOCc1cnc(-c2ccc(OC)cc2)c(-c2ccc(CCC(=O)O)cc2)c1] | 1H-NMR (DMSO-D6) δ: 0.88 (3H, t, J = 7.4 Hz), 1.50-1.61 (2H, m), 2.48-2.54 (2H, m), 2.80 (2H, t, J = 7.5 Hz), 3.44 (2H, t, J = 6.6 Hz), 3.71 (3H, s), 4.55 (2H, s), 6.79 (2H, d, J = 9.0 Hz), 7.08 (2H, d, J = 8.1 Hz), 7.17 (2H, d, J = 8.3 Hz), 7.21 (2H, d, J = 9.0 Hz), 7.64 (1H, d, J = 2.3 Hz), 8.54 (1H, d, J = 2.1 Hz), 12.09 (1H, br s). | 406 | 404 |

TABLE 1-19

| Ex. | Structure | NMR | MS (M + H) | MS (M − H) |
|---|---|---|---|---|
| 145 | 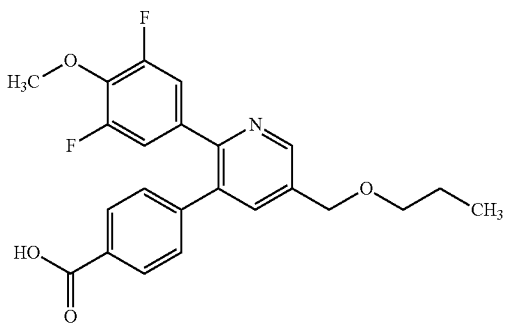 [SMILES: CCCOCc1cnc(-c2cc(F)c(OC)c(F)c2)c(-c2ccc(C(=O)O)cc2)c1] | 1H-NMR (DMSO-D6) δ: 0.88 (3H, t, J = 7.4 Hz), 1.51-1.62 (2H, m), 3.46 (2H, t, J = 6.6 Hz), 3.90 (3H, s), 4.59 (2H, s), 6.97 (2H, d, J = 9.7 Hz), 7.35 (2H, d, J = 8.3 Hz), 7.78 (1H, d, J = 2.1 Hz), 7.91 (2H, d, J = 8.6 Hz), 8.65 (1H, d, J = 2.1 Hz), 12.99 (1H, br s). | 414 | 412 |
| 146 | 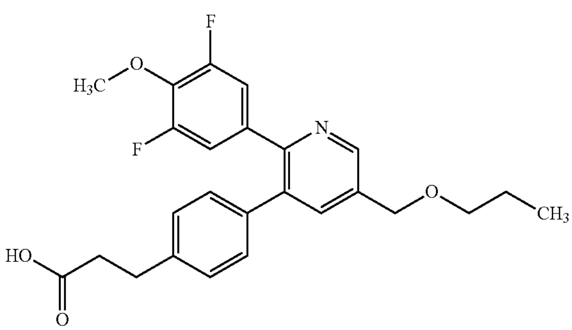 [SMILES: CCCOCc1cnc(-c2cc(F)c(OC)c(F)c2)c(-c2ccc(CCC(=O)O)cc2)c1] | 1H-NMR (DMSO-D6) δ: 0.88 (3H, t, J = 7.4 Hz), 1.51-1.62 (2H, m), 2.50-2.55 (2H, m), 2.83 (2H, t, J = 7.6 Hz), 3.45 (2H, t, J = 6.6 Hz), 3.90 (3H, s), 4.57 (2H, s), 6.96 (2H, d, J = 9.7 Hz), 7.12 (2H, d, J = 8.3 Hz), 7.23 (2H, d, J = 8.3 Hz), 7.71 (1H, d, J = 2.1 Hz), 8.59 (1H, d, J = 1.8 Hz), 12.12 (1H, brs). | 442 | 440 |
| 147 | 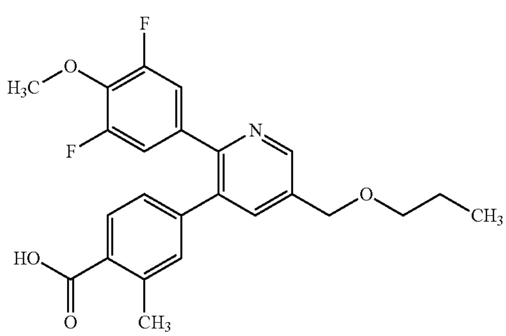 [SMILES: CCCOCc1cnc(-c2cc(F)c(OC)c(F)c2)c(-c2ccc(C(=O)O)c(C)c2)c1] | 1H-NMR (DMSO-D6) δ: 0.88 (3H, t, J = 7.4 Hz), 1.51-1.62 (2H, m), 2.49 (3H, s), 3.45 (2H, t, J = 6.6 Hz), 3.91 (3H, s), 4.59 (2H, s), 6.99 (2H, d, J = 9.7 Hz), 7.05 (1H, dd, J = 8.0, 1.5 Hz), 7.23 (1H, d, J = 1.4 Hz), 7.72-7.78 (2H, m), 8.63 (1H, d, J = 2.1 Hz), 12.89 (1H, br s). | 428 | 426 |

| Ex. | Structure | NMR | MS (M + H) | MS (M − H) |
|---|---|---|---|---|
| 148 | 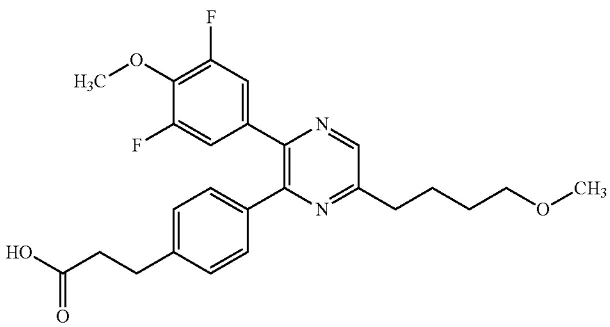 [SMILES: COCCCCc1cnc(-c2cc(F)c(OC)c(F)c2)c(-c2ccc(CCC(=O)O)cc2)n1] | 1H-NMR (DMSO-D6) δ: 1.56-1.63 (2H, m), 1.74-1.82 (2H, m), 2.54 (2H, t, J = 7.6 Hz), 2.83-2.89 (4H, m), 3.21 (3H, s), 3.36 (2H, t, J = 6.5 Hz), 3.94 (3H, s), 7.09 (2H, d, J = 9.5 Hz), 7.25 (2H, d, J = 8.3 Hz), 7.33 (2H, d, J = 8.3 Hz), 8.58 (1H, s), 12.13 (1H, s). | 457 | 455 |
| 149 | 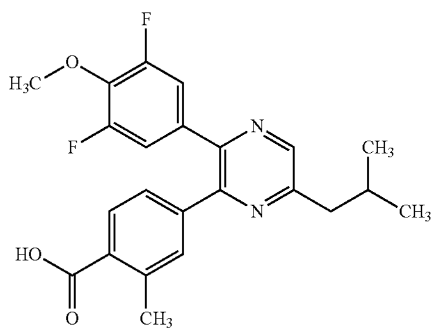 [SMILES: COc1c(F)cc(-c2ncc(CC(C)C)nc2-c2ccc(C(=O)O)c(C)c2)cc1F] | 1H-NMR (DMSO-D6) δ: 0.94 (6H, d, J = 6.7 Hz), 2.07-2.18 (1H, m), 2.49 (3H, s), 2.75 (2H, d, J = 7.2 Hz), 3.93 (3H, s), 7.10 (2H, d, J = 9.5 Hz), 7.22 (1H, dd, J = 8.1, 1.4 Hz), 7.40 (1H, d, J = 1.6 Hz), 7.76 (1H, d, J = 8.1 Hz), 8.59 (1H, s), 12.91 (1H, br s). | 413 | 411 |
| 150 | 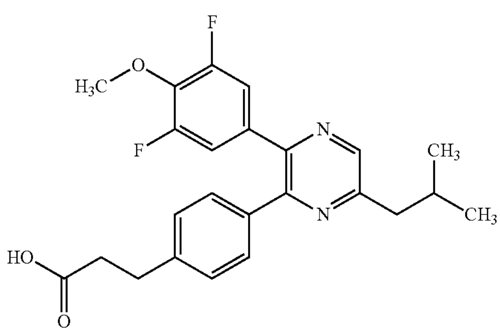 [SMILES: COc1c(F)cc(-c2ncc(CC(C)C)nc2-c2ccc(CCC(=O)O)cc2)cc1F] | 1H-NMR (DMSO-D6) δ: 0.94 (6H, d, J = 6.7 Hz), 2.06-2.17 (1H, m), 2.52 (2H, t, J = 7.6 Hz), 2.72 (2H, d, J = 7.2 Hz), 2.83 (2H, t, J = 7.5 Hz), 3.93 (3H, s), 7.08 (2H, d, J = 9.5 Hz), 7.23 (2H, d, J = 8.3 Hz), 7.32 (2H, d, J = 8.3 Hz), 8.53 (1H, s), 12.13 (1H, br s). | 427 | 425 |
| 151 | 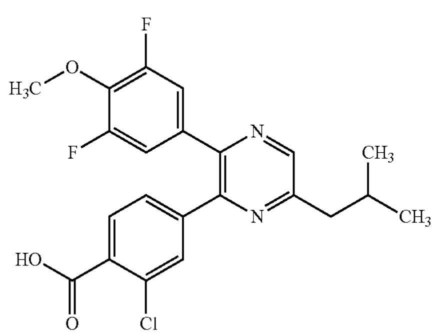 [SMILES: COc1c(F)cc(-c2ncc(CC(C)C)nc2-c2ccc(C(=O)O)c(Cl)c2)cc1F] | 1H-NMR (DMSO-D6) δ: 0.94 (6H, d, J = 6.5 Hz), 2.07-2.19 (1H, m), 2.76 (2H, d, J = 7.2 Hz), 3.94 (3H, s), 7.16 (2H, d, J = 9.5 Hz), 7.35 (1H, dd, J = 8.1, 1.8 Hz), 7.61 (1H, d, J = 1.6 Hz), 7.74 (1H, d, J = 8.1 Hz), 8.62 (1H, s), 13.50 (1H, br s). | 433 | 431 |

TABLE 1-19-continued

| Ex. | Structure | NMR | MS (M + H) | MS (M − H) |
|---|---|---|---|---|
| 152 | 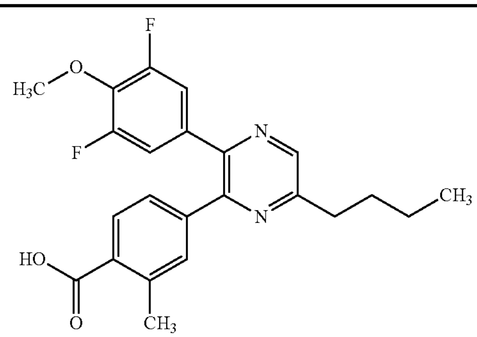 | 1H-NMR (DMSO-D6) δ: 0.93 (3H, t, J = 7.4 Hz), 1.35-1.44 (2H, m), 1.70-1.77 (2H, m), 2.51 (3H, s), 2.88 (2H, t, J = 7.6 Hz), 3.95 (3H, s), 7.11 (2H, d, J = 9.5 Hz), 7.23 (1H, dd, J = 8.1, 1.5 Hz), 7.42 (1H, d, J = 1.5 Hz), 7.77 (1H, d, J = 8.1 Hz), 8.64 (1H, s), 12.95 (1H, s). | 413 | 411 |

TABLE 1-20

| Ex. | Structure | NMR | MS (M + H) | MS (M − H) |
|---|---|---|---|---|
| 153 | 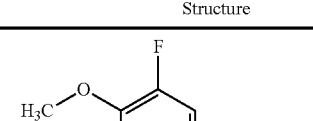 | 1H-NMR (DMSO-D6) δ: 0.93 (3H, t, J = 7.4 Hz), 1.34-1.43 (2H, m), 1.69-1.77 (2H, m), 2.54 (2H, t, J = 7.6 Hz), 2.83-2.88 (4H, m), 3.94 (3H, s), 7.09 (2H, d, J = 9.2 Hz), 7.25 (2H, d, J = 8.3 Hz), 7.33 (2H, d, J = 8.3 Hz), 8.58 (1H, s), 12.12 (1H, s). | 427 | 425 |

The formulation examples of the present invention include the following formulations. However, the present invention is not limited by such formulation examples.

Formulation Example 1 (Production of Capsule)

| 1) Compound of Example 1 | 30 mg |
|---|---|
| 2) Microcrystalline cellulose | 10 mg |
| 3) Lactose | 19 mg |
| 4) Magnesium stearate | 1 mg |

1), 2), 3) and 4) are mixed and filled in a gelatin capsule.

Formulation Example 2 (Production of Tablet)

| 1) Compound of Example 1 | 10 g |
|---|---|
| 2) Lactose | 50 g |
| 3) Corn starch | 15 g |
| 4) Carmellose calcium | 44 g |
| 5) Magnesium stearate | 1 g |

The total amount of 1), 2), 3) and 30 g of 4) are kneaded with water, vacuum dried and sieved. The sieved powder is mixed with 14 g of 4) and 1 g of 5), and the mixture is tableted by a tableting machine. In this way, 1000 tablets containing 10 mg of the compound of Example 1 per tablet are obtained.

Test Example 1

Evaluation of Human GLUT9 Inhibitory Activity

A method for measuring GLUT9 inhibitory activity using human GLUT9 expressing cells transduced with Uricase/Hyper is shown hereinafter. GLUT9 inhibitory activity ($IC_H$ value) of the test compound was calculated based on the intracellular uptake amount of labeled uric acid ([$^{14}C$] uric acid) transported by GLUT9.

1. Preparation of Human GLUT9 Expression Plasmid

Human GLUT9S coding region (NM_001001290.1) was amplified by PCR method using PrimeSTAR MAX DNA Polymerase (Takara Bio). The obtained PCR product was subjected to agarose gel electrophoresis, and the desired size of PCR product was purified by QIAquick Gel Extraction Kit (QIAGEN). Next, pEBMulti-Bsd vector (Wako Pure Chemical Industries, Ltd.) was subjected to digestion using restriction enzymes SalI and EcoR V, and linked to the PCR product containing GLUT9S by In-Fusion reaction using In-Fusion HD Cloning Kit (Takara Bio). XL10-Gold Competent Cells (Agilent Technologies) were transformed in In-Fusion reaction solution, and the obtained transfectants were cultured with shaking overnight in LB medium to which Blasticidin S HCl (Thermo Fisher Scientific) was added. Human GLUT9 expression plasmid DNA was prepared from the collected transfectants using EndoFree Plasmid Kit (Takara Bio).

2. Establish of Human GLUT9 Stably Expressing Cell

HEK293T cells (American Type Culture Collection, DS Pharma Biomedical) were seeded in a 6 well plate at $1\times10^6$ cells/well. Next day, human GLUT9 expression plasmid was transfected by using Lipofectamine 3000 Reagent (Thermo Fisher Scientific) as follows. Lipofectamine 3000 Reagent (5 μL) was diluted with Opti-MEM (125 μL, Thermo Fisher Scientific). Separately, plasmid DNA (2.5 μg) was diluted with Opti-MEM (125 μL), and P3000 Reagent (5 μL) was added thereto. The obtained solution was mixed with the previously obtained diluted solution, and the mixture was left stand at room temperature for 5 min, and added to the cells. Next day, the transfected cells were diluted and reseeded in a 6 well plate at $4\times10^5$ cells/well, and drug selection was performed in the presence of 30 μg/mL of Blasticidin S HCl, and thereby, Blasticidin-resistant human GLUT9 stably expressing cell line was established. Mock cells were prepared by introducing pEBMulti-Bsd vector into HEK293T cells in a similar manner.

3. Preparation of Uricase/Hyper Expression Plasmid

Uricase/Hyper expression plasmid was prepared by linking the coding regions of Aspergillus Flavus-derived uricase gene and pHyPer-Cyto vector (Evrogen) HyPer gene to the pEBMulti-Hyg vector (Wako Pure Chemical Industries, Ltd.) and then introducing it. The preparation method was performed by reference to Gout and Nucleic Acid Metabolism 2013, 37(2), 93-101, and seven repeated linker sequence of glycine-glycine-glycine-serine was prepared herein.

4. Preparation of Human GLUT9-Uricase/Hyper Coexpressing Cell

Human GLUT9 stably expressing cells were seeded at $3.6\times10^7$ cells per 225 cm² flask. Next day, Uricase/Hyper expression plasmid was transfected by using Lipofectamine 3000 Reagent as follows. Lipofectamine 3000 Reagent (40 μL) was diluted with Opti-MEM (750 μL). Separately, plasmid DNA (20 μg) was diluted with Opti-MEM (750 μL), and P3000 Reagent (40 μL) was added thereto. The obtained solution was mixed with the previously obtained diluted solution, and the mixture was left stand at room temperature for 5 min, and added to the cells. Next day, transfected cells were collected to prepare human GLUT9-Uricase/Hyper coexpressing cells.

5. Evaluation of GLUT9 Inhibitory Activity

Uricase/Hyper transiently-transfected human GLUT9 stably expressing cells or mock cells (blank) were seeded in a 96 well plate (Corning) at $1.6\times10^5$ cells/well, and cultured overnight at 37° C., 5% $CO_2$. D-MEM/high glucose (Wako Pure Chemical Industries, Ltd.) containing 10% Fetal Bovine Serum (Lifetechnology) and 100 units/ml penicillin/100 μg/ml streptomycin (GIBCO) was used as a medium. High $K^-$ buffer (129.8 mM KCl, 1.2 mM $KH_2PO_4$, 1.2 mM $MgSO_4.7H_2O$, 1.3 mM $CaCl_2$. $2H_2O$, 25 mM HEPES, pH 7.4 with 1 M Tris) and the medium were mixed in equal amount to prepare Assay Buffer. The medium in each well was removed, and the test compound solution (final 1% DMSO) diluted with Assay Buffer was added thereto at 50 μl/well, and the mixture was left stand at room temperature for 30 to 60 min. For the solvent control and blank, Assay Buffer containing DMSO alone was added at 50 μl/well, and the mixture was left stand at room temperature for 30 to 60 min. In addition, uric acid solution (containing [$^{14}$C]uric acid as a tracer) diluted with Assay Buffer was added to each well at 15 μl/well (final 300 μM uric acid), and the uptake reaction was performed at room temperature for 6 min. After the completion of the reaction, the cells were washed three times with ice-cooled Wash Buffer (Hank's Balanced Salt Solution containing 0.01% Bovine Serum Albumin) at 150 μl/well, and 0.1N aqueous NaOH solution was added thereto at 25 μl/well to dissolve the cell. MicroScint-20 (Perkin-Elmer) was added thereto at 150 μl/well, the plate was shaked, and CPM of [$^{14}$C] was measured by TopCount NXT (Perkin-Elmer).

Data was obtained by deducting average of CPM in blank well from average of CPM in each treated well. The inhibitory rate of the test compound in each concentration was calculated from the following formula: $[(A-B)/A]\times100$, A is data of solvent control, B is data of test compound treatment. $IC_{50}$ value (50% inhibition concentration) of the test compound was obtained by applying the inhibitory rate of the test compound in each concentration to logistic curve.

The results are shown in Table 2-1 to Table 2-6. With regard to Examples 7, 15, 22, 33, 47, 54, 60 and 76 in tables, the GLUT9 inhibitory rate at 10 μM of compound are shown therein.

TABLE 2-1

| Example | humans GLUT9 inhibitory activity ($IC_{50}$ value (μM)) |
|---|---|
| 1 | 0.0807 |
| 2 | 0.9461 |
| 3 | 0.1341 |
| 4 | 0.6124 |
| 5 | 0.0626 |
| 6 | 0.1409 |
| 7 | 9% inhibition at 10 μM |
| 8 | 0.1504 |
| 9 | 0.4831 |
| 10 | 1.7769 |
| 11 | 0.0659 |
| 12 | 5.0637 |
| 13 | 0.2188 |
| 14 | 0.0914 |
| 15 | 5% inhibition at 10 μM |
| 16 | 0.0819 |
| 17 | 0.6922 |
| 18 | 0.0942 |
| 19 | 3.0737 |
| 20 | 0.1198 |
| 21 | 0.0607 |
| 22 | 9% inhibition at 10 μM |
| 23 | 0.9916 |
| 24 | 0.1342 |
| 25 | 0.0837 |
| 26 | 0.1543 |
| 27 | 0.2548 |
| 28 | 4.2515 |
| 29 | 0.1578 |
| 30 | 0.0892 |

TABLE 2-2

| Example | humans GLUT9 inhibitory activity ($IC_{50}$ value (μM)) |
|---|---|
| 31 | 0.1336 |
| 32 | 0.0888 |
| 33 | 28% inhibition at 10 μM |
| 34 | 0.1241 |
| 35 | 0.1193 |
| 36 | 0.1891 |
| 37 | 0.1106 |
| 38 | 0.8652 |
| 39 | 1.4456 |
| 40 | 0.3405 |
| 41 | 0.0890 |
| 42 | 6.5049 |
| 43 | 7.1322 |
| 44 | 1.6522 |
| 45 | 0.0506 |

TABLE 2-2-continued

| Example | humans GLUT9 inhibitory activity (IC$_{50}$ value (μM)) |
|---|---|
| 46 | 2.7530 |
| 47 | 47% inhibition at 10 μM |
| 48 | 7.1178 |
| 49 | 0.2005 |
| 50 | 0.1333 |
| 51 | 0.9618 |
| 52 | 0.1186 |
| 53 | 0.4600 |
| 54 | 43% inhibition at 10 μM |
| 55 | 3.9895 |
| 56 | 0.1798 |
| 57 | 0.3443 |
| 58 | 0.0520 |
| 59 | 0.1315 |
| 60 | 45% inhibition at 10 μM |

TABLE 2-3

| Example | humans GLUT9 inhibitory activity (IC$_{50}$ value (μM)) |
|---|---|
| 61 | 5.5905 |
| 62 | 0.1267 |
| 63 | 0.6586 |
| 64 | 0.0987 |
| 65 | 0.0946 |
| 66 | 0.0770 |
| 67 | 0.1024 |
| 68 | 0.0578 |
| 69 | 0.8563 |
| 70 | 1.6718 |
| 71 | 0.1318 |
| 72 | 0.5258 |
| 73 | 0.1044 |
| 74 | 0.1410 |
| 75 | 0.0844 |
| 76 | 10% inhibition at 10 μM |
| 77 | 0.0585 |
| 78 | 2.2102 |
| 79 | 0.3686 |
| 80 | 0.8421 |
| 81 | 0.1924 |
| 82 | 0.2450 |
| 83 | 0.0662 |
| 84 | 0.1167 |
| 85 | 0.8527 |
| 86 | 1.8180 |
| 87 | 1.7851 |
| 88 | 0.9282 |
| 89 | 1.7982 |
| 90 | 0.1397 |

TABLE 2-4

| Example | humans GLUT9 inhibitory activity (IC$_{50}$ value (μM)) |
|---|---|
| 91 | 0.2470 |
| 92 | 0.1810 |
| 93 | 0.1837 |
| 94 | 0.0918 |
| 95 | 0.0576 |
| 96 | 0.0887 |
| 97 | 0.0795 |
| 98 | 0.0605 |
| 99 | 0.0514 |
| 100 | 0.0820 |
| 101 | 0.1642 |
| 102 | 0.7899 |
| 103 | 0.0720 |
| 104 | 0.1388 |
| 105 | 0.4533 |

TABLE 2-4-continued

| Example | humans GLUT9 inhibitory activity (IC$_{50}$ value (μM)) |
|---|---|
| 106 | 0.1007 |
| 107 | 0.0627 |
| 108 | 0.0712 |
| 109 | 0.0799 |
| 110 | 0.2649 |
| 111 | 0.0826 |
| 112 | 0.5607 |
| 113 | 1.0001 |
| 114 | 0.0604 |
| 115 | 0.0497 |
| 116 | 0.0684 |
| 117 | 0.5432 |
| 118 | 0.1078 |
| 119 | 0.5012 |
| 120 | 0.5391 |

TABLE 2-5

| Example | humans GLUT9 inhibitory activity (IC$_{50}$ value (μM)) |
|---|---|
| 121 | 0.5007 |
| 122 | 0.2579 |
| 123 | 0.0589 |
| 124 | 0.1826 |
| 125 | 0.2287 |
| 126 | 0.0497 |
| 127 | 0.0688 |
| 128 | 0.0732 |
| 129 | 0.0569 |
| 130 | 0.0521 |
| 131 | 0.1552 |
| 132 | 0.0519 |
| 133 | 0.3134 |
| 134 | 0.5248 |
| 135 | 0.0613 |
| 136 | 0.2502 |
| 137 | 0.0917 |
| 138 | 0.4993 |
| 139 | 0.1672 |
| 140 | 0.0713 |
| 141 | 0.0639 |
| 142 | 0.2263 |
| 143 | 0.1253 |
| 144 | 0.3270 |
| 145 | 0.1065 |
| 146 | 0.1387 |
| 147 | 0.0868 |
| 148 | 0.0807 |
| 149 | 0.0574 |
| 150 | 0.1018 |

TABLE 2-6

| Example | humans GLUT9 inhibitory activity (IC$_{50}$ value (μM)) |
|---|---|
| 151 | 0.1064 |
| 152 | 0.0590 |
| 153 | 0.1023 |

INDUSTRIAL APPLICABILITY

Since Compound [I] or a pharmaceutically acceptable salt thereof has a GLUT9 inhibitory activity, it may be useful for the treatment or prophylaxis of a disease selected from the group consisting of hyperuricemia and gout.

The invention claimed is:
1. A compound of Formula [I], or a pharmaceutically acceptable salt thereof:

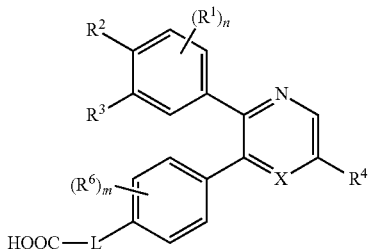

[I]

wherein
=X— is =C($R^5$)— or =N—;
-L-COOH is
(1) —COOH,
(2) —C($R^{71}$)($R^{72}$)—COOH,
(3) —C($R^{73}$)($R^{74}$)—C($R^{75}$)($R^{76}$)—COOH, or
(4) —O—C($R^{77}$)($R^{78}$)—COOH;
n is 0, 1, or 2;
m is 0, 1, 2, or 3;
$R^1$ is each independently halogen or $C_{1-3}$ alkyl;
$R^2$ is
(1) halogen,
(2) hydroxy,
(3) cyano,
(4) $C_{1-6}$ alkyl optionally substituted with 1 to 3 substituents independently selected from the group consisting of cyano and $C_{1-3}$ alkoxy,
(5) halo $C_{1-6}$ alkyl,
(6) $C_{1-6}$ alkoxy,
(7) halo $C_{1-6}$ alkoxy,
(8) —COO$R^{21}$ wherein $R^{21}$ is hydrogen or $C_{1-3}$ alkyl,
(9) —CON($R^{22}$)($R^{23}$) wherein $R^{22}$ and $R^{23}$ are each independently hydrogen or $C_{1-3}$ alkyl,
(10) $C_{3-6}$ cycloalkyl or
(11) a 4- to 6-membered saturated heterocyclic group containing 1 or 2 hetero atom as a ring atom in addition to the carbon atoms, wherein the hetero atom is independently selected from the group consisting of oxygen, nitrogen and sulfur atoms, and
$R^3$ is
(1) hydrogen,
(2) halogen,
(3) cyano,
(4) $C_{1-3}$ alkyl,
(5) halo $C_{1-3}$ alkyl,
(6) $C_{1-3}$ alkoxy, or
(7) —COO$R^{31}$ wherein $R^{31}$ is hydrogen or $C_{1-3}$ alkyl or
$R^2$ and $R^3$, together with the carbon atoms that they are bonded to, form a 4- to 6-membered saturated heterocycle containing 1 or 2 hetero atom as a ring atom in addition to the carbon atoms, wherein the hetero atom is independently selected from the group consisting of oxygen, nitrogen and sulfur atoms;
$R^4$ is
(1) $C_{1-8}$ alkyl optionally substituted with 1 to 3 substituents independently selected from the following Group A,
(2) halo $C_{1-6}$ alkyl,
(3) CON($R^{41}$)($R^{42}$) wherein $R^{41}$ and $R^{42}$ are each independently hydrogen or $C_{1-6}$ alkyl,
(4) $C_{3-6}$ cycloalkyl optionally substituted with 1 to 3 substituents independently selected from $C_{1-3}$ alkoxy, or
(5) a 4- to 6-membered saturated heterocyclic group containing 1 or 2 hetero atom as a ring atom in addition to the carbon atoms, wherein the hetero atom is independently selected from the group consisting of oxygen, nitrogen and sulfur atoms, and wherein the ring atom in the heterocyclic group bonded to

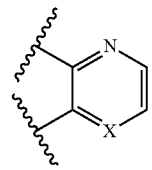

is a carbon atom, and
Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl optionally substituted with one hydroxy, and
(e) phenyl, and
$R^5$ is hydrogen, halogen or $C_{1-3}$ alkyl or
$R^4$ and $R^5$, together with the carbon atoms that they are bonded to, form $C_{3-6}$ cycloalkane;
$R^6$ are each independently halogen, hydroxy, $C_{1-3}$ alkyl or $C_{1-3}$ alkoxy; and
$R^{71}$, $R^{72}$, $R^{73}$, $R^{74}$, $R^{75}$, $R^{76}$, $R^{77}$, and $R^{78}$ are each independently hydrogen or $C_{1-3}$ alkyl.

2. The compound according to claim 1 or a pharmaceutically acceptable salt thereof, wherein -L-COOH is —COOH.

3. The compound according to claim 1 or a pharmaceutically acceptable salt thereof, wherein n is 0 or 1.

4. The compound according to claim 1 or a pharmaceutically acceptable salt thereof, wherein m is 0 or 1.

5. The compound according to claim 1 or a pharmaceutically acceptable salt thereof, wherein $R^3$ is (1) hydrogen or (2) halogen.

6. The compound according to claim 1 or a pharmaceutically acceptable salt thereof, wherein
$R^4$ is
(1) $C_{1-8}$ alkyl optionally substituted with 1 to 3 substituents independently selected from the following Group A,
(2) halo $C_{1-6}$ alkyl, or
(3) CON($R^{41}$)($R^{42}$) wherein $R^{41}$ and $R^{42}$ are each independently hydrogen or $C_{1-6}$ alkyl, and Group A consists of
(a) hydroxy,
(b) $C_{1-3}$ alkoxy optionally substituted with one hydroxy or one $C_{1-3}$ alkoxy,
(c) halo $C_{1-3}$ alkoxy,
(d) $C_{3-6}$ cycloalkyl optionally substituted with one hydroxy, and
(e) phenyl.

7. A compound of the following formula or a pharmaceutically acceptable salt thereof:

8. A compound of the following formula or a pharmaceutically acceptable salt thereof:

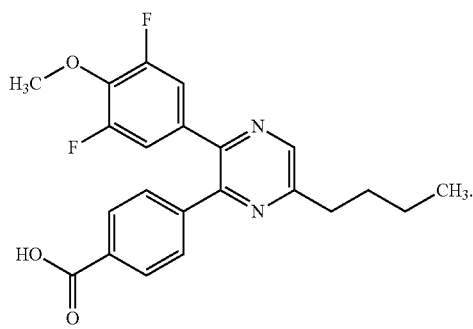 [SMILES: CCCCc1cnc(-c2cc(F)c(OC)c(F)c2)c(-c2ccc(C(=O)O)cc2)n1]

9. A compound of the following formula or a pharmaceutically acceptable salt thereof:

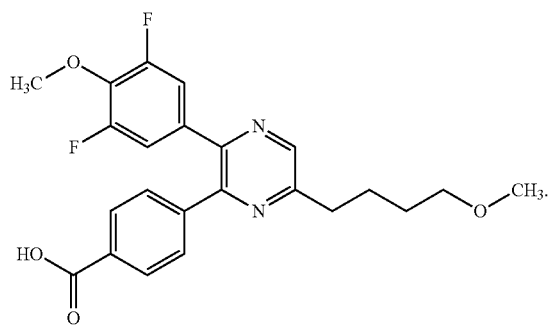 [SMILES: COCCCCc1cnc(-c2cc(F)c(OC)c(F)c2)c(-c2ccc(C(=O)O)cc2)n1]

10. A compound of the following formula or a pharmaceutically acceptable salt thereof:

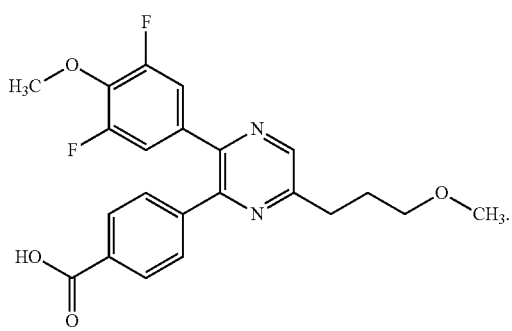 [SMILES: COCCCc1cnc(-c2cc(F)c(OC)c(F)c2)c(-c2ccc(C(=O)O)cc2)n1]

11. A compound of the following formula or a pharmaceutically acceptable salt thereof:

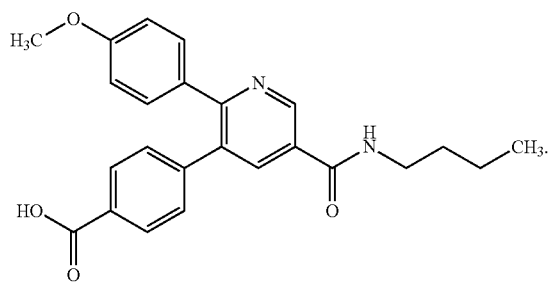 [SMILES: CCCCNC(=O)c1cnc(-c2ccc(OC)cc2)c(-c2ccc(C(=O)O)cc2)c1]

12. A compound of the following formula or a pharmaceutically acceptable salt thereof:

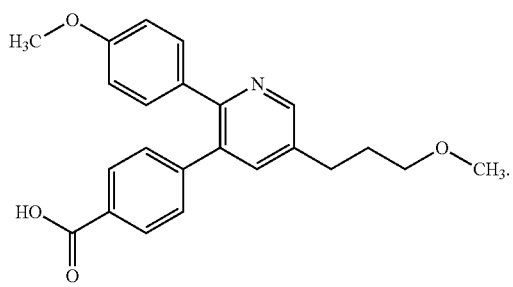 [SMILES: COCCCc1cnc(-c2ccc(OC)cc2)c(-c2ccc(C(=O)O)cc2)c1]

13. A compound of the following formula or a pharmaceutically acceptable salt thereof:

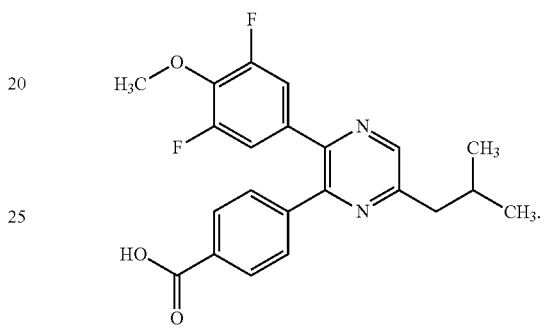

14. A compound of the following formula or a pharmaceutically acceptable salt thereof:

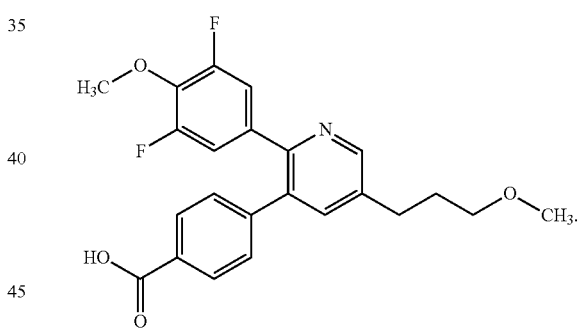

15. A compound of the following formula or a pharmaceutically acceptable salt thereof:

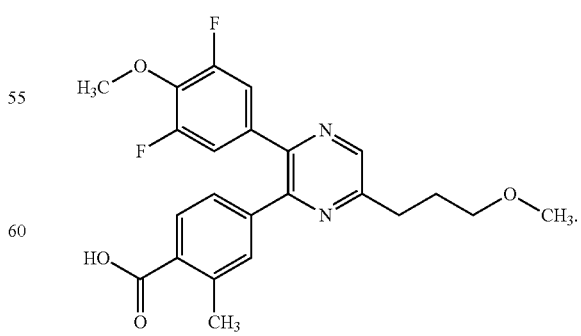

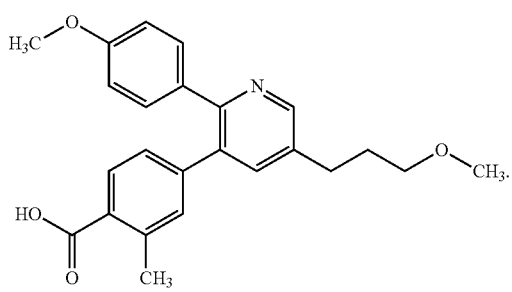 [SMILES: COCCCc1cnc(-c2ccc(OC)cc2)c(-c2ccc(C(=O)O)c(C)c2)c1]

16. A compound of the following formula or a pharmaceutically acceptable salt thereof:

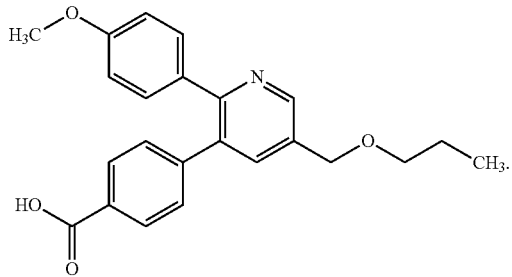 [SMILES: CCCOCc1cnc(-c2ccc(OC)cc2)c(-c2ccc(C(=O)O)cc2)c1]

17. A compound of the following formula or a pharmaceutically acceptable salt thereof:

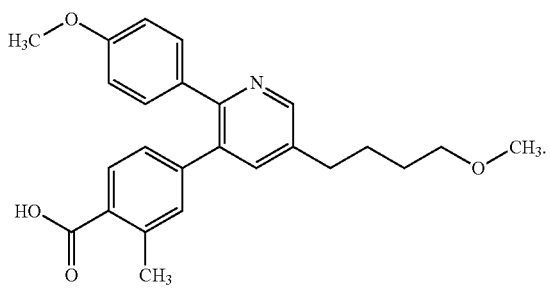 [SMILES: COCCCCc1cnc(-c2ccc(OC)cc2)c(-c2ccc(C(=O)O)c(C)c2)c1]

18. A pharmaceutical composition comprising the compound according to any one of claims 1 and 7-17 or a pharmaceutically acceptable salt thereof, and a pharmaceutically acceptable carrier.

19. A method for the treatment or prophylaxis of a disease selected from the group consisting of hyperuricemia, gout, and chronic kidney disease in a mammal in need of such treatment or prophylaxis, which comprises administering a pharmaceutically effective amount of the compound according to any one of claims 1 and 7-17 or a pharmaceutically acceptable salt thereof to the mammal.

20. A compound of the following formula:

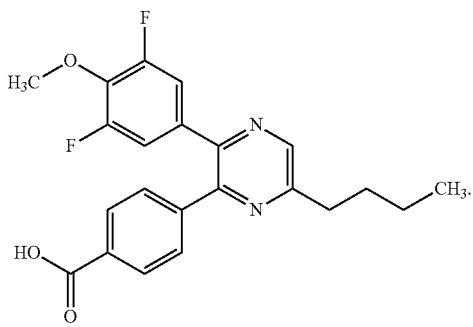

21. A compound of the following formula:

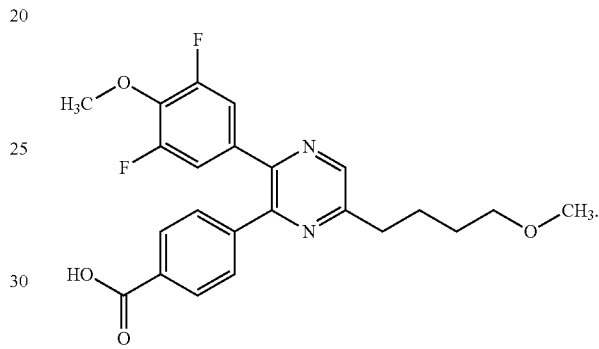

22. A compound of the following formula:

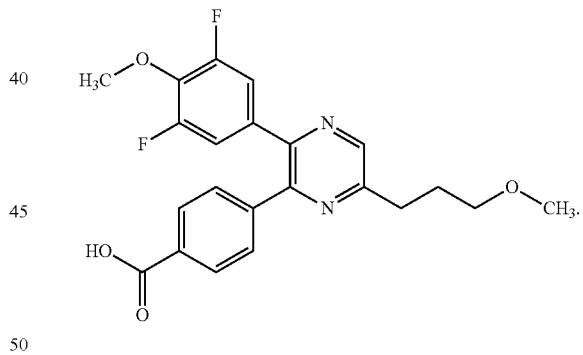

23. A compound of the following formula:

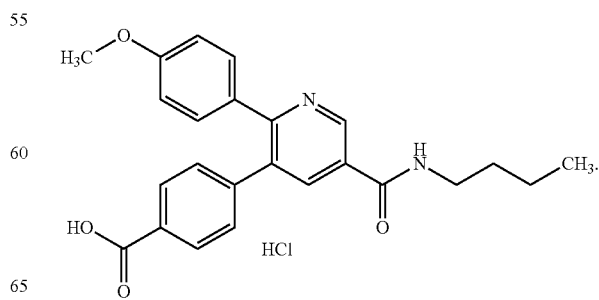

24. A compound of the following formula:

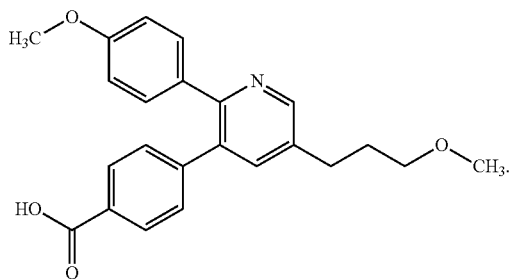 [SMILES: COCCCc1cnc(-c2ccc(OC)cc2)c(-c2ccc(C(=O)O)cc2)c1]

25. A compound of the following formula:

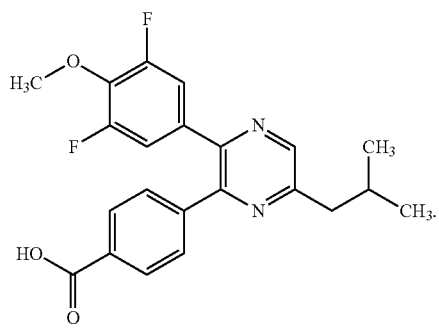 [SMILES: COc1c(F)cc(-c2ncc(CC(C)C)nc2-c2ccc(C(=O)O)cc2)cc1F]

26. A compound of the following formula:

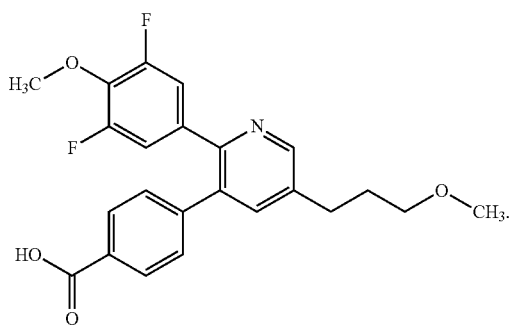 [SMILES: COCCCc1cnc(-c2cc(F)c(OC)c(F)c2)c(-c2ccc(C(=O)O)cc2)c1]

27. A compound of the following formula thereof:

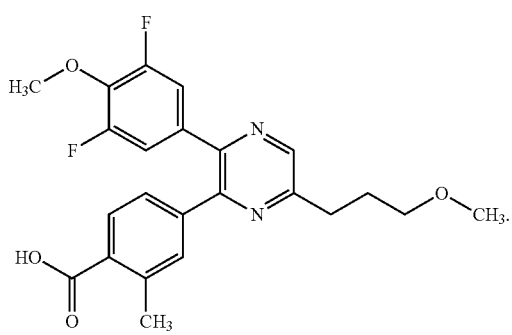 [SMILES: COCCCc1cnc(-c2cc(F)c(OC)c(F)c2)c(-c2ccc(C(=O)O)c(C)c2)n1]

28. A compound of the following formula:

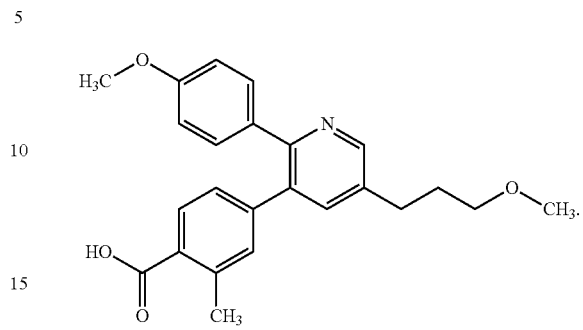

29. A compound of the following formula:

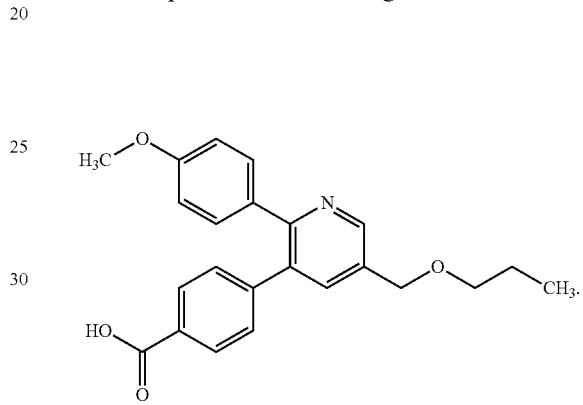

30. A compound of the following formula:

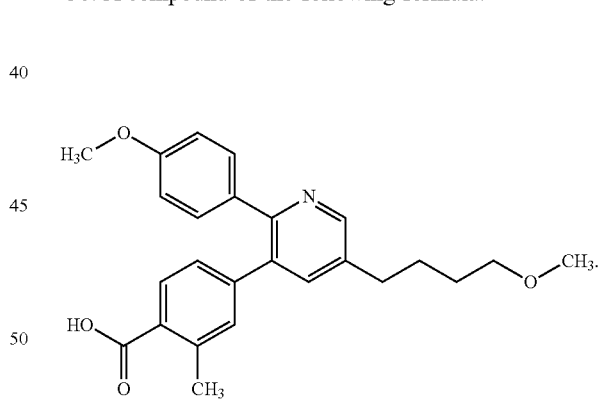

31. A pharmaceutical composition comprising the compound according to any one of claims 20-30 and a pharmaceutically acceptable carrier.

32. A method for the treatment or prophylaxis of a disease selected from the group consisting of hyperuricemia, gout, and chronic kidney disease in a mammal in need of such treatment or prophylaxis, which comprises administering a pharmaceutically effective amount of the compound according to any one of claims 20-30 to the mammal.

* * * * *